US012655202B2

(12) United States Patent
Fellouse et al.

(10) Patent No.: US 12,655,202 B2
(45) Date of Patent: **\*Jun. 16, 2026**

---

(54) SYNTHETIC ANTIBODIES AGAINST VEGF AND THEIR USES

(71) Applicants: Saksin Lifesciences Pvt Ltd, Chennai (IN); THE GOVERNING COUNCIL OF THE UNIVERSITY OF TORONTO BANTING INSTITUTE, Toronto (CA)

(72) Inventors: Frederic Fellouse, Toronto (CA); Jason Moffat, Toronto (CA); Sachdev Sidhu, Toronto (CA); Chaniyilparampi Nanappan Ramchand, Chennai (IN); Ravikant Harit, Chennai (IN); Reena Arora, Chennai (IN); Aju Antony, Chennai (IN); Santhi Vinodh, Chennai (IN)

( \* ) Notice: Subject to any disclaimer, the term of this patent is extended or adjusted under 35 U.S.C. 154(b) by 772 days.

This patent is subject to a terminal disclaimer.

(21) Appl. No.: 17/529,586

(22) Filed: Nov. 18, 2021

(65) Prior Publication Data

US 2022/0235123 A1 Jul. 28, 2022

Related U.S. Application Data

(62) Division of application No. 16/331,512, filed as application No. PCT/IB2017/001166 on Sep. 7, 2017, now Pat. No. 11,254,738.

(60) Provisional application No. 62/384,644, filed on Sep. 7, 2016.

(51) Int. Cl.

| | |
|---|---|
| *C07K 16/00* | (2006.01) |
| *A61K 39/395* | (2006.01) |
| *A61P 27/02* | (2006.01) |
| *A61P 35/00* | (2006.01) |
| *C07K 16/22* | (2006.01) |
| *C12N 15/85* | (2006.01) |
| *A61K 39/00* | (2006.01) |

(52) U.S. Cl.
CPC .............. *C07K 16/22* (2013.01); *A61P 27/02* (2018.01); *A61P 35/00* (2018.01); *C12N 15/85* (2013.01); *A61K 2039/507* (2013.01); *C07K 2317/10* (2013.01); *C07K 2317/24* (2013.01); *C07K 2317/33* (2013.01); *C07K 2317/55* (2013.01); *C07K 2317/565* (2013.01); *C07K 2317/76* (2013.01); *C07K 2317/92* (2013.01); *C12N 2015/8518* (2013.01)

(58) Field of Classification Search
None
See application file for complete search history.

(56) References Cited

U.S. PATENT DOCUMENTS

| | | |
|---|---|---|
| 7,740,844 B2 | 6/2010 | Hong et al. |
| 2004/0260068 A1 | 12/2004 | Tsurushita et al. |
| 2007/0237764 A1 | 10/2007 | Birtalan et al. |
| 2014/0154255 A1 | 6/2014 | Akamatsu et al. |
| 2015/0086568 A1 | 3/2015 | Fuh et al. |
| 2015/0232549 A1 | 8/2015 | Fuh et al. |

FOREIGN PATENT DOCUMENTS

| | | |
|---|---|---|
| CN | 1863818 | 11/2006 |
| WO | PCT/US2004/024662 | 2/2005 |
| WO | WO201673918 | 5/2016 |

OTHER PUBLICATIONS

Holm et al., Molecular Immunology, 2007, vol. 44, pp. 1075-1084.\*
International Search Report dated Nov. 2, 2018 in connection with WO 2018/046997.
Written Opinion of the International Searching Authority dated Nov. 2, 2018 in connection WO2018/046997.
International Search Report dated Jul. 3, 2019 in connection with WO 2018/046997.
Paul, Fundamental Immunology, 3rd Edition, 1993, pp. 292-295.
Rudikoff et al., Proc. Natl. Acad. Sci. USA, 79(6): 1979-1983, Mar. 1982.
Colman P. M. Research in Immunology, 145:33-36, 1994.
Maccallum et al., J. Mol. Biol., 262, 732-745, 1996.
Pascalis et al., Journal of Immunology, 2002, vol. 169, pp. 3076-3084.
Casset et al., Biochemical and Biophysical Research Communications, 2003. vol. 307, pp. 198-205.
Holz Frank G et al: "Single-Chain Antibody Fragment VEGF Inhibitor RTH258 for Neovascular Age-Related Macular Degeneration A Randomized Controlled Study", Ophthalmology, Elsevier, Amsterdam, NL, vol. 123, No. 5, Feb. 20, 2016 (Feb. 20, 2016), pp. 1080-1089, XP029516946, ISSN: 0161-6420. DOI: 10.1016/J. OPHTHA.2015.12.030.
Wang, Q et al.: "Pharmacological characteristics and efficacy of a novel antiangiogenic antibody FD006 in corneal neovascularization", BMC Biotechnology. vol. 14, Feb. 27, 2014 (Feb. 27, 2014), XP021178366.

\* cited by examiner

*Primary Examiner* — Mark Halvorson
(74) *Attorney, Agent, or Firm* — ADRIANO & ASSOCIATES

(57) ABSTRACT

The invention provides novel synthetic antibodies directed against VEGF and uses thereof.

17 Claims, 31 Drawing Sheets

Figure 4B:
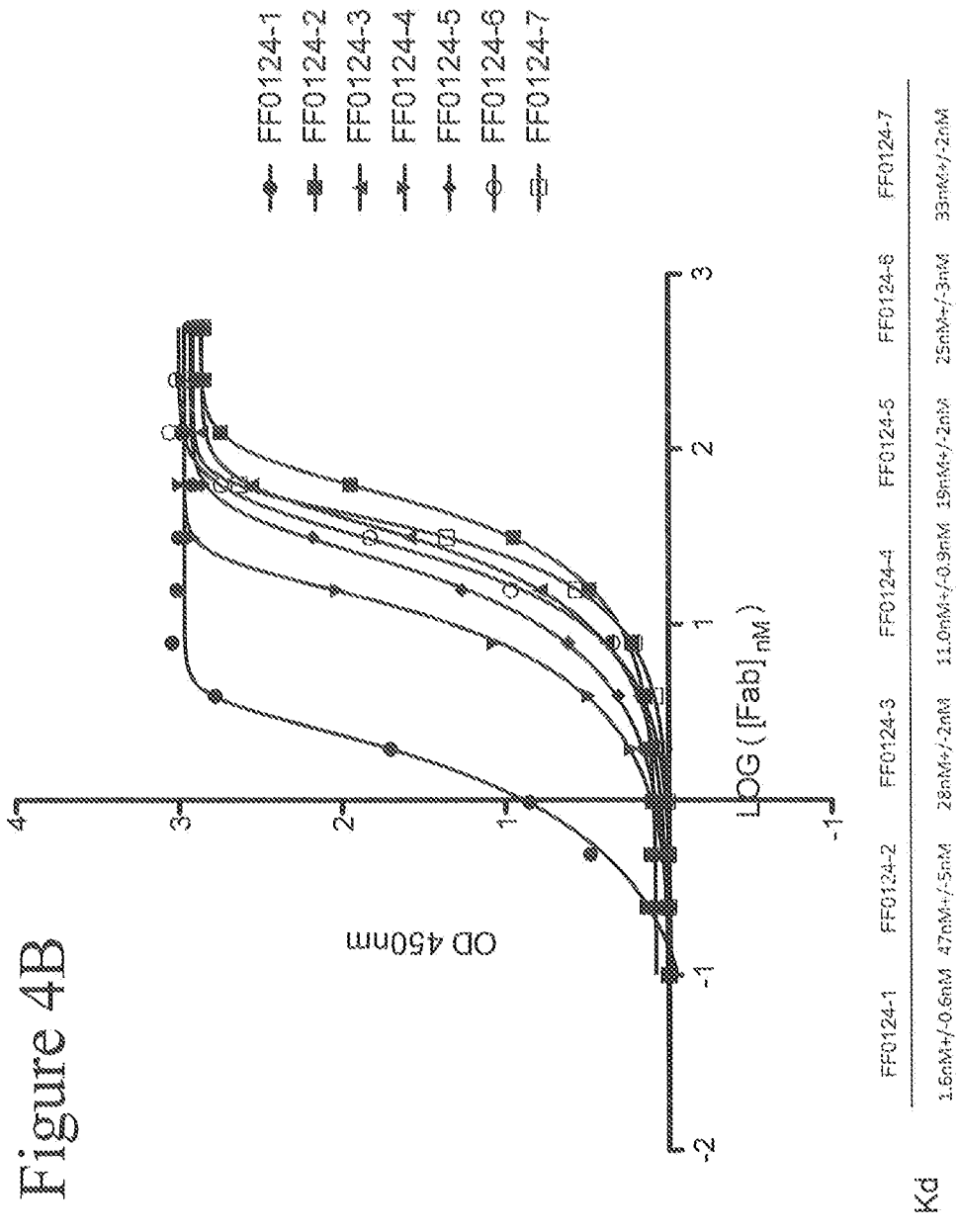

Specification includes a Sequence Listing.

Figure 1: BSA standard curve for the quantification through Bradford method with absorbance determined at 595 nm
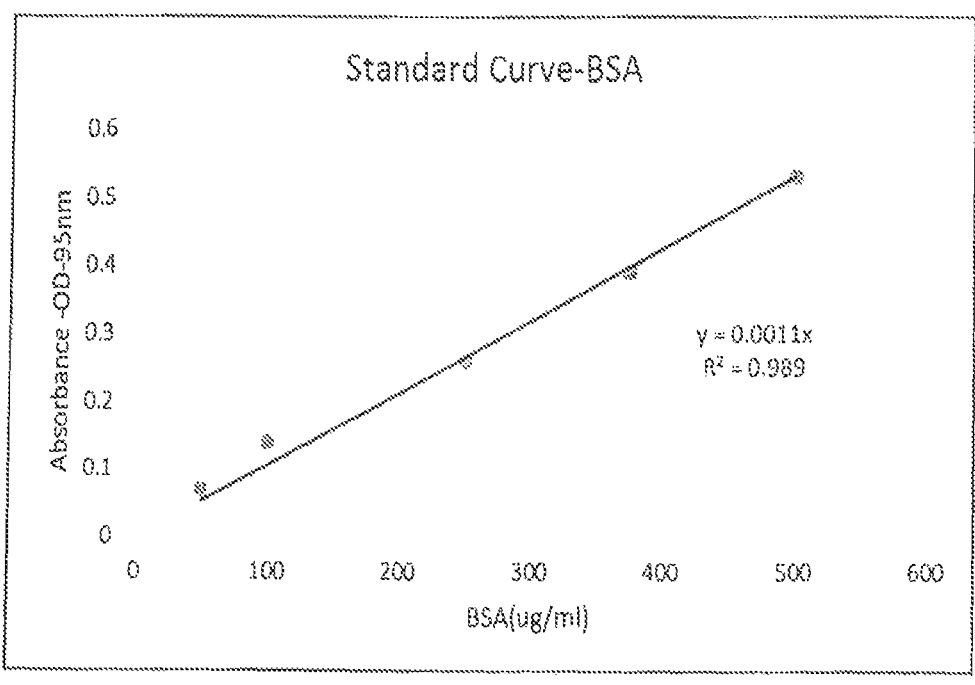

Figure 2: ELISA standard curve prepared using Lucentis for quantification of Fab
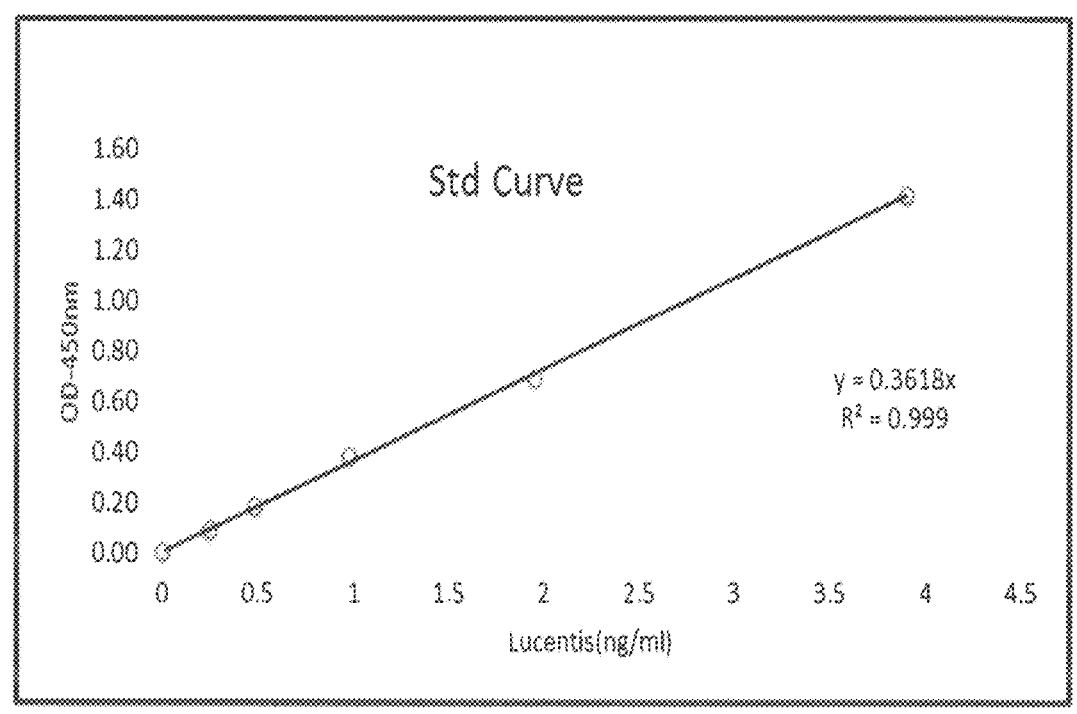

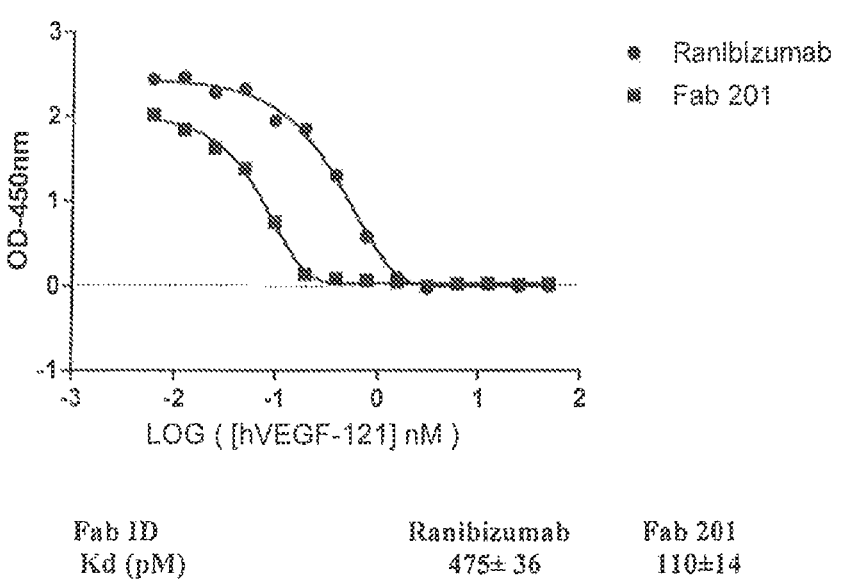
Figure 3: Competitive ELISA
| Fab ID | Ranibizumab | Fab 201 |
|---|---|---|
| Kd (pM) | 475± 36 | 110±14 |

Figure 4A-B. CDR sequences of Fabs issued from the selection of the naïve antibody library

Fig 4A

| Fab ID | TRAC Fab ID | CDR-L1 | CDR-L2 | CDR-L3 | CDR-H1 | CDR-H2 | CDR-H3 |
|--------|-------------|--------|--------|--------|--------|--------|--------|
| 1. FF0124-1 | F2078 | RASQSVSSAVA | SASSLYS | QQGGWLLIT | GFNLYYYSIH | YIYPSYGYTYYADSVKG | HAWYSGWAMDY |
| 2. FF0124-2 | F2083 | RASQSVSSAVA | SASSLYS | QQSGPLFT | GFNLYYYSSMH | SISPSSSYTYYADSVKG | YYWWHSPFWAYSGLDY |
| 3. FF0124-3 | F2086 | RASQSVSSAVA | SASSLYS | QQSSYSLIT | GFNLSYSSIH | SISSYYSYTYYADSVKG | SFGWPWGWAMDY |
| 4. FF0124-4 | F2088 | RASQSVSSAVA | SASSLYS | QQGYGPFYSLIT | GFNLYSYSIH | SIYSYSGYTYYADSVKG | GGWYALDY |
| 5. FF0124-5 | F2091 | RASQSVSSAVA | SASSLYS | QQFWAGYGLIT | GFNISSYYMH | SIYSYSGYTSYADSVKG | HSVYYWYGSYWYPSSAMDY |
| 6. FF0124-6 | F2094 | RASQSVSSAVA | SASSLYS | QQSGHVHYPFT | GFNIYYYSMH | SISSYSGYTSYADSVKG | YPYYYWAFDY |
| 7. FF0124-7 | F2116 | RASQSVSSAVA | SASSLYS | QQHYGPIT | GFNLYYSYMH | SISSYSGYTSYADSVKG | GFYGGWYGIIDY |

1. SEQ ID NO.: 39
2. SEQ ID NO.: 40
3. SEQ ID NO.: 41
4. SEQ ID NO.: 42
5. SEQ ID NO.: 43
6. SEQ ID NO.: 44
7. SEQ ID NO.: 45

Figure 5. Competitive Fab-ELISA.
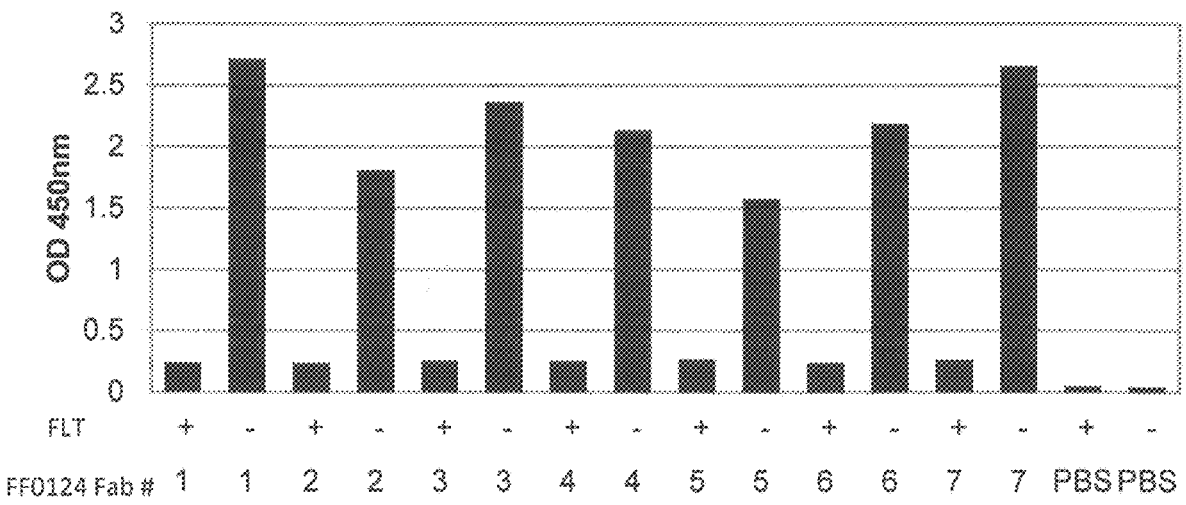

Figure 6A–C

Figure 7A. CDR sequences of Fabs obtained from screening libraries based on FF0158-C4 Fab sequence for higher hVEGF-binding affinity and improved yield.

| Fab ID | CDR-L3 | CDR-H1 | CDR-H2 | CDR-H3 | Yield in ug per liter of culture | Single point competitive ELISA 1nM (% residual binding) | Affinity measured by competitive ELISA |
|---|---|---|---|---|---|---|---|
| 1. FF0158-C4 | QQRGWYLFT | GFNLXYYSIH | YIYPSYGYTYYADSVKG | HAWYSGWAMDY | 220 | 18 | 150+/-30pM |
| 2. FF0187-B3 | QQRGWYLFT | GFDLWYYSIH | YIYPSYGYTYYADSVKG | HAWYSGWAMDY | 440 | 35 | |
| 3. FF0187-C1 | QQRGWYLFT | GFDLWYYSIH | YIYPSYGYTYYADSVKG | HAWYSGWAMDY | 440 | N.D. | |
| 4. FF0187-A12 | QQRGWYLFT | GFDLWYYSIH | YIYPSYGYTYYADSVKG | HAWYSGWAMDY | 660 | 26 | |
| 5. FF0187-H3 | QQRGWYLFT | GFDLWYYSIH | YIYPSYGYTYYADSVKG | HAWYSGWAMDY | 440 | N.D. | |
| 6. FF0187-A8 | N.D. | | | | 220 | 18 | |
| 7. FF0188-H5 | QQRGWYLFT | GFDLFHYSIH | YIYPSYGYTYYADSVKG | HAWYSGWAMDY | 3300 | 31 | 450+/-30pM |
| 8. FF0188-B10 | QQRGWYLFT | GFDLFHYSIH | YIYPSYGYTYYADSVKG | HAWYSGWAMDY | 3080 | N.D. | 410+/-10pM |
| 9. FF0188-F12 | QQRGWYLFT | GFDLYHYSIH | YIYPSYGYTYYADSVKG | HAWYSGWAMDY | 2200 | 30 | |
| 10. FF0188-B6 | QQRGWYLFT | GFDLWYYSIH | YIYPSYGYTYYADSVKG | HAWYSGWAMDY | 1540 | N.D. | |
| 11. FF0188-A2 | QQRGWYLFT | GFDLFFYSIH | YIYPSYGYTYYADSVKG | HAWYSGWAMDY | 660 | 32 | |
| 12. FF0188-A9 | QQRGWYLFT | GFDLYFYSIH | YIYPSYGYTYYADSVKG | HAWYSGWAMDY | 440 | N.D. | |

1. SEQ ID NO:84
2. SEQ ID NO:85
3. SEQ ID NO:86
4. SEQ ID NO:87
5. SEQ ID NO:88
6. SEQ ID NO:89
7. SEQ ID NO:90
8. SEQ ID NO:91
9. SEQ ID NO:92
10. SEQ ID NO:93
11. SEQ ID NO:94

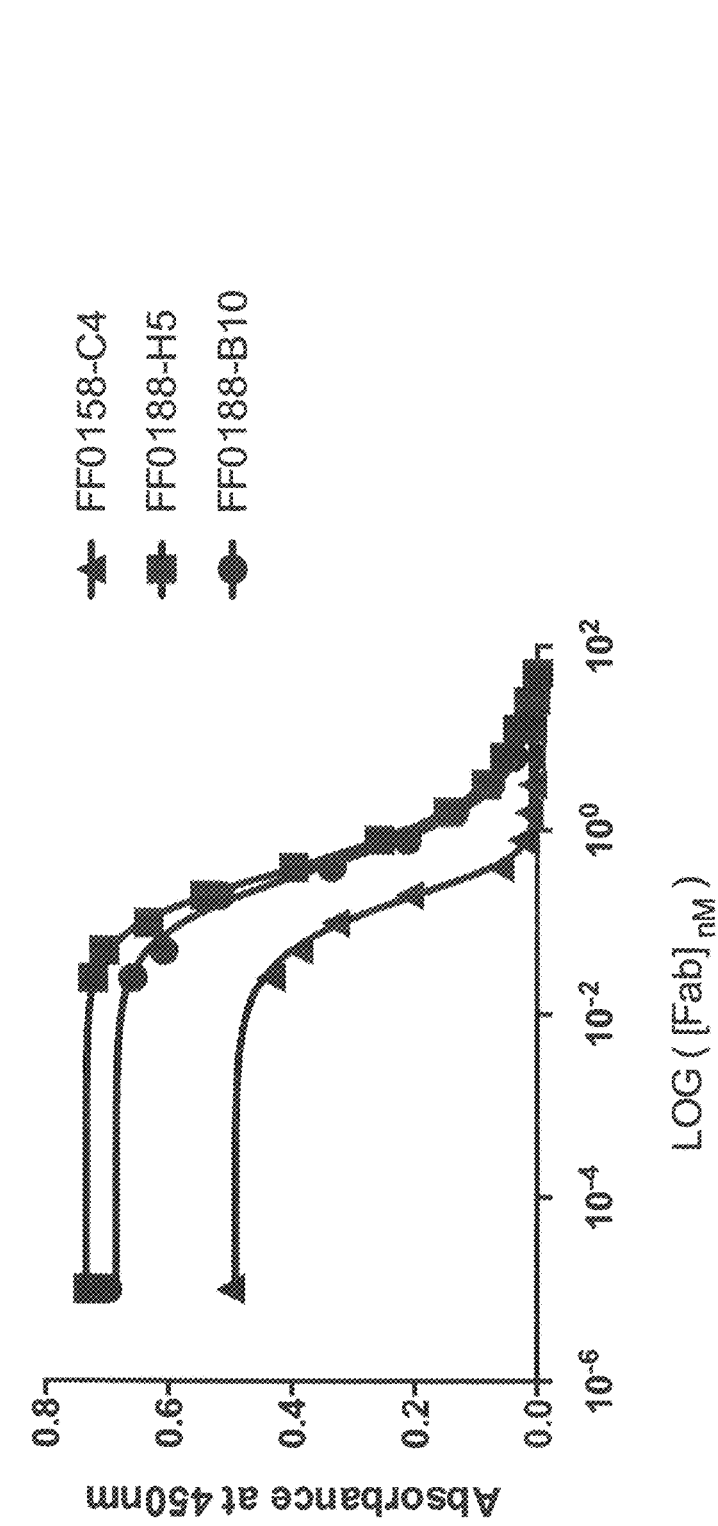
Figure 7B. CDR sequences of Fabs obtained from screening libraries based on FF0158-C4 Fab sequence for higher hVEGF-binding affinity and improved yield.

Figure 8. CDR sequences of Fabs obtained from screening libraries based on FF0188-H5 Fab sequence for higher hVEGF-binding affinity.

| Fab ID | CDR-L3 | CDR-H1 | CDR-H2 | CDR-H3 | Residual binding of competitive phage-ELISA 1nM | Yield in mg per liter of culture | Affinity (KD) by competitive Fab-ELISA in pM | Tm by thermal shift assay in °C |
|---|---|---|---|---|---|---|---|---|
| FF0117-A3 | QQRGWYLFT | GFDLFHYSIH | YIYPSYGVTYYADSVKG | HAWYYSWALDY | 7% | 1.9 | 60+/-20 | |
| FF0117-A5 | QQRGWYLFT | GFDLFHYSIH | YIYPSYGVTYYADSVKG | HAWYYCWGLDY | 14% | 5.4 | 80+/-40 | 77 |
| FF0117-A8 | QQRGWYLFT | GFDLFHYSIH | YIYPSYGVTYYADSVKG | HAWYSGWALDY | 17% | 1.6 | 130+/-50 | |
| FF0117-A10 | QQRGWYLFT | GFDLFHYSIH | YIYPSYGVTYYADSVKG | HAWYYSWALRY | 7% | 2.9 | N.D. | |
| FF0117-A11 | QQRGWYLFT | GFDLFHYSIH | YIYPSYGVTYYADSVKG | HAWYWGWALDY | 5% | 3.7 | 30+/-30 | 77 |
| FF0117-A12 | QQRGWYLFT | GFDLFHYSIH | YIYPSYGVTYYADSVKG | HAWYFKWALDY | 12% | 3.5 | 70+/-40 | |
| FF0117-B5 | QQRGWYLFT | GFDLFHYSIH | YIYPSYGVTYYADSVKG | HAWYYCWGLDY | 18% | 4.0 | 170+/-190 | |
| FF0117-B9 | QQGWYLIT | GFDLFHYSIH | YIYPSYGVTYYADSVKG | HAWYYCWAMDY | 15% | 7.3 | N.D. | 83.5 |
| FF0117-B11 | QQGWYLFT | GFDLFHYSIH | YIYPSNGNTYYADSVKG | HAWYYGWAMDY | 19% | 5.0 | 150+/-80 | 73.5 |
| Ranibizumab | | | | | N.D. | N.D. | 530+/-90 | |
| FF0188-H5 | QQRGWYLFT | GFDLFHYSIH | YIYPSYGVTYYADSVKG | HAWYSGWAMDY | N.D. | N.D. | 400+/-500 | 81 |
| Trastuzumab Fab | | | | | N.D. | N.D. | N.D. | |

1. SEQ ID NO.:55
2. SEQ ID NO.:56
3. SEQ ID NO.:57
4. SEQ ID NO.:58
5. SEQ ID NO.:59
6. SEQ ID NO.:60
7. SEQ ID NO.:61
8. SEQ ID NO.:62
9. SEQ ID NO.:63
10. SEQ ID NO.:64

Figure 9A-C. CDR sequences of Fabs issued from the selection of libraries based on FF0117-A5 Fab sequence. Fabs CDR sequences, production yield and hVEGF binding kinetic parameters are shown.

9A

| Fab ID | CDR-L1 | CDR-L2 | CDR-L3 | CDR-H1 | CDR-H2 | CDR-H3 | Yield in mg per liter of culture | Off rate (s⁻¹) measured by SPR | Off rate (s⁻¹) standard error | Tm by thermal shift assay in °C |
|---|---|---|---|---|---|---|---|---|---|---|
| 1. FF03033-1 | RASQYMSNTA | AASYL.V | QQRGMYLFT | GFDLFHYSIH | YIYPSGYTYYADSVKG | HAWYGMGLDY | N.D. | | | |
| 2. FF03033-2 | RASCTAPTNVA | DASIL.R | QQRGMYLFT | GFDLFHYSIH | YIYPSGYTYYADSVKG | HAWYGMGLDY | 700 | 2.36E-04 | 4.E-06 | |
| 3. FF03033-3 | RASQPVGYRVA | GASSL.A | QQRGMYLFT | GFDLFHYSIH | YIYPSGYTYYADSVKG | HAWYGMGLDY | 840 | 1.46E-04 | 4.E-06 | |
| 4. FF03033-4 | RASQRGWTNVA | SLSQL.A | QQRGMYLFT | GFDLFHYSIH | YIYPSGYTYYADSVKG | HAWYGMGLDY | 1370 | <1E-05 | N.A. | |
| 5. FF03033-5 | RASTGYGERVA | MASRL.A | QQRGMYLFT | GFDLFHYSIH | YIYPSGYTYYADSVKG | HAWYGMGLDY | 4525 | 1.68E-04 | 4.E-06 | |
| 6. FF03033-6 | RASQFKDKVA | RASTL.A | QQRGMYLFT | GFDLFHYSIH | YIYPSGYTYYADSVKG | HAWYGMGLDY | 5160 | 2.84E-04 | 4.E-06 | |
| 7. FF03033-8 | RASQAAYGRVA | RASEL.A | QQRGMYLFT | GFDLFHYSIH | YIYPSGYTYYADSVKG | HAWYGMGLDY | 800 | <1E-06 | N.A. | |
| 8. FF03046-2 | RASQAAYGRVA | KASELXA | QQRGMYLFT | GFDLFHYSIH | YINPSGYTYYADSVKG | HAWYGMGLDY | 2900 | <1E-06 | N.A. | 75 |
| 9. FF0117-A5 | RASQSVSSAVA | SASSLYS | QQRGMYLFT | GFDLFHYSIH | YIYPSGYTYYADSVKG | HAWYGMGLDY | 4140 | 2.55E-04 | 4.E-06 | 75 |
| Ranibizumab | | | | | | | N.D. | <1E-06 | N.A. | 73.5 |

1. SEQ ID NO:65
2. SEQ ID NO:66
3. SEQ ID NO:67
4. SEQ ID NO:68
5. SEQ ID NO:69
6. SEQ ID NO:70
7. SEQ ID NO:71
8. SEQ ID NO:72
9. SEQ ID NO:73

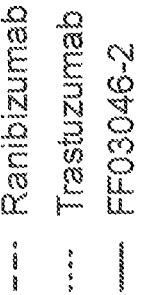
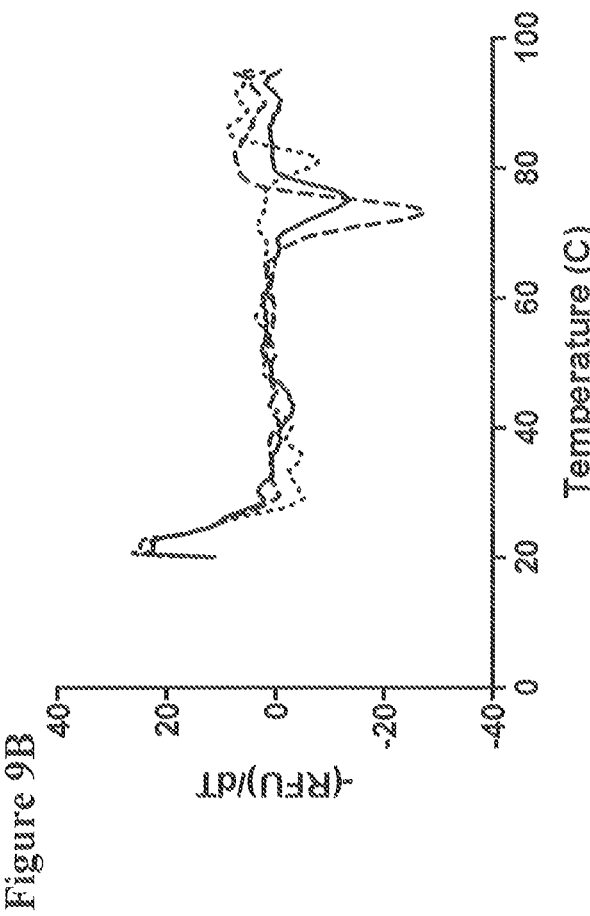
Figure 9B

Figure 9C

Light chain (hK) amino acid sequence (CDR sequences defined in accordance with IMGT® are shown in bold. CDR sequences defined in accordance with Kabat are underlined. Amino acid sequence of the Fab constant region is shown in italic):

DIQMTQSPSSLSASVGDRVTITCRASQAAYGRVAWYQQKPGKAPKLLIYKASELYAGVPSRFSGSRSGTDF
TLTISSLQPEDFATYYCQQRGWYLPTFGQGTKVEIKRTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGE
C (SEQ ID NO.: 76)

Light chain (hK) nucleic acid sequence (DNA sequence coding for the CDR sequences defined in accordance with IMGT® are shown in bold. DNA sequence coding for CDR sequences defined in accordance with Kabat are underlined. DNA sequence coding for Fab the constant region is shown in italic):
GATATCCAGATGACCCAGTCCCCGAGCTCCCTGTCCGCCTCTGTGGGCGATAGGGTCACCATCACCTGCCG
GGCCAGTCAGGCCGCCTACGGCCGCGTAGCCTGGTATCAACAGAAACCAGGAAAAGCTCCGAAGCTTCTGA
TTTACAAAGCATCCGAACTCTACGCCGGAGTCCCTTCTCGCTTCTCTGGTAGCCGTTCCGGGACGGATTTC
ACTCTGACCATCAGCAGTCTGCAGCCGGAAGACTTCGCAACTTATTACTGTCAGCAACGTGGCTGGTATCT
GTTCACGTTCGGACAGGGTACCAAGGTGGAGATCAAACGTACGGTGGCTGCACCATCTGTCTTCATCTTCC
CGCCATCTGATGAGCAGTTGAAATCTGGAACTGCCTCTGTTGTGTGCCTGCTGAATAACTTCTATCCCAGA
GAGGCCAAAGTACAGTGGAAGGTGGATAACGCCCTCCAATCGGGTAACTCCCAGGAGAGTGTCACAGAGCA
GGACAGCAAGGACAGCACCTACAGCCTCAGCAGCACCCTGACGCTGAGCAAAGCAGACTACGAGAAACACA
AAGTCTACGCCTGCGAAGTCACCCATCAGGGCCTGAGCTCGCCCGTCACAAAGAGCTTCAACAGGGGAGAG
TGT (SEQ ID NO.: 77)

Heavy chain amino acid sequence (CDR sequences defined in accordance with IMGT® are shown in bold. CDR sequences defined in accordance with Kabat are underlined. Amino acid sequence of the Fab constant region is shown in italic):

EVQLVESGGGLVQPGGSLRLSCAASGFDLFHYSIHWVRQAPGKGLEWVAYIYPSYGYTYYADSVKGRFTIS
ADTSKNTAYLQMNSLRAEDTAVYYCARHAWYYGWGLDYWGQGTLVTVSSASTKGPSVFPLAPSSKSTSGGT
AALGCLVKDYFPEPVTVSWNSGALTSGVHTFPAVLQSSGLYSLSSVVTVPSSSLGTQTYICNVNHKPSNTK
VDKKVEPKSCDKTHT (SEQ ID NO.: 78)

Heavy chain nucleic acid sequence: (DNA sequence coding for the CDR sequences defined in accordance with IMGT® are shown in bold. DNA sequence coding for CDR sequences defined in accordance with Kabat are underlined. DNA sequence coding for the Fab constant region is shown in italic)
GAGGTTCAGCTGGTGGAGTCTGGCGGTGGCCTGGTGCAGCCAGGGGGCTCACTCCGTTTGTCCTGTGCAGC
TTCTGGCTTCGATTTATTTCATTATTCTATACACTGGGTGCGTCAGGCCCCGGGTAAGGGCCTGGAATGGG
TTGCATACATTTACCCGTCTTATGGCTATACTTATTATGCCGATAGCGTCAAGGGCCGTTTCACTATAAGC
GCAGACACATCCAAAAACACAGCCTACCTACAAATGAACAGCTTAAGAGCTGAGGACACTGCCGTCTATTA
TTGTGCTCGCCATGCGTGGTATTATGGGTGGGGTTTGGACTACTGGGGTCAAGGAACCCTGGTCACCGTCT
CCTCGGCTAGCACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAACTCAGGCGCCCT
GACCAGCGGCGTGCACACCTTCCCGGCTGTCCTACAGTCCTCAGGACTCTACTCCCTCAGCAGCGTGGTGA
CCGTGCCCTCCAGCAGCTTGGGCACCCAGACCTACATCTGCAACGTGAATCACAAGCCCAGCAACACCAAG
GTGGACAAGAAAGTTGAGCCCAAATCTTGTGACAAAACTCACACA (SEQ ID NO.: 79)

Figure 10. hVEGF-dependent Huvec assay
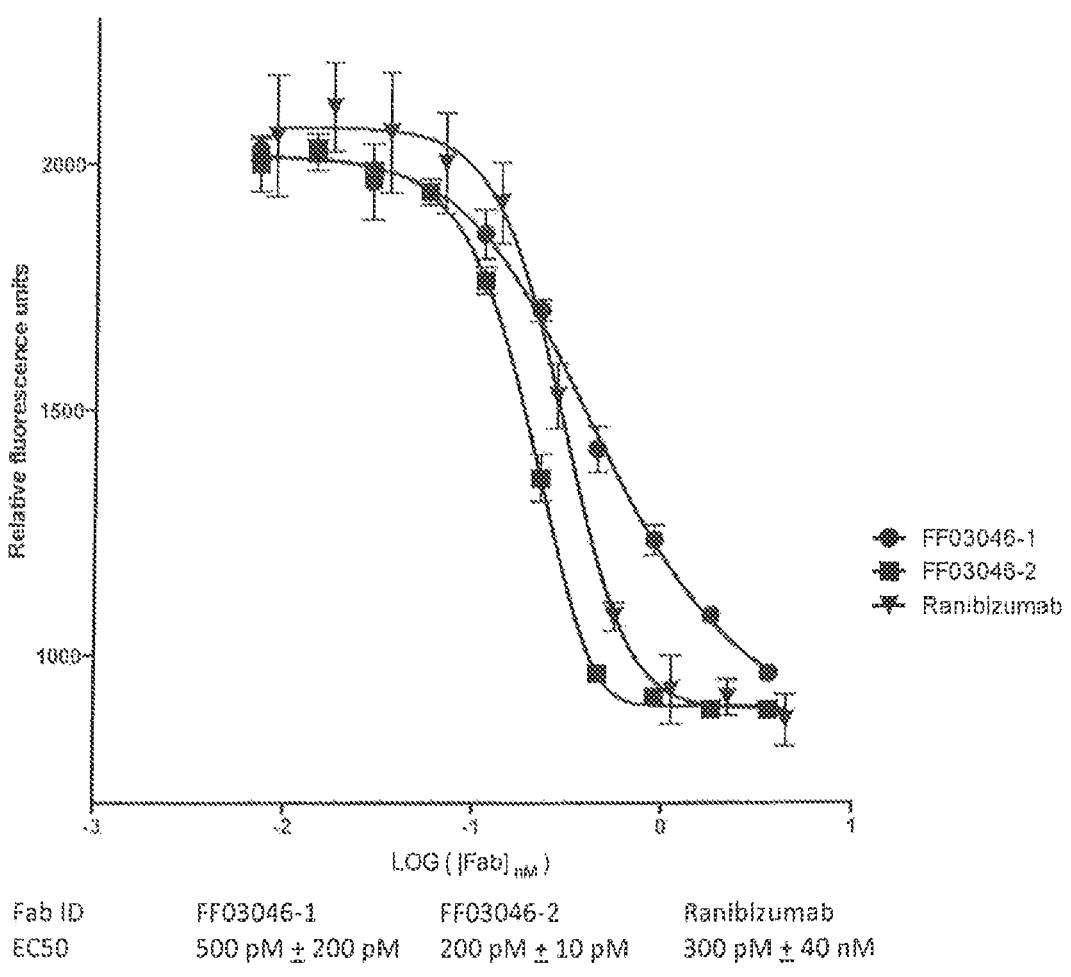
| Fab ID | FF03046-1 | FF03046-2 | Ranibizumab |
|--------|-----------|-----------|-------------|
| EC50 | 500 pM ± 200 pM | 200 pM ± 10 pM | 300 pM ± 40 nM |

Figure 11.  Competitive Fab-ELISA
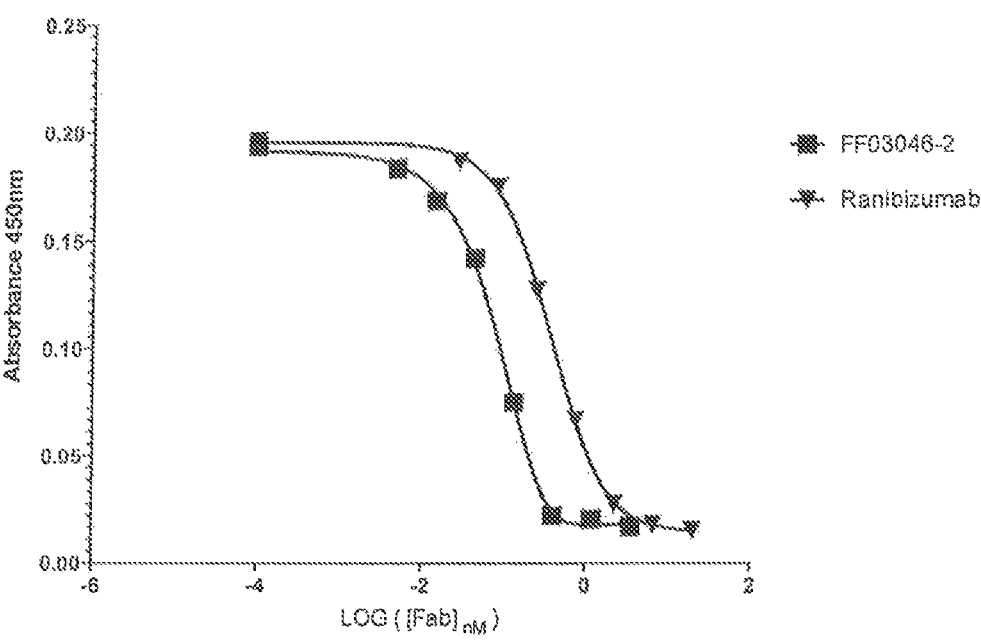
| Fab ID | FF03046-2 | Ranibizumab |
|--------|-----------|-------------|
| Kd | 90 pM +/- 20 pM | 390 pM +/- 50 pM |

Figure 12. Protein and DNA sequence of FF03092-I, the anti-VEGF Fc-Fab fusion Light chain (hK) amino acid sequence (CDR sequences defined in accordance with IMGT® are shown in bold. CDR sequences defined in accordance with Kabat are underlined. The amino acid sequence of the Fab constant domain is shown in italic):

DIQMTQSPSSLSASVGDRVTITCRASQAAYGRVAWYQQKPGKAPKLLIYKASELYAGVPSRFSGSRSGTDF
TLTISSLQPEDFATYYCQQRGYLFTFGQGTKVEIK*RTVAAPSVFIFPPSDEQLKSGTASVVCLLNNFYPR
EAKVQWKVDNALQSGNSQESVTEQDSKDSTYSLSSTLTLSKADYEKHKVYACEVTHQGLSSPVTKSFNRGE
C* (SEQ ID NO:76)

Light chain (hK) nucleic acid sequence (DNA sequence coding for the CDR sequences defined in accordance with IMGT® are shown in bold. DNA sequence coding for CDR sequences defined in accordance with Kabat are underlined. The DNA sequence coding for the Fab constant domain is shown in italic):

GATATCCAGATGACCCAGTCTCCGAGCTCCCTGTCCGCCTCTGTGGGCGATAGGGTCACCATCACCTGCCG
TGCCAGTCAGGCCGCCTACGGCCGGGGTAGCCTGGTATCAACAGAAACCAGGAAAAGCTCCGAAGCTTCTGA
TTTACAAAGCATCCGAACTCTACGCCGGGAGTCCCTTCTCGCTTCTCTGGTAGCCGTTCCGGCACGGATTTC
ACTCTGACCATCAGCAGTCTGCAGCCGGAAGACTTCGCAACTTATTACTGTCAGCAACGTGGCTGGTATCT
GTTCACGTTCGGACAGGGTACCAAGGTGGAGATCAAACGTACGGTGGCTGCACCATCTGTCTTCATCTTCC
CGCCATCTGATGAGCAGTTGAAATCTGCAACTGCCTCTGTTGTGTCCCTGCTGAATAACTTCTATCCCAGA
GAGGCCAAAGTACAGTGGAAGGTGGATAACGCCCTCCAATCGGGTAACTCCCAGGAGAGTGTCACAGAGCA
GGACAGCAAGGACAGCACCTACAGCCTCAGCAGCACCCTGACGCTGAGCAAAGCAGACTACGAAAAACATA
AAGTCTACGCCTGCGAAGTCACCCATCAGGGCCTGAGCTCGCCCGTCACAAAGAGCTTCAACAGGGGAGAG
TGT (SEQ ID NO:77)

Heavy chain nucleic acid sequence (the Fab HC fusion sequence is underlined, the Fc sequence is in italic; the linker between the Fc and the Fab HC is in italic and in bold; DNA coding sequences and amino acid sequences corresponding to the CDRs defined in accordance with IMGT® are shown in bold; DNA sequence coding for CDR sequences defined in accordance with Kabat are double underlined):

*TGCCCACCGTGCCCAGCACCTGAACTCCTGGGCGGACCGTCAGTCTTCCTCTTCCCCCCAAAACCCAAGGA
CACCCTCATGATCTCCCGGACCCCTGAGGTCACATGCGTGGTGGTGGACGTGAGCCACGAAGACCCTGAGG
TCAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGGCAGCCTC
GAGAACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTCACCGTGGACAAGA
GCAGGTGGCAGCAGGGGAACGTCTTCTCATGCTCCGTGATGCATGAGGCTCTGCACAACCACTACACGCAG
AAGAGCCTCTCGCTGAGCCCTGGAAAAGGT*GGCGGAGGATCTGGCGGCGGAGGAAGCGGTGGAGGCGGAAG
CGGAGGCGGAGAAGTGCAGCTGGTGGAATCAGGCGGCGGACTGGTGCAGCCTGGCGGAAGCTTAAGACTGA
GCTGCGCCGCCAGCGGCTTCGACCTGTTCCACTACTCTATCCACTGGGTCCGACAGGCCCCTGGCAAGGGA
CTGGAATGGGTGGCCTACATCTACCCCAGCTACGGCTACACCTACTACGCCGACAGCGTGAAGGGCCGGTT
CACCATCAGCGCCGACACCAGCAAGAACACCGCCTACCTGCAGATGAACAGCCTGAGAGCCGAGGACACCG
CCGTGTACTACTGTGCCAGACACGGCTGGTACTACGGCTGGCCGCTGGATTATTGGGGCCAGGGCACCCTG
GTCACCGTGTCTAGCGCCCTCTACAAAGGGCCCCAGCGTGTTCCCTCTGGCCCCTAGCAGCAAGAGCACATC
TGGCGGAACAGCCGCCCTGGGCTGCCTGGTCAAGGACTACTTTCCCGAGCCCGTGACCGTGTCCTGGAACT
CTGGTGCCCTGACCAGCGGCGTGCACACCTTTCCAGCTGTGCTGCAGAGCAGCGGCCTGTACAGCCTGTCC*

Figure 12 (Continued)

AGCGTGGTCACAGTGCCAAGCAGCACCTGCGCACCCAGAGCCTACATCTGCAACGTGAACCACAAGCCCAG
CAACACCAAGGTGGACAAGAAGGTGGAACCCAAGAGCTGCGACAAGACCCACACC (SEQ ID NO.: 5)

Heavy chain amino acid sequence:
CPPCPAPELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQ
KSLSLSPGKGGGGSGGGGSGGGGSGGGGEVQLVESGGGLVQPGGSLRLSCAASGFDLFRYSIHWVRQAPGKG
LEWVAYIYPSYGYTYYADSVKGRFTISADTSKNTAYLQMNSLRAEDTAVYYCARHAWYYGWGLDYWGQGTL
VTVSSASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHT (SEQ ID NO.: 6)

Figure 13. DNA and protein sequence of FF03077-4, the anti-VEGF Fc-scFv fusion

Single chain nucleic acid sequence (the scFv fusion sequence is underlined; the Fc sequence is in italic; the linker between the Fc and the scFv is in italic and in bold; DNA coding sequences and amino acid sequences corresponding to the CDRs defined in accordance with IMGT are shown in bold; DNA coding sequences and amino acid sequences corresponding to CDR sequences of Fab FF03046-2 defined in accordance with Kabat in the scFv are double underlined):

CPPCPAPELLGGPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRWQQGNVFSCSVMHEALHNHYTQ KSLSLSPGKGGGGSGGGGSGGGGSGGGGDIQMTQSPSSLSASVGDRVTITCRASQAAYGRVAWYQQKPGKAP KLLIYKASELYAGVPSRFSGSRSGTDFTLTISSLQPEDFATYYCQQRGWLPTFGGGTKVEIKGTTAASGS SGGGSSSGAEVQLVESGGGLVQPGGSLRLSCAASGFDLFHSIHWVRQAPGKGLEWVAYIYPSYGYTYYADS VKGRFTISADTSKNTAYLQMNSLRAEDTAVYYCARHAWYSWGLDYWGQGTLVTVSS (SEQ ID NO.:75)

Figure 14.  Competitive ELISA
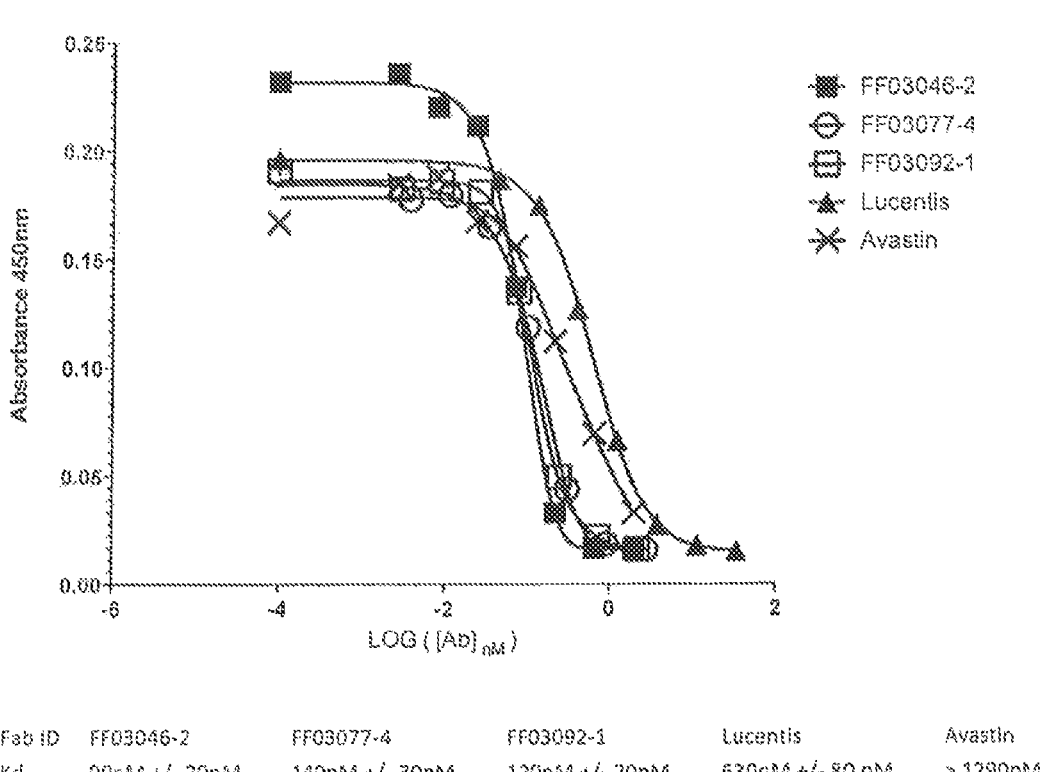
| Fab ID | FF03046-2 | FF03077-4 | FF03092-1 | Lucentis | Avastin |
|--------|-----------|-----------|-----------|----------|---------|
| Kd | 90pM +/- 20pM | 140pM +/- 30pM | 120pM +/- 20pM | 630pM +/- 80 pM | > 1290pM |

Figure 15. Protein and DNA sequence of FF03092-3, the anti-VEGF full length mature IgG1

Light chain (hK) amino acid sequence (CDR sequences defined in accordance with
IMGT® are shown in bold. CDR sequences defined in accordance with Kabat are
underlined. Amino acid sequence of the Fab constant region is shown in italic):

DIQMTQSPSSLSASVGDRVTITCRASQAAYGRVAWYQQKPGKAPKLLIYKASEL
YAGVPSRFSGSRSGTDFTLTISSLQPEDFATYYCQQRGWYLFTFGQGTKVEIKRT
10   VAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO.: 76)

Light chain (hK) nucleic acid sequence (DNA sequence coding for the CDR sequences
defined in accordance with IMGT® are shown in bold. DNA sequence coding for CDR
sequences defined in accordance with Kabat are underlined. DNA sequence coding for the
Fab constant region is shown in italic):

GATATCCAGATGACCCAGTCCCCGAGCTCCCTGTCCGCCTCTGTGGGCGATA
GGGTCACCATCACCTGCCGTGCCAGTCAGGCCGCCTACGGCCGCGTAGCCT
GGTATCAACAGAAACCAGGAAAAGCTCCGAAGCTTCTGATTTACAAAGCATC
CGAACTCTACGCCGGAGTCCCTTCTCGCTTCTCTGGTAGCCGTTCCGGGACGG
ATTTCACTCTGACCATCAGCAGTCTGCAGCCGGAAGACTTCGCAACTTATTAC
TGTCAGCAACGTGGCTGGTATCTGTTCACGTTCGGACAGGGTACCAAGGT
GGAGATCAAACGTACGGTGGCTGCACCATCTGTCTTCATCTTCCCGCCATCTGAT
25   GAGCAGTTGAAATCTGGAACTGCCTCTGTTGTGTGCCTGCTGAATAACTTCTATCC
CAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAG
TCACCCATCAGGGCCTGAGCTCGCCCGTCACAAAGAGCTTCAACAGGGGAGAGTG
30   T (SEQ ID NO.: 77)

Heavy chain amino acid sequence (CDR sequences defined in accordance with IMGT®
are shown in bold. CDR sequences defined in accordance with Kabat are underlined.
35   Amino acid sequence of the Fab constant region is shown in italic):

EVQLVESGGGLVQPGGSLRLSCAASGFDLFHYSIHWVRQAPGKGLEWVAYIYP
SYGYTYYADSVKGRFTISADTSKNTAYLQMNSLRAEDTAVYYCARHAWYYG
WGLDYWGQGTLVTVSSASTKGPSVFPLAPSSKSTSGGTAALGCLVKDYFPEPVTVS
40   WNSGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPG
K (SEQ ID NO.: 12)

Figure 15 continued. Protein and DNA sequence of FF03092-3, the anti-VEGF full length mature IgG1

Heavy chain nucleic acid sequence (DNA sequence coding for the CDR sequences defined in accordance with IMGT® are shown in bold. DNA sequence coding for CDR sequences defined in accordance with Kabat are underlined. DNA sequence coding for the Fab constant region is shown in italic):

GAGGTTCAGCTGGTGGAGTCTGGCGGTGGCCTGGTGCAGCCAGGGGGCTCAC
TCCGTTTGTCCTGTGCAGCTTCTGGCTTCGATTTATTTCATTATTCTATACA
CTGGGTGCGTCAGGCCCCGGGTAAGGGCCTGGAATGGGTTGCA*TACATTTAC*
***CCGTCTTATGGCTATACT*TATTATGCCGATAGCGTCAAGGGCCGTTTCACTA
TAAGCGCAGACACATCCAAAAACACAGCCTACCTACAAATGAACAGCTTAAG
AGCTGAGGACACTGCCGTCTATTATTGTGCTCGCCATGCGTGGTATTATGG**
GTGGGGTTTGGACTACTGGGGTCAAGGAACCCTGGTCACCGTCTCCTCGGC
*TAGCACCAAGGGCCCATCGGTCTTCCCCCTGGCACCCTCCTCCAAGAGCACCTCT*
*GGGGGCACAGCGGCCCTGGGCTGCCTGGTCAAGGACTACTTCCCCGAACCGGTG*
*ACGGTGTCGTGGAACTCAGGCGCCCTGACCAGCGGCGTGCACACCTTCCCGGCT*
*GTCCTACAGTCCTCAGGACTCTACTCCCTCAGCAGCGTGGTGACCGTGCCCTCCA*
*GCAGCTTGGGCACCCAGACCTACATCTGCAACGTGAATCACAAGCCCAGCAACAC*
*CAAGGTGGACAAGAAAGTTGAGCCCAAATCTTGTGACAAAACTCACACATGCCCAC*
*CGTGCCCAGCACCTGAACTCCTGGGGGGACCGTCAGTCTTCCTCTTCCCCCCAAA*
*ACCCAAGGACACCCTCATGATCTCCCGGACCCCTGAGGTCACATGCGTGGTGGTG*
*GACGTGAGCCACGAAGACCCTGAGGTCAAGTTCAACTGGTACGTGGACGGCGTG*
*GAGGTGCATAATGCCAAGACAAAGCCGCGGGAGGAGCAGTACAACAGCACGTAC*
*CGTGTGGTCAGCGTCCTCACCGTCCTGCACCAGGACTGGCTGAATGGCAAGGAGT*
*ACAAGTGCAAGGTCTCCAACAAAGCCCTCCCAGCCCCCATCGAGAAAACCATCTC*
*CAAAGCCAAAGGGCAGCCCCGAGAACCACAGGTGTACACCCTGCCCCCATCCCG*
*GGAGGAGATGACCAAGAACCAGGTCAGCCTGACCTGCCTGGTCAAAGGCTTCTAT*
*CCCAGCGACATCGCCGTGGAGTGGGAGAGCAATGGGCAGCCGGAGAACAACTAC*
*AAGACCACGCCTCCCGTGCTGGACTCCGACGGCTCCTTCTTCCTCTACAGCAAGC*
*TCACCGTGGACAAGAGCAGGTGGCAGCAGGGGAACGTCTTCTCATGCTCCGTGAT*
*GCATGAGGCTCTGCACAACCACTACACGCAGAAGAGCCTCTCCCTGTCTCCGGGT*
*AAA* (SEQ ID NO.: 11)

Figure 16. Protein and DNA sequence of anti-VEGF Fab #216 with an alternative coding sequence from Example 3

Light chain (hK) amino acid sequence (CDR sequences defined in accordance with IMGT® are shown in bold. CDR sequences defined in accordance with Kabat are underlined. Amino acid sequence of the Fab constant region is shown in italic):

DIQMTQSPSSLSASVGDRVTITCRASQAAYGRVAWYQQKPGKAPKLLIYKASELYAGVPSRFSGSRSGTDF
TLTISSLQPEDFATYYCQQRGWYLPTFGQGTKVEIKRTVAAPSVFIFPPSDSQLKSGTASVVCLLNNFYPR
EAKVQWKVDNALQSGNSQESVTEQDSKDSTYSLSSTLTLSKADYEKHKVYACEVTHQGLSSPVTKSFNRGE
C (SEQ ID NO.:76)

Light chain (hK) nucleic acid sequence (DNA sequence coding for the CDR sequences defined in accordance with IMGT® are shown in bold. DNA sequence coding for CDR sequences defined in accordance with Kabat are underlined. DNA sequence coding for Fab the constant region is shown in italic. Differences from the coding sequence provided for anti-VEGF Fab #216 in Example 3 are indicated by double underline):

GATATCCAGATGACCCAGTCCCCGAGCTCCCTGTCCGCCTCTGTGGGCGATAGGGTCACCATCACCTGCCG
TGCCAGTCAGGCCGCCTACGGCCGCGTAGCCTGGTATCAACAGAAACCAGGAAAAGCTCCGAAGCTTCTGA
TTTACAAAGCATCCAACTCTACGCCCGGAGTCCCTTCTCGCTTCTCTGGTAGCCGTTCCGGGACGGATTTC
ACTCTGACCATCAGCAGTCTGCAGCCCGAAGACTTCGCAACTTATTACTGTCAGCAACGTGGCTGGTATCT
GTTCACGTTCGGACAGGGTACCAAGGTGGAGATCAAACGTACCGTGGCCTGCACCATCTGTCTTCATCTTCC
CGCCATCTGATTCACAGTTGAAATCTGGAACTGCTCTGTTGTGTGCCTGCTGAATAACTTCTATCCCAGA
GAGGCCAAAGTACAGTGGAAGGTGGATAACGCCCTCCAATCGGGTAACTCCCAGGAGAGTGTCACAGAGCA
GGACAGCAAGGACAGCACCTACAGCCTCAGCAGCACCCTGACGCTGAGCAAAGCAGACTACGAGAAACACA
AAGTCTACGCCTGCGAAGTCACCCATCAGGGCCTGAGCTCGCCCGTCACAAAGAGCTTCAACAGGGGAGAG
TGT (SEQ ID NO.:77)

Heavy chain amino acid sequence (CDR sequences defined in accordance with IMGT® are shown in bold. CDR sequences defined in accordance with Kabat are underlined. Amino acid sequence of the Fab constant region is shown in italic):

EVQLVESGGGLVQPGGSLRLSCAASGFDLDHYSIHWVRQAPGKGLEWVAYIYPSYGYTYYADSVKGRFTIS
ADTSKNTAYLQMNSLRAEDTAVYYCARHAWYYGWCLDYWGQGTLVTVSSASTKGPSVFPLAPSSKSTSGGT
AALGCLVKDYFPEPVTVSWNSGALTSGVHTFPAVLQSSGLYSLSSVVTVPSSSLGTQTYICNVNHKPSNTK
VDKKVEPKSCDKTHT (SEQ ID NO.:78)

Heavy chain nucleic acid sequence (DNA sequence coding for the CDR sequences defined in accordance with IMGT® are shown in bold. DNA sequence coding for CDR sequences defined in accordance with Kabat are underlined. DNA sequence coding for the Fab constant region is shown in italic. Differences from the coding sequence provided for anti-VEGF Fab #216 in Example 3 are indicated by double underline):

GAGGTTCAGCTGGTGGAGTCTGGCGGTGGCCTGGTGCAGCCACGGGGCCTCACTCCGTTTGTCCTGTGCAGC
TTCTGGCTTCGATTTAGATCATTATTCTATACACTGGCTGCGTCAGGCCCCGGGTAAGGGCCTGGAATGGG
TTGCATACATTTACCCGTCTTATGGCTATACTTATTATGCCGATAGCGTCAAGGGCCGTTTCACTATAAGC
GCAGACACATCCAAAAACACAGCCTACCTACAAATGAACAGCTTAAGAGCTGAGGACACTGCCGTCTATTA
TTGTGCTCGCCATGCCTGGTATTATGGGTGGGGTTTGGACTACTGGGGTCAAGGAACCCTGGTCACCGTCT
CCTCGGCTAGCACCAAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACGGGTGACGGTGTCGTGGAACTCAGGCGCCCT

Figure 16 (Continued)

GACCAGCGGCGTGCACACCTTCCCGGCTGTCCTACAGTCCTCAGGACTCTACTCCCTCAGCAGCGTGGTCA
CCGTGCCCTCCAGCAGCTTGGGCACCCAGACCTACATCTGCAACGTGAATCACAAGCCCAGCAACACCAAG
GTGGACAACAAACTTGAGCCCAAATCTTGTGACAAAACTCACACA (SEQ ID NO.:79)

Figure 17. Schematic representation of expression plasmid for anti-VEGF Fab 201
Vector map of the clone #201
Vector features:
Bases 7-274 – phoA promoter sequence
Bases 275-988 – DNA sequence coding for light chain of Fab#201
Bases 1102-1857 – DNA sequence coding for heavy chain of Fab#201
Bases 989-1101 – Intercistronic region
Bases 1858-2132 – rrnB Termination sequence
Bases 2695-3902 – pBR322 origin
Bases 5038-4073 – Ampicillin resistance ORF

Figure 18. Schematic representation of expression plasmid for anti-VEGF Fab 216
Vector map of the clone #216
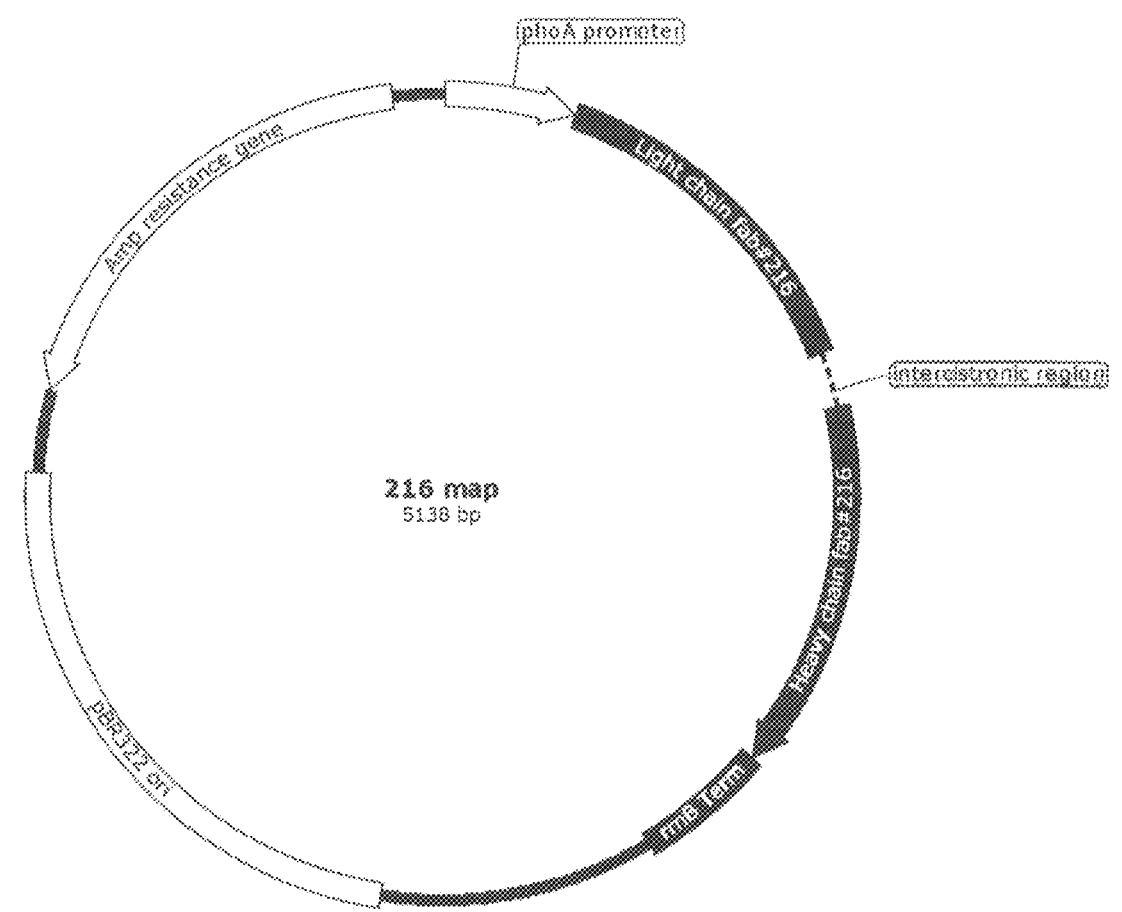
Vector features:
Bases 7-274 – phoA promoter sequence
Bases 275-988 – DNA sequence coding for light chain of Fab#216
Bases 1102-1857 – DNA sequence coding for heavy chain of Fab#216
Bases 989-1101 – Intercistronic region
Bases 1858-2132 – rrnB Termination sequence
Bases 2695-3902 – pBR322 origin
Bases 5038-4073 – Ampicillin resistance ORF

Figure 19.  Competitive ELISA:
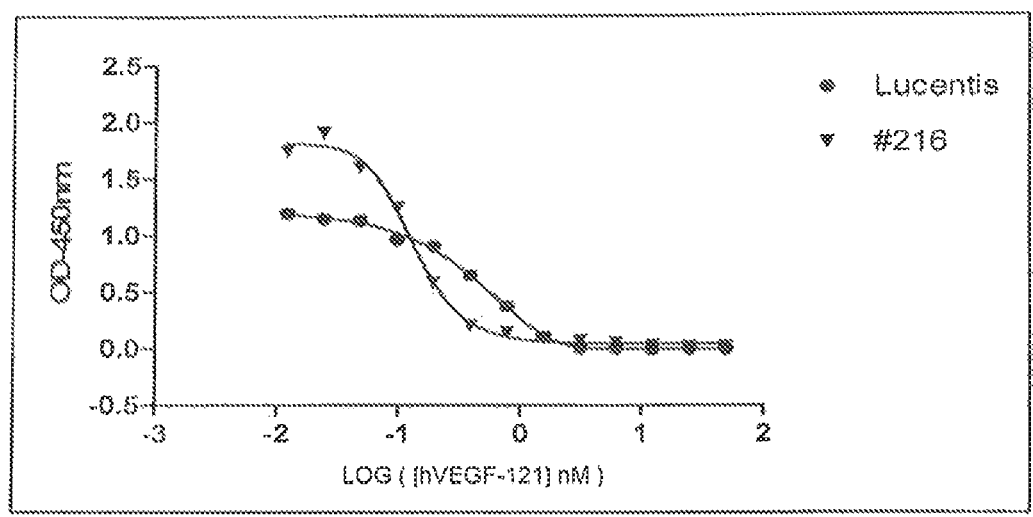
| | Kd (pM) |
|---|---|
| Lucentis | 540 ± 44 |
| Fab #216 | 94 ± 12 |

Figure 20.  Competitive Fab-ELISA
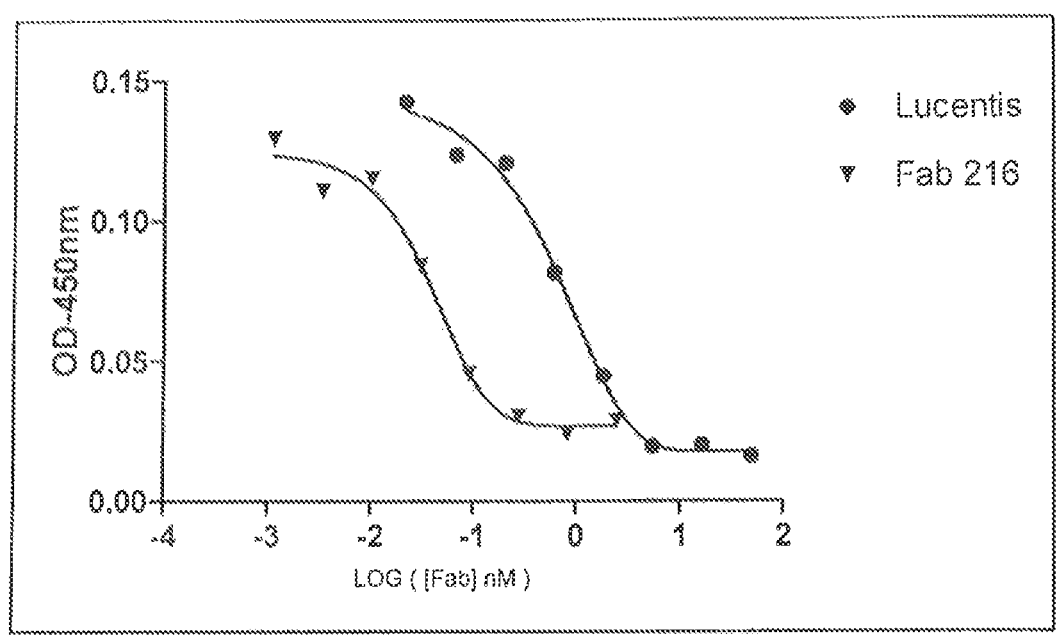
| Kd(pM) | |
|---|---|
| Fab 216 | Lucentis |
| 35±4 | 591±60 |

Figure 21.  Fermentation data and expression yield for anti-VEGF Fab
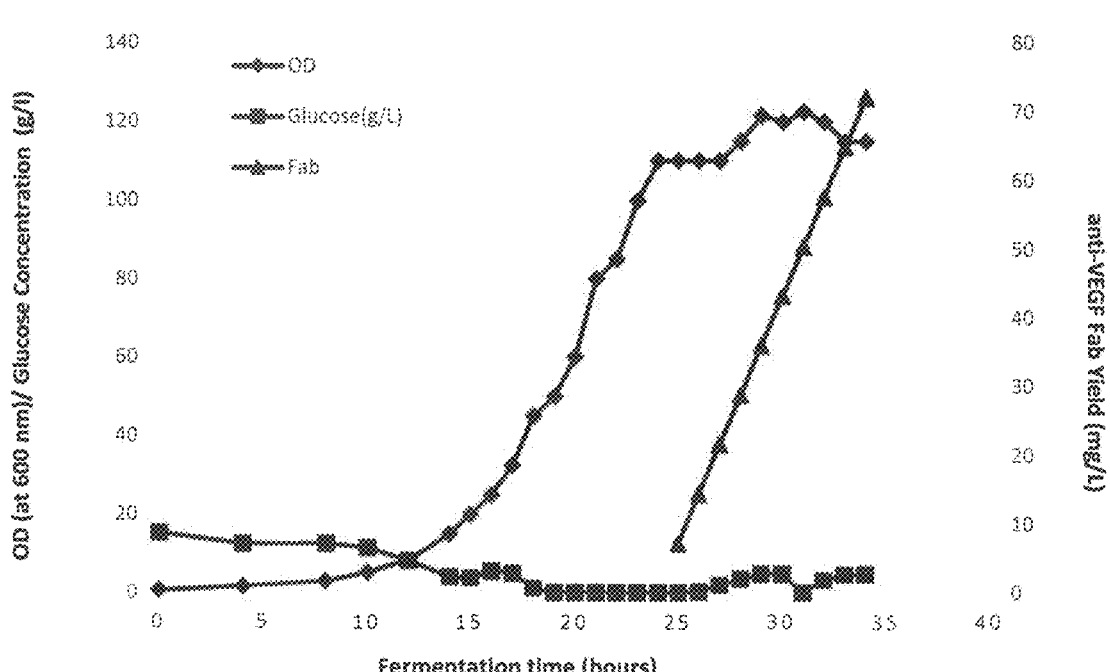
S Figure 22.  Stability of drug product Fab 201 at 4°C
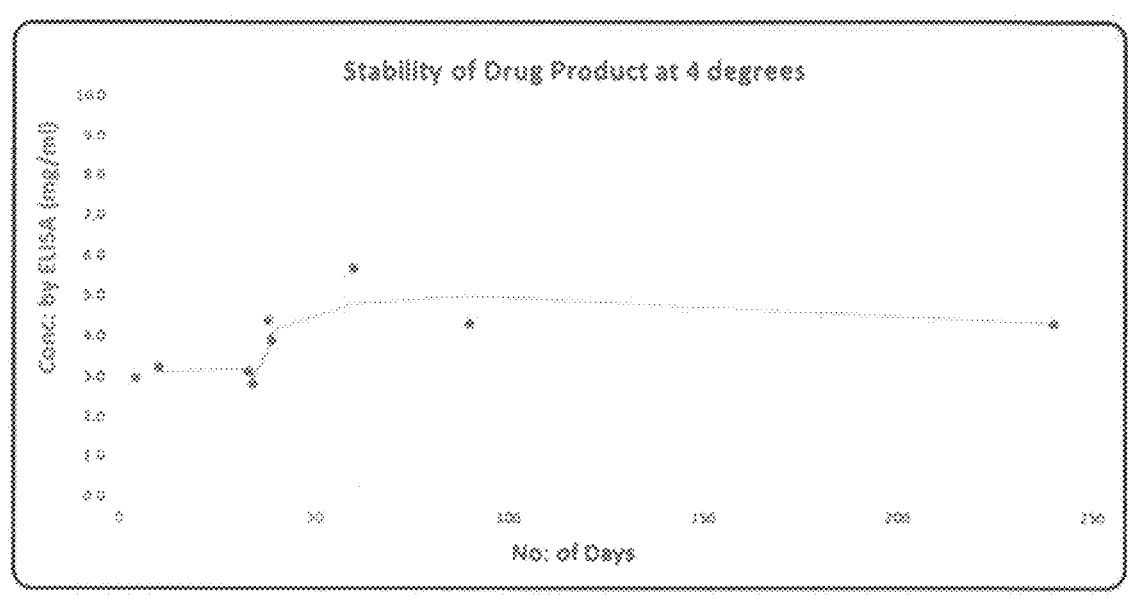
5

Figure 23:
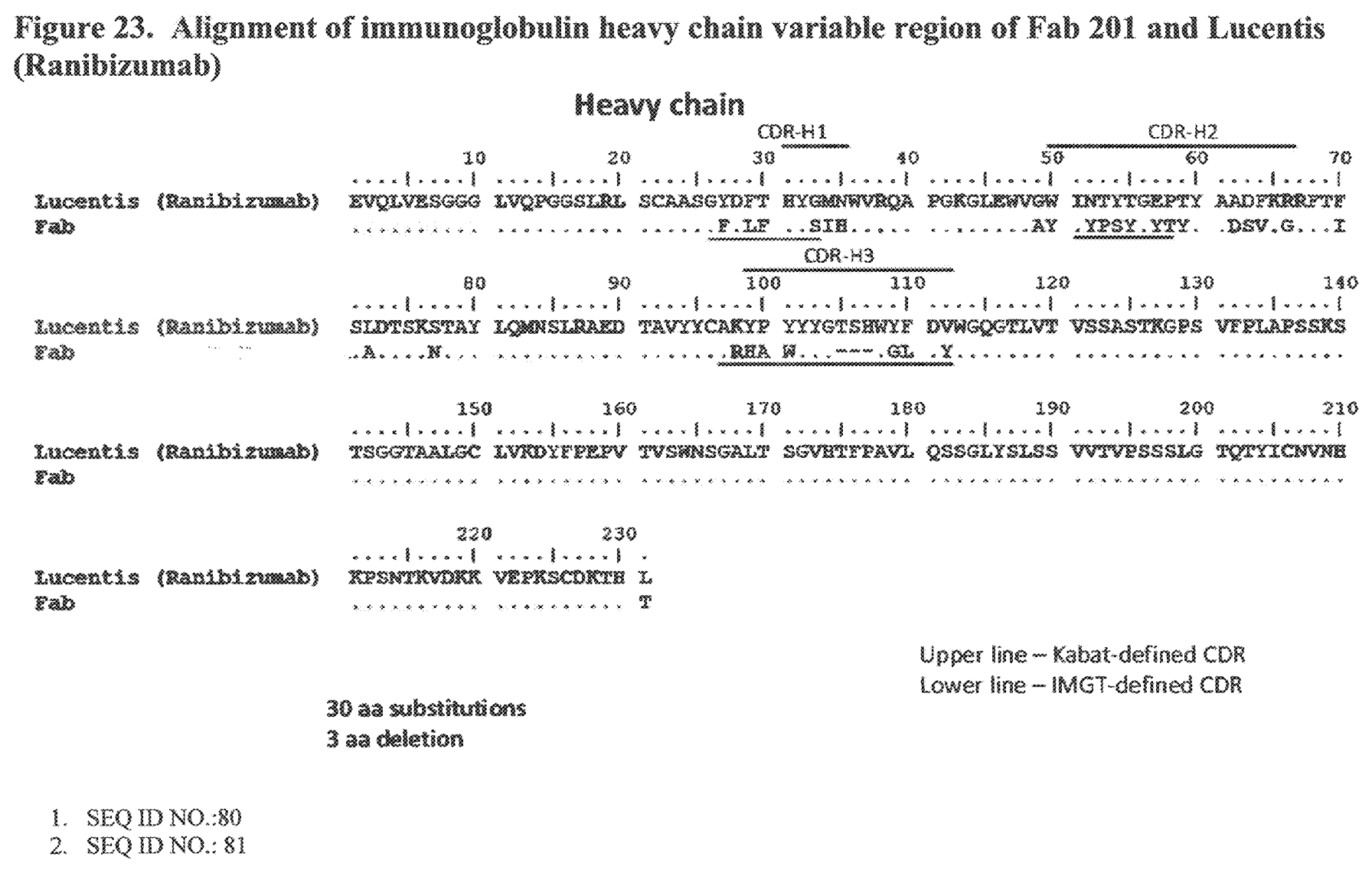

Figure 23. Alignment of immunoglobulin heavy chain variable region of Fab 201 and Lucentis (Ranibizumab)

Heavy chain 30 aa substitutions
3 aa deletion

Upper line – Kabat-defined CDR
Lower line – IMGT-defined CDR

1. SEQ ID NO: 80
2. SEQ ID NO: 81

Figure 24:
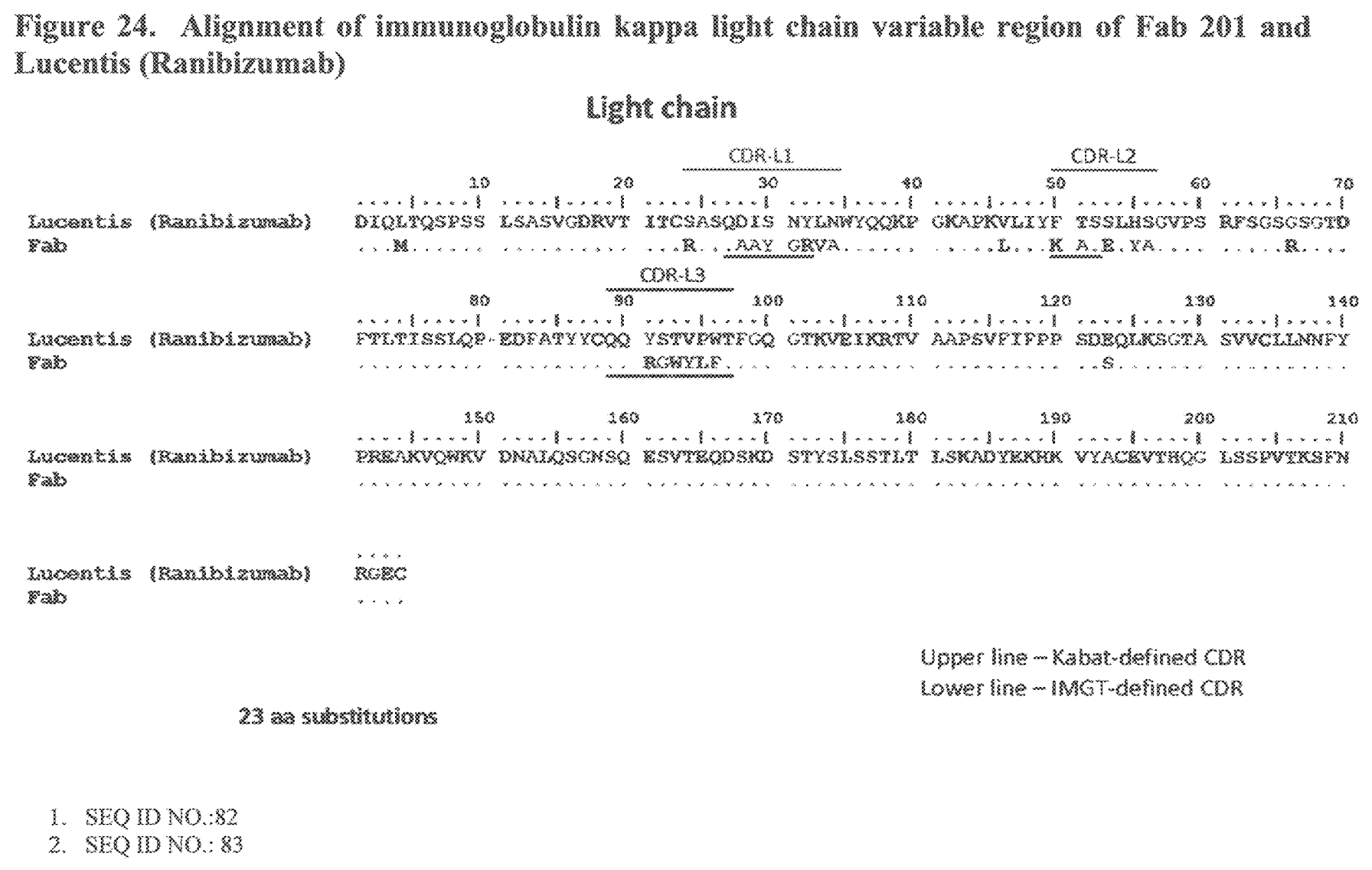

Figure 24. Alignment of immunoglobulin kappa light chain variable region of Fab 201 and Lucentis (Ranibizumab)

Light chain

|  |  |  | CDR-L1 | | | | | |
|---|---|---|---|---|---|---|---|---|
| | 10 | 20 | 30 | 40 | 50 | 60 | 70 | |

Lucentis (Ranibizumab)  DIQLTQSPSS LSASVGDRVT IICSASQDIS NYLNWYQQKP GKAPKVLIYF TSSLHSGVPS RFSGSGSGTD
Fab                     .......M.. ..........  ....R...AAY GRVA...... .......L.. ...K.A.B.YA ....R.....

|  |  |  |  |  |  |  |
|---|---|---|---|---|---|---|
| | 80 | 90 | 100 | 110 | 120 | 130 | 140 |

Lucentis (Ranibizumab)  FTLTISSLQP EDFATYYCQQ YSTVPWTFGQ GTKVEIKRTV AAPSVFIFPP SDEQLKSGTA SVVCLLNNFY
Fab                     .......... .........  RGNYLF.... .......... .......... ......S... ..........

CDR-L3 / CDR-L2 markers as shown.

|  |  |  |  |  |  |  |
|---|---|---|---|---|---|---|
| | 150 | 160 | 170 | 180 | 190 | 200 | 210 |

Lucentis (Ranibizumab)  PREAKVQWKV DNALQSGNSQ ESVTEQDSKD STYSLSSTLT LSKADYEKHK VYACEVTHQG LSSPVTKSFN
Fab                     .......... .......... .......... .......... .......... .......... ..........

Lucentis (Ranibizumab)  RGEC
Fab                     ....

23 aa substitutions

Upper line — Kabat-defined CDR
Lower line — IMGT-defined CDR

1. SEQ ID NO:82
2. SEQ ID NO: 83

SYNTHETIC ANTIBODIES AGAINST VEGF AND THEIR USES

Throughout this application, various publications are referenced within parentheses. The disclosures of these publications are hereby incorporated by reference herein in their entireties.

BACKGROUND OF THE INVENTION

Age-related macular degeneration (AMD), is the leading cause of vision loss and blindness among people with age 60 and above. AMD is diagnosed as either dry (non-neovascular) or wet (neovascular) AMD. About 85 to 90 percent of AMD patients are diagnosed with dry AMD. It is an early stage of disease which may result from the aging and thinning of macular tissues, resulting in deposition of pigment characterized by yellow spots called drusen in macula. Gradual central vision loss may occur with dry macular degeneration but usually is not nearly as severe as wet AMD.

In a significant proportion of cases, dry AMD progresses to the more advanced and damaging form of the disease, wet AMD, leading to serious vision loss. Wet AMD is characterized by the process of choroidal neovascularization which involves the formation of new blood vessels (angiogenesis) beneath the retina resulting in leakage of blood and fluid. This leakage causes permanent damage to light-sensitive retinal cells, resulting in vision loss. Vascular endothelial growth factor (VEGF) appears to play a pivotal role in the pathogenesis of choroidal neovascularization.

Treatment methods for wet AMD include laser photocoagulation, photodynamic laser therapy with Visudyne® (Valeant Pharmaceuticals International) and anti-VEGF drugs. The discovery of anti-VEGF agents has revolutionized treatment of the condition. Currently, the four anti-VEGF agents either approved or in common use include pegaptanib (Macugen®, Valeant Pharmaceuticals International), ranibizumab (Lucentis®, Novartis and Roche), aflibercept or VEGF Trap-Eye (EYLEA®, Bayer and Regeneron Pharmaceuticals) and bevacizumab (Avastin®, Roche).

Anti-VEGF therapy may be used for treating wet AMD. However, current treatment involves giving frequent injections of the anti-VEGF drug into the affected eye once a month for three months and then, monitoring the treatment to give further injections. The frequent administration of injections leads to complications such as macular edema and stress in the eyes of patients. If macular edema is prolonged, retinal thinning, scarring or retinal hole can eventually form. As such there remains an urgent need for improved drugs and methods for treating diseases associated with abnormal vascularization, such as wet AMD.

SUMMARY OF THE INVENTION

This invention encompasses novel anti-VEGF antibodies; and polynucleotides comprising sequences encoding such novel anti-VEGF antibodies and compositions, including pharmaceutical compositions, comprising them and uses thereof.

The present invention also provides using the novel anti-VEGF antibodies, polynucleotides comprising sequences encoding such novel anti-VEGF antibodies and compositions, including pharmaceutical compositions in methods for inhibiting or treating diseases such as wet age related macular degeneration (AMD), diabetic maculopathy, proliferative diabetic retinopathy, macular edema in retinal vein occlusion (RVO), iris neovascularization, choroidal neovascularisation caused by pathological myopia, retinopathy of maturity, neovascular glaucoma and cancer.

BRIEF DESCRIPTION OF THE FIGURES AND SEQUENCE LISTING

FIG. 1. Standard curve for determining Fab protein concentration based on bovine serum albumin (BSA) as a reference standard and absorbance at 595 nm using the Bradford protein assay showing linearity from 50 µg/mL to 500 µg/mL of BSA.

FIG. 2. Standard curve for quantifying amount of Fab with anti-VEGF activity relative to known concentrations of anti-VEGF Fab (Lucentis®, Novartis and Roche) in an ELISA format with immobilized human VEGF (hVEGF) 121 isoform and horse radish peroxidase (HRP)-conjugated anti-kappa light chain antibody to detect soluble anti-VEGF Fab bound to immobilized hVEGF and generate a colorimetric product with absorbance at 450 nm.

FIG. 3. Competitive binding assay to determine the half maximal inhibitory concentration (IC50) of ranibizumab and Fab Clone #201 (Fab 201) for hVEGF-121. The Fabs were incubated in two separate experiments with various concentration of hVEGF-121 reported in the x-axis. The unbound fraction of each Fab was captured with a hVEGF-121 coated plate and quantified with anti-Kappa-light-chain-HRP-conjugated antibody, as shown on the y-axis. 100 pM of each Fab was incubated with serial dilutions of hVEGF-121. Unbound Fabs were captured with immobilized hVEGF-121 and detected with anti-Kappa-light-chain-HRP-conjugated antibody. Kd estimated from the IC50 calculated from the data fitted with a 5 parameter asymmetric model with Prism software are shown in Table 3.

FIG. 4a-b. CDR sequences of Fabs obtained from screening a naïve synthetic antibody fragment (Fab) phage display library with recombinant hVEGF 121 isoform (A), and analysis of binding affinity using immobilized hVEGF and serial dilutions of soluble selected Fabs from the naïve phage display library in a Fab-ELISA format (B). Amino acid sequences corresponding to the CDR according to Kabat are underlined (A) and titration by Fab-ELISA performed as follows: increasing concentration of Fabs were incubated on wells coated with 2 ug/mL of hVEGF-121. The bound Fabs were detected with anti-Kappa-light-chain-HRP-conjugated antibody (B). The dissociation constant (Kd) was estimated from the 50% effective maximal concentration (EC50) and reported in the table below the line graph.

FIG. 5. A bar graph showing inhibition of binding of selected Fabs to immobilized hVEGF in the presence (+) or the absence (−) of FLT, a VEGF natural receptor, as a competitor in a competitive Fab-ELISA format, consistent with the 6 Fabs and FLT having overlapping binding sites on hVEGF. Wells of a microtiter plate were coated with 2 ug/mL of hVEGF. Washed wells were pre-incubated with either 500 nM FLT (R&D systems, catalog number 321-FL-250) in PBT (+) or PBT alone (−) for 1 hour. Sub-saturating amounts of Fabs were then added to either the FLT− or the FLT+ wells and plates were incubated for 15 minutes and washed. The identity of the Fab added to the well is identified on the y-axis. Bound Fabs were then detected with an anti-Kappa-light-chain-HRP antibody. The background subtracted OD 450 nm measurement is reported on the y-axis.

Figure 6A:
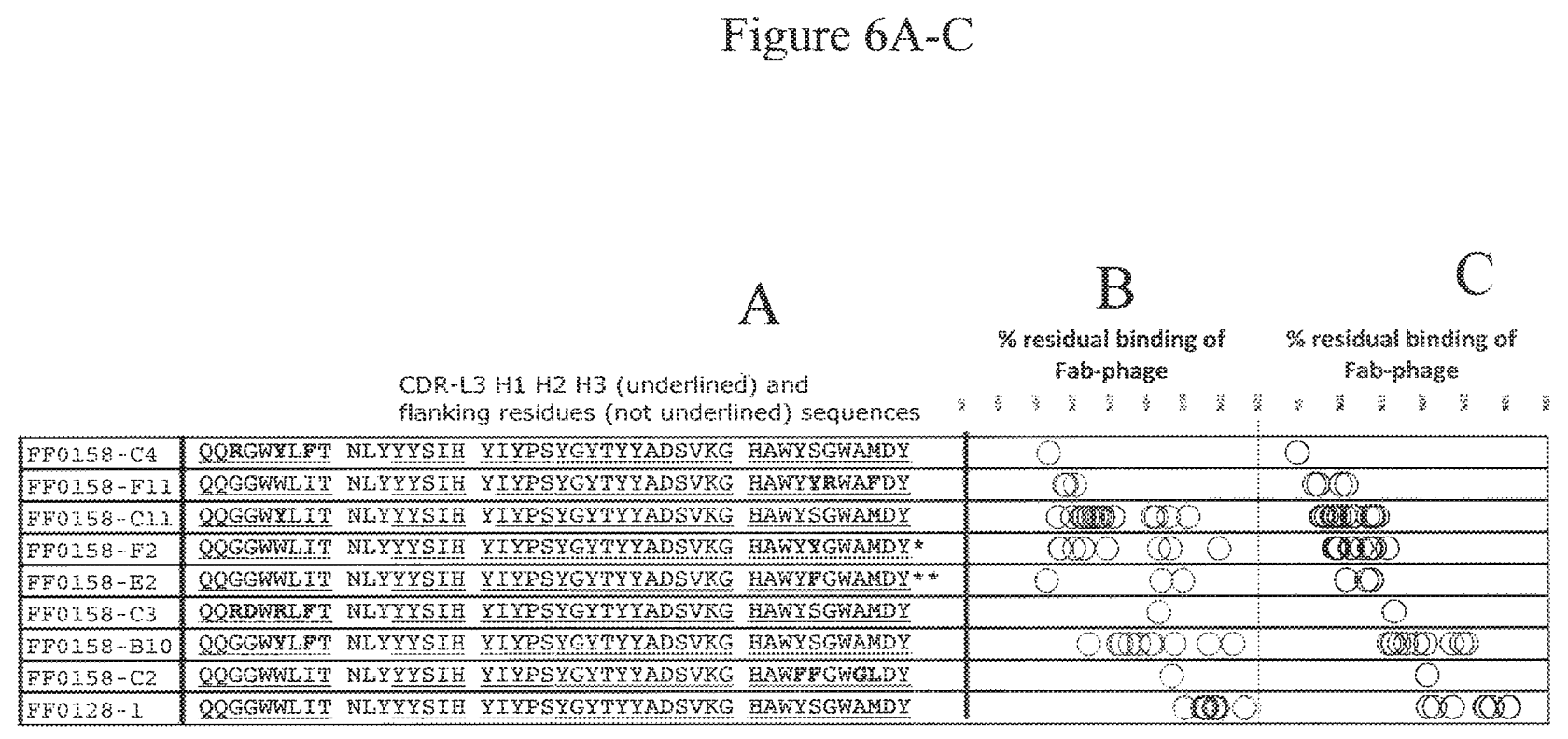

FIG. 6a-c. (A) CDR sequences of Fabs issued from the selection of libraries based on FF0124-1 Fab sequence. Fabs are ranked by residual binding observed in the competition-phage-ELISA when 10 nM of hVEGF was preincubated with the Fab-phage. (B and C) Competitive Phage-ELISA results for different clones with the sequence listed in panel A. The residual binding of the Fab-phage to immobilized hVEGF after preincubation with 1 nM (B) or 10 nM (C) of hVEGF is shown in percentage of binding without hVEGF preincubation. (*) CDR-H3 (defined by Kabat) also had "HAWYYGWAFDY" (SEQ ID NO: 150) sequences in this group of clones. (**) CDR-H3 (defined by Kabat) also had "HAWYYGWALDY" (SEQ ID NO: 151) and "HAWYYG-WAFDY" (SEQ ID NO: 150) sequences in this group of clones. The sequence and competitive phage ELISA for the parental Fab, FF0124-1, is shown for comparison. Amino acid sequences corresponding to the CDR accordingly to Kabat are underlined. Amino acid sequences that are different from the parental Fab (FF0124-1) are highlighted in bold.

FIG. 7a-b. (A) CDR sequences of Fabs issued from the selection of libraries based on FF0158-C4 Fab sequence, yields in shake flasks and affinity measurements by single point competitive ELISA and/or competitive ELISA (Kd—data and fit shown in B). Amino acid sequences corresponding to the CDR accordingly to Kabat are underlined. Amino acid sequences different from the parental Fab (FF0158-C4) are highlighted in bold.

FIG. 8. CDR sequences of Fabs issued from the selection of libraries based on FF0188-H5 Fab sequence, production yields in shake flasks, affinity measurements by single point competitive ELISA and/or competitive ELISA and melting temperature (Tm). Amino acid sequences corresponding to the CDR accordingly to Kabat are underlined. Amino acid sequences different from the parental Fab (FF0188-H5) are highlighted in bold.

FIG. 9a-c. Fabs CDR sequences, production yield and hVEGF binding kinetic parameters are shown. (A) Table with CDR sequences, yields in shake flasks, hVEGF-121 binding off rates measured by SPR and melting temperature (Tm)—data shown in B. Amino acid sequences corresponding to the CDR accordingly to Kabat are underlined Amino acid sequences different from the parental Fab (FF0117-A5) are highlighted in bold. (B) Thermal shift assay. (C) Example of full length sequences for Fab FF03046-2.

FIG. 10. Inhibition of hVEGF-dependent human vascular endothelium cell (HUVEC) proliferation by anti-VEGF Fabs, FF03046-1, FF03046-2 and Ranibizumab (Lucentis®; Novartis and Roche) in which recombinant human VEGF 165 isoform is used to stimulate proliferation of HUVEC cells. $2 \times 10^5$ cells/ml of log-phase Huvec cells were added to serial dilutions of Fabs pre-incubated with 260 pM of rhVEGF-165. Cells were then incubated at 37° C. for 3 days before. The number of live cells was assessed by resazurin staining.

FIG. 11. Competitive Fab-ELISA. 5 pM of hVEGF-165 was incubated with serial dilutions of anti-VEGF antibody as described in the figure legend. Pre-formed hVEGF-165/anti-VEGF antibody complexes along with any unbound hVEGF-165 in the binding solution are transferred into a 96-well polystyrene microplate coated with a monoclonal antibody specific for human VEGF, as provided in the Quantikine® ELISA Human VEGF Immunoassay (R&D Catalog Number: SVE00). hVEGF-165 bound to the plate is detected using a polyclonal anti-hVEGF antibody conjugated to horseradish peroxidase and tetramethylbenzidine as a chromagen to quantify hVEGF-165 bound to the plate as provided in the Quantikine® assay kit. Kd calculated from the data fitted with a 5 parameter asymmetric model with Prism software are shown in the table at the bottom of the figure.

FIG. 12. DNA and protein sequence of FF03092-1, the anti-VEGF Fc-Fab fusion.

FIG. 13. DNA and protein sequence of FF03077-4, the anti-VEGF Fc-scFv fusion. Single chain nucleic acid sequence: the scFv fusion sequence is underlined; the Fc sequence is in italic; the linker between the Fc and the scFv is underlined and in bold DNA coding sequences and amino acid sequences corresponding to the CDRs defined in accordance with IMGT® are shown in bold; DNA coding sequences and amino acid sequences corresponding to CDR sequences of Fab FF03046-2 defined in accordance with Kabat in the scFv are double underlined.

FIG. 14. Competitive ELISA. 5 pM of hVEGF-165 was incubated with serial dilutions of anti-VEGF antibody as described in the figure legend. Pre-formed hVEGF-165/anti-VEGF antibody complexes along with any unbound hVEGF-165 in the binding solution are transferred into a 96-well polystyrene microplate coated with a monoclonal antibody specific for human VEGF, as provided in the Quantikine® ELISA Human VEGF Immunoassay (R&D Catalog Number: SVE00). hVEGF-165 bound to the plate is detected using a polyclonal anti-hVEGF antibody conjugated to horseradish peroxidase and tetramethylbenzidine as a chromagen to quantify hVEGF-165 bound to the plate as provided in the Quantikine® assay kit. Kd calculated from the data fitted with a 5 parameter asymmetric model with Prism software are shown in the table at the bottom of the figure.

FIG. 15. DNA and protein sequence of FF03092-3, the anti-VEGF full length mature IgG1.

FIG. 16. DNA and protein sequence of anti-VEGF Fab #216 with an alternative embodiment coding sequence from Example 3 indicated by a double underline.

FIG. 17. Schematic representation of expression plasmid for anti-VEGF Fab 201.

FIG. 18. Schematic representation of expression plasmid for anti-VEGF Fab 216.

FIG. 19. Competitive binding assay to determine the half maximal inhibitory concentration (IC50) of Lucentis (Ranibizumab, Novartis and Roche) and Fab Clone #216 (Fab 216) for hVEGF-121. The Fabs were incubated in two separate experiments with various concentration of hVEGF-121 (Peprotech, Cat-100-20A) reported in the x-axis. The unbound fraction of each Fab was captured with a hVEGF-121 coated plate and quantified with anti-Kappa-light-chain-HRP-conjugated antibody, as shown on the y-axis. 100 pM of each Fab #216 was incubated with serial dilutions of hVEGF-121. Unbound Fabs were captured with immobilized hVEGF-121 and detected with anti-Kappa-light-chain-HRP-conjugated antibody. Kd estimated from the IC50 calculated from the data fitted with a 5 parameter asymmetric model with Prism software are shown in the table at the bottom of the figure FIG. 20. Competitive-ELISA. 10 pM of hVEGF-165 was incubated with serial dilutions of anti-VEGF antibody, Fab 216. Pre-formed hVEGF-165/anti-VEGF antibody complexes along with any unbound hVEGF-165 in the binding solution are transferred into a 96-well polystyrene microplate coated with a monoclonal antibody specific for human VEGF, as provided in the Quantikine® ELISA Human VEGF immunoassay (R&D Catalog Number: SVE00). hVEGF-165 bound to the plate is detected using a polyclonal anti-hVEGF antibody conjugated to horseradish peroxidase and tetramethylbenzidine as a chromagen to quantify hVEGF-165 bound to the plate as provided in the Quantikine® assay kit. Kd was estimated using IC50 calculated from the data fitted with a 5 parameter asymmetric model with Prism software are shown in the table at the bottom of the figure.

FIG. 21. Fermentation data and expression yield for anti-VEGF Fab.

FIG. 22. Stability of drug product Fab 201 at 4° C.

FIG. 23. Alignment of immunoglobulin heavy chain variable region of Fab 201 and Lucentis® (ranibizumab). Lines above and below the aligned immunoglobulin heavy chain variable region sequences indicate the location of the CDRs of Fab 201 as defined by Kabat and IMGT® methods, respectively, and given in SEQ ID NO: 16. Sequence of Lucentis® (ranibizumab) is obtained from GenBank Accession Number APZ76728.1 and APZ76729.1.

FIG. 24. Alignment of immunoglobulin kappa light chain variable region of Fab 201 and Lucentis® (ranibizumab). Lines above and below the aligned kappa light chain variable region sequences indicate the location of the CDRs of Fab 201 as defined by Kabat and IMGT® methods, respectively, and given in SEQ ID NO: 16. Sequence of Lucentis® (ranibizumab) is obtained from GenBank Accession Number APZ76728.1 and APZ76729.1.

| SEQUENCES in the patent application | Sequence Listing |
|---|---|
| Nucleic acid sequence encoding an Ig heavy chain fragment of Fab FF03046-2 antibody comprising a variable region with an optimized human framework and affinity matured CDR-H1, -H2 & -H3 against mouse and human VEGF and a constant region with a CH1 domain | SEQ ID NO: 1 |
| Amino acid sequence of heavy chain variable domain encoded by SEQ ID NO: 1 | SEQ ID NO: 2 |
| Nucleic acid sequence encoding an Ig Sight chain of a synthetic humanized anti-VEGF Fab antibody fragment, Fab FF03046-2, comprising a variable region with an optimized human framework and affinity matured CDR-L1, L2 and L3 against mouse and human VEGF and a kappa light chain constant region | SEQ ID NO: 3 |
| Amino acid sequence of light chain variable domain encoded by SEQ ID NO: 3 | SEQ ID NO: 4 |
| Nucleic acid sequence encoding a synthetic humanized antibody FF03092-1 heavy chain fusion used to form a humanized anti-VEGF Fc-Fab fusion comprising an amino terminal humanized immunoglobulin Fc fragment fused to a humanized Fab fragment | SEQ ID NO: 5 |
| Amino acid sequence of a synthetic humanized antibody FF03092-1 heavy chain fusion encoded by SEQ ID NO: 5 | SEQ ID NO: 6 |
| Nucleic acid sequence encoding a synthetic humanized antibody FF03092-1 kappa light chain used to form a humanized anti-VEGF Fc-Fab fusion comprising an amino ::terminal humanized immunoglobulin Fc fragment fused to a humanized Fab fragment | SEQ ID NO: 7 |
| Amino acid sequence of a synthetic humanized antibody FF03092-1 kappa light chain encoded by SEQ ID NO: 7 | SEQ ID NO: 8 |
| Nucleic acid sequence encoding a synthetic humanized antibody FF03077-4 comprising an amino-terminal humanized Fc fragment fused to a humanized anti-VEGF single chain Fv (scFv) directed against human and mouse VEGF | SEQ ID NO: 9 |
| Amino acid sequence of a synthetic humanized antibody FF03077-4 encoded by SEQ ID NO: 9, comprising an amino-terminal humanized Fc fragment fused to a humanized anti-VEGF single chain Fv (scFv) directed against human and mouse VEGF | SEQ ID NO: 10 |
| Nucleic Acid sequence encoding a synthetic humanized anti-VEGF full length mature IgG1 antibody, FF03092-3, heavy chain comprising an optimized human framework and affinity matured CDR-H1, CDR-H2 and CDR-H3 directed against mouse and human VEGF | SEQ ID NO: 11 |
| Amino acid sequence of a synthetic humanized anti-VEGF full length mature igG1 antibody, FF03092-3, heavy chain encoded by SEQ ID NO: 11, comprising an optimized human framework and affinity matured CDR-H1, CDR-H2 and CDR-H3 directed against mouse and human VEGF | SEQ ID NO: 12 |
| Nucleic acid sequence of a synthetic humanized full length mature IgG1 antibody, FF03092-3, kappa light chain comprising an optimized human framework and affinity matured CDR-L1, CDR-L2 and CDR-L3 directed against mouse and human VEGF | SEQ ID NO: 13 |
| Amino acid sequence of a synthetic humanized full length mature IgG1 antibody, FF03092-3, kappa light chain encoded by SEQ ID NO: 13, comprising an optimized human framework and affinity matured CDR-L1, CDR-L2 and CDR-L3 directed against mouse and human VEGF | SEQ ID NO: 14 |
| Nucleic acid sequence of *E. coli* Pho A promoter | SEQ ID NO: 15 |
| Nucleic acid sequence enoding a synthetic humanized Fab anti-VEGF antibody fragment with amino-terminal secretory signal along with non-coding intercistronic | SEQ ID NO: 16 |

-continued

| SEQUENCES in the patent application | Sequence Listing |
|---|---|
| region directed against mouse and human VEGF present in expression plasmid Clone #201 | |
| Amino acid sequence of an Ig kappa light chain of a synthetic humanized anti-VEGF Fab antibody fragment directed against mouse and human VEGF along with amino-terminal secretory signal encoded by expression plasmid Clone #201 | SEQ ID NO: 17 |
| Amino acid sequence of an Ig heavy chain fragment of a synthetic humanized anti-VEGF Fab antibody fragment directed against mouse and human VEGF along with amino-terminal secretory signal encoded by expression plasmid Clone #201 | SEQ ID NO: 18 |
| Nucleic acid sequence of the ribosomal RNA gene terminator used to terminate transcription of Ig coding sequence in expression plasmid Clone #201 | SEQ ID NO: 19 |
| Nucleic acid sequence of pBR322 (GenBank Accession No: J01749.1) from nucleotide position 1353 to 4361 in which the tetracycline resistance gene of pBR322 has been deleted, which is used to construct expression plasmid Clone #201 | SEQ ID NO: 20 |
| Variant 201 | SEQ ID NO: 21 |
| Variant 202 | SEQ ID NO: 22 |
| Variant 203 | SEQ ID NO: 23 |
| Variant 204 | SEQ ID NO: 24 |
| Variant 205 | SEQ ID NO: 25 |
| Variant 206 | SEQ ID NO: 26 |
| Variant 207 | SEQ ID NO: 27 |
| Variant 208 | SEQ ID NO: 28 |
| Variant 209 | SEQ ID NO: 29 |
| Variant 212 | SEQ ID NO: 30 |
| Variant 213 | SEQ ID NO: 31 |
| Variant 214 | SEQ ID NO: 32 |
| Variant 215 | SEQ ID NO: 33 |
| Variant 216 | SEQ ID NO: 34 |
| Variant 217 | SEQ ID NO: 35 |
| Variant 218 | SEQ ID NO: 36 |
| Variant 219 | SEQ ID NO: 37 |
| Variant 220 | SEQ ID NO: 38 |
| FF0124-1 F2078 FIG. 4 | SEQ ID NO: 39 |
| FF0124-2 F2083 FIG. 4 | SEQ ID NO: 40 |
| FF0124-3 F2086 FIG. 4 | SEQ ID NO: 41 |
| FF0124-4 F2088 FIG. 4 | SEQ ID NO: 42 |
| FF0124-5 F2091 FIG. 4 | SEQ ID NO: 43 |
| FF0124-6 F2094 FIG. 4 | SEQ ID NO: 44 |
| FF0124-7 F2116 FIG. 4 | SEQ ID NO: 45 |
| FF0158-C4 FIG. 6 | SEQ ID NO: 46 |
| FF0158-F11 FIG. 6 | SEQ ID NO: 47 |
| FF0158-C11 FIG. 6 | SEQ ID NO: 48 |
| FF0158-F2 FIG. 6 | SEQ ID NO: 49 |
| FF0158-E2 FIG. 6 | SEQ ID NO: 50 |
| FF0158-C3 FIG. 6 | SEQ ID NO: 51 |
| FF0158-B10 FIG. 6 | SEQ ID NO: 52 |
| FF0158-C2 FIG. 6 | SEQ ID NO: 53 |
| FF0128-1 FIG. 6 | SEQ ID NO: 54 |
| FF0158-C4 (2) FIG. 7 | SEQ ID NO: 84 |
| FF0187-B3 FIG. 7 | SEQ ID NO: 85 |
| FF0187-C1 FIG. 7 | SEQ ID NO: 86 |

-continued

| SEQUENCES in the patent application | Sequence Listing |
|---|---|
| FF0187-A12<br>FIG. 7 | SEQ ID NO: 87 |
| FF0187-H3<br>FIG. 7 | SEQ ID NO: 88 |
| FF0188-H5<br>FIG. 7 | SEQ ID NO: 89 |
| FF0188-B10<br>FIG. 7 | SEQ ID NO: 90 |
| FF0188-F12<br>FIG. 7 | SEQ ID NO: 91 |
| FF0188-B6<br>FIG. 7 | SEQ ID NO: 92 |
| FF0188-A2<br>FIG. 7 | SEQ ID NO: 93 |
| FF0188-A9<br>FIG. 7 | SEQ ID NO: 94 |
| FF0117-A3<br>FIG. 8 | SEQ ID NO: 55 |
| FF0U7-A5<br>FIG. 8 | SEQ ID NO: 56 |
| FF0117-A8<br>FIG. 8 | SEQ ID NO: 57 |
| FF0117-A10<br>FIG. 8 | SEQ ID NO: 58 |
| FF0117-A11<br>FIG. 8 | SEQ ID NO: 59 |
| FF0117-A12<br>FIG. 8 | SEQ ID NO: 60 |
| FF0117-B5<br>FIG. 8 | SEQ ID NO: 61 |
| FF0117-B9<br>FIG. 8 | SEQ ID NO: 62 |
| FF0117-B11<br>FIG. 8 | SEQ ID NO: 63 |
| FF0188-H5(2)<br>FIG. 8 | SEQ ID NO: 64 |
| FF03033-1<br>FIG. 9A | SEQ ID NO: 65 |
| FF03033-2<br>FIG. 9A | SEQ ID NO: 66 |
| FF03033-3<br>FIG. 9A | SEQ ID NO: 67 |
| FF03033-4<br>FIG. 9A | SEQ ID NO: 68 |
| FF03033-5<br>FIG. 9A | SEQ ID NO: 69 |
| FF03033-6<br>FIG. 9A | SEQ ID NO: 70 |
| FF03033-8<br>FIG. 9A | SEQ ID NO: 71 |
| FF03046-2<br>FIG. 9A | SEQ ID NO: 72 |
| FF0117-A5 (2)<br>FIG. 9A | SEQ ID NO: 73 |
| FF03077-4 anti-VEGF Fc-scFv fusion<br>Single chain nucleic acid sequence:<br>FIG. 13 | SEQ ID NO: 74 |
| FF03077-4 anti-VEGF Fc-scFv fusion<br>Single chain amino acid sequence:<br>FIG. 13 | SEQ ID NO: 75 |
| Anti-VEGF Fab 216<br>Light chain (hK) amino acid sequence:<br>FIG. 16 | SEQ ID NO: 76 |
| Anti-VEGF Fab 216<br>Light chain (hK) nucleic acid sequence:<br>FIG. 16 | SEQ ID NO: 77 |
| Anti-VEGF Fab 216<br>Heavy chain amino acid sequence:<br>FIG. 16 | SEQ ID NO: 78 |
| Anti-VEGF Fab 216<br>Heavy chain Nucleic acid sequence:<br>FIG. 16 | SEQ ID NO: 79 |
| Lucentis (Ranibizumab) Heavy Chain<br>(GenBank Accession Number: APZ76728.1)<br>FIG. 23 | SEQ ID NO: 80 |
| Fab 201 Heavy Chain<br>FIG. 23 | SEQ ID NO: 81 |

-continued

| SEQUENCES in the patent application | Sequence Listing |
| --- | --- |
| Lucentis (Ranibizumab) Light Chain FIG. 24 (GenBank Accession Number: APZ76729.1) | SEQ ID NO: 82 |
| Fab 201 Light Chain FIG. 24 | SEQ ID NO: 83 |

DETAILED DESCRIPTION OF THE INVENTION

Definitions

Unless defined otherwise, all technical and scientific terms used herein have the same meaning as is commonly understood by one of ordinary skill in the art to which relevant embodiments of the invention belong.

It must be noted that, as used herein and in the appended claims, the singular forms "a," "or," and "the" include plural referents unless the context clearly dictates otherwise. Thus, for example, "an antibody" includes a plurality of such antibodies. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

As used herein, the term "substantially free" includes being free of a given substance or cell type or nearly free of that substance or cell type, e.g. having less than about 1% of the given substance or cell type.

As used herein, the term vascular endothelial growth factor "VEGF" refers, unless specifically or contextually indicated otherwise, to any native, variant or synthetic VEGF polypeptide, or fragment thereof, of the VEGF family which comprises seven members: VEGF-A, VEGF-B, VEGF-C, VEGF-D, VEGF-E, VEGF-G and PLGF, wherein all members have a common VEGF homology domain composed of a cysteine knot motif with eight invariant cysteine residues involved in inter- and intramolecular disulfide bonds at one end of a conserved central four stranded β-sheet within each monomer, which dimerize in an anti-parallel, side-by-side orientation, and participate in angiogenesis (reviewed in Hoeben, A., et al. (2004) Vascular endothelial growth factor and angiogenesis. Pharmacol. Rev. 56, 549-580; see FIG. 1 of Hoeben et al. (2004) for a 3D structure of cysteine knot motif with inter- and intramolecular disulfide bonds). Each member within the VEGF family is encoded by a distinct gene; however, each member may comprise a number of different isoforms due to alternative splicing or proteolysis.

In a preferred embodiment, VEGF is VEGF-A and its isoforms that play a role in promoting or maintaining angiogenesis. For example, alternative splicing of the primary transcript of the VEGF-A gene, also referred to in the literature as VEGF without reference to "-A", produces different VEGF-A mRNAs encoding different VEGF-A isoforms, indicated often simply as VEGF followed by a number, with different isoforms having a pro-angiogenic or anti-angiogenic property depending on the presence of an alternatively spliced exon 8a or 8b of the VEGF-A gene. Of particular interests are VEGF-A isoforms obtained from translation of the alternative spliced exon 8a, which are generally pro angiogenic, in contrast to those with exon 8b, which are generally anti-angiogenic. In humans, the exon 8a-containing VEGF-A isoforms from alternative splicing comprise: VEGF-$A_{121}$ (also, often called VEGF$_{121}$), VEGF-$A_{145}$ (also, often called VEGF$_{145}$), VEGF-$A_{148}$ (also, often called VEGF$_{148}$), VEGF-$A_{165}$ (also, often called VEGF$_{165}$), VEGF-$A_{183}$ (also, often called VEGF$_{183}$), VEGF-$A_{189}$ (also, often called VEGF$_{189}$) and VEGF-$A_{206}$ (also, often called VEGF$_{206}$) (Nowak, D. G., et al. (2008) Expression of pro- and anti-angiogenic isoforms of VEGF is differentially regulated by splicing and growth factors. *J. Cell Sci.* 121, 3487-3495). The number following VEGF in each isoform of VEGF-A refers to the number of amino acids, atter signal sequence cleavage following secretion; this number may be a subscript or inline, such as VEGF$_{121}$ or VEGF121, respectively. In rodents, such as mouse, orthologs of these VEGF isoforms contain one less amino acid. VEGF is normally a homodimeric glycoprotein with its isoforms differing in their abilities to bind heparin. The larger highly basic VEGF$_{189}$ and VEGF$_{206}$ isoforms bind tightly to cell-surface heparin-containing proteoglycans in the extracellular matrix (ECM); whereas, the acidic VEGF$_{121}$ isoform lacks ability to bind heparin and is freely diffusible. VEGF$_{165}$ isoform has intermediate properties with a significant fraction bound to heparin and ECM. In addition to VEGF isoforms produced by alternative splicing, the ECM-bound VEGF isoforms may undergo proteolysis to generate a bioactive fragment with high mitogenic activity such as VEGF$_{110}$ or VEGF100 from proteolysis of VEGF165 or VEGF189 of human VEGF-A isoforms (Ferrara, N., Gerber, H.-P., and LeCouter, J. (2003) The biology of VEGF and its receptors. *Nature Medicine* 9, 669-676; also, see Hoeben, A., et al. (2004) above). In addition to VEGF100, any fragment of VEGF protein derived from the VEGF family of genes, either through natural proteolysis or man made, may be considered as VEGF so long as an antibody may be raised against or be directed to it, and the VEGF protein fragment has a role in promoting or maintaining angiogenesis, macular degeneration, tumor or human disease.

In addition to isolating VEGF protein from a subject or cultured cells, VEGF protein may be produced by recombinant DNA methods. For example, VEGF protein for any VEGF isoform or fragment or variant may be produced in a bacterium, a yeast, an insect cell or a mammalian cell or be produced in vitro in cell-free translation extract or coupled transcription-translation extract, as is known in the art. In the case of production in a bacterial cell, the resulting recombinant VEGF protein produced in bacterium can have the same primary amino acid sequence but may lack post translational modification such as glycosylation unlike VEGF protein isolated from mammalian cells. Nevertheless, the present disclosure encompasses VEGF produced in a bacterial cell, produced in vitro, such as using an in vitro cell-free translation system or coupled transcription-translation system, or produced by recombinant methods, in addition to VEGF isolated from a natural source. A VEGF antigen may be naturally occurring, recombinant or synthetic VEGF molecule. The VEGF antigen may be present on an intact VEGF protein, VEGF isoform, a fragment of VEGF or a peptide with a sequence derived from a portion of VEGF.

As used herein, "wild type VEGF sequence" generally refers to a primary amino acid sequence found in a naturally occurring VEGF isoform or derived from translation of the VEGF mRNA following processing of the primary VEGF gene transcript in a mammalian cell or derived from the translation of any VEGF cDNA. The VEGF cDNA may be obtained, for example, by reverse transcription of polysomal VEGF mRNA from a mammalian cell, such as a mouse or human cell.

As used herein, "antibody" includes monoclonal antibodies (e.g., full length or intact monoclonal antibodies), polyclonal antibodies, multivalent antibodies (e.g., antibodies with more than one antigen binding site of the same specificity so as to permit association with more than one antigen depending on the valency and increased avidity observed for example for bivalent IgG antibody versus its monovalent Fab antibody fragment), multispecific antibodies (e.g., bispecific antibodies so long as they exhibit the desired biological activity) and may also include certain antibody fragments (as described in greater detail herein). An antibody can be human, humanized, affinity matured and/or synthetic. An antibody may be produced by any method known in the art, such as, for example in vivo in an animal, in tissue or cell culture, or in vitro protein synthesis systems by enzymatic and/or chemical synthesis methods. Recombinant DNA methods may be used in the production of an antibody, and the resulting antibody may be considered to be a recombinant antibody. A recombinant antibody may be produced free of animal products such as produced in a bacterium. An antibody or its fragment may be displayed on the surface of a bacteriophage.

"Antibody fragment" or "antibody fragments" are only a portion of an antibody, wherein the portion retains at least one, preferably many or all, of the functions normally associated with that portion when present in an intact antibody. Examples of antibody fragments include Fab, Fab', F(ab')2, and Fv fragments; diabodies; linear antibodies; single-chain antibody molecules including single-chain Fv (scFv) antibody molecule; multivalent antibodies formed from multiple copies of the same antibody fragment with the same specificity; and multispecific antibodies formed from antibody fragments.

A synthetic human anti-VEGF antibody includes an "affinity matured" antibody which includes one or more changes in one or more hypervariable regions or complementarity determining regions (CDRs) thereof, which result in an improvement in the affinity of the antibody for VEGF, compared to a parent antibody which does not possess those changes. CDRs found in the variable region of an antibody may be defined by Kabat method or IMGT method (Martin, A. C. R. (1996) Accessing the Kabat Antibody Sequence Database by Computer *PROTEINS: Structure, Function and Genetics* 25: 130-133; Johnson, G. and Wu, T. T. (2004) The Kabat Database and a Bioinformatics Example. *Methods in Molecular Biology* 248: 11-25; Kabat, E. A., Wu, T. T., Perry, H., Gottesman, K., and Foeller, C. (1991) *Sequences of Proteins of Immunological Interest,* 5th ed., NIH Publication No. 91-3242, Bethesda, MD.; MacCallum, R. M., Martin, A. C. R. and Thornton, J. T. (1996) Antibody-antigen interactions: Contact analysis and binding site topography. *J. Mol. Biol.* 262, 732-745; Lefranc, M.-P., Pommié, C., Ruiz, M., Giudicelli, V., Foulquier, E., Truong, L., Thouvenin-Contet, V. and Lefranc, G. (2003) IMGT unique numbering for immunoglobulin and T cell receptor variable domains and Ig superfamily V-like domains. *Dev. Comp. Immunol.* 27: 55-77; and Lefranc, M.-P. (2005) IMGT, the international ImMunoGeneTics information System®. *Nucleic Acids Res.* 33: D593-D597; Lefranc, M.-P. et al. (2009) IMGT®, the international ImMunoGeneTics information System®. *Nucleic Acids Res.* 37:D1006-D1012). The specificity of an antibody may be defined or described by a set of CDRs which may be defined by a number of methods including Kabat or IMGT® method.

The antigen-binding region of an antibody may include an antigen-binding site formed by the CDRs of the light chain variable region and heavy chain variable region.

A disorder or disease is a condition that would benefit from treatment with anti-VEGF antibodies/compositions or method of the invention. This includes chronic and acute disorders or diseases including those pathological conditions which predispose the mammal to the disorder in question. Non-limiting examples of disorders to be treated herein include cell proliferative disorders. The cell proliferative disorder may include a disease such as wet age related macular degeneration, diabetic maculopathy, proliferative diabetic retinopathy, macular edema in retinal vein occlusion (RVO), iris neovascularization, choroidal neovascularisation caused by pathological myopia, retinopathy of maturity, neovascular glaucoma, diabetic retinopathy, retinal neovascularization, pars plana vitrectomy (PPV), diabetic macular edema (DME) or cancer.

As used herein, "treating" means using a therapy to ameliorate a disease or disorder or one or more of the biological manifestations of the disease or disorder; to directly or indirectly interfere with (a) one or more points in the biological cascade that leads to, or is responsible for, the disease or disorder or (b) one or more of the biological manifestations of the disease or disorder; to alleviate one or more of the symptoms, effects or side effects associated with the disease or disorder or one or more of the symptoms or disorder or treatment thereof; or to slow the progression of the disease or disorder or one or more of the biological manifestations of the disease or disorder. Treatment includes eliciting a clinically significant response. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder. For example, treatment of an eye condition may improve the symptoms of the condition, reduce the severity of a condition, alter the course of condition's progression and/or improve the basic condition. Treatment may also include improving quality of life for a subject afflicted with the disease or disorder (e.g., a subject afflicted with a cancer may receive a lower dose of an anti-cancer drug that cause side-effects when the subject is immunized with a composition of the invention described herein). Throughout the specification, compositions of the invention and methods for the use thereof are provided and are chosen to provide suitable treatment for subjects in need thereof.

A "subject" may be a vertebrate, preferably a mammal, and more preferably a human. Mammals include, but are not limited to, farm animals (such as cows, sheeps, and goats), sport animals, pets (such as cats, dogs and horses), primates (such as, monkeys, gorillas and chimpanzees), mice and rats.

As used herein, an "effective amount" refers to an amount effective, at dosages and for periods of time necessary, to achieve the desired therapeutic or prophylactic result.

In order that the invention herein described may be more fully understood the following description is set forth. Compositions of the Invention and Methods of Making Same This invention encompasses novel anti-VEGF antibodies; and polynucleotides comprising sequences encoding such novel anti-VEGF antibodies and compositions, including pharmaceutical compositions, comprising them. The terms "pharmaceutical formulations", "pharmaceutical compositions" and "dosage forms" are used interchangeably herein and refer to a composition containing the active ingredient(s) of the invention in a form suitable for administration to a subject.

As used herein, compositions comprise one or more antibodies of the invention that bind to VEGF, and/or one or more polynucleotides comprising sequences encoding one or more antibodies that bind to VEGF. These compositions may further comprise suitable carriers, such as pharmaceutically acceptable excipients, including buffers, which are well known in the art.

Merely by way of example, an antibody is a protein that may take the shape of a Y which may be created by joining two immunoglobulin light chains and two immunoglobulin heavy chains, wherein one light chain associates with one heavy chain to form one arm of the protein. The two arms join through the association of one heavy chain to the other. Typically, each arm of the antibody recognizes the same antigen and binds an epitope on the antigen through the antigen binding site formed by the variable region of the associated light and heavy chain. The portion of the variable region of the light and heavy chain that bind to the epitope are called hypervariable regions or "complementarity determining regions (CDRs)." An antibody's specificity for a particular antigen depends on the amino acid sequences of the hypervariable region or CDRs, which show greatest variability between antibodies of different binding specificities. The remaining non-hypervariable regions or non-CDRs called the framework regions (FRs). For example, there may be three CDRs from amino-to-carboxyl terminal of a variable region called CDR1-3 for each light chain and each heavy chain, which are separated by four FRs, namely, FR1-4. To distinguish the light chain CDR from heavy chain CDR, the light chain CDR1-3 are designated CDRL1-CDRL3, or alternatively CDR-L1 to CDR-L3. Similarly, the heavy chain CDR1-3 are designated CDRH1-CDRH3 or CDR-H1 to CDR-H3. The four FRs in the light chain variable region are designated FRL1-FRL4 or FR-L1 to FR-L4. Further, the four FRs in the heavy chain variable region are designed FRH1-FRH4 or FR-H1 to FR-H4. Accordingly, the typical variable region is formed by attaching from the amino-to-carboxyl terminus for the light chain in the order FRL1-CDRL1-FRL2-CDRL2-FRL3-CDRL3-FRL4. Similarly, the heavy chain is formed in the order FRH1-CDRH1-FRH2-CDRH2-FRH3-CDRH3-FRH4. The light chain variable region is followed by a kappa or lambda light chain constant region, which completes the light chain. Whereas, the heavy chain variable region is joined at its C-terminus to constant regions, CH1, CH2 and CH3 along with a hinge region between CH1 and CH2 with cysteine residue(s) that participate in an interstrand crosslink with the hinge region of the second heavy chain. Sequence of the heavy chain constant region determines the class of immunoglobulin (IgA, IgD, IgE, IgG, or IgM) and within each class determines the subclass (e.g., for IgG class, the IgG1, IgG2, IgG3 or IgG4 subclass).

The complementarity determining region (CDR) or hypervariable region of an immunoglobulin light and heavy chains may be defined based on sequence comparison as by Elvin A. Kabat and colleagues (Kabat, E. A., Wu, T. T., Perry, H. M., Gottesman, K. S. and Foeller, C. (1991) Sequences of Proteins of Immunological Interest, Volumes 1-3. 5th edition. NIH Publication No. 91-3242 (ISBN: 094137565X, 9780941375658), with non-CDR sequences designed as specific FRs, depending on the relationship to each CDR. Alternatively, another method for identification of CDRs in immunoglobulin was developed by Marie-Paule Lefranc and colleagues to produce the IMGT® charts and methods for identifying CDRs (Lefranc, M.-P., et al. (1999) IMGT, the international ImMunoGeneTics database. *Nucl. Acids Res.* 27, 209-212; Lefranc, M.-P., et al. (2015) IMGT®, the international ImMunoGeneTics® information system 25 years on. *Nucl. Acids Res.* 43, D413-D422). Both the Kabat method and IMGT method for identifying CDRs are used herein. Both methods produce either identical CDR sequences or overlaps between CDR sequences or one CDR sequence contained in its entirety with the CDR sequence determined for the corresponding CDR by the other method. In cases where the CDR sequences identified by both methods failed to yield same length or are overlapping, the framework regions (by default the region outside of the CDR or between CDRs in the variable region) are not identical in size or similarly will have overlapping sequences.

In one embodiment, the invention provides an isolated anti-VEGF antibody or portion or variant thereof having a heavy chain variable domain comprising the following hypervariable region or complementarity determining region (CDR) amino acid sequences: CDRH1 comprising histidine at amino acid position 31 to histidine at amino acid position 35 (SEQ ID NO: 1), CDRH2 comprising tyrosine at amino acid position 50 to glycine at amino acid position 66 (SEQ ID NO: 1) and CDRH3 comprising histidine at amino acid position 99 to tyrosine at amino acid position 109 (SEQ ID NO: 1).

A variant of an anti-VEGF antibody of the invention may include antibodies that comprise an amino acid sequence wherein one or more amino acid residues are different relative to the amino acid sequences of any of the Y variants disclosed herein, (e.g., see Example 3 and FIGS. 9C and 16) e.g., changes due to amino acid residues that are inserted into, deleted from and/or substituted in the framework region but no amino acid residues are inserted into, deleted from and/or substituted in the CDR regions (e.g. either as defined by Kabat numbering or IMGT numbering; or any other CDR identification system such as Chothia nomenclature). Variants include antibody fragments, such as Fab fragment and single chain Fv (scFv) fragment. Variants may further include fusion proteins, such as e.g., in FIGS. 12 and 13. Variants and antibodies of disclosed herein may be produced by recombination DNA methods.

A portion of an isolated antibody of the invention includes useful immunologically functional fragments or provides specificity of binding an antigen or epitope on an antigen (e.g. recognizes and binds a VEGF) such as a CDR region, a variable domain of a heavy and/or light chain or a portion of an antibody chain that binds a VEGF. It would be clear to one skilled in the art that the antibodies of the invention can be camelized.

For example, an isolated antibody or portion or variant thereof is one which has been separated and/or recovered from its production environment. The production environment may be cell-based, e.g., cells, or may be cell free, e.g., in vitro translation or coupled transcription-translation cell-free system. In preferred embodiments, the antibody will be purified (a) to greater than about 95% by weight of antibody as determined by, e.g., the Lowry method, and most preferably more than about 99% by weight or (b) to homogeneity by SDS-PAGE under reducing or nonreducing conditions. As used herein, the term "about" when used before a numerical designation, e.g., temperature, time, amount, concentration, and such other, including a range, indicates approximations which may vary by (+) or (−) 10%, 5% or 1%.

In another embodiment, the invention provides an isolated anti-VEGF antibody or portion or variant thereof having a light chain variable domain comprising the following hypervariable region or complementarity determining region (CDR) amino acid sequences: CDRL1 comprising arginine at amino acid position 24 to alanine at amino acid position 34 (SEQ ID NO: 3), CDRL2 comprising lysine at amino acid position 50 to alanine at amino acid position 56 (SEQ ID NO: 3), and CDRL3 comprising glutamine at amino acid position 89 to threonine at amino acid position 97 (SEQ ID NO: 3).

In yet an additional embodiment, the anti-VEGF antibody or portion thereof may further comprise a heavy chain variable domain comprising the following CDR amino acid sequences defined in accordance with IMGT numbering shown in bold in FIG. 16: CDRH1 comprising amino acid sequences GFDLDHYS (SEQ ID NO: 152), CDRH2 comprising amino acid sequences IYPSYGYT (SEQ ID NO: 153) and CDRH3 comprising amino acid sequences ARHAWYYGWGLDY (SEQ ID NO: 154); and a light chain variable domain comprising the following CDR amino acid sequences defined in accordance with IMGT numbering shown in bold in FIG. 16: CDRL1 comprising amino acid sequences QAAYGR (SEQ ID NO: 155), CDRL2 comprising amino acid sequences KAS and CDRL3 comprising amino acid sequences QQRGWYLFT (SEQ ID NO: 142)

An additional embodiment provides the anti-VEGF antibody or portion thereof further comprising a heavy chain variable domain comprising the following CDR amino acid sequences: CDRH1 comprising histidine at amino acid position 31 to histidine at amino acid position 35 (SEQ ID NO: 1), CDRH2 comprising tyrosine at amino acid position 50 to glycine at amino acid position 66 (SEQ ID NO: 1) and CDRH13 comprising histidine at amino acid position 99 to tyrosine at amino acid position 109 (SEQ ID NO: 1).

The invention provides a humanized anti-VEGF antibody or portion thereof. The anti-VEGF antibody of the invention inhibits VEGF-induced angiogenesis in vivo.

Also, the invention provides synthetic human anti-VEGF antibodies or portion or variant thereof. In one embodiment, it comprises a light chain variable domain having the following hypervariable region or complementarity determining region (CDR) amino acid sequences: a CDRL1 which comprises arginine at amino acid position 24 to alanine at amino acid position 34 (SEQ ID NO: 3) or a portion thereof, a CDRL2 which comprises lysine at amino acid position 50 to alanine at amino acid position 56 (SEQ ID NO: 3) or a portion thereof, and a CDRL3 which comprises glutamine at amino acid position 89 to threonine at amino acid position 97 (SEQ ID NO: 3) or a portion thereof; and a heavy chain variable domain having the following hypervariable region or complementarity determining region (CDR) amino acid sequences: a CDRH1 which comprises histidine at amino acid position 31 to histidine at amino acid position 35 (SEQ ID NO: 1) or a portion thereof, a CDRH2 which comprises tyrosine at amino acid position 50 to glycine at amino acid position 66 (SEQ ID NO: 1) or a portion thereof and a CDRH3 which comprises histidine at amino acid position 99 to tyrosine at amino acid position 109 (SEQ ID NO: 1) or a portion thereof.

Examples of anti-VEGF antibodies of the invention include, but are not limited to, variants 201, 202, 203, 204, 205, 206, 207, 208, 209, 212, 213, 214, 215, 216, 217, 218, 219 and 220 as shown in SEQ ID NOS: 21-28, respectively.

In yet an additional embodiment, the anti-VEGF antibody may further comprise a heavy chain framework region (FR) 1, FRH1, amino sequence comprising glutamic acid at amino acid position 1 to phenylalanine at amino acid position 30 (SEQ ID NO: 1).

In yet an additional embodiment, the anti-VEGF antibody may further comprise a heavy chain framework region (FR) 2, FRH2, amino sequence comprising tryptophan at amino acid position 36 to alanine at amino acid position 49 (SEQ ID NO: 1).

In yet an additional embodiment, the anti-VEGF antibody may further comprise a heavy chain framework region (FR) 3, FRH13, amino sequence comprising arginine at amino acid position 67 to arginine at amino acid position 98 (SEQ ID NO: 1).

In yet an additional embodiment, the anti-VEGF antibody may further comprise a heavy chain framework region (FR) 4, FRH4, amino sequence comprising tryptophan at amino acid position 110 to serine at amino acid position 120 (SEQ ID NO: 1).

In yet an additional embodiment, the anti-VEGF antibody may further comprise the following heavy chain framework region (FR) amino acid sequences: FRH1 comprising glutamic acid at amino acid position 1 to phenylalanine at amino acid position 30 (SEQ ID NO: 1), FRH2 comprising tryptophan at amino acid position 36 to alanine at amino acid position 49 (SEQ ID NO: 1), FRH3 comprising arginine at amino acid position 67 to arginine at amino acid position 98 (SEQ ID NO: 1) and FRH4 comprising tryptophan at amino acid position 110 to serine at amino acid position 120 (SEQ ID NO: 1).

In yet an additional embodiment, the anti-VEGF antibody may further comprise a light chain framework region (FR) 1, FRL1, amino sequence comprising aspartic acid at amino acid position 1 to cysteine at amino acid position 23 (SEQ ID NO: 3).

In yet an additional embodiment, the anti-VEGF antibody may further comprise a light chain framework region (FR) 2, FRL2, amino sequence comprising tryptophan at amino acid position to tyrosine at amino acid position 49 (SEQ ID NO: 3).

In yet an additional embodiment, the anti-VEGF antibody may further comprise a light chain framework region (FR) 3, FRL3, amino sequence comprising glycine at amino acid position 57 to cysteine at amino acid position 88 (SEQ ID NO: 3).

In yet an additional embodiment, the anti-VEGF antibody may further comprise a light chain framework region (FR) 4, FRL4, amino sequence comprising phenylalanine at amino acid position 98 to lysine at amino acid position 107 (SEQ ID NO: 3).

In yet an additional embodiment, the anti-VEGF antibody may further comprise the following light chain framework region (FR) amino acid sequences: FRL1 comprising aspartic acid at amino acid position 1 to cysteine at amino acid position 23 (SEQ ID NO: 3), FRL2 comprising tryptophan at amino acid position 35 to tyrosine at amino acid position 49 (SEQ ID NO: 3), FRL3 comprising glycine at amino acid position 57 to cysteine at amino acid position 88 (SEQ ID NO: 3) and FRL4 comprising phenylalanine at amino acid position 98 to lysine at amino acid position 107 (SEQ ID NO: 3).

In yet an additional embodiment, the anti-VEGF antibody or portion or variant thereof may further comprise: (c) a light chain variable domain having the following framework region amino acid sequences: a FRL1 which comprises aspartic acid at amino acid position 1 to cysteine at amino acid position 23 (SEQ ID NO: 3) or a portion thereof, FRL2 which comprises tryptophan at amino acid position 35 to tyrosine at amino acid position 49 (SEQ ID NO: 3) or a portion thereof, FRL3 which comprises glycine at amino acid position 57 to cysteine at amino acid position 88 (SEQ ID NO: 3) or a portion thereof, and FRL4 which comprises phenylalanine at amino acid position 98 to lysine at amino acid position 107 (SEQ ID NO: 3) or a portion thereof; and (d) a heavy chain variable domain having the following framework region amino acid sequences: a FRH1 which comprises glutamic acid at amino acid position 1 to phenylalanine at amino acid position 30 (SEQ ID NO: 1) or a portion thereof, FRH2 which comprises tryptophan at amino acid position 36 to alanine at amino acid position 49 (SEQ ID NO: 1) or a portion thereof, FRH3 which comprises arginine at amino acid position 67 to arginine at amino acid position 98 (SEQ ID NO: 1) or a portion thereof, and FRH4 which comprises tryptophan at amino acid position 110 to serine at amino acid position 120 (SEQ ID NO: 1) or a portion thereof.

The invention also encompasses isolated anti-VEGF antibody and polynucleotide embodiments. The invention also encompasses substantially pure antibody and polynucleotide embodiments.

The anti-VEGF antibodies of the invention may be monoclonal (e.g., full length or intact monoclonal antibodies). In an embodiment of the invention, the anti-VEGF antibody of the invention is a full length antibody. Further, in one example, the full length antibody comprises a light chain comprising the amino acid sequence shown in SEQ ID NO:3 and a heavy chain shown in SEQ ID NO:1. In another embodiment, the full length antibody comprises a light chain comprising the amino acid sequence shown in SEQ ID NO:3 and a heavy chain shown in SEQ ID NO:1, a light chain comprising the aspartic acid at amino acid position 24 to cysteine at amino acid position 237 (SEQ ID NO:17) and a heavy chain comprising the glutamic acid at amino acid position 24 to threonine at amino acid position 251 (SEQ ID NO:18) (e.g. heavy chain Fab 216; FIG. 16), or a light chain comprising the aspartic acid at amino acid position 24 to cysteine at amino acid position 237 (SEQ ID NO:76) (e.g., light chain Fab 216; FIG. 16) and a heavy chain comprising the glutamic acid at amino acid position 24 to threonine at amino acid position 251 (SEQ ID NO:78) (e.g., heavy chain Fab 216; FIG. 16)

Also encompassed within the scope of the invention are Fab, Fab', Fab'-SH and F(ab')2 fragments of the anti-VEGF antibodies provided herein. These antibody fragments can be created by traditional means, such as enzymatic digestion, or may be generated by recombinant techniques, as well as through the use of chemical methods. For example, Fab'-SH, Fab' with reduced —SH group such as at the cysteine that plays a role in interstrand cross link between two heavy chains, may be produced by recombinant techniques or by chemical methods by reducing the disulfide bonds of F(ab')₂ antibody fragment. Such antibody fragments may be chimeric or humanized. Fab and scFv fragments may be engineered to form dimers, trimers or tetramers by chemical or genetic crosslinks to improve retention and internalization properties as compared with the parent IgG. These fragments are useful for the diagnostic and therapeutic purposes set forth below.

A Fv fragment contains a complete antigen-recognition and -binding site. In a single-chain Fv species, a single heavy- and a single light-chain variable domain may be covalently linked by a peptide linker such that the light and heavy chains may associate in a "dimeric" structure. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

A Fab fragment contains a single antigen-binding site, and a residual "Fc" fragment. The Fab fragment also contains the constant domain of the light chain and the first constant domain (CH1) of the heavy chain. Fab' fragments are encompassed herein and differ from Fab fragments by the addition of a few residues at the carboxy terminus of the heavy chain CH1 domain including one or more cysteines from the antibody hinge region. F(ab')₂ antibody fragments are encompassed herein and are a pair of Fab' fragments which have hinge cysteines between them. Other chemical couplings of antibody fragments are known and encompassed herein.

Depending on the amino acid sequence of the constant domain of their heavy chains, immunoglobulins can be assigned to different classes. For example, the antibodies of the invention may be any of immunoglobulin class: IgA, IgD, IgE, IgG, and IgM. Moreover, within these classes, they can be further divided into subclasses (isotypes) including any of, e.g., IgG₁, IgG₂, IgG₃, IgG₄, IgA₁, and IgA₂. The heavy-chain constant domains that correspond to the different classes of immunoglobulins may be any of α, δ, ε, γ, and μ, respectively.

Monoclonal antibodies are obtained from a population of substantially homogenous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-VEGF monoclonal antibodies of the invention can be made using the hybridoma method first described by Kohler et al., Nature, 256:495 (1975), or may be made by recombinant DNA methods.

Additionally, the anti-VEGF antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-VEGF antibodies of the invention can be obtained by designing a suitable antigen screening procedure to select for the phage clone of interest followed by construction of a full length anti-VEGF antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

Chimeric antibodies of the invention are immunoglobulin molecules that comprise a human and non-human portion. The antigen combining region (variable region) of a chimeric antibody can be derived from a non-human source (e.g. murine) and the constant region of the chimeric antibody which confers biological effector function to the immunoglobulin can be derived from a human source. The chimeric antibody should have the antigen binding specificity of the non-human antibody molecule and the effector function conferred by the human antibody molecule.

In general, the procedures used to produce chimeric antibodies can involve the following steps:

a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;

b) cloning the gene segments encoding the constant region or desired part thereof;

c) ligating the variable region with the constant region so that the complete chimeric antibody is encoded in a form that can be transcribed and translated;

d) ligating this construct into a vector containing a selectable marker and gene control regions such as promoters, enhancers and poly(A) addition signals;

e) amplifying this construct in bacteria;

f) introducing this DNA into eukaryotic cells (transfection) most often mammalian lymphocytes;

g) selecting for cells expressing the selectable marker;

h) screening for cells expressing the desired chimeric antibody; and k) testing the antibody for appropriate binding specificity and effector functions.

The invention encompasses multiple types of vectors. The term vector is any molecule or entity used to transfer protein coding information into a host cell including, but not limited to, plasmids, bacteriophage, virus, cosmids, and phagemids. Moreover, certain vectors are capable of directing the expression of genes to which they are operatively linked. Such vectors are referred to herein as recombinant expression vectors or expression vectors. In general, expression vectors for use in recombinant DNA techniques may be in the form of plasmids.

Antibodies of several distinct antigen binding specificities have been manipulated by these protocols to produce chimeric proteins [e.g. anti-TNP: Boulianne et al., *Nature* 312:643 (1984); and anti-tumor antigens: Sahagan et al., *J. Immunol.* 137:1066 (1986)]. Likewise, several different effector functions have been achieved by linking new sequences to those encoding the antigen binding region. Some of these include enzymes [Neuberger et al., *Nature* 312:604 (1984)], immunoglobulin constant regions from another species and constant regions of another immunoglobulin chain [Sharon et al., *Nature* 309:364 (1984); Tan et al., *J. Immunol.* 135:3565-3567 (1985)]. Additionally, procedures for modifying antibody molecules and for producing chimeric antibody molecules using homologous recombination to target gene modification have been described (Fell et al., *Proc. Natl. Acad. Sci. USA* 86:8507-8511 (1989)).

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently. "Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. As used herein, scFv encoding phage clones and Fab encoding phage clones are collectively referred to as "Fv phage clones" or "Fv clones".

"Hypervariable regions" are the regions of an antibody variable domain which are hypervariable in sequence and/or form structurally defined loops. In general, antibodies may comprise six hypervariable regions. These include three regions in the variable heavy chain (VH) which are designated H1, 1H2, H3. Additionally, there are three in the variable light chain (VL) which are designated L1, L2, L3. A number of hypervariable region delineations are in use and are encompassed herein. For example, the Kabat Complementarity Determining Regions (CDRs) are based on sequence variability and may be used (Kabat et al., *Sequences of Proteins of Immunological Interest,* 5th Ed. Public Health Service, National Institutes of Health, Bethesda, Md. (1991)).

Repertoires of VH and VL genes can be separately cloned by polymerase chain reaction (PCR). Then the clones may be recombined randomly in phage libraries and searched for antigen-binding clones. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization. Finally, naive libraries can also be made synthetically by cloning the unrearranged V-gene segments from stem cells, and using PCR primers containing random sequence to encode the highly variable CDR3 regions and to accomplish rearrangement in vitro.

Filamentous phage may be used to display antibody fragments. The antibody fragments then can be displayed as single chain Fv fragments. The VB and VL domains may be connected on the same polypeptide chain by a flexible polypeptide spacer, or as Fab fragments, in which one chain is fused to pIII of the filamentous phage and the other is secreted into the bacterial host cell periplasm where assembly of a Fab-coat protein structure which becomes displayed on the phage surface by displacing some of the wild type coat proteins.

In general, nucleic acids encoding antibody gene fragments are obtained from immune cells harvested from humans or animals. If a library biased in favor of anti-VEGF clones is desired, the subject is immunized with VEGF to generate an antibody response, and spleen cells and/or circulating B cells other peripheral blood lymphocytes (PBLs) are recovered for library construction. In a preferred embodiment, a human antibody gene fragment library biased in favor of anti-VEGF clones is obtained by generating an anti-VEGF antibody response in transgenic mice carrying a functional human immunoglobulin gene array (and lacking a functional endogenous antibody production system) such that VEGF immunization gives rise to B cells producing human antibodies against VEGF. The generation of human antibody-producing transgenic mice is described below.

Nucleic acids (also referred to herein as polynucleotides) refer to polymers of nucleotides of any length, and include DNA and RNA. The nucleotides can be ribonucleotides, deoxyribonucleotides, modified nucleotides or bases, and/or their analogs. A polynucleotide may comprise modified nucleotides, such as methylated nucleotides and their analogs. The sequence of nucleotides may be interrupted by non-nucleotide components. A polynucleotide may be further modified after synthesis, including, for example, via conjugation with a label.

Percent amino acid sequence identity in connection with a peptide or polypeptide sequence of the invention means the percentage of amino acid residues in a candidate sequence that shares identity with the amino acid residues in the specific peptide or polypeptide sequence of the invention, after aligning the sequences and, if necessary, including gaps to obtain the maximum percent sequence identity.

In another embodiment, the invention embodies an amino acid sequence with a percent identity of at least 91%. In another embodiment, the invention embodies an amino acid sequence with a percent identity of a range of about 92-98%. In another embodiment, the invention embodies an amino acid sequence with a percent identity of at least 99%. In one embodiment, the amino acid sequence of the invention comprises only a portion of the entire sequence as provided in the invention, e.g., a deletion. Such a deletion may be internal or at an end. In one embodiment, the amino acid sequence of the invention comprises additional amino acids wherein the additional amino acids are inserted within the amino acid sequence of the invention or are attached to the end. In one embodiment, the invention embodies an amino acid substitution wherein the substitution does not interfere with the binding to VEGF or neutralizing VEGF function. Such substitutions are often conservative amino acid substitution wherein the substituting amino acid has functionally equivalent physiochemical properties, such as aliphatic (glycine, alanine, valine, leucine, isoleucine), hydroxyl or sulfur/selenium-containing (serine cysteine, selenocysteine, threonine, methionine), cyclic (proline), aromatic (phenylalanine, tyrosine, tryptophan), basic (histidine, lysine, arginine) and acidic and their amide (aspartate, glutamate, asparagine, and glutamine).

Nucleic acid encoding antibody variable gene segments (including VH and VL segments) may be recovered from the cells of interest and amplified. For example, the antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries. Additionally, affinity maturation can be performed by randomly mutating one or more CDRs, e.g. using PCR with primers carrying random sequence spanning the CDR of interest, in selected individual Fv clones and screening for higher affinity clones. Another effective approach is to recombine the VH or VL domains selected by phage display with repertoires of naturally occurring V domain variants obtained from unimmunized donors and screen for higher affinity in several rounds of chain reshuffling. This technique allows the production of antibodies and antibody fragments with higher affinities with $K_d$ in the about $10^{-9}$ M range.

For example, an anti-VEGF antibody, portion or variant thereof of the invention may bind human VEGF with a $K_{(d)}$ value of no more than about 50 nM. In an another embodiment, the anti-VEGF antibody, portion or variant thereof binds human VEGF with a $K_{(d)}$ value of no more than about nM. In yet another embodiment, the anti-VEGF antibody, portion or variant thereof binds human VEGF with a $K_{(d)}$ value of no more than about 2.5 nM. In yet a further embodiment, the anti-VEGF antibody, portion or variant thereof binds human VEGF with a $K_{(d)}$ value of no more than about 0.5 nM. In an additional embodiment, the anti-VEGF antibody, portion or variant thereof binds human VEGF with a $K_{(d)}$ value of no more than about 0.15 nM. In yet additional embodiment, the anti-VEGF antibody, portion or variant thereof binds human VEGF with a $K_{(d)}$ value between 5 pM and 150 pM. In a further embodiment, the anti-VEGF antibody, portion or variant thereof binds human VEGF with a $K_{(d)}$ value of about 0.15 nM. In another further embodiment, the anti-VEGF antibody, portion or variant thereof of the invention binds human VEGF with a $K_{(d)}$ value of 90 pM±20 pM. In still a further embodiment, the anti-VEGF antibody, portion or variant thereof binds human VEGF with a $K_{(d)}$ value of about 25 pM. In an embodiment, the anti-VEGF antibody, portion or variant thereof binds human VEGF with a $K_{(d)}$ value of about 10 pM. In yet another embodiment, the anti-VEGF antibody, portion or variant thereof of the invention has a higher affinity for human VEGF than ranibizumab (Lucentis®; Novartis and Roche) or bevacizumab (Avastin®; Roche) with more than 3-fold lower $K_{(d)}$ value than that for ranibizumab or bevacizumab. In yet a further embodiment, the antibody or portion or variant thereof has a relative $K_{(d)}$ value for human VEGF that is more than 4-fold lower than ranibizumab (Lucentis®; Novartis and Roche). In another embodiment, the antibody or portion or variant thereof has a relative $K_{(d)}$ value for human VEGF that is more than 10-fold lower than ranibizumab (Lucentis®; Novartis and Roche). In another embodiment, the antibody or portion or variant thereof has a relative $K_{(d)}$ value for human VEGF that is more than 50-fold lower than ranibizumab (Lucentis®; Novartis and Roche). In another embodiment, the antibody or portion or variant thereof has a relative $K_{(d)}$ value for human VEGF that is about 55-fold lower than ranibizumab (Lucentis®; Novartis and Roche). In still another embodiment, the antibody or portion or variant thereof has a relative $K_{(d)}$ value for human VEGF that is more than 10-fold lower than bevacizumab (Avastin®; Roche). In another embodiment, the antibody or portion or variant thereof has a relative $K_{(d)}$ value for human VEGF that is more than 50-fold lower than bevacizumab (Avastin®; Roche). In another embodiment, the antibody or portion or variant thereof has a relative $K_{(d)}$ value for human VEGF that is more than 100-fold lower than bevacizumab (Avastin®; Roche). In another embodiment, the antibody or portion or variant thereof has a relative $K_{(d)}$ value for human VEGF that is about 110-fold lower than bevacizumab (Avastin®; Roche).

In yet a further embodiment, the antibody or portion or variant thereof has an IC50 value of no more than about 200 pM for inhibiting VEGF-induced proliferation of endothelial cells in vitro. Further, an additional embodiment, the antibody or portion or variant thereof is more effective at inhibiting VEGF-induced proliferation of endothelial cells in vitro than ranibizumab (Lucentis®; Novartis and Roche). In a further embodiment the relative IC50 value for inhibiting VEGF-induced proliferation of endothelial cells in vitro is about 1.5-fold lower than ranibizumab (Lucentis®; Novartis and Roche).

In an embodiment, the invention provides antibodies which have increased stability. In one embodiment, the anti-VEGF antibody or portion of variant thereof, has greater stability than ranibizumab (Lucentis®; Novartis and Roche). In another embodiment, the anti-VEGF antibody or portion of variant thereof, has greater storage life than ranibizumab (Lucentis®; Novartis and Roche).

In an embodiment, the invention provides antibodies which have increased thermal stability than ranibizumab (Lucentis®; Novartis and Roche). For example, the melting temperature of the humanized anti-VEGF antibody of the invention may be about 1.5° C. higher than that of ranibizumab (Lucentis®; Novartis and Roche).

In one embodiment, an anti-VEGF antibody of the invention, or portion or variant thereof, does not bind BSA or Fc.

Following construction of the DNA molecule encoding the antibodies against VEGF of the invention, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell. Methods for transfection are well known in the art.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the antibodies against VEGF of the invention can be cultured as described generally in Sambrook et al., supra.

Mammalian host cells may be used to produce the antibodies against VEGF and may be cultured in a variety of media, which is well known in the art and some of which is described herein.

The host cells referred to in this disclosure encompass cells in in vitro culture as well as cells that are within a host animal. Purification of antibodies against VEGF of the invention may be accomplished using art-recognized methods, some of which are described herein. The purified antibodies can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones.

Phage library samples may be contacted with immobilized VEGF under conditions suitable for binding of at least a portion of the phage particles with a solid phase. Normally, the conditions, including pH, ionic strength, temperature and the like are selected to mimic physiological conditions. The phages bound to the solid phase may be washed and then eluted. Phages can be enriched in a single round of selection; and if enriched, can be grown in bacterial culture and subjected to further rounds of selection. It is possible to select between phage antibodies of different affinities, even with affinities that differ slightly, for VEGF.

Reactivity of anti-VEGF mAbs against the target antigen may be established by a number of well known means, including Western blot, immunoprecipitation, ELISA, and FACS analyses using, as appropriate, VEGF proteins, peptides, VEGF-expressing cells or extracts thereof. Examples of such assays are presented in Example 1, infra.

The antibody or fragment thereof of the invention may be cytostatic to the cell, to which it binds. As used herein, "cytostatic" means that the antibody can inhibit growth, but not necessarily kill, VEGF-positive cells.

DNA encoding the Fv clones of the invention can be combined with known DNA sequences encoding heavy chain and/or light chain constant regions to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. In a preferred embodiment, a Fv clone derived from human variable DNA is fused to human constant region DNA to form coding sequence(s) for all human, full or partial length heavy and/or light chains.

Antibody Fragments

The present invention encompasses antibody fragments. The smaller size of the antibody fragments compared to whole antibodies have certain advantages. For example, fragments may allow for more rapid clearance, and may lead to improved access to sites of interest when compared with whole antibodies.

For example, in one embodiment, the antibody fragment is a Fab which comprises a light chain variable domain comprising the amino acid sequence beginning at aspartic acid at position 1 and ending at lysine at position 107 of SEQ ID NO:3 and a heavy chain variable domain comprising the amino acid sequence beginning at glutamic acid at position 1 and ending at serine at position 120 of SEQ ID NO:1.

In another embodiment, the Fab fragment is joined to a Fc region which comprises the amino acid shown in SEQ ID NO:5.

In yet another embodiment, the variant of the antibody is a recombinant protein comprising the antigen-binding region of the antibody of the invention. For example, the variant may be a scFv which comprises the amino acid sequence beginning at aspartic acid at position 241 and ending at serine at position 483 of SEQ ID NO:9. In a further embodiment of the invention, the scFv is joined to a Fc region. Merely by way of example, the scFv joined to a Fc region may comprise the amino acid shown in SEQ ID NO:9.

There are various techniques for the production of antibody fragments. The antibodies or fragments may be produced by recombinant means. For example, these fragments can be produced directly by recombinant host cells. Fab, Fv and ScFv antibody fragments can all be expressed in and secreted from, e.g., *E. coli*, thus allowing the relatively easy production of large amounts of these fragments. Antibody fragments can be isolated from the antibody phage libraries discussed herein. Alternatively, Fab'-SH fragments can be directly recovered from *E. coli* and chemically coupled to form F(ab')$_2$ fragments. According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv.

Synthetic Human Anti-VEGF Antibodies

The invention further provides antibodies (e.g., polyclonal, monoclonal, chimeric, synthetic and humanized antibodies) that bind to VEGF. The most preferred antibodies will selectively bind to VEGF and will not bind (or will bind weakly) to non-VEGF proteins. The most preferred antibodies will specifically bind to VEGF. It is intended that the term "specifically bind" means that the antibody predominantly binds to VEGF. Anti-VEGF antibodies that are particularly contemplated include monoclonal and polyclonal antibodies as well as fragments thereof (e.g., recombinant proteins) containing the antigen binding domain and/or one or more complement determining regions of these antibodies. These antibodies can be from any source, e.g., rat, dog, cat, pig, horse, mouse or human.

In one embodiment, the anti-VEGF antibodies of the invention may be anti-VEGF neutralizing antibodies. In one embodiment, the anti-VEGF antibodies of the invention specifically bind to the VEGF protein and, e.g., inhibits VEGF-induced angiogenesis in vivo. As will be understood by those skilled in the art, the regions or epitopes of a VEGF protein to which an antibody of the invention is directed may vary with the intended application.

For example, antibodies intended for use in an immunoassay for the detection of membrane-bound VEGF on viable cancer cells or ocular cells should be directed to an accessible epitope on membrane-bound VEGF. Different VEGF isoforms may have different potential for cell membrane binding. For example, the larger highly basic VEGF$_{189}$ and VEGF$_{206}$ isoforms (isoforms of VEGF-A$_{121}$) bind tightly to cell-surface heparin-containing proteoglycans in the extracellular matrix (ECM) and hence is found tightly bound to cells; whereas, the acidic VEGF$_{121}$ isoform (VEGF-A$_{121}$) lacks ability to bind heparin and is freely diffusible. VEGF$_{165}$ isoform *VEGF-A$_{165}$) has intermediate properties with a significant fraction bound to heparin and ECM. Examples of such antibodies are described in the Examples which follow. Antibodies that recognize other epitopes may be useful for the identification of VEGF within damaged or dying cells, for the detection of secreted VEGF proteins or fragments thereof.

Anti-VEGF antibodies of the invention may be particularly useful in diagnostic assays, imaging methodologies, treatment of eye disease, treatment of vision impairment, prevention of blindness and therapeutic methods in the management of cancer. The invention provides various immunological assays useful for the detection of VEGF proteins and for the diagnosis of cancer. Such assays generally comprise one or more anti-VEGF antibodies capable of recognizing and binding a VEGF protein, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. Cancer Research 58: 4055-4060 (1998), immunohistochemical analysis and the like.

In one embodiment, anti-VEGF antibodies of the invention and fragments thereof (e.g., Fv, Fab', F(ab')2) and variants thereof (e.g., scFv) are used therapeutically to treat a disease selected from retinal disorder, age-related macular degeneration (AMD), macular degeneration, wet age-related macular degeneration, diabetic retinopathy, diabetic maculopathy, proliferative diabetic retinopathy, macular edema in retinal vein occlusion (RVO), macular edema secondary to Retinal vein Occlusion (RVO), iris neovascularization, retinal neovascularization, choroidal neovascularization caused by pathological myopia, macular edema, retinopathy of prematurity (ROP), retinopathy of maturity, pars plana vitrectomy (PPV), neovascular glaucoma, diabetic macular edema (DME) and eye disease associated with angiogenesis. The anti-VEGF antibodies of the invention and fragments thereof and variants thereof may be used to prevent or stop progression of the forementioned diseases or conditions.

A therapeutically effective amount of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A prophylactically effective amount refers to an amount effective, at dosages and for periods of time necessary, to achieve the desired prophylactic result. Typically but not necessarily, since a prophylactic dose is used in subjects prior to or at an earlier stage of disease, the prophylactically effective amount may be less than the therapeutically effective amount.

In one embodiment, anti-VEGF antibodies of the invention and fragments thereof (e.g., Fv, Fab', F(ab')2) are used for detecting the presence of a cancer. The anti-VEGF antibodies of the invention and fragments thereof may be used to detect the presence of an ocular cell- or endothelial cell-expressing VEGF, -responding to VEGF, or -participating in VEGF-dependent angiogenesis. The presence of such VEGF positive (+) cells within various biological samples, including serum, vitreous humor, eye, prostate and other tissue biopsy specimens, other tissues such as bone, urine, etc., may be detected with VEGF antibodies. In addition, anti-VEGF antibodies may be used in various imaging methodologies, such as immunoscintiography with Indium-111 (or other isotope) conjugated antibody.

Anti-VEGF antibodies may also be used in methods for purifying VEGF proteins and peptides and for isolating VEGF homologues and related molecules. For example, in one embodiment, the method of purifying a VEGF protein comprises incubating an anti-VEGF antibody, which has been coupled to a solid matrix, with a lysate or other solution containing VEGF under conditions which permit the anti-VEGF antibody to bind to VEGF; washing the solid matrix to eliminate impurities; and eluting the VEGF from the coupled antibody. Additionally, anti-VEGF antibodies may be used to isolate VEGF positive cells using cell sorting and purification techniques.

In one embodiment, an isolated human anti-VEGF antibody or portion or variant thereof that specifically recognizes and binds a VEGF comprising a light chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Tables 5a and 5c. In another embodiment, an isolated human anti-VEGF antibody or portion or variant thereof that specifically recognizes and binds a VEGF comprising a heavy chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Tables 5b and 5d.

In one embodiment, an isolated human anti-VEGF antibody or portion or variant thereof that specifically recognizes and binds a VEGF comprising any of the light chain of variant 201, 202, 203, 204, 205, 206, 207, 208, 209, 212, 213, 214, 215, 216, 217, 218, 219, or 220 comprising amino acid sequence as provided in Table 5a or 5c. In another embodiment, an isolated human anti-VEGF antibody or portion or variant thereof that specifically recognizes and binds a VEGF comprising any of the heavy chain of variant 201, 202, 203, 204, 205, 206, 207, 208, 209, 212, 213, 214, 215, 216, 217, 218, 219, or 220 comprising amino acid sequence as provided in Table 5b or 5d.

In one embodiment, an isolated human anti-VEGF antibody or portion or variant thereof that specifically recognizes and binds a VEGF comprising: a light chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Table 5a, and a corresponding heavy chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Table 5b.

In one embodiment, an isolated human anti-VEGF antibody or portion or variant thereof that specifically recognizes and binds a VEGF comprising a light chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Table 5c, and a corresponding heavy chain variable domain comprising the following hypervariable region or complementarity determining region (CDR) amino acid sequences of variant 201, 202, 203, 204, 205, 206, 207, 208, 209, 212, 213, 214, 215, 216, 217, 218, 219, or 220 as shown in Table 5d.

Humanized and Human Antibodies

The present invention encompasses novel humanized anti-VEGF antibodies. Humanized antibodies are chimeric antibodies that contain sequence derived from non-human immunoglobulin. For example, humanized antibodies are human immunoglobulins (recipient antibody) wherein residues from a hypervariable region of a recipient are replaced by residues from a hypervariable region of a non-human species (donor antibody) such as a nonhuman primate, mouse, rat or rabbit having the desired specificity, affinity, and capacity. In some cases, framework region (FR) residues of the human immunoglobulin may be replaced by corresponding non-human residues. Further, humanized antibodies may comprise residues that are not found in the recipient antibody or in the donor antibody in order to further refine antibody performance. The humanized antibody may also comprise at least a portion of an immunoglobulin constant region (Fc), typically that of a human immunoglobulin. Chimeric antibodies may have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Methods for producing fully human anti-VEGF monoclonal antibodies of the invention, include phage display and transgenic methods. For example, fully human anti-VEGF monoclonal antibodies of the invention may be generated using cloning technologies employing large human Ig gene combinatorial libraries (i.e., phage display). Fully human anti-VEGF monoclonal antibodies of the invention may also be produced using transgenic mice engineered to contain a human immunoglobulin gene.

Bispecific Antibodies

Bispecific antibodies are anti-VEGF monoclonal, preferably human or humanized, antibodies of the invention that have binding specificities for at least two different antigens. In the present case, one of the binding specificities is for VEGF and the other is for any other antigen. Exemplary bispecific antibodies may bind to two different epitopes of the VEGF protein.

In one embodiment of the invention, the bispecific antibody has a binding specificity for two different antigens, one of the antigens being that with which the antibody of invention binds. For example, the bispecific antibody may comprises an amino acid sequence comprising the amino acid sequence for CDRH1 (e.g., amino acid position 31 to histidine at amino acid position 35 (SEQ ID NO: 1)) or a portion thereof, CDRH2 (e.g., tyrosine at amino acid position 50 to glycine at amino acid position 66 (SEQ ID NO: 1)) or a portion thereof, CDRH3 (e.g., histidine at amino acid position 99 to tyrosine at amino acid position 109 (SEQ ID NO: 1)) or a portion thereof, CDRL1 (e.g., arginine at amino acid position 24 to alanine at amino acid position 34 (SEQ ID NO: 3)) or a portion thereof, CDRL2 (e.g., lysine at amino acid position 50 to alanine at amino acid position 56 (SEQ ID NO: 3)) or a portion thereof, or CDRL3 (e.g., glutamine at amino acid position 89 to threonine at amino acid position 97 (SEQ ID NO: 3)) or a portion thereof, or a combination thereof.

Bispecific antibodies may also be used to localize cytotoxic agents to cells which express VEGF. These antibodies possess an VEGF-binding arm and an arm which binds the cytotoxic agent (e.g. saporin, anti-interferon-.alpha., vinca alkaloid, ricin A chain, methotrexate or radioactive isotope hapten). Bispecific antibodies can be prepared as full length antibodies or antibody fragments (e.g. F(ab')$_2$ bispecific antibodies). Methods for making bispecific antibodies are known in the art. Antibodies with more than two valencies are contemplated. For example, trispecific antibodies can be prepared.

Antibody Variants

In some embodiments, amino acid sequence modification(s) of the anti-VEGF antibodies described herein are contemplated. Amino acid sequence variants of the antibody may be prepared by, e.g., introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics.

Further, the contemplates Fc region variants that may be obtained by introducing one or more amino acid modifications in an Fc region of the immunoglobulin polypeptides of the invention. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine. In accordance with this description and the teachings of the art, it is contemplated that in some embodiments, an antibody used in methods of the invention may comprise one or more alterations as compared to the wild type counterpart antibody, e.g. in the Fc region.

Nucleic Acids, Vectors, Host Cells and Recombinant Methods

Another aspect of the invention provides various nucleic acid molecules encoding anti-VEGF antibody and fragments thereof, preferably in isolated form, including DNA, RNA, DNA/RNA hybrid, and related molecules, nucleic acid molecules complementary to the anti-VEGF antibody-coding sequence or a part thereof, and those which hybridize to the anti-VEGF antibody-encoding nucleic acids. Particularly preferred nucleic acid molecules will have a nucleotide sequence substantially identical to or complementary to the human or murine DNA sequences herein disclosed. Specifically contemplated are genomic DNA, cDNAs, ribozymes, and antisense molecules, as well as nucleic acids based on an alternative backbone or including alternative bases, whether derived from natural sources or synthesized.

The invention further provides fragments of the anti-VEGF antibody-encoding nucleic acid molecules of the present invention. As used herein, a fragment of an anti-VEGF antibody-encoding nucleic acid molecule refers to a small portion of the entire anti-VEGF antibody-encoding sequence. The size of the fragment will be determined by its intended use.

In one embodiment, the invention provides an isolated nucleic acid encoding an immunoglobulin heavy chain or a portion thereof, an immunoglobulin light chain or a portion thereof, or both, of a specific binding member that binds to human VEGF. In an embodiment of the invention, said specific binding member comprises an antigen-binding portion of an antibody, wherein the immunoglobulin heavy chain or a portion thereof, of the antigen-binding portion of the antibody comprises an immunoglobulin heavy chain CDRH1 comprising the nucleic acid sequence beginning at cytosine at position 91 and ending at cytosine at position 105 (SEQ ID NO: 1) or a portion thereof, an heavy chain CDRH2 comprising the nucleic acid sequence beginning at thymine at position 148 and ending at cytosine at position 198 (SEQ ID NO: 1) or a portion thereof, and an heavy chain CDRH3 comprising the nucleic acid sequence beginning at cytosine at position 295 and ending at cytosine at position 327 (SEQ ID NO: 1) or a portion thereof; and/or wherein the immunoglobulin light chain or portion thereof, of the antigen-binding portion of the antibody comprises a light chain CDRL1 comprising the nucleic acid sequence beginning at cytosine at position 70 and ending at cytosine at position 102 (SEQ ID NO: 3) or a portion thereof, a light chain CDRL2 comprising the nucleic acid sequence beginning at adenine at position 148 to cytosine at position 168 (SEQ ID NO: 3) or a portion thereof, and a light chain CDRL3 comprising the nucleic acid sequence beginning at cytosine at position 265 and ending at guanine at position 291 (SEQ ID NO: 3) or a portion thereof.

For example, a nucleic acid molecule encoding an anti-VEGF antibody of the invention may be considered isolated when the nucleic acid molecule is substantially separated from contaminant nucleic acid molecules that encode polypeptides other than a VEGF antibody. A skilled artisan can readily employ nucleic acid isolation procedures to obtain an isolated VEGF antibody-encoding nucleic acid molecule. While achieving a high degree of purity is desirable, isolated nucleic acid need not be pure or achieve absolute purity in order to be an isolated nucleic acid.

In another embodiment, any of the nucleic acid sequence as provided in (a) or (b) above may be replaced with an equivalent nucleic acid sequence encoding for same amino acid sequence. In yet an additional embodiment, the antibody further comprises a human or humanized constant region. For example, the human or humanized constant region may be an IgG1 constant region. In another example, the human or humanized constant region is an IgG4 constant region.

In one embodiment of the invention, the isolated nucleic acid comprises the sequence shown in SEQ ID NO: 16.

In still another embodiment, the isolated nucleic acid sequence encodes a specific binding member which is a single chain Fv molecule comprising the nucleic acid sequence beginning at guanine at position 721 to thymine at position 1449 as shown in SEQ ID NO: 9 or a portion thereof. In still another additional embodiment, the specific binding member is a Fab comprising the nucleic acid sequences shown in SEQ ID NOS: 1 and 3 or a portion(s) thereof. In a further embodiment, the heavy chain of the antibody comprises a FR amino acid sequence comprising the amino acid sequence beginning at guanine at position 70 to thymine at position 711 as shown in SEQ ID NO: 16 and the nucleic acid sequence beginning at guanine at position 897 to adenine at position 1580 in SEQ ID NO: 16 or a portion(s) thereof. In another embodiment, the specific binding member is a Fab comprising the nucleic acid sequence beginning at adenine at position 1 to thymine at position 711 as shown in SEQ ID NO: 16 and the nucleic acid sequence beginning at adenine at position 828 to adenine at position 1580 in SEQ ID NO: 16 or a portion(s) thereof.

In still another embodiment, the specific binding member is a Fab comprising the nucleic acid sequences shown in SEQ ID NO: 16 or a portion thereof.

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin heavy chain framework region (FR) 1, FRH1, comprising the nucleic acid sequence beginning at guanine at position 1 and ending at thymine at position 90 (SEQ ID NO: 1) encoding an amino acid sequence glutamic acid at amino acid position 1 to phenylalanine at amino acid position 30 (SEQ ID NO: 1).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin heavy chain framework region (FR) 2, FRH2, comprising the nucleic acid sequence beginning at thymine at position 106 and ending at adenine at position 147 (SEQ ID NO: 1) encoding an amino acid sequence tryptophan at amino acid position 36 to alanine at amino acid position 49 (SEQ ID NO: 1).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin heavy chain framework region 3, FRH3, comprising the nucleic acid sequence beginning at cytosine at position 199 and ending at cytosine at position 294 (SEQ ID NO: 1) encoding an amino acid sequence arginine at amino acid position 67 to arginine at amino acid position 98 (SEQ ID NO: 1).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin heavy chain framework region 4, FRH4, comprising the nucleic acid sequence beginning at thymine at position 328 and ending at guanine at position 360 (SEQ ID NO: 1) encoding an amino acid sequence tryptophan at amino acid position 110 to serine at amino acid position 120 (SEQ ID NO: 1).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises a heavy chain framework region FRH1 comprising the nucleic acid sequence beginning at guanine at position 1 and ending at thymine at position 90 (SEQ ID NO: 1) encoding an amino acid sequence glutamic acid at amino acid position 1 to phenylalanine at amino acid position 30 (SEQ ID NO: 1), a heavy chain framework region FRH2 comprising the nucleic acid sequence beginning at thymine at position 106 and ending at adenine at position 147 (SEQ ID NO: 1) encoding an amino acid sequence tryptophan at amino acid position 36 to alanine at amino acid position 49 (SEQ ID NO: 1), a heavy chain framework region FRH3 comprising the nucleic acid sequence beginning at cytosine at position 199 and ending at cytosine at position 294 (SEQ ID NO: 1) encoding an amino acid sequence arginine at amino acid position 67 to arginine at amino acid position 98 (SEQ ID NO: 1), and a heavy chain framework region FRH4 comprising the nucleic acid sequence beginning at thymine at position 328 and ending at guanine at position 360 (SEQ ID NO: 1) encoding an amino acid sequence tryptophan at amino acid position 110 to serine at amino acid position 120 (SEQ ID NO: 1), wherein the nucleic acid sequences encoding the heavy chain framework regions, FRH1 to FRH4, and the heavy chain complementarity determining regions, CDRH1 to CDRH3, are joined in the order FRH1-CDRH1-FRH2-CDRH2-FRH3-CDRH3-FRH4.

In one embodiment, the isolated nucleic acid comprises the nucleic acid sequence for a heavy chain variable region beginning at guanine at position 1 and ending at guanine at position 360 (SEQ ID NO: 1) encoding an amino acid sequence glutamic acid at amino acid position 1 to serine at amino acid position 120 (SEQ ID NO: 1).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin light chain framework region 1, FRL1, comprising the nucleic acid sequence beginning at guanine at position 1 and ending at cytosine at position 69 (SEQ ID NO: 3) encoding an amino acid sequence aspartic acid at amino acid position 1 to cysteine at amino acid position 23 (SEQ ID NO: 3).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin light chain framework region 2, FRL2, comprising the nucleic acid sequence beginning at thymine at position 103 and ending at cytosine at position 147 (SEQ ID NO: 3) encoding an amino acid sequence tryptophan at amino acid position 35 to tyrosine at amino acid position 49 (SEQ ID NO: 3).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin light chain framework region 3, FRL3, comprising the nucleic acid sequence beginning at guanine at position 169 and ending at thymine at position 264 (SEQ ID NO: 3) encoding an amino acid sequence glycine at amino acid position 57 to cysteine at amino acid position 88 (SEQ ID NO: 3).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises an immunoglobulin light chain framework region 4, FRL4, comprising the nucleic acid sequence beginning at thymine at position 292 and ending at adenine at position 321 (SEQ ID NO: 3) encoding an amino acid sequence phenylalanine at amino acid position 98 to lysine at amino acid position 107 (SEQ ID NO: 3).

In an embodiment, the isolated nucleic acid encoding an immunoglobulin heavy chain or a portion thereof, an immunoglobulin light chain or a portion thereof, or both, of a specific binding member that binds to human VEGF, said specific binding member comprising an antigen-binding portion of an antibody additionally comprises a light chain framework region FRL1 comprising the nucleic acid sequence beginning at guanine at position 1 and ending at cytosine at position 69 (SEQ ID NO: 3) encoding an amino acid sequence aspartic acid at amino acid position 1 to cysteine at amino acid position 23 (SEQ ID NO: 3), a light chain framework FRL2 comprising the nucleic acid sequence beginning at thymine at position 103 and ending at cytosine at position 147 (SEQ ID NO: 3) encoding an amino acid sequence tryptophan at amino acid position 35 to tyrosine at amino acid position 49 (SEQ ID NO: 3), a light chain framework FRL3 comprising the nucleic acid sequence beginning at guanine at position 169 and ending at thymine at position 264 (SEQ ID NO: 3) encoding an amino acid sequence glycine at amino acid position 57 to cysteine at amino acid position 88 (SEQ ID NO: 3), a light chain framework FRL4 comprising the nucleic acid sequence beginning at thymine at position 292 and ending at adenine at position 321 (SEQ ID NO: 3) encoding an amino acid sequence phenylalanine at amino acid position 98 to lysine at amino acid position 107 (SEQ ID NO: 3), wherein the nucleic acid sequences encoding the light chain framework regions FRL1 to FRL4 and the light chain complementarity determining regions CDRL1 to CDRL3 are joined in the order FRL1-CDRL1-FRL2-CDRL2-FRL3-CDRL3-FRL4.

In one embodiment, the isolated nucleic acid encoding for each CDR and each FR amino acid sequence is defined by IMGT method are the following: IMGT-defined CDRH1 comprising the nucleic acid sequence beginning at guanine at position 76 and ending at thymine at position 99 (SEQ ID NO: 79); IMGT-defined CDRH2 comprising the nucleic acid sequence beginning at adenine at position 151 and ending at thymine at position 174 (SEQ ID NO: 79); IMGT-defined CDRH3 comprising the nucleic acid sequence beginning at guanine at position 289 and ending at cytosine at position 327 (SEQ ID NO: 79); IMGT-defined CDRL1 comprising the nucleic acid sequence beginning at cytosine at position 79 and ending at cytosine at position 96 (SEQ ID IMGT-defined CDRL2 comprising the nucleic acid sequence beginning at adenine at position 148 and ending at cytosine at position 156 (SEQ ID NO: 77); IMGT-defined CDRL3 comprising the nucleic acid sequence beginning at cytosine at position 265 and ending at guanine at position 291 (SEQ ID NO: 77); IMGT-defined FRH1 comprising the nucleic acid sequence beginning at guanine at position 1 and ending at thymine at position 75 (SEQ ID NO: 79) encoding an amino acid sequence glutamic acid at amino acid position 1 to serine at amino acid position 25 (SEQ ID NO: 79); IMGT-defined FRH2 comprising the nucleic acid sequence beginning at adenine at position 100 and ending at cytosine at position 150 (SEQ ID NO: 79) encoding an amino acid sequence isoleucine at amino acid position 34 to tyrosine at amino acid position 50 (SEQ ID NO: 79); IMGT-defined FRH3 comprising the nucleic acid sequence beginning at thymine at position 175 and ending at thymine at position 288 (SEQ ID NO: 79) encoding an amino acid sequence tyrosine at amino acid position 59 to cysteine at amino acid position 96 (SEQ ID NO: 79); IMGT-defined FRH4 comprising the nucleic acid sequence beginning at thymine at position 328 and ending at guanine at position 360 (SEQ ID NO: 79) encoding an amino acid sequence tryptophan at amino acid position 110 to serine at amino acid position 120 (SEQ ID NO: 79); IMGT-defined FRL1 comprising the nucleic acid sequence beginning at guanine at position 1 and ending at thymine at position 78 (SEQ ID NO: 77) encoding an amino acid sequence aspartic acid at amino acid position 1 to serine at amino acid position 26 (SEQ ID NO: 77); IMGT-defined FRL2 comprising the nucleic acid sequence beginning at guanine at position 97 and ending at cytosine at position 147 (SEQ ID NO: 77) encoding an amino acid sequence valine at amino acid position 33 to tyrosine at amino acid position 49 (SEQ ID NO: 77); IMGT-defined FRL3 comprising the nucleic acid sequence beginning at guanine at position 157 and ending at thymine at position 264 (SEQ ID NO:77) encoding an amino acid sequence glutamic acid at amino acid position 53 to cysteine at amino acid position 88 (SEQ ID NO: 77); and/or IMGT-defined FRL4 comprising the nucleic acid sequence beginning at thymine at position 292 and ending at adenine at position 321 (SEQ ID NO: 77) encoding an amino acid sequence phenylalanine at amino acid position 98 to lysine at amino acid position 107 (SEQ ID NO: 77).

In one embodiment, the isolated nucleic acid comprises the nucleic acid sequence for a light chain variable region beginning at guanine at position 1 and ending at adenine at position 321 (SEQ ID NO: 3) encoding an amino acid sequence aspartic acid at amino acid position 1 to lysine at amino acid position 107 (SEQ ID NO: 3).

In an additional embodiment of the invention, the nucleic acid encodes a specific binding member which is an anti-body.

In yet another embodiment, the heavy chain of the anti-body comprises the FF03046-2 $V_H$ domain from glutamic acid at amino acid position 1 to serine at amino acid position 120 (SEQ ID NO: 1) and a CH1 domain of a human IgG1 constant region from alanine at amino acid position 121 to valine at amino acid position 218 (SEQ ID NO: 1), and wherein the light chain of the antibody comprises the FF03046-2 $V_L$ domain from aspartic acid at amino acid position 1 to lysine at amino acid position 107 (SEQ ID NO: 3) and a human kappa light chain constant region from arginine at amino acid position 108 to cysteine at amino acid position 214 (SEQ ID NO: 3).

In yet another embodiment, the heavy chain of the anti-body comprises the FF03046-2 $V_H$ domain from glutamic acid at amino acid position 1 to serine at amino acid position 120 (SEQ ID NO: 1), a CH1 domain of a human IgG1 constant region from alanine at amino acid position 121 to valine at amino acid position 218 (SEQ ID NO: 1), and a portion of a hinge region of a human IgG1 constant region from glutamic acid at amino acid position 219 to threonine at amino acid position 228 (SEQ ID NO: 1), and wherein the light chain of the antibody comprises the FF03046-2 VL domain from aspartic acid at amino acid position 1 to lysine at amino acid position 107 (SEQ ID NO: 3) and a human kappa light chain constant region from arginine at amino acid position 108 to cysteine at amino acid position 214 (SEQ ID NO: 3).

Also, the invention provides an embodiment wherein the heavy chain of the antibody comprises the FF03046-2 $V_H$ domain from glutamic acid at amino acid position 261 to serine at amino acid position 380 (SEQ ID NO: 16) and a CH1 domain of a human IgG1 constant region from alanine at amino acid position 381 to valine at amino acid position 478 (SEQ ID NO: 16), and wherein the light chain of the antibody comprises the FF03046-2 $V_L$ domain from aspartic acid at amino acid position 24 to lysine at amino acid position 130 (SEQ ID NO: 16) and a human kappa light chain constant region from arginine at amino acid position 131 to cysteine at amino acid position 237 (SEQ ID NO: 16).

The invention provides an embodiment wherein the heavy chain of the antibody comprises the FF03046-2 $V_H$ domain from glutamic acid at amino acid position 261 to serine at amino acid position 380 (SEQ ID NO: 16), a CH1 domain of a human IgG1 constant region from alanine at amino acid position 381 to valine at amino acid position 478 (SEQ ID NO: 16), and a portion of a hinge region of a human IgG1 constant region from glutamic acid at amino acid position 479 threonine at amino acid position 488 (SEQ ID NO: 16), and wherein the light chain of the antibody comprises the FF03046-2 $V_L$ domain from aspartic acid at amino acid position 24 to lysine at amino acid position 130 (SEQ ID NO: 16) and a human kappa light chain constant region from arginine at amino acid position 131 to cysteine at amino acid position 237 (SEQ ID NO: 16).

The invention provides an isolated nucleic acid having a sequence as provided in SEQ ID NO: 16.

In one embodiment, a constitutive promoter is used to the control the expression of the antibody, portion or variant thereof of the invention. In a separate embodiment, a regu-latable or an inducible promoter is use to express the antibody, portion or variant thereof of the invention. In one embodiment, the regulatable or an inducible promoter is a pho A promoter. The invention provide an isolated nucleic acid, wherein the pho A promoter comprises a nucleic acid sequence as provided in SEQ ID NO: 15 or a portion thereof.

The invention provides an isolated nucleic acid sequence, wherein termination of transcription of the nucleic acid is under the control of a transcriptional terminator. In one embodiment, the transcriptional terminator is a ribosomal RNA gene terminator. In one embodiment, the ribosomal RNA gene terminator comprises a nucleic acid sequence as provided in SEQ ID NO: 19 or a portion thereof.

The invention provides an isolated nucleic acid sequence wherein the isolated nucleic acid sequence is in a vector. In one embodiment, the vector comprises an origin of replication. In another embodiment, the vector comprises a colE1 origin of replication.

In one embodiment, the vector comprises a selectable marker or a screening marker. In one embodiment, the selectable marker or screening marker is selected from the group consisting of a drug selectable marker, a fluorescent protein, a cell surface marker, an enzyme, a luminescent protein, a metabolic marker, a growth factor and a resistance factor. In one embodiment, the vector is pBR322 deleted of tetracycline resistance gene as provided in SEQ ID NO: 20.

The invention provides an isolated nucleic acid, wherein the nucleic acid encoding the antibody of the invention does not bind BSA or Fc.

For recombinant production of an antibody of the invention, the nucleic acid encoding it may be isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

The isolated nucleic acid encoding an anti-VEGF antibody of the invention may have a silent mutation or mutations. Additionally, the isolated nucleic acid of the invention may have a missense mutation or mutations, wherein the nucleotide substitution results in a change in the identity of the amino acid but not in a prematurely truncated polypeptide due to the substitution leading to specification of a translation termination codon. The isolated nucleic acid of the invention may have an inframe deletion or insertion, wherein the deletion or insertion occurs as a multiple of 3 bases or basepairs.

Also provided are recombinant DNA molecules (rDNAs) that contain an anti-VEGF antibody-encoding sequences as herein described, or a fragment thereof. As used herein, a rDNA molecule is a DNA molecule that has been subjected to molecular manipulation in vitro. Methods for generating rDNA molecules are well known in the art, for example, see Sambrook et al., *Molecular Cloning* (1989). In the preferred rDNA molecules of the present invention, an anti-VEGF-antibody encoding DNA sequence that encodes an anti-VEGF antibody or a fragment thereof, is operably linked to one or more expression control sequences and/or vector sequences. The rDNA molecule can encode either the entire VEGF antibody, or can encode a fragment of the VEGF antibody.

The choice of vector and/or expression control sequences to which the VEGF antibody-encoding sequence is operably linked depends directly, as is well known in the art, on the functional properties desired. e.g., protein expression, and the host cell to be transformed. A vector contemplated by the present invention is at least capable of directing the replication or insertion into the host chromosome, and preferably also expression, of the VEGF antibody-encoding sequence included in the rDNA molecule.

Expression control elements that are used for regulating the expression of an operably linked protein encoding sequence are known in the art and include, but are not limited to, inducible promoters, constitutive promoters, secretion signals, enhancers, transcription terminators and other regulatory elements. For example, the transcription of the nucleic acid of the invention may be under the control of a ribosomal RNA terminator. In one embodiment, the ribosomal RNA terminator comprises a nucleic acid sequence as provided in SEQ ID NO: 19 or a portion thereof.

In one embodiment, the vector containing an anti-VEGF antibody-encoding nucleic acid molecule will include a prokaryotic replicon, i.e., a DNA sequence having the ability to direct autonomous replication and maintenance of the recombinant DNA molecule intrachromosomally in a prokaryotic host cell, such as a bacterial host cell, transformed therewith. Such replicons are well known in the art. In addition, vectors that include a prokaryotic replicon may also include a gene whose expression confers a detectable or selectable marker such as a drug resistance. Typical bacterial drug resistance genes are those that confer resistance to ampicillin or tetracycline.

Expression vectors compatible with eukaryotic cells, preferably those compatible with vertebrate cells, can also be used to insert an anti-VEGF antibody-encoding sequence and express anti-VEGF antibody of the invention. Eukaryotic cell expression vectors are well known in the art and are available from several commercial sources. Typically, such vectors are provided containing convenient restriction sites for insertion of the desired DNA segment. Such vectors may supply a promoter/enhancer combination for either constitutive or regulatable expression of the anti-VEGF antibody. In addition, such vectors may include a transcription terminator effective in a eukaryotic cell.

Eukaryotic cell expression vectors used to construct the rDNA molecules of the present invention may further include a selectable marker that is effective in an eukaryotic cell, preferably a drug resistance selection marker.

In accordance with the practice of the invention, the vector can be a plasmid, a cosmid, a viral vector or phage vector containing the anti-VEGF antibody-encoding sequences of the invention or a portion thereof. Additionally, the invention anticipates a host-vector system comprising the plasmid, cosmid, viral vector or phage vector transfected into a suitable eukaryotic host cell. Examples of suitable eukaryotic host cells include a yeast cell, a plant cell, or an animal cell, such as a mammalian cell. The host-vector system is useful for the production of an anti-VEGF antibody or portion or variant thereof. Alternatively, the host cell can be prokaryotic, such as a bacterial cell, as provided in the invention.

Many vectors that are available and known in the art can be used for the purpose of the present invention. The vector components generally include, but are not limited to: an origin of replication, a selection marker gene, a promoter, a ribosome binding site (RBS), a signal sequence, the heterologous nucleic acid insert and a transcription termination sequence. For example, the nucleic acid may be expressed under the control of a pho A promoter. In one embodiment, the pho A promoter comprises a nucleic acid sequence as provided in SEQ ID NO: 15 or a portion thereof. Pho A promoter may be induced to transcribe downstream nucleic acid sequences (such as a nucleic acid sequence of the invention) under low phosphate condition (such as a phosphate concentration of below 0.05 mM).

The expression vector of the invention may comprise two or more promoter-cistron pairs, encoding each of the polypeptide components. Alternatively, the expression vector may comprise one promoter with more than one cistron to encode more than one polypeptide component. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

In one embodiment of the invention, an inducible promoter, such as a pho A promoter, is placed upstream and operationally linked to a nucleic acid encoding both immunoglobulin light chain and immunoglobulin heavy chain or portion or variant thereof. Induction of the pho A promoter by low phosphate condition results in transcription of downstream nucleic sequences and production of a RNA transcript, which in the case of a pho A promoter placed upstream and operationally linked to a nucleic acid encoding both immunoglobulin light chain and immunoglobulin heavy chain results in the production of a bicistronic mRNA. In one embodiment, translation of the bicistronic mRNA results in the production of both an immunoglobulin heavy chain and an immunoglobulin light chain, as in the case of Clone #201.

Variant clone #201, comprising Fab 201 coding sequences (SEQ ID NO: 16) and can be used for bacterial expression of Fab 201 (FIG. 17), was deposited on Sep. 5, 2017, with the American Type Culture Collection (ATCC), 10801 University Blvd., Manassas, VA 20110-2209, under the provisions of the Budapest Treaty, and have been accorded ATCC deposit numbers Not Yet Known.

A large number of promoters recognized by a variety of potential host cells are well known. In some embodiments, heterologous promoters are utilized, as they generally permit greater transcription and higher yields of expressed target gene as compared to the native target polypeptide promoter. In addition to naturally occurring promoters from a host cell or non-host cell, viral promoters and artificial promoter are known in the art. In eukaryotic cells (such as yeast, insect or mammalian cells), promoters are used in combination with transcription enhancers.

Transformed Host Cells

The invention further provides host cells transformed with a nucleic acid molecule that encodes an anti-VEGF antibody or a fragment thereof. The host cell can be either prokaryotic or eukaryotic. Eukaryotic cells useful for expression of an anti-VEGF antibody are not limited, so long as the cell line is compatible with cell culture methods and compatible with the propagation of the expression vector and expression of an anti-VEGF antibody gene. Preferred eukaryotic host cells include, but are not limited to, yeast, insect and mammalian cells, preferably vertebrate cells such as those from a mouse, rat, monkey or human cell line. Preferred vertebrate cell lines include, but are not limited to, CHO and HEK293. Most preferred vertebrate cell lines are those approved for the manufacture or production of biologics. The preferred prokaryotic host is either *E. coli*, or *B. subtili*.

Transformation, transfection or transduction of appropriate cell hosts with an rDNA molecule of the present invention is accomplished by well known methods that typically depend on the type of vector used and host system employed. With regard to transformation of prokaryotic host cells, electroporation and salt-heat shock treatment methods are typically employed, see, for example, Cohen et al., *Proc Acad Sci USA* (1972) 69:2110; and Maniatis et al., *Molecular Cloning, A Laboratory Manual*, Cold Spring Harbor Laboratory, Cold Spring Harbor, NY (1982). In addition, prokaryotic host cells may be infected or transduced with a phage comprising a nucleic acid encoding an anti-VEGF antibody of the invention. With regard to transfection of vertebrate cells with vectors containing rDNAs, electroporation, cationic lipid or salt treatment methods are typically employed, see, for example, Graham et al., *Virol* (1973) 52:456; Wigler et al., *Proc Natl Acad Sci USA* (1979) 76:1373-76. In addition, vertebrate cells may be infected or transduced with an eukaryotic viral particle comprising a nucleic acid encoding an anti-VEGF antibody. Such a viral particles may be DNA or RNA viral particles, and may include, but are not limited to, adenoviral, adenovirus-associated viral, retroviral and lentiviral particles.

Successfully transformed, transfected or transduced cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method. Alternatively, sister cells may be analyzed may be analyzed by highly sensitive methods known in the art for the presence of foreign nucleic acid. The transformed, transfected or transduced cells may also be isolated or identified on the basis of markers (either drug selectable markers, imaging markers or detectable markers) present on the same nucleic acid introduced into the cell or on separate nucleic acid co-introduced into the cell.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*). Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus.*

Antibody Production

Various methods for the preparation of antibodies are well known in the art. For example, host cells may be transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells.

Prokaryotic cells used to produce the polypeptides of the invention are grown in media known in the art and suitable for culture of the selected host cells. Examples of suitable media include Luria broth (LB) plus necessary nutrient supplements.

Antibody Purification

Standard protein purification methods known in the art can be employed. The following procedures are exemplary of suitable purification procedures: fractionation on immunoaffinity or ion-exchange columns, SDS-PAGE, ammonium sulfate precipitation, reverse phase HPLC, chromatography on silica or on a cation-exchange resin such as DEAE, and gel filtration using, for example, Sephadex G-75.

Immunoconjugates

The invention also provides immunoconjugates (interchangeably termed "antibody-drug conjugates" or "ADC"), comprising any of the anti-VEGF of the invention (including e.g., a portion or variant thereof described herein) conjugated to a cytotoxic or therapeutic agent such as a chemotherapeutic agent, a drug, a growth inhibitory agent, a toxin (e.g., an enzymatically active toxin of bacterial, fungal, plant, or animal origin, or fragments thereof), or a radioactive agent (i.e., a radioconjugate). For example, the therapeutic agent includes, but is not limited to, an anti-tumor drug, a cytokine, a second antibody, or portion of an antibody (e.g., Fc). Further, the invention provides an embodiment wherein the antibody of the invention is linked to an enzyme that converts a prodrug into a cytotoxic drug. In accordance with the practice of the invention, the portion of the antibody may be selected from the group consisting of scFv, Fv, Fab, Fab', and F(ab')$_2$ fragments.

A growth inhibitory agent refers to a compound or composition which inhibits growth of a cell either in vitro or in vivo. Examples of growth inhibitory agents include agents that block cell cycle progression, such as classical M-phase blockers which include the vincas (vincristine and vinblastine), taxanes, and topoisomerase II inhibitors such as doxorubicin, epirubicin, daunorubicin, etoposide, and bleomycin. Additional suitable agents include, for example, DNA alkylating agents such as tamoxifen, prednisone, dacarbazine, mechlorethamine, cisplatin, methotrexate, 5-fluorouracil, and ara-C.

The antibody or fragment thereof of the invention may be labeled with a detectable marker thereby resulting in an immunoconjugate, e.g., a diagnostic immunoconjugate.

The immunoconjugate can be used for targeting the second molecule to a VEGF positive cell (Vitetta, E. S. et al., 1993, Immunotoxin therapy, in DeVita, Jr., V. T. et al., eds, *Cancer: Principles and Practice of Oncology*, 4th ed., J.B. Lippincott Co., Philadelphia, 2624-2636).

Examples of cytotoxic agents include, but are not limited to ricin, ricin A-chain, doxorubicin, daunorubicin, taxol, ethidium bromide, mitomycin, etoposide, tenoposide, vincristine, vinblastine, colchicine, dihydroxy anthracin dione, actinomycin D, diptheria toxin, *Pseudomonas* exotoxin (PE) A, PE40, abrin, abrin A chain, modeccin A chain, alpha-sarcin, gelonin, mitogellin, restrictocin, phenomycin, enomycin, curicin, crotin, calicheamicin, *Saponaria officinalis* inhibitor, maytansinoids, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer prodrug activating enzyme capable of converting the pro-drug to its active form.

Additionally, the recombinant protein of the invention comprising the antigen-binding region of any of the monoclonal antibodies or recombinant antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin or toxin. Suitable toxins include those described above.

Techniques for conjugating or joining therapeutic agents to antibodies are well known (see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al, (eds.), pp. 475-506 (1985); and Thorpe et al., "The Preparation And Cytotoxic Properties Of Antibody-Toxin Conjugates", *Immunol. Rev.*, 62:119-58 (1982)). The use of VEGF antibodies as therapeutic agents is further described herein.

Methods for Isolating Other Anti-VEGF Antibody-Encoding Nucleic Acid Molecules

The anti-VEGF antibody-encoding nucleic acid molecules described herein enable the isolation of anti-VEGF antibody homologues, alternatively sliced isoforms, allelic variants, and mutant forms of the anti-VEGF antibody of the invention as well as their coding and gene sequences.

For example, a portion of the anti-VEGF antibody-encoding sequence herein described can be synthesized and used as a probe to retrieve DNA encoding a member of the anti-VEGF antibody family of proteins from organisms other than human, allelic variants of the human VEGF protein herein described, and genomic sequence containing the anti-VEGF antibody gene. Oligomers (or oligonucleotides) containing approximately 16-21 nucleotides (encoding about a 5-7 amino acid stretch) may be prepared and used to screen genomic DNA or cDNA libraries to obtain hybridization under stringent conditions or conditions of sufficient stringency to eliminate an undue level of false positives. Oligomers of particular interest are those that encode for the amino acid sequence of the hypervariable region or complementarity determining region (CDR) of the anti-VEGF antibodies of the invention. The oligomers may be prepared from a CDR sequence described herein or a portion of such a CDR sequence. The oligomers may be prepared from recoding an amino acid sequence of a CDR described herein or a portion thereof, such that translation of the oligomer or its complement encodes for a CDR described herein or a portion thereof.

Additionally, pairs of oligonucleotide primers may be prepared for use in a polymerase chain reaction (PCR) to selectively amplify/clone an anti-VEGF antibody-encoding nucleic acid molecule, or fragment thereof. A PCR denature/anneal/extend cycle for using such PCR primers is well known in the art and can readily be adapted for use in isolating other anti-VEGF antibody-encoding nucleic acid molecules.

Non-human homologues of anti-VEGF antibody-encoding sequences, naturally occurring allelic variants of anti-VEGF antibody-encoding sequences and genomic anti-VEGF antibody-encoding sequences will share a high degree of homology to the human anti-VEGF-antibody sequences in CDR portions of the antibody herein described. In general, such nucleic acid molecules will hybridize to the human VEGF sequence under stringent conditions. Such sequences will typically contain at least 70% homology, preferably at least 80%, most preferably at least 90% homology to the human anti-VEGF antibody-encoding sequence.

Stringent conditions are those that (1) employ low ionic strength and high temperature for washing, for example, 0.015M NaCl/0.0015M sodium nitrate/0.1% SDS at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

Other anti-VEGF-antibody-encoding nucleic acid molecules may be obtained through mutagenesis of the CDR-coding region or FR-coding region and characterizing the resulting antibodies for ability to bind VEGF. For the FR-coding region, nucleotides adjacent to the CDR-coding region may be preferred sites of mutagenesis except for those encoding cysteines that participate in intrastrand disulfide bond formation and a conserved tryptophan at the amino terminal end of FRH4, immediately following CDRH3.

Assay for Identifying Competitive Inhibition Antibodies

Another aspect of the invention relates to assays and methods that can be used to detect and identify additional anti-VEGF antibodies that bind to the same or overlapping epitopes to VEGF as recognized and bound by the antibodies of the invention. Specifically, anti-VEGF antibodies and other agents and cellular constituents that bind to VEGF can be identified by the ability of the anti-VEGF antibodies to bind to VEGF and/or the ability to inhibit/stimulate VEGF activity. Assays for VEGF-binding activity may require VEGF protein or its fragment or its peptide are suitable for use in high through-put screening methods.

Alternatively, antibodies immunoreactive with critical position of the VEGF protein (recognized by any of the antibodies of the invention) may be selected from an antibody library, such as a naïve synthetic Fab phage display library. Following initial screening, focused mutagenesis of the CDR sequences may be performed and additional rounds of screening done with limited VEGF protein or portion of VEGF protein to select out improved anti-VEGF antibodies with desirable activity (e.g., high affinity antibodies for VEGF). Additional rounds of mutagenesis and screenings may be performed with the selected Fab sequences present in the selected phages until the desired outcome is reached.

Diagnostic Uses of the Invention

There are multiple diagnostic uses of the invention. For example, the invention provides methods for diagnosing in a subject, e.g., an animal or human subject, macular degeneration or vision impairment or loss (actual or potential) associated with excess production of VEGF in an eye, or cancer associated with the presence of the VEGF protein. In one embodiment, the method comprises quantitatively determining the number of VEGF protein in the sample (e.g., cell or biological fluid sample) using any one or combination of the antibodies of the invention. Then the number so determined can be compared with the amount in a sample from a normal subject. The presence of a measurably different amount (i.e., the number of VEGF in the test sample exceeds the number from a normal sample) in the samples indicating the presence or increased risk of macular degeneration or vision impairment or loss or the presence of the cancer. VEGF is overexpressed by a cell when the number of VEGF in the test sample exceeds the number from a normal sample.

In another embodiment, diagnosis involves quantitatively determining in a sample from the subject the amount of RNA encoding the VEGF protein using the nucleic acid of the invention. The amount so determined can be compared with the amount of RNA in a sample from a normal subject. Once again, the presence of a measurable different amount indicating the presence or increased risk of macular degeneration or vision impairment or loss or the presence of the cancer.

Further, the invention provides a method for diagnosing a neoplastic or preneoplastic condition in a subject. This method comprises obtaining from the subject a sample of a tissue, detecting a difference in the amount and/or distribution of VEGF in the using the method above, a distinct measurable difference being indicative of such neoplastic or pre-neoplastic condition.

In accordance with the practice of the invention, the antibody of the invention can be directed to the epitope to which any of the monoclonal antibodies of the invention is directed. Further, the tissue section can be from the bladder, prostate, bone, lymphatic tissues, pancreas, other organs, or muscle.

Further, the invention provides a method for diagnosing macular degeneration or vision impairment or loss associated with the presence of excess VEGF in an eye of a subject. This method comprises obtaining from the subject a sample of an eye tissue or cell, detecting a difference in the amount of VEGF in the tissue or cell using the method above, a distinct measurable difference being indicative of macular degeneration or vision impairment or loss associated with the presence of excess VEGF in an eye of a subject.

The invention also provides methods of detecting and quantitatively determining the concentration of VEGF in a biological fluid sample. In one embodiment the method comprises contacting a solid support with an excess of one or more monoclonal antibodies of the invention which forms (preferably specifically forms) a complex with VEGF under conditions permitting the monoclonal antibody to attach to the surface of the solid support. The resulting solid support to which the monoclonal antibody is attached is then contacted with a biological fluid sample so that the VEGF in the biological fluid binds to the antibody and forms a VEGF-antibody complex. The complex can be labeled directly or indirectly with a detectable marker. Alternatively, either the VEGF or the antibody can be labeled before formation of the complex. The complex can then be detected and quantitatively determined thereby detecting and quantitatively determining the concentration of VEGF in the biological fluid sample. A high concentration of VEGF in the sample relative to a biological fluid of a normal control being indicative of a neoplastic or preneoplastic condition. Alternatively, a high concentration of VEGF in the sample relative to a biological fluid of a normal control being indicative of presence or increased risk of macular degeneration or visual impairment or loss. In the latter case, the biological fluid is obtained from an eye.

In accordance with the practice of the invention, the biological fluid includes but is not limited to vitreous humor, tissue extract, urine, blood, serum, and phlegm. Further, the detectable marker includes but is not limited to an enzyme, biotin, a fluorophore, a chromophore, a heavy metal, a paramagnetic isotope, or a radioisotope.

Further, the invention provides a diagnostic kit comprising an antibody of the invention that recognizes and binds VEGF (an anti-VEGF antibody); and a conjugate of a detectable label and a specific binding partner of the anti-VEGF antibody. In accordance with the practice of the invention the label includes, but is not limited to, enzymes, radiolabels, chromophores and fluorescers.

Methods for Monitoring the Course of a Disease Associated with VEGF

Additionally, the invention provides methods for monitoring the course of macular degeneration or vision impairment, or cancer (e.g., prostate, bone metastases of prostate cancer, bladder, pancreatic cancer) or disorders associated with VEGF in a subject by measuring the amount of VEGF in a sample from the subject at various points in time. This is done for purposes of determining a change in the amount of VEGF in the sample e.g., to determine whether the change is a small change in the amount or a large change, i.e., overexpression of VEGF. In one embodiment, the method comprises quantitatively determining in a first sample from the subject the presence of a VEGF protein and comparing the amount so determined with the amount present in a second sample from the subject, such samples being taken at different points in time, a difference in the amounts determined being indicative of the course of the macular degeneration or vision impairment or the cancer.

In another embodiment, monitoring is effected by quantitatively determining in a first sample from the subject the presence of a VEGF RNA and comparing the amount so determined with the amount present in a second sample from the subject, such samples being taken at different points in time, a difference in the amounts determined being indicative of the course of the macular degeneration or vision impairment or the cancer (e.g, prostate, bone metastases of prostate cancer, bladder and pancreatic cancer).

The sample can be from an animal or a human. Further, the sample can be a cell sample. For example, using the methods of the invention, organ tissues such as eye tissue or cell, prostate tissue, bladder tissue, pancreatic tissue, neuroendocrine tissue, and bone (any tissue where carcinomas can metastasize, e.g., node, lung, liver, pancreas) can be evaluated for the presence or increased risk of macular degeneration or vision impairment or loss, or the presence of cancer or metastatic lesion. Alternatively, the sample can be a biological fluid, e.g., extracellular fluid of the eye, vitreous humor, urine, blood sera or plasma.

In accordance with the practice of the invention, detection can be effected by immunologic detection means involving histology, blotting, ELISA, and ELIFA. When the sample is a tissue or cell sample it can be formalin-fixed, paraffin-embedded or frozen.

The invention additionally provides methods of determining a difference in the amount and distribution of VEGF in tissue sections from an eye or a neoplastic tissue to be tested relative to the amount and distribution of VEGF in tissue sections from a normal tissue. In one embodiment, the method comprises contacting both the tissue to be tested and the normal tissue with a monoclonal antibody of the invention that specifically forms a complex with VEGF and thereby detecting the difference in the amount and distribution of VEGF.

Cancer Therapy and Therapy of Disorders associated with VEGF such as Macular Degeneration or Eye Disease/Disorder Associated with VEGF The invention provides anti-VEGF antibodies of the invention that may be used, e.g., systemically, to treat diseases associated with VEGF such as Wet Age Related Macular Degeneration, Diabetic Maculopathy, Proliferative Diabetic Retinopathy, Macular edema in Retinal Vein Occlusion (RVO), Iris neovascularization, Choroidal neovascularisation caused by pathological myopia, Retinopathy of Maturity, Neovascular glaucoma and/or cancer.

Antibodies which target the disease cells but not the surrounding non-diseased cells and tissue are preferred. Thus, the invention provides a method of treating a patient susceptible to or having a disease which expresses VEGF antigen, comprising administering to said patient an effective amount of an antibody of the invention which binds specifically to the VEGF protein. In another approach, the invention provides a method of inhibiting the growth of tumor cells expressing VEGF, comprising administering to a patient an antibody which binds specifically to the VEGF in an amount effective to inhibit growth of the tumor cells. VEGF mAbs of the invention may also be used in a method for selectively inhibiting the growth of or killing a cell expressing VEGF antigen comprising reacting a VEGF antibody immunoconjugate or immunotoxin of the invention with the cell in an amount sufficient to inhibit the growth of or kill the cell.

For example, unconjugated anti-VEGF antibody of the invention (including monoclonal, polyclonal, chimeric, humanized, fully human and fragments thereof (e.g., recombinant proteins)) may be introduced into a patient such that the antibody binds to VEGF on disease cells and mediates growth inhibition of such cells (including the destruction thereof), and the tumor, by mechanisms which may include complement-mediated cytolysis, antibody-dependent cellular cytotoxicity, altering the physiologic function of VEGF, and/or the inhibition of ligand binding or signal transduction pathways. In addition to unconjugated anti-VEGF antibodies, fragments thereof, and recombinant proteins of the invention, anti-VEGF antibodies conjugated to toxic agents such as ricin may also be used therapeutically to deliver the toxic agent directly to VEGF-bearing tumor cells and thereby destroy the tumor.

For example, one way to apply monoclonal antibodies of the invention clinically is to administer them in unmodified form, using monoclonal antibodies of the invention which display cell inhibition/killing activity (e.g., ADCC and CDC activity). In one embodiment, to detect ADCC and CDC activity, anti-VEGF antibodies of the invention can be tested for lysing cultured $^{51}$Cr-labeled tumor target cells over a 4-hour incubation period. Target cells may be labeled with $^{51}$Cr and then can be exposed for a few hours (e.g., four hours) to a combination of effector cells (in the form of human lymphocytes purified by the use of a lymphocyte-separation medium) and antibody, which is added in concentrations, e.g., varying between 0.1 μg/ml and 10 μg/ml. The release of $^{51}$Cr from the target cells may be measured as evidence of tumor-cell lysis (cytotoxicity). The total amount of $^{51}$Cr that can be released may be measured and ADCC may be calculated as the percent killing of target cells observed with monoclonal antibody plus effector cells as compared to target cells being incubated alone.

In the practice of the method of the invention, anti-VEGF antibodies capable of inhibiting the growth of diseased cells expressing VEGF on the cell surface are administered in a therapeutically effective amount to patients having a disease as described herein whose diseased cells express or over-express VEGF. The anti-VEGF mAb therapy method of the invention may provide remarkable growth inhibition of diseased cells in vivo. The antibody therapy methods of the invention may be combined with a chemotherapeutic, radiation, and/or other therapeutic regimen.

Patients may be evaluated for the presence and level of VEGF overexpression in diseased cells, preferably using immunohistochemical assessments of diseased tissue, quantitative VEGF imaging, or other techniques capable of reliably indicating the presence and degree of VEGF expression. Immunohistochemical analysis of cell biopsies or surgical specimens may be preferred for this purpose. Methods for immunohistochemical analysis of diseased tissues are well known in the art.

The methods of the invention contemplate the administration of single anti-VEGF antibody of the invention as well as combinations, or "cocktails, of different individual anti-VEGF antibodies such as those recognizing different epitopes. Such mAbs in combination may exhibit synergistic therapeutic effects. In addition, the administration of anti-VEGF mAbs may be combined with other therapeutic agents, including but not limited to various cytotoxic agents. The anti-VEGF mAbs may be administered in their unconjugated form, or may have therapeutic agents conjugated to them.

The anti-VEGF monoclonal antibodies used in the practice of the method of the invention may be formulated into pharmaceutical compositions comprising a carrier suitable for the desired delivery method. Suitable carriers include any material which when combined with the anti-VEGF mAbs retains the anti-disease function of the antibody and is non-reactive with the subject's immune systems. Examples include, but are not limited to, any of a number of standard pharmaceutical carriers such as sterile phosphate buffered saline solutions, and the like.

The present invention provides various methods, local or systemic, for administering the anti-VEGF antibody formulations of the invention to the disease site. As is standard practice in the art, the compositions of the invention may be administered to the subject in any pharmaceutically acceptable form.

Potentially effective routes of administration include, but are not limited to, injections, such as intraocular injections, intravenous, intramuscular, intraperitoneal, oral, inhalation and subcutaneous methods, as well as by implantable pump, continuous infusion, gene therapy, liposomes, suppositories, topical contact, vesicles, capsules, biodegradable polymers, hydrogels, and controlled release patch. The composition of the invention, compounded with a carrier, may be packaged as a sterile solution to be administered directly to a disease site, e.g., an eye.

In accordance with the invention, administering of the compositions of the invention can comprise co-administration, e.g. concomitantly or in sequence, of a therapeutically effective amount of a composition of the invention, with one or more additional compositions of the invention. Administration can also comprise a continuous release (time-release) of the agent(s), for example, the agent(s) can be embedded in a time-release capsule or other continuous release material.

Generally, treatment may involve the administration of the anti-VEGF antibody of the invention by means of an acceptable route of administration at an effective dose. Dosages will depend upon various factors generally appreciated by those of skill in the art, including without limitation the type of disease and the severity, grade, or stage of the disease, the binding affinity and half life of the anti-VEGF antibody of the invention used, the degree of VEGF expression in the patient, the desired steady-state antibody concentration level, frequency of treatment, and, when used, the influence of chemotherapeutic agents used in combination with the treatment method of the invention. Typical daily doses may range from about 0.1 to 100 mg/kg. The primary determining factor in defining the appropriate dose is the amount of a particular antibody necessary to be therapeutically effective in a particular context. Repeated administrations may be required in order to achieve disease inhibition or regression.

Binding affinity generally refers to the strength of the sum total of noncovalent interactions between a single binding site of a molecule (e.g., an antibody) and its binding partner (e.g., an antigen). Affinity can be measured by common methods known in the art, including those described herein. A variety of methods of measuring binding affinity are known in the art, any of which can be used for purposes of the present invention.

Direct administration of VEGF mAbs is also possible and may have advantages in certain contexts. For example, for the treatment of macular degeneration, VEGF antibodies of the invention may be injected directly into the macula area of the eye.

The invention further provides methods for inhibiting cellular activity (e.g., cell proliferation, activation, or propagation) of a cell expressing multiple VEGF antigens on its cell surface. This method comprises reacting the immunoconjugates of the invention (e.g., a heterogeneous or homogenous mixture) with the cell so that the VEGF antigen on the cell surface forms a complex with the immunoconjugate. The greater the number of VEGF antigens on the cell surface, the greater the number of VEGF-antibody complexes form. The greater the number of VEGF-antibody complexes the greater the cellular activity that is inhibited. A subject with a disease, such as a neoplastic or preneoplastic condition, can be treated in accordance with this method when the inhibition of cellular activity results in cell inhibition or death.

The invention further provides methods for inhibiting the biological activity of VEGF by blocking VEGF from binding its receptor or a VEGF partner. The methods comprises contacting an amount of VEGF with an antibody or immunoconjugate of the invention under conditions that permit a VEGF-immunoconjugate or VEGF-antibody complex thereby blocking VEGF from binding its receptor or a VEGF-partner and inhibiting the activity of VEGF.

In another embodiment, the invention provides methods for selectively inhibiting a cell expressing VEGF antigen by reacting any one or a combination of the immunoconjugates of the invention with the cell in an amount sufficient to inhibit the cell. Such amounts include an amount to kill the cell or an amount sufficient to inhibit cell growth or proliferation. As discussed supra the dose and dosage regimen will depend on the nature of the disease or disorder to be treated associated with VEGF, its population, the site to which the antibodies are to be directed, and the patient.

Pharmaceutical Compositions

The present invention provides compositions comprising any of the novel anti-VEGF antibodies of the invention. The phrase "pharmaceutically acceptable carrier" refers to any carrier known to those skilled in the art to be suitable for the particular mode of administration. In addition, the novel anti-VEGF antibodies of the invention may be formulated as the sole pharmaceutically active ingredient in the composition or may be combined with other active ingredients.

The compositions herein may comprise one or more novel anti-VEGF antibodies of the invention. The novel anti-VEGF antibodies of the invention are, in one embodiment, formulated into suitable pharmaceutical preparations such as in sterile solutions or suspensions for parenteral administration.

In the compositions, effective concentrations of one or more novel anti-VEGF antibodies of the invention may be mixed with a suitable pharmaceutical carrier. The amount or concentration of the anti-VEGF antibodies of the invention in the compositions are effective for delivery of an amount, upon administration, that treats, prevents, or ameliorates one or more of the symptoms of diseases or disorders to be treated.

In one embodiment, a therapeutically effective dosage may produce a serum concentration of active ingredient of from about 0.1 ng/ml to about 50-100 µg/mL The pharmaceutical compositions, in another embodiment, may provide a dosage of from about 0.001 mg to about 2000 mg of compound per kilogram of body weight per day. Pharmaceutical dosage unit forms are prepared and may provide from about 0.01 mg, 0.1 mg or 1 mg to about 500 mg, 1000 mg or 2000 mg, and in one embodiment from about 0.5 mg to about 500 mg of the active ingredient or a combination of essential ingredients per dosage unit form.

In one embodiment, the composition comprises an anti-VEGF antibody or portion or variant thereof, polysorbate 20, sucrose, sodium chloride, and a buffer. In one embodiment, the composition comprises a phosphate buffer. In one embodiment, the phosphate buffer has a pH between 5.0 and 6.0. In another embodiment, the composition comprises a buffer (e.g., a histidine buffer). In one embodiment, the histidine buffer has a pH between about 5.0 and 6.5 (preferably at about pH 6.0). In another embodiment, the composition comprises a citrate buffer. In another embodiment, the composition comprises a sodium citrate buffer. In one embodiment, the sodium citrate buffer has a pH between about 5.0 and 6.5 (preferably at about pH 6.0).

In one embodiment, the composition comprises an ani-VEGF antibody or portion or variant thereof at a concentration of about 2 mg/ml to about 100 mg/ml). In one embodiment, the composition comprises polysorbate 20 at a concentration of 0.1% to 0.04%. In one embodiment, the composition comprises sucrose at a concentration of 1% to 20%. In one embodiment, the composition comprises sodium chloride at a concentration of 10 mM to 80 mM. In one embodiment, the composition comprises a phosphate buffer at a concentration of 10 mM to 100 mM. In one embodiment, the composition comprises a histidine buffer at a concentration of 5 mM to 50 mM. In one embodiment, the composition comprises a sodium citrate buffer at a concentration of 5 mM to 20 mM.

In one embodiment, the composition comprises an anti-VEGF antibody or portion or variant thereof at a concentration of about 5 mg/mL 0.03% polysorbate 20, 5% sucrose. 40 mM sodium chloride, and 10 mM phosphate buffer (pH 5.8). In another embodiment, the composition comprises an anti-VEGF antibody or portion or variant thereof at a concentration of about 5 mg/ml, 0.03% polysorbate 20, 5% sucrose, 40 mM sodium chloride, and 10 mM histidine buffer (pH 5.8). In one embodiment, the composition comprises an anti-VEGF antibody or portion or variant thereof at a concentration of about 5 mg/mL 0.03% polysorbate 20, 5% sucrose, 40 mM sodium chloride, and 10 mM sodium citrate buffer (pH 5.0).

The active ingredient or agents (i.e., the novel anti-VEGF antibodies of the invention) may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the active agents, the resulting mixture may be a solution, suspension, emulsion or the like. The form of the resulting mixture depends upon a number of factors, including the intended mode of administration and the solubility of the active agents in the selected carrier or vehicle.

The pharmaceutical compositions are provided for administration to humans and animals in unit dosage forms, such as sterile parenteral solutions or suspensions, and injectable solutions or suspensions containing suitable quantities of the compositions of the invention or active agent. The injectables, solutions and emulsions also contain one or more excipients. Suitable excipients are, for example, polysorbate 20, sucrose, sodium chloride, phosphate buffer, histidine buffer, sodium citrate buffer, water, saline, dextrose, glycerol or ethanol.

Liquid pharmaceutically administrable compositions can, for example, be prepared by dissolving, dispersing, or otherwise mixing an active agent as defined above and optional pharmaceutical adjuvants in a carrier or excipient, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Encompassed within the invention are also lyophilized powders, which can be reconstituted for administration as solutions, emulsions and other mixtures. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined. These solutions, particularly those intended for ophthalmic use, may be formulated as about 0.01% to 10% (vol %) isotonic solutions, pH about 5 to 7, with appropriate salts.

Kits

According to another aspect of the invention, kits are provided. Kits according to the invention include package(s) comprising compositions of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering active agents or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include active agents in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In other embodiments, compounds are provided in an injectable means.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

EXAMPLES

Example 1

Identification and Molecular Characterization of Novel Synthetic Antibodies Directed Against VEGF The overall process involves selection of Fab using phage display technology, selection of clones followed by several rounds of affinity maturation for selection of clones with highest binding affinity. The sequences obtained are cloned in a Pho A-based vector followed by expression in *E. coli*, protein purification and affinity determination. Detailed Protocols are below.

1. Phage Display Technology

Construction of Synthetic phage libraries is based on structural and functional characterization of naturally occurring antibodies, bacteriophage coat protein structure and assembly, bacteriophage biology and host cell biology. Based such knowledge, infective bacteriophages displaying synthetic Fab antibody fragments on the phage surface are produced. For any single Fab phage display library, the synthetic Fab antibody fragment portion of the chimeric Fab-phage coat protein fusion protein may have specific human framework region (FR) or human consensus sequences FR to which complementarity determining region (CDR) loops with various sequences or random sequences may be joined. Since the CDRs plays a critical role in binding to an antigen, the phages are screened against an antigen, such as VEGF, to identify synthetic Fab phages that bind VEGF and hence select out phages with the CDRs that play a role in binding to VEGF. Improvements to VEGF-binding by the selected Fab phages may require directed mutagenesis of the selected CDRs and further rounds of phage selection. Alternatively, directed mutagenesis to the FR sequences may be performed especially for the amino acid residues adjacent to a CDR sequence except for the cysteines that participate in intrastrand disulfide formation and highly conserved amino acids, such as, for example, the invariant tryptophan of heavy chain FR-14 of human IgG1.

Framework region or FR residues are those variable domain residues other than the hypervariable region residues, as herein defined. Since the designation of the hypervariable residues or CDRs sequences can differ between Kabat method or IMGT® method for identifying CDRs, the sequences of the framework regions may be different. In particular, the FR sequences between Kabat nomenclature and IMGT® nomenclature may be identical, overlapping, or contained within one or the other.

An acceptor human framework region (for the CDR sequences) comprises the amino acid sequence of a VL or VH framework region derived from a human immunoglobulin framework region, or from a human consensus framework region. For example, using the Kabat nomenclature, the human framework region sequences of the heavy chain variable region are: FRH1 comprising glutamic acid at amino acid position 1 to phenylalanine at amino acid position (SEQ ID NO: 1), FRH2 comprising tryptophan at amino acid position 36 to alanine at amino acid position 49 (SEQ ID NO: 1), FRH3 comprising arginine at amino acid position 67 to arginine at amino acid position 98 (SEQ ID NO: 1) and FRH4 comprising tryptophan at amino acid position 110 to serine at amino acid position 120 (SEQ ID NO: 1).

An acceptor human framework region derived from a human immunoglobulin framework or human consensus framework may comprise the same amino acid sequence thereof, or may contain amino acid sequence changes. Preferably no more than 5 and preferably 4 or less, or 3 or less, amino acid changes are present or made.

An example, using the Kabat nomenclature, the human framework region sequences of the light chain variable region are: FRL1 comprising aspartic acid at amino acid position 1 to cysteine at amino acid position 23 (SEQ ID NO: 3), FRL2 comprising tryptophan at amino acid position 35 to tyrosine at amino acid position 49 (SEQ ID NO: 3), FRL3 comprising glycine at amino acid position 57 to cysteine at amino acid position 88 (SEQ ID NO: 3) and FRL4 comprising phenylalanine at amino acid position 98 to lysine at amino acid position 107 (SEQ ID NO: 3).

In the case of the framework region sequences identified by the IMGT® method for the same Fab heavy chain sequence (SEQ ID NO: 1), the IMGT®-defined framework region sequences of the heavy chain variable region are: IMGT-defined FRH1 comprising glutamic acid at amino acid position 1 to serine at amino acid position 25 (SEQ ID NO: 1); IMGT-defined FRH2 comprising isoleucine at amino acid position 34 to tyrosine at amino acid position 50 (SEQ ID NO: 1); IMGT-defined FRH3 comprising tyrosine at amino acid position 59 to cysteine at amino acid position 96 (SEQ ID NO: 1), and IMGT-defined FRH4 comprising tryptophan at amino acid position 110 to serine at amino acid position 120 (SEQ ID NO: 1). In the case of the framework region sequences identified by the IMGT® method for the same Fab light chain sequence (SEQ ID NO: 3), the IMGT®-defined framework region sequences of the light chain variable region are: IMGT-defined FRL1 comprising aspartic acid at amino acid position 1 to serine at amino acid position 26 (SEQ ID NO: 3); IMGT-defined FRL2 comprising valine at amino acid position 33 to tyrosine at amino acid position 49 (SEQ ID NO: 3); IMGT-defined FRL3 comprising glutamic acid at amino acid position 53 to cysteine at amino acid position 88 (SEQ ID NO: 3); and IMGT-defined FRL4 comprising phenylalanine at amino acid position 98 to lysine at amino acid position 107 (SEQ ID NO: 3).

In the variable region, the arrangement of the FRs and CDRs are: FRH1-CDRH1-FRH2-CDRH2-FRH3-CDRH3-FRH4 for the heavy chain variable region and FRH1-CDRL1-FRL2-CDRL2-FRL3-CDRL3-FRL4 for the light chain variable region.

The Fab phage display library is constructed in a filamentous phage vector system (such as M13 bacteriophage), a phagemid, which contains a coding sequence for an antibody light chain and a coding sequence for a Fab antibody fragment heavy chain fused to a coat protein. Once the library is constructed, it is transformed into E. coli and the phagemids replicate (using dsDNA origin, such as colE1) and expresses the antibody light chain and the heavy chain-coat protein fusion protein. On co-infection with helper phages (KO7), using the ssDNA origin, phagemids replicate as single stranded DNA packaged into virions decorated with heavy chain-coat fusion protein from the phagemid and wild-type coat protein from the helper phage. The helper phages provide genetic information required for wild-type coat protein synthesis and replication/packaging through the M13/f1 phage origin in the phagemid.

Phagemid virions are extruded from the host cell, and each phage particle displays a unique antibody/Fab whose coding sequences are encapsulated within the phage particle. These phage particles are challenged with VEGF protein, selected for VEGF binding, and amplified by infecting its bacterial host cells, permitting further Fab characterization and isolation of the Fab nucleic acid sequences.

Phagemid clones are further subjected to affinity maturation, which includes further fine tuning amino acid combinations in the antigen binding regions, preparing libraries followed by phage-display library, screening, enrichment and validation. Several rounds of affinity maturations might be essential to come up with clones having desired affinity.

From the billions of Fab pool, few (~100) binders having highest affinity to the desired antigen protein is screened in round one. Further enrichment of the clones is performed in an antigen-guided fashion in subsequent rounds of selection, where from 100, we find best binders having good affinity (~10). Best clones with best affinities (nM) are then sub-cloned into expression vector and expressed to screen out clones with best yield. The clones with good affinity and yield are selected, and based on the application, the affinity has to be further improved to pM range.

The basic vector backbone is same for all the Fab constructs. Change is only in the CDR. There are 3 such CDR regions. L chain—CDR-L1, L2 and L3 and H chain—CDR-H1, 112 and H3. One or a combination of these CDR's are changed to come up with billions of possibilities in the library 2. Cloning of Fab in Pho A-Based Vector A DNA construct of 2140 bp was gene-synthesised, and this construct comprised sequences of phoA promoter, Fab coding sequence of clone #121 (Fab-A5) and rrnB terminator. The construct was cloned into the modified pBR322 vector at the EcoRI/NotI site to generate the clone #121. Clone #121 was subsequently modified by deletion of tet$^R$ resistance gene of 1454 bp size to generate the clone #131.

The DNA sequence of Fab-F8.y corresponding to the amino acid region from 8$^{th}$ to 203$^{rd}$ position was gene-synthesised and this DNA fragment was replaced into the clone #131 using standard cloning techniques, to make the clone #201. It is to be noted that Fab 201 produced from clone #201 is identical in amino acid sequence to Fab FF03046-2 except for a single amino acid change at amino acid 123 in the mature kappa light chain constant region, wherein a glutamic acid in Fab FF03046-2 (see FIG. 9C) is changed to a serine in clone #201 (see FIG. 16). Fab variant #216 derived from clone #201 has the same serine at amino acid 123 of the mature kappa light chain constant region (see FIG. 16), corresponding to amino acid 146 of an unprocessed, translated kappa light chain as provided in e.g. SEQ ID NO:16 or SEQ ID NO:17 with an amino terminal secretory signal extension. It is also noted that an alternative coding sequence for Fab 216 is provided in FIG. 16. Schematic representation of the expression plasmids for anti-VEGF Fab 201 and anti-VEGF Fab 216 are provided in FIGS. 17 and 18.

3. Transformation & Expression of Recombinant Fab

Transformation of recombinant Fab was done in E. coli Dh5α & BL21.

Glycerol Stock Revival

Glycerol vials from −80° C. are thawed in ice for 10 mins. 50 μl Carbenicillin from 100 mg/ml or Ampicillin 100 mg/ml is added to 50 ml of Luria Broth (LB). 7 μl of thawed glycerol stock culture was taken and inoculated in 50 ml LB broth with antibiotic. The culture was grown in incubator shaker for overnight at 37° C. and 210 rpm.

Plasmid Isolation 5 ml of overnight grown culture is taken and the plasmid is isolated using Qiagen QIAprep Spin Miniprep Kit (Catalog Number: 27104).

Competent Cell Preparation:

Bacteria from frozen stock are plated with adequate antibiotic (Carbencillin/Ampicillin). A single colony is picked and cells are grown in LB with antibiotic till the 01) at 600 nm reaches 0.4-0.6. Culture is spin down for 10 min at 4000 g at 4° C. The pellet is resuspended in 1/20 volume of TSB at 4° C. Cells are incubated on ice for 10 min and added 10% sterile glycerol final concentration. Cells are aliquoted in individual tubes (100 ul of cells) and frozen in liquid nitrogen or dry ice. Tubes are stored at −80° C.

Transformation

Diluted DNA is mixed with 10 μl of 1× KCM in 1.5 mL tube. Tube is chilled on ice for 2-5 mins before adding the same volume of competent cells (10 ul). Tube is further incubated on ice for 20 mins, and then incubated at room temperature for 10 mins. 200 ul of Super Optimal Broth with Catabolite Repression (SOC) or LB medium (ThermoFisher) is added and the cells are allowed to recover by shaking at 37° C. for 1 hour. 100-200 ul of above culture is taken, grown on LB agar plate with adequate antibiotic (Carbencillin/Ampicillin) for overnight at 37° C.

Master Cell Bank Preparation from Transformants

Pre-Inoculum is prepared (LB medium pH 7.0, 10 mL+10 μl Carbencillin from 100 mg/ml stocks). The culture is grown overnight at 37° C./210 rpm. 1 mL overnight grown culture is subcultured in 100 mL fresh LB medium (100 mL LB medium, pH 7.0+100 μl Carbencillin from 100 mg/ml stocks). Culture is grown at 37° C./210 rpm till OD$_{600}$ reaches between 0.4 to 0.6. Culture is spun at 4000 rpm under sterile conditions. The pellet is resuspended in 6 ml, sterile LB medium pH 7.0+4 mL, 50% sterile glycerol in the ratio of 60:40 (grown culture:glycerol) under sterile conditions. Multiple glycerol stocks are prepared and stored first at −20° C. and then later transferred to −80° C. The glycerol stocks are revived periodically.

Pre-Inoculum Preparation:

Single colony of freshly transformed 201 in *E. coli* BL21 from LB agar plate was picked. *E. coli* BL21-201 was inoculated in LB broth (10 mL) contains carbenicillin antibiotic (10 μl). The culture was kept in orbital shaker at 37° C. at 210 rpm for 16 hrs. OD of the culture at 600 nm was checked after 16 hrs.

Growth and Induction in Minimal Medium:

500 mL growth and production medium were prepared. The medium pH was adjusted to 7.0. Before inoculation, 500 μL carbenicillin (from 100 mg/mL stocks), 500 μL Thiamine HCL (from 1M sterile stocks), 2.5 mL sterile glucose (from 40% sterile stocks) and 320 μL potassium phosphate (from 1 M $KH_2PO_4$) were added. The growth medium was inoculated with 8% of overnight grown culture (Pre-inoculum). The initial OD (at 600 nm), Glucose concentration and Phosphate concentration of the culture in the Growth medium were checked simultaneously. The culture flask was kept in orbital shaker at 37° C. at 210 rpm till 01) reach in between 2-2.5. The OD (at 600 nm) was checked to estimate glucose concentration and phosphate concentration of the culture in the growth medium. The culture was spun at 4000 rpm, +25° C. for 15 mins. The cell pellet was washed in sterile condition and spun at 4000 rpm for 15 mins. The cell pellet was resuspended in 500 mL production medium with low phosphate concentration (0.064 mM working concentration). The production culture flask was kept at 30° C. at 210 rpm for 20 hrs. Simultaneously, the OD (at 600 nm), WCW, DCW, glucose and phosphate concentration of the culture in the production medium were analyzed. Expressed culture was spun at 4300 g at +4° C. for 30 mins.

Purification of Fab

Process Followed for the Extraction of Protein from 100 ml Culture

Bacterial pellet lysis was carried out using 20 mM phosphate buffer containing 140 mM Sodium chloride and 1 mM phenyl methane sulfonyl fluoride (PMSF). For a 20 g pellet from a 100 ml culture, 4 L of lysis buffer was used. Pellet wash was given using 2 L of lysis buffer wherein the pellet was suspended and centrifuged at 4,300 g for 15 minutes at 4° C. The pellet was then suspended in 2 L of lysis buffer at 4° C. and preheated for 5 minutes at 65° C. water bath. After a short mixing step, Triton X 100 was added in a ratio of 0.1% and mixed for 5 minutes. The suspension was then transferred to water bath maintained at 65° C. for 40 minutes followed by chilling of the lysate on ice.

Clarification of pellet was done by centrifuging the lysate at 4,300 g for 10 minutes and further clarifying the supernatant at 17,000 g for 30 minutes at 4° C. The final supernatant was filtered through 0.45 μm PES membrane filter. The filtrate was purified through Capto L (GE) affinity chromatography, in which fab was eluted with 0.2 M Glycine-HCl buffer containing 2% sucrose at pH 2.0. The eluted fab was immediately neutralized with 1.5 M Tris-Cl buffer of pH 8.8. The neutralized fab was exchanged with 20 mM phosphate buffer of pH 6.0 followed by endotoxin removal through Cellufine ET Clean L resin. Purified fraction was analysed quantitatively by Bradford assay and qualitatively by reducing and non-reducing SDS-PAGE using Silver staining and active protein was analysed using ELISA. The level of endotoxin was analysed using Thermo Scientific Pierce LAL kit.

The BSA standard curve (FIG. 1) for the quantification through Bradford method was done as follows. The BSA samples were serially diluted in order to make concentrations ranging from 50 ug/ml to 500 μg/mL Briefly, for the assay, 10 ul of each standard was mixed with working Bradford reagent, incubated for 5 min at room temperature and absorbance measured at 595 nm in multi-plate reader.

TABLE 1

| Table used for plotting standard curve in FIG. 1 | |
|---|---|
| Conc. BSA ug/ml | OD at 595 |
| 50 | 0.07 |
| 100 | 0.14 |
| 250 | 0.26 |
| 375 | 0.39 |
| 500 | 0.53 |

Yield Quantitation & Activity Determination for Purified Fab

For quantification of yield of Fab from the expressed clones in shake flask & after purification. Standard Curve of Lucentis was prepared & was used for determination of the concentration of Fab in cell lysates and the eluate after column chromatography (protein purification).

Quantitative ELISA Protocol

Buffers were prepared (Wash Buffer (PT), Dilution Buffer (PBT) and Blocking Buffers). VEGF-121 (human VEGF-A121) was used to coat Nunc 96 well MaxiSorp plates at a final concentration of 50 ng/100 ul per well for 2 hrs at PBS with mild shaking. hVEGF was removed from coated plates. 200 ul of blocking buffer was added, and the plate was incubated for 1 hr at RT with mild shaking. Blocking Buffer was removed by dumping on filter paper. Plates were washed 3 times with 200 ul Wash Buffer. From a stock solution of 20 μg/mL Lucentis® (ranibizumab; Novartis and Roche) was diluted to 500 ng/ml in Dilution Buffer. Using the 500 ng/ml of the diluted Lucentis®, a series of serial dilutions of Lucentis was performed to obtain diluted Lucentis® at: 200 ng/mL 100 ng/mL, . . . , 0.39 ng/mL 100 ul of the serially diluted Lucentis® was added to a well in triplicates, and the plate incubated for 1 hr, RT with mild shaking. Solution in the wells of the plates were dumped, and the plates are washed 3× with 200 ul of Wash buffer. 100 ul of anti-kappa light chain antibody-HRP conjugate (1:5000 in Dilution Buffer) was added and incubated for 1 hr at RT. Plates were washed 3× with Wash Buffer and 2× with PBS and dumped on filter paper to remove the buffer completely. 100 ul of TMB substrate was added to each well, and colorimetric reaction was allowed to develop for 5 minutes. 100 ul of 1N sulfuric acid was added to stop the reaction. The plates were read in a Multimode plate Reader at 450 nm. For unknown samples, several dilutions are made and the values are extrapolated using standard curve (FIG. 2 and Table 2).

TABLE 2

| Values used for plotting standard curve (Quantitative ELISA) in FIG. 2 | |
|---|---|
| Conc. ng/ml | OD-450 nm |
| 0 | 0 |
| 0.244 | 0.09 |
| 0.488 | 0.18 |
| 0.976 | 0.38 |
| 1.952 | 0.69 |
| 3.904 | 1.41 |
| 7.808 | 2.75 |

Affinity Assay

The steps in the affinity assay are as follows. Buffers were prepared (Wash Buffer (PBST), Dilution Buffer (PBT), Blocking Buffer and Stop Buffers). Wells of a Nunc 384 well plate were coated with hVEGF in PBS at final concentration of 50 ng/25 ul per well for 2 hrs at 150 rpm, RT. After two hours, hVEGF was removed from the coated plate. 75 ul of blocking buffer was added and incubated for 1 hr at 200 rpm, RT with mild shaking. Blocking Buffer was removed and the plate was washed 6× with 75 ul of PBST and tapped dry on a tissue towel. In the meantime, in a non-stick plate/Eppendorf hVEGF starting conc. 2X (100 nM, 50 nM, 25 nM, 12.5 nM, 6.25 nM . . . ) were prepared in PBT so that final conc of VEGF X is 50 nM, 25 nM. 12.5 nM, 6.25 nM . . . ). 200 pM Lucentis (2X) Fab was prepared in PBT so that final X concentration is 100 pM. 50 ul of 100 pM hVEGF (2X) (100 nM, 50 nM, 25 nM, 12.5 nM, 6.25 nM . . . ) was mixed with 50 ul of 200 pM Lucentis (2×) so that final conc X is (50 nM, 25 nM, 12.5 nM, 6.25 . . . ) and incubated for 1 hr at 200 rpm, RT with mild shaking. Similar steps were followed for Fab molecule also. 25 ul of this serially diluted hVEGF/Fab mixture was added to the plate and incubated for 30 mins at 200 rpm, RT with mild shaking. Primary Antibody not immobilized on the plate was removed and the plate was washed 6× with 75 ul of PBST and tapped dry on a tissue towel. 25 ul anti-kappa light chain IRP (1:5000 in PBT) was added and incubated for 45 mins at 200 rpm, RT with mild shaking. Secondary antibody not immobilized on the plate was removed and the plate was washed 6× with 75 ul of PBST and 2× with PBS in each well and tapped dry on a tissue towel. 25 ul of TMB substrate was added and incubated for 5 mins at 200 rpm, RT with mild shaking. 25 ul 1N sulfuric acid was added to the plate to stop the reaction. Plate was read at 450 nm in Multimode Plate Reader (See FIG. 3 and Table 3).

TABLE 3

| | Fab ID | |
| --- | --- | --- |
| | Ranibizumab | Fab 201 |
| Kd (pM) | 475 ± 36 | 110 ± 14 |

Competitive-ELISA Using hVEGF-165 Quantikine® ELISA Human VEGF Immunoassay Kit (R&D Systems, Inc.)

Briefly, 10 pM of hVEGF-165 was incubated with serial dilutions of anti-VEGF antibody as described in the figure legend. Pre-formed hVEGF-165/anti-VEGF antibody complexes along with any unbound hVEGF-165 in the binding solution are transferred into a 96-well polystyrene microplate coated with a monoclonal antibody specific for human VEGF, as provided in the Quantikine® ELISA Human VEGF Immunoassay (R&D Systems, Inc.; Catalog Number: SVE00). hVEGF-165 bound to the plate is detected using a polyclonal anti-hVEGF antibody conjugated to horseradish peroxidase and tetramethylbenzidine as a chromagen to quantify hVEGF-165 bound to the plate as provided in the Quantikine® assay kit. Kd calculated from the data fitted with a 5 parameter asymmetric model with Prism software.

The following are the coding sequences of Promoter-phoA, Fab-F8.y and Terminator-rrnB.

```
Promoter-phoA
                                       (SEQ ID NO: 15)
GACCAACAGCGGTTGATTGATCAGGTAGAGGGGGCGCTGTACGAGGTAAAGCCCG

ATGCCAGCATTCCTGACGACGATACGGAGCTGCTGCGCGATTACGTAAAGAAGTTA

TTGAAGCATCCTCGTCAGTAAAAAGTTAATCTTTTCAACAGCTGTCATAAAGTTGTC

ACGGCCGAGACTTATAGTCGCTTTGTTTTTATTTTTTAATGTATTTGTAACTAGTACG

CAAGTTCACGTAAAAAGGGTATGTAGAGGTTGAGGTGATTTT

Coding sequence of Fab-F8.y
                                       (SEQ ID NO: 16)
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGGACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAAGAGGGGAGAGTGTTAATACTCGAGGCTGAGCAAA

GCAGACTACTCAATAACATAAAGTCTACGCCGGACGCATCGTGGCCCTAGTACGCAA
```

-continued

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Terminator-rrnB (SEQ ID NO: 19)
CGTTTTACAACGTCGTGACTGGGAAAACATCCATGCGTTAACGCGAGAGTAGGGAA

CTGCCAGGCATCAAATAAAACGAAAGGCTCAGTCGGAAGACTGGGCCTTTCGTTTT

ATCTGTTGTTTGTCGGTGAACGCTCTCCTGAGTAGGACAAATCCGCCGGGAGCGGA

TTTGAACGTTGTGAAGCAACGGCCCGGAGGGTGGCGGGCAGGACGCCCGCCATAA

ACTGCCAGGCATCAAACTAAGCAGAAGGCCATCCTGACGGATGGCCTTTTT

Nucleic acid sequence of pBR322 (GenBank Accession No:
J01749.1) from nucleotide position 1353 to 4361 in which
the tetracycline resistance gene of pBR322 has been deleted
GAATGCGCAAACCAACCCTTGGCAGAACATATCCATCGCGTCCGCCATCTCCAGCA

GCCGCACGCGGCGCATCTCGGGCAGCGTTGGGTCCTGGCCACGGGTGCGCATGATC

GTGCTCCTGTCGTTGAGGACCCGGCTAGGCTGGCGGGGTTGCCTTACTGGTTAGCA

GAATGAATCACCGATACGCGAGCGAACGTGAAGCGACTGCTGCTGCAAAACGTCTG

CGACCTGAGCAACAACATGAATGGTCTTCGGTTTCCGTGTTTCGTAAAGTCTGGAA

ACGCGGAAGTCAGCGCCCTGCACCATTATGTTCCGGATCTGCATCGCAGGATGCTG

CTGGCTACCCTGTGGAACACCTACATCTGTATTAACGAAGCGCTGGCATTGACCCTG

AGTGATTTTTCTCTGGTCCCGCCGCATCCATACCGCCAGTTGTTTACCCTCACAACG

TTCCAGTAACCGGGCATGTTCATCATCAGTAACCCGTATCGTGAGCATCCTCTCTCG

TTTCATCGGTATCATTACCCCCATGAACAGAAATCCCCCTTACACGGAGGCATCAGT

GACCAAACAGGAAAAAACCGCGCTTAACATGGCCCGCTTTATCAGAAGCCAGACAT

TAACGCTTCTGGAGAAACTCAACGAGCTGGACGCGGATGAACAGGCAGACATCTGT

GAATCGCTTCACGACCACGCTGATGAGCTTTACCGCAGCTGCCTCGCGCGTTTCGGT

GATGACGGTGAAAACCTCTGACACATGCAGCTCCCGGAGACGGTCACAGCTTGTCT

GTAAGCGGATGCCGGGAGCAGACAAGCCCGTCAGGGCGCGTCAGCGGGTGTTGGC

GGGTGTCGGGGCGCAGCCATGACCCAGTCACGTAGCGATAGCGGAGTGTATACTGG

CTTAACTATGCGGCATCAGAGCAGATTGTACTGAGAGTGCACCATATGCGGTGTGA

AATACCGCACAGATGCGTAAGGAGAAAATACCGCATCAGGCGCTCTTCCGCTTCCT

-continued

```
CGCTCACTGACTCGCTGCGCTCGGTCGTTCGGCTGCGGCGAGCGGTATCAGCTCACT

CAAAGGCGGTAATACGGTTATCCACAGAATCAGGGGATAACGCAGGAAAGAACAT

GTGAGCAAAAGGCCAGCAAAAGGCCAGGAACCGTAAAAAGGCCGCGTTGCTGGCG

TTTTTCCATAGGCTCCGCCCCCCTGACGAGCATCACAAAAATCGACGCTCAAGTCA

GAGGTGGCGAAACCCGACAGGACTATAAAGATACCAGGCGTTTCCCCCTGGAAGCT

CCCTCGTGCGCTCTCCTGTTCCGACCCTGCCGCTTACCGGATACCTGTCCGCCTTTCT

CCCTTCGGGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGACAGTAT

TTGGTATCTGCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTC

TGACGCTCAGTGGAACGAAAACTCACGTTAAGGGATTTTGGTCATGAGATTATCAA

AAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCT

ATCTCAGCGATCTGTCTATTTCGTECATCCATAGTTGCCTGACTCCCCGTCGTGTAG

ATAACTACGATACGGGAGGGCTTACCATCTGGCCCCAGTGCTGCAATGATACCGCG

AGACCCACGCTCACCGGCTCCAGATTTTATCAGCAATAAACCAGCCAGCCGGAAGGG

CCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCC

ATTGCTGCAGGCATCGTGGTGTCACGCTCGTCGTTTGTATGGCTTCATTCAGCTCC

GGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACT

CATGGTTATGGCAGCACTGCATAATTCTCTTACTGTCATGCCATCCGTAAGATGCTT

TTCTGTGACTGGTGAGTACTCAACCAAGTCATTCTGAGAATAGTGTATGCGGCGAC

CGAGTTGCTCTTGCCCGGCGTCAACACGGGATAATACCGCGCCACATAGCAGAACT

TTAAAAGTGCTCATCATTGGAAAACGTTCTTCGGGGCGAAAACTCTCAAGGATCTT

ACCGCTGTTGAGATCCAGTTCGATGTAACCCACTCGTGCACCCAACTGATCTTCAGC

ATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTT

CAATATTATTGAAGCATTTATCAGGGTTATTGTCTCATGAGCGGATACATATTTGAA

TGTATTTAGAAAAATAAACAAATAGGGGTTCCGCGCACATTTCCCCGAAAAGTGCC

ACCTGACGTCTAAGAAACCATTATTATCATGACATTAACCTATAAAAATAGGCGTA

TCACGAGGCCCTTTCGTCTTCAAGAATTC
```

Example 2

First Generation Anti-VEGF Fab Selection—Naïve Antibody Library Selection and Cross-Species Reactivity and Specificity of Selected Fabs.

The antibody fragment (Fab) phage library F (H. Persson, Et. al., J Mol Biol, vol. 425, no. 4, pp. 803-811, 2013.) was selected against recombinant human vascular endothelial growth factor (hVEGF) 121 from Preprotech (catalog number 100-20A). Fabs were screened for binding to mouse VEGF (mVEGF) from Preprotech (catalog number 450-32) and to hVEGF and for absence of binding to antibody crystallisable fragment (Fc) and to bovine serum albumin (BSA). A total of 7 Fabs were selected, 6 of them (referred as FF0124-1, FF0124-3, FF0124-4, FF0124-5, FF0124-6 and FF0124-7) bind to both hVEGF and mVEGF and not to Fc and BSA. The affinity of these Fabs for hVEGF was estimated by Fab-ELISA (FIG. 4).

Ability of the Fabs to Block hVEGF Binding to hVEGF Receptor, FLT and Affinity Ranking.

FLT is one of VEGF natural receptors. The 6 Fabs bind less hVEGF when preincubated with FLT (FIG. 5), which suggests that the 6 Fabs and FLT have overlapping binding sites on hVEGF, and that they have the potential to inhibit FLT binding to hVEGF. Five Fabs were used as a template to make libraries based on FF0124-1, FF0124-3, FF0124-4, FF0124-6 and FF0124-7 sequences. These libraries were selected for higher affinity for hVEGF.

Second Generation Anti-VEGF Fab Selection—Affinity Maturation of First Generation Anti-VEGF Antibodies.

The next generation libraries were based on Fabs FF0124-1, FF0124-3, FF0124-4, FF0124-6 and FF0124-7. The diversity of each library ranged from $1 \times 10^9$ to $4 \times 10^9$. The five libraries were pooled (total diversity of $10^{10}$) and produced as previously described. The pooled Fab-phage library was then selected, and the sequence of selected clones ranked by their estimated affinity is reported in FIG. 6. Based on the 10 nM single point competition ELISA, Fabs FF0158-C4, FF0158-F11 and FF0158-C11 bind hVEGF with the lowest affinity. These were produced in bacteria as soluble proteins as described previously. Affinities for hVEGF in solution were measured by competitive Fab-ELISA (FIG. 7).

The yield of production of FF0158-C4 and C11 were 5 to 10 times lower than usually observed. To identify which amino acid position is responsible for this drop in production yield, we replaced each one of FF0158-C4 and FF0158-C11 CDR sequences by the CDR sequence of a high yield Fab, an anti-maltose-binding-protein (MBP)-antibody. Both CDR-H1 and CDR-H2 when mutated back to the anti-MBP Fab CDR respective sequences restored yields of FF0158-C4 production to normal level.

Third Generation Anti-VEGF Fab—Affinity Maturation and Yield Improvement of Second Generation Anti-VEGF Antibodies Since the mutation of CDR-H1 or CDR-H2 can improve the production yield of FF0158-C4, we generated two different libraries with diversity focused on CDR-H1 and CDR-H2. The libraries were built from the anti-MBP Fab phagemid with a pTac promoter and an amber stop between the heavy chain and the pIII coding sequence. In this format, Fabs are displayed on phage when expressed in an Amber suppressor bacterial strain and secreted in soluble form when expressed in a non-Amber suppressor bacterial strains. Phage displayed Fabs were selected for affinity, while secreted Fabs were screened for protein yield.

In order to generate Fab displaying phage particles, phage produced after electroporation by SR320 were infected into the amber stop suppressor strain, Omnimax™ (Thermo Fisher Scientific). The library with a $9 \times 10^9$ diversity was selected for binding to hVEGF-121, and clones were screened for production yield improvement in small scale bacterial culture. Interestingly, the two Fabs with the greatest yield improvement (Fabs FF0188-H5/FF01088-B10 and FF0188-F12) carry a phenylalanine to histidine amino acid mutation at the heavy chain CDR-H1 (as defined in the Kabat® numbering). A phenylalanine residue at position 31 (Fab FF0188-A9 and FF0188-A2) does not lead to a large yield improvement (2 and 3 fold improvement, respectively), as shown in FIG. 7. The thermostability is identical for all three Fabs: FF0158-C4, FF0188-F12 and FF0188-H5: 74.5° C.

Fourth Generation Anti-VEGF Fab—Affinity Maturation and Yield Improvement of Third Generation Anti-VEGF Antibodies In order to affinity improve the yield-improved anti-VEGF Fab FF0188-H5, we designed a new library with FF0188-H5 sequence as a template. Stop codons in the diversified CDR were added to the template to limit the number of parental sequence in the two libraries.

The diversity of the library was $6 \times 10^9$. The phage library was amplified in the amber suppressor strain Omnimax™, to be able to produce phage displayed Fabs. The library was then selected against hVEGF-121, and 64 selected clones were screened by single point competitive phage-ELISA. The 20 clones that showed the lowest residual binding after 1 nM hVEGF competition were sequenced and characterized (FIG. 8 shows the sequence and further characterization of the 9 unique clones). FF0117-A5 has a 5.4 mg per liter yield, an affinity of 80+/−40 pM for hVEGF, a Tm of 77° C. FF0117-A5 is superior to ranibizumab in terms of affinity and thermal stability: the affinity of FF0117-A5 in competitive Fab-ELISA is 4 to 15 times higher than ranibizumab and the Tm of FF0117-A5 is 3.5° C. higher.

Fifth Generation Anti-VEGF Fab—Affinity Maturation of Fourth Generation Anti-VEGF Antibodies In order to further affinity improve anti-VEGF Fab FF0117-A5, we designed a new library with FF0117-A5 sequence as a template: FF0117-A5 was mutagenized to introduce stop codons in CDR-L1 and CDR-L2, and to modify the sequence coding for the C-terminal end of the HC of the Fab, to allow monovalent display instead of bivalent display. The library diversity is $6 \times 10^9$. $10^{10}$ phage particles were used to infect 500 mL of the amber-suppressor strain Omnimax™ culture to make Fab display phage particles.

Library FF01159-1 was selected, and Fab-phage clones that showed binding to hVEGF were sequenced and produced as soluble Fabs (FIG. 9). Since library FF01159-1 was designed with a deletion of one residue near the end of CDR-L2 (Kabat), the selected Fabs FF03033-4 and FF03033-8 were mutagenized to reintroduce previously deleted tyrosine residue back at the deleted position. The resulting Fabs are named FF03046-1 and FF03046-2. Fab FF03046-2 CDR sequence, thermal stability, production yield and binding affinity for hVEGF are shown in FIG. 9. The ability of FF03046-2 Fab to block hVEGF-dependent human vascular endothelium cells (HUVEC) proliferation is reported in FIG. 10. 260 pM of hVEGF-165 was used in the HUVEC proliferation assay. The EC50 of FF03046-2 (200 pM+/−10 pM) is below the concentration of hVEGF-165 used in the assay, meaning that the EC550 of FF03046-2 could actually be underestimated by this HUVEC assay. The affinity of FF03046-2 Fab for hVEGF was also measured in solution. hVEGF-165 was used and detected with a Quantikine assay. This allowed us to lower the working concentration of hVEGF to 5 pM (FIG. 11). In this assay, the affinity of FF03046-2 for hVEGF-165 is well below Ranibizumab. (90 pM+/−20 pM versus 390 pM+/−50 pM).

C-Terminal Fc Fusion of Anti-VEGF scFv and Fab.

We have then fused the scFv or Fab version of FF03046-2 onto the C-terminus of a human Fc. We expect the fusion proteins to have slower clearance, higher affinity because of their ability to clamp a single molecule of VEGF with each one of the Fab/scFv fused to the C-terminal of the Fc. This facilitates the generation of multispecific entities, as the N-terminus of the Fc can be fused with a scFv or Fab to bind other proteins of interest.

The sequence of the Fab and scFv Fc fusions are shown in FIGS. 12 and 13, respectively. The affinities of the Fab and scFv fusions for hVEGF-165 in comparison with other anti-VEGF proteins are shown in FIG. 14. The affinity of FF03077-4 and FF03092-1 for hVEGF is similar to the one of the Fab FF03046-2. The sequence of the full length IgG version of Fab FF0346-2 (FF03092-3) is shown in FIG. 15.

Taken together, FF03092-1, FF03077-4, and FF03046-2 are three different anti-VEGF entities that could have different pharmacokinetic profiles that could translate into different efficacy in vivo. In order to further improve the solubility and yield of production of FF03046-2, several variants (e.g., sequences shown in Example 3) were designed to be tested for production yield, solubility and hVEGF binding affinity.

Example 3

```
SEQUENCE OF Y VARIANTS
Variant 201
                                        (SEQ ID NO: 21)
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTGAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTGACGTAAAAAGGGTAACTAGAGGTTGAGGTGATTTTATGAAAAAGAATATCGC

ATTTCTTCTTGCATCTTATGTTCGTTTTTTCTATTGCTACAAACGCGTACGCTGAGGTT

CAGCTGGTGGAGTCTGGCGGTGGCCTGGTGCAGCCAGGGGGCTCACTCCCTTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCACCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTTGAATCACAAGCCC

AGCAACACCAAGGTCGACAAGAAAGTTGAGCCCAAATCTTGTGACAAAACTCACA

CATAA

Variant 202
                                        (SEQ ID NO: 22)
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC
```

-continued

```
TGGTATCAACAGAAACCAGGAAAAGCTCCGAAGCTTCTGATTTACAAAGCATCCGA

ACTCGACGCCGGAGTCCCTTCTCGCTTCTCTGGTAGCCGTTCCGGGACGGATTTCAC

TCTGACCATCAGCAGTCTCCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATGTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCGATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGCACAAAACTCACA

CATAA
```

Variant 203
                                                    (SEQ ID NO: 23)
```
ATGAAAAAGAATATCGCATTTCTTCTTGCATTCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

TCTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGTCCTCTTGTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA
```

-continued

```
GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTYTTTCTATTGCTACAAACGCGTACGCTGAGGTT

CAGCTGGTGGAGTCTGGCCTGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCCTTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCCTTGGAACTCAGGCCTCCCTGACCAGCGGCGTGCACA

CCTTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA
```

Variant 204

(SEQ ID NO: 24)

```
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCAGACGA

ACTCTACGCCCTGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT
```

-continued

CCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGGAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Variant 205

(SEQ ID NO: 25)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGATTCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Variant 206

(SEQ ID NO: 26)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACGATGCATCCGA

-continued

```
ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGaiCACAGCGGCCCTGGGCTGCCTGGTCAAGGACTACTT

CCCCGAACCGGTGACCTGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA
```

Variant 207

(SEQ ID NO: 27)
```
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTCCAGTCAGGCCGCCTACGGCCGCGTAGCC

TGGTATCAACAGAAACCAGGAAAAGCTCCGAAGCTTCTGATTGACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGAGAGCACCTACAGCCTCAGCAGCACCCTGACGCTGAGCAAAGCA

GACTACGAAAAACATAAAGTCTACGCCTGCGAACTTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC
```

-continued

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCACACCTACATCTGCAACGTGAATCACAAGCCC

AGCAACACCAAGGTCGACAAGAAAGTTGAGCCCAAATCTTGTGACAAAACTCACA

CATAA

Variant 208

(SEQ ID NO: 28)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCGATGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

-continued

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Variant 209

(SEQ ID NO: 29)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGATGCCGCCTACGGCCGCGTA

GCCTGGTATCAACAGAAACCAGGAAAAGCTCCGAAGCTTCTGATTTACAAAGCATC

CGAACTCTACGCCGGAGTCCCTTCTCGCTTCTCTGGTAGCCGTTCCGGGACGGATTT

CACTCTGACCATCAGCAGTCTGCAGCCGGAAGACTTCGCAACTTATTACTGTCAGC

AACGTGGCTGGTATCTGTTCACGTTCGGACAGGGTACCAAGGTGGAGATCAAACGA

AGTGTGGCTGCACCATCTGTCTTCATCTTCCCGCCATCTGATTCACAGTTGAAATCT

GGAACTGCCTCTTGTTGTCTGCCTGCTGAATAACTTCTATCCCAGAGAGGCCAAAGT

ACAGTGGAAGGTGGATAACGCCCTCCAATCGGGTAACTCCCAGGAGAGTGTCACAG

AGCAGGACAGCAAGGACAGCACCTACAGCCTCAGCAGCACCCTGACGCTGAGCAA

AGCAGACTACGAAAAACATAAAGTCTACGCCTGCGAAGTCACCCATCAGGGCCTGA

GCTCGCCCGTCACAAAGAGCTTCAACAGGGGAGAGTGTTAATACTCGAGGCTGAGC

AAAGCAGACTACTAATAACATAAAGTCTACGCCGGACGCATCGTGGCCCTAGTACG

CAAGTTCACGTAAAAAGGGTAACTAGAGGTTGAGGTGATTTTATGAAAAAGAATAT

CGCATTTCTTCTTGCATCTATGTTCGTTTTTTCTATTGCTACAAACGCGTACGCTGAG

GTTCAGCTGGTGGAGTCTGGCGGTGGCCTGGTGCAGCCAGGGGGCTCACTCCGTTT

GTCCTGTGCAGCTTCTGGCTTCGATTTATTTCATTATTCTATACACTGGGTGCGTCAG

GCCCCGGGTAAGGGCCTGGAATGGGTTGCATACATTTACCCGTCTTATGGCTATACT

TATTATGCCGATAGCGTCAAGGGCCGTTTCACTATAAGCGCAGACACATCCAAAAA

CACAGCCTACCTACAAATGAACAGCTTAAGAGCTGAGGACACTGCCGTCTATTATT

GTGCTCGCCATGCGTGGTATTATGGGTGGGGTTTGGACTACTGGGGTCAAGGAACC

CTGGTCACCGTCTCCTCGGCCTCCACCAAGGGTCCATCGGTCTTCCCCCTGGCACCC

TCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGC

ACACCTTCCCGGCTGTCCTACAGTCCTCAGGACTCTACTCCCTCAGCAGCGTGGTGA

CCGTGCCCTCCAGCAGCTTGGGCACCCAGACCTACATCTGCAACGTGAATCACAAG

CCCAGCAACACCAAGGTCGACAAGAAAGTTGAGCCCAAATCTTGTGACAAAACTCA

CACATAA

Variant 212

(SEQ ID NO: 30)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCCTCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGCAAGACTTCGCAACTTATTACTGTCAGCAAC

-continued

GTGGCTGGTATCTGTTCACGTTCGGACAGGGTACCAAGGTGGAGATCAAACCTAACT

GTGGCTGCACCATCTGTCTTCATCTTCCCGCCATCTGATTCACAGTTGAAATCTGGA

ACTGCCTCTGTTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGACTCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATAGACTGGGTGCGTCAGGC

CCCGGGTAAGGCCTGGAATGGGTTGCATACATTTACCCCTTCTTATGGCTATACTTA

TTATGCCGATAGCGTCAAGGGCCGTTTCACTATAAGCGCAGACACATCCAAAAACA

CAGCCTACCTACAAATGAACAGCTTAACTAGCTGAGGACACTGCCGTCTATTATTGT

GCTCGCCATGCGTGGTATTATGGGTGGGGTTTGGACTACTGGGGTCAAGGAACCCT

GGTCACCGTCTCCTCGGCCTCCACCAAGGGTCCATCGGTCTTCCCCCTGGCACCCTC

CTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCC

CAGCAACACCAAGGTCGACAAGAAAGTTGAGCCCAAATCTTGTGACAAAACTCAC

ACATAA

Variant 213

(SEQ ID NO: 31)
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCCTGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

-continued
```
CAGCTGGTGGAGTCTGGCGGTGGCCTGGTGCAGCCAGGGGGCTCACTCCGTTTGTC

CTGTGCAGGTTCTGGCTTCGATTTATTTCATTATGATATACACTGGGTGCGTCAGGC

CCCGGGTAAGGGCCTGGAATGGGTTGCATACATTTACCCGTCTTATGGCTATACTTA

TTATGCCGATAGCGTCAAGGGCCGTTTCACTATAAGCGCAGACACATCCAAAAACA

CAGCCTACCTACAAATGAACAGCTTAAGAGCTGAGGACACTGCCGTCTATTATTGT

GCTCGCCATGCGTGGTATTATGGGTGGGGTTTGGACTACTGGGGTCAAGGAACCCT

GGTCACCGTCTCCTCGGCCTCCACCAAGGGTCCATCGGTCTTCCCCCTGGCACCCTC

CTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCC

CAGCAACACCAAGGTCGACAAGAAAGTTGAGCCCAAATCTTGTGACAAAACTCAC

ACATAA
```

Variant 214
```
                                              (SEQ ID NO: 32)
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATGATTCTATACACTGGGTGCGTCAGGC

CCCGGGTAAGGGCCTGGAATGGGTTGCATACATTTTACCCGTCTTATGGCTATACTTA

TTATGCCGATAGCGTCAAGGGCCGTTTCACTATAAGCGCAGACACATCCAAAAACA

CAGCCTACCTACAAATGAACAGCTTAAGAGCTGAGGACACTGCCGTCTATTATTGT

GCTCGCCATGCGTGGTATTATGGGTGGGGTTTGGACTACTGGGGTCAAGGAACCCT

GGTCACCGTCTCCTCGGCCTCCACCAAGGGTCCATCGGTCTTCCCCCTGGCACCCTC

CTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACC
```

-continued

```
GTGCCCTCCAGCAGCTTGGGCACCGAGACCTACATCTGCAACGTGAATCACAAGCC

CAGCAACACCAAGGTCGACAAGAAAGTTGAGCCCAAATCTTGTGACAAAACTCAC

ACATAA
```

Variant 215

(SEQ ID NO: 33)
```
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCACTTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTGATTATTCTATACACTGGGTGCGTCAGGC

CCCGGGTAAGGGCCTGGAATGGGTTGCATACATTTACCCGTCTTATGGCTATACTTA

TTATGCCGATAGCGTCAAGGGCCGTTTCACTATAAGCGCAGACACATCCAAAAACA

CAGCCTACCTACAAATGAACAGCTTAAGAGCTGAGGACACTGCCGTCTATTATTGT

GCTCGCCATGCGTGGTATTATGGGTGGGGTTTGGACTACTGGGGTCAAGGAACCCT

GGTCACCGTCTCCTCGGCCTCCACCAAGGGTCCATCGGTCTTCCCCCTGGCACCCTC

CTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCC

CAGCAACACCAAGGTCGACAAGAAAGTTGAGCCCAAATCTTGTGACAAAACTCAC

ACATAA
```

Variant 216

(SEQ ID NO: 34)
```
ATGAAAAAGAATATCGCATTTCTTCTTGCATCTATGTTCGTTTTTTCTATTGCTACAA

ATGCCTATGCAGATATGCAGATGACCCAGTCCCCGAGCTCCCTGTCCGCCTCTGTGG

GCGATAGGGTCACCATCACCTGCCGTGCCAGTCAGGCCGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT
```

-continued

```
GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTAGATCATTATTCTATACACTGGGTGCGTCAGGC

CCCGGGTAAGGGCCTGGAATGGGTTGCATACATTTACCCGTCTTATGGCTATACTTA

TTATGCCGATAGCGTCAAGGGCCGTTTCACTATAAGCGCAGACACATCCAAAAACA

CAGCCTACCTACAAATGAACAGCTTAAGAGCTGAGGACACTGCCGTCTATTATTGT

GCTCGCCATGCGTGGTATTATGGGTGGGGTTTGGACTACTGGGGTCAAGGAACCCT

GGTCACCGTCTCCTCGGCCTCCACCAAGGGTCCATCGGTCTTCCCCCTGGCACCCTC

CTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCC

CAGCAACACCAAGGTCGACAAGAAAGTTGAGCCCAAATCTTGTGACAAAACTCAC

ACATAA
```

Variant 217

(SEQ ID NO: 35)
```
ATGAAAAAGAATATCGCATTTCTTCTTGCATGTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGACGCCTACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTGTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC
```

-continued

```
CTGTGCAGCTTCTGGCTTCGATTTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAACTGGCCGTTTCACTATAAGCGCACTACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGCKTGTCAAGGAACCCTG

GTCACCGTCTCCTCGGCCTCCACCAAGGGTCCATCGGTCTTCCCCCTGGCACCCTCC

TCCAAGAGCACCTCTCTGGGGCACAGCGGCCCTGGGCTGCCTGGTCAAGGAATACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA
```

Variant 218

(SEQ ID NO: 36)

```
ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCGACGGCCGCGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTVTTGCATCTATGTTCGTTTTTTCTATTGCTACAAACGCGTACGCTGAGGTT

CAGCTGGTGGAGTCTGGCGGTGGCCTGGTGCAGCCAGGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCCTTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG
```

-continued

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Variant 219

(SEQ ID NO: 37)

ATGAAAAAGAATATCGCATTTCTTCTTGCATCTATGTTCGTTTTTTCTATTGCTACAA

ATGCCTATGGAGATATCCAGATGACCCAGTCCCCGAGCTCCCTGTCCGCCTCTGTGG

GCGATAGGGTCACCATCACCTGCCGTGCCAGTCAGGCCGCCTACGACCGCGTAGCC

TGGTATCAACAGAAACCAGGAAAAGCTCCGAAGCTTGTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

GTGGCTGCACCATCTGTCTTCATCTTCCCGCCATCTGATTCACAGTTCTAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGGGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTCTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACTCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA

Variant 220

(SEQ ID NO: 38)

ATGAAAAAGAATATCGCATTTCTTCTTGCATCTATGTTCGTTTTTTCTATTGCTACAA

ATGCCTATGCAGATATCCAGATGACCCAGTCCCCGAGCTCCCTGTCCGCCTCTGTGG

GCGATAGGGTCACCATCACCTGCCGTGCCAGTCAGGCCGCCTACGGCGACGTAGCC

TGGTATCAACAGAAACCAGGAAAAGCTCCGAAGCTTCTGATTTACAAAGCATCCGA

ACTCTACGCCGGAGTCCCTTCTCGCTTCTCTGGTAGCCGTTCCGGGACGGATTTCAC

TCTGACCATCAGCAGTCTGCAGCCGGAAGACTTCGCAACTTATTACTGTCAGCAAC

GTGGCTGGTATCTGTTCACGTTCGGACAGGGTACCAAGGTGGAGATCAAACGAACT

-continued

```
GTGGCTGCACCATCTGTCTTCATCTTCCCGCCATCTGATTCACAGTTGAAATCTGGA

ACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCA

GGACAGCAAGGACAGCACCTACAGCCTCAGCAGCACCCTGACGCTGAGCAAAGCA

GACTACGAAAAACATAAAGTCTACGCCTGCGAAGTCACCCATCAGGGCCTGAGCTC

GCCCGTCACAAAGAGCTTCAACAGQGGAGAGTGTTAATACTCGAGGCTGAGCAAA

GCAGACTACTAATAACATAAAGTCTACGCCGGACGCATCGTGGCCCTAGTACGCAA

GTTCACGTAAAAAGGGTAACTAGAGGTTGAGGTGATTTTATGAAAAAGAATATCGC

ATTTCTTCTTGCATCTATGTTCGTTTTTTCTATTGCTACAAACGCGTACGCTGAGGTT

CAGCTGGTGGAGTCTGGCGGTGGCCTGGTGCAGCCAGGGGGCTCACTCCGTTTGTC

CTGTGCAGCTTCTGGCTTCGATTTATTTCATTATTCTATACACTGGGTGCGTCAGGCC

CCGGGTAAGGGCCTGGAATGGGTTGCATACATTTACCCGTCTTATGGCTATACTTAT

TATGCCGATAGCGTCAAGGGCCGTTTCACTATAAGCGCAGACACATCCAAAAACAC

AGCCTACCTACAAATGAACAGCTTAAGAGCTGAGGACACTGCCGTCTATTATTGTG

CTCGCCATGCGTGGTATTATGGGTGGGGTTTGGACTACTGGGGTCAAGGAACCCTG

GTCACCGTGTCCTCGGCCTCCACCAAGGGTCCATCGGTCTTCCCCCTGGCACCCTCC

TCCAAGAGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCGTGCACA

CCTTCCCGGCTGTCCTACAGTCCTCAGGACCCTACTCCCTCAGCAGCGTGGTGACCG

TGCCCTCCAGCAGCTTGGGCACCCAGACCTACATCTGCAACGTGAATCACAAGCCC

AGCAACACCAAGGTCGACAAGAAAGTTGAGCCCAAATCTTGTGACAAAACTCACA

CATAA
```

Immunoglobulin light chain and heavy chain fragments encoded by the nucleic acid sequences of the Y variants above are shown in FIGS. 4, 6-9, and 12-16 along with the CDRs as defined by Kabat or IMGT® nomenclatures.

The Fab variants based on the Fab produced by Clone #201 showed a variety of binding affinities for VEGF-165 as shown below in Table 4. Two of the variants (S1. No. 3 and 9) showed a higher affinity for human VEGF-165 isoform than the starting Fab of Clone #201, indicating that further improvement in the Kd of the Fab for VEGF may be obtained, as these two variants have Kd values of about 12 pM and 14 pM.

Fab variant 216 derived from mutagenesis of Clone #201 has a single amino acid change from a phenylalanine to an aspartic acid residue in the heavy chain CDR1 sequence (as defined by IMGT® method) such that GFDLFHYS (SEQ ID NO: 156), CDR-H1 of Fab 201 from Clone #201, is GFDLDHYS (SEQ ID NO: 152), CDR-H1 of Fab variant 216. As shown in FIGS. 19 and 20 and Table 4, presence of the phenylalanine to aspartic acid change in Fab 216 reduces its binding affinity for VEGF slightly, compared to the parental Fab 201 (Kd of approximately 35±4 pM for Fab 216 versus 25±2 pM for Fab 201; see Table 4), but like Fab 201, the dissociation constant Kd of Fab 216 is about 5-16× less than the Kd of Lucentis (see FIGS. 19 and 20).

TABLE 4

| Kd VALUES OF CLONE #201 VARIANTS Quantikine kit(VEGF-165)-10 pM VEGF | |
| --- | --- |
| Y variants | Kd(pM) |
| 201 | 25 ± 2 |
| 205 | 62 |
| 206 | 14 |
| 209 | 28 |
| 212 | 1276 |
| 213 | 91 |
| 215 | 27 |
| 216 | 35 ± 4 |
| 219 | 12 |
| 220 | 26 |
| Lucentis | 591 ± 60 |

The Sequence Alignment for the Y Variants are Shown
Below in Tables 5a-d.

TABLE 5a

Multiple sequence alignment for light chain of variants 201-220
as indicated in right-hand column (CDR sequences
defined in accordance with IMGT ® are underlined)

```
201   MKKNIAFLLASMFVFSIATNAYADIQMTQSPSSLSASVGDRVTITCRASQ-AAYGRVAWY    59
202   MKKNIAFLLASMFVFSIATNAYADIQMTQSPSSLSASVGDRVTITCRASQ-AAYGRVAWY    59
203   MKKNIAFLLASMFVFSIATNAYADIQMTQSPSSLSASVGDRVTITCRASQ-AAYGRVAWY    59
204   MKKNIAFLLASMFVFSIATNAYADIQMTQSPSSLSASVGDRVTITCRASQ-AAYGRVAWY    59
205   MKKNIAFLLASMFVFSIATNAYADIQMTQSPSSLSASVGDRVTITCRASQ-AAYGRVAWY    59
206   MKKNIAFLLASMFVFSIATNAYADIQMTQSPSSLSASVGDRVTITCRASQ-AAYGRVAWY    59
207   MKKNIAFLLASMFVFSIATNAYADIQMTQSPSSLSASVGDRVTITCRASQ-AAYGRVAWY    59
208   MKKNIAFLLASMFVFSIATNAYADIQMTQSPSSLSASVGDRVTITCRASQ-AAYGRVAWY    59
209   MKKNIAFLLASMFVFSIATNAYADIQMTQSPSSLSASVGDRVTITCRASQDAAYGRVAWY    60
212   MKKNIAFLLASMFVFSIATNAYADIQMTQSPSSLSASVGDRVTITCRASQ-AAYGRVAWY    59
213   MKKNIAFLLASMFVFSIATNAYADIQMTQSPSSLSASVGDRVTITCRASQ-AAYGRVAWY    59
214   MKKNIAFLLASMFVFSIATNAYADIQMTQSPSSLSASVGDRVTITCRASQ-AAYGRVAWY    59
215   MKKNIAFLLASMFVFSIATNAYADIQMTQSPSSLSASVGDRVTITCRASQ-AAYGRVAWY    59
216   MKKNIAFLLASMFVFSIATNAYADIQMTQSPSSLSASVGDRVTITCRASQ-AAYGRVAWY    59
217   MKKNIAFLLASMFVFSIATNAYADIQMTQSPSSLSASVGDRVTITCRASQ-DAYGRVAWY    59
218   MKKNIAFLLASMFVFSIATNAYADIQMTQSPSSLSASVGDRVTITCRASQ-AADGRVAWY    59
219   MKKNIAFLLASMFVFSIATNAYADIQMTQSPSSLSASVGDRVTITCRASQ-AAYDRVAWY    59
220   MKKNIAFLLASMFVFSIATNAYADIQMTQSPSSLSASVGDRVTITCRASQ-AAYGDVAWY    59
      **********************************************  ***   *  .  ****

201   QQKPGKAPKLLIYKASELYAGVPSRFSGSRSGTDFTLTISSLQPEDFATYYCQQRGWYLF    119
202   QQKPGKAPKLLIYKASELDAGVPSRFSGSRSGTDFTLTISSLQPEDFATYYCQQRGWYLF    119
203   QQKPGKAPKLLIYKASELYAGVPSRFSGSRSGTDFTLTISSLQPEDFATYYCQQRGWYLF    119
204   QQKPGKAPKLLIYKADELYAGVPSRFSGSRSGTDFTLTISSLQPEDFATYYCQQRGWYLF    119
205   QQKPGKAPKLLIYKDSELYAGVPSRFSGSRSGTDFTLTISSLQPEDFATYYCQQRGWYLF    119
206   QQKPGKAPKLLIYDASELYAGVPSRFSGSRSGTDFTLTISSLQPEDFATYYCQQRGWYLF    119
207   QQKPGKAPKLLIDKASELYAGVPSRFSGSRSGTDFTLTISSLQPEDFATYYCQQRGWYLF    119
208   QQKPGKAPKLLIYKASELYAGVPSRFSGSRSGTDFTLTISSLQPEDFATYYCQQRGWYLF    119
209   QQKPGKAPKLLIYKASELYAGVPSRFSGSRSGTDFTLTISSLQPEDFATYYCQQRGWYLF    120
212   QQKPGKAPKLLIYKASELYAGVPSRFSGSRSGTDFTLTISSLQPEDFATYYCQQRGWYLF    119
213   QQKPGKAPKLLIYKASELYAGVPSRFSGSRSGTDFTLTISSLQPEDFATYYCQQRGWYLF    119
214   QQKPGKAPKLLIYKASELYAGVPSRFSGSRSGTDFTLTISSLQPEDFATYYCQQRGWYLF    119
215   QQKPGKAPKLLIYKASELYAGVPSRFSGSRSGTDFTLTISSLQPEDFATYYCQQRGWYLF    119
216   QQKPGKAPKLLIYKASELYAGVPSRFSGSRSGTDFTLTISSLQPEDFATYYCQQRGWYLF    119
217   QQKPGKAPKLLIYKASELYAGVPSRFSGSRSGTDFTLTISSLQPEDFATYYCQQRGWYLF    119
218   QQKPGKAPKLLIYKASELYAGVPSRFSGSRSGTDFTLTISSLQPEDFATYYCQQRGWYLF    119
219   QQKPGKAPKLLIYKASELYAGVPSRFSGSRSGTDFTLTISSLQPEDFATYYCQQRGWYLF    119
220   QQKPGKAPKLLIYKASELYAGVPSRFSGSRSGTDFTLTISSLQPEDFATYYCQQRGWYLF    119
      ***********  .  .:*  *****************************************

201   TFGQGTKVEIKRTVAAPSVFIFPPSDSQLKSGTASVVCLLNNFYPREAKVQWKVDNALQS    179
202   TFGQGTKVEIKRTVAAPSVFIFPPSDSQLKSGTASVVCLLNNFYPREAKVQWKVDNALQS    179
203   TFGQGTKVEIKRTVAAPSVFIFPPSDSQLKSGTASVVCLLNNFYPREAKVQWKVDNALQS    179
204   TFGQGTKVEIKRTVAAPSVFIFPPSDSQLKSGTASVVCLLNNFYPREAKVQWKVDNALQS    179
205   TFGQGTKVEIKRTVAAPSVFIFPPSDSQLKSGTASVVCLLNNFYPREAKVQWKVDNALQS    179
206   TFGQGTKVEIKRTVAAPSVFIFPPSDSQLKSGTASVVCLLNNFYPREAKVQWKVDNALQS    179
207   TFGQGTKVEIKRTVAAPSVFIFPPSDSQLKSGTASVVCLLNNFYPREAKVQWKVDNALQS    179
208   TFGQGTKVEIKRTVAAPSVFIFPPSDSQLKSGTASVVCLLNNFYPREAKVQWKVDNALQS    179
209   TFGQGTKVEIKRTVAAPSVFIFPPSDSQLKSGTASVVCLLNNFYPREAKVQWKVDNALQS    180
212   TFGQGTKVEIKRTVAAPSVFIFPPSDSQLKSGTASVVCLLNNFYPREAKVQWKVDNALQS    179
213   TFGQGTKVEIKRTVAAPSVFIFPPSDSQLKSGTASVVCLLNNFYPREAKVQWKVDNALQS    179
214   TFGQGTKVEIKRTVAAPSVFIFPPSDSQLKSGTASVVCLLNNFYPREAKVQWKVDNALQS    179
215   TFGQGTKVEIKRTVAAPSVFIFPPSDSQLKSGTASVVCLLNNFYPREAKVQWKVDNALQS    179
216   TFGQGTKVEIKRTVAAPSVFIFPPSDSQLKSGTASVVCLLNNFYPREAKVQWKVDNALQS    179
217   TFGQGTKVEIKRTVAAPSVFIFPPSDSQLKSGTASVVCLLNNFYPREAKVQWKVDNALQS    179
218   TFGQGTKVEIKRTVAAPSVFIFPPSDSQLKSGTASVVCLLNNFYPREAKVQWKVDNALQS    179
219   TFGQGTKVEIKRTVAAPSVFIFPPSDSQLKSGTASVVCLLNNFYPREAKVQWKVDNALQS    179
220   TFGQGTKVEIKRTVAAPSVFIFPPSDSQLKSGTASVVCLLNNFYPREAKVQWKVDNALQS    179
      ***********************************************************

201   GNSQESVTEQDSKDSTYSLSSTLTLSKADYEKHKVYACEVTHQGLSSPVTKSFNRGEC    237
202   GNSQESVTEQDSKDSTYSLSSTLTLSKADYEKHKVYACEVTHQGLSSPVTKSFNRGEC    237
203   GNSQESVTEQDSKDSTYSLSSTLTLSKADYEKHKVYACEVTHQGLSSPVTKSFNRGEC    237
204   GNSQESVTEQDSKDSTYSLSSTLTLSKADYEKHKVYACEVTHQGLSSPVTKSFNRGEC    237
205   GNSQESVTEQDSKDSTYSLSSTLTLSKADYEKHKVYACEVTHQGLSSPVTKSFNRGEC    237
206   GNSQESVTEQDSKDSTYSLSSTLTLSKADYEKHKVYACEVTHQGLSSPVTKSFNRGEC    237
207   GNSQESVTEQDSKDSTYSLSSTLTLSKADYEKHKVYACEVTHQGLSSPVTKSFNRGEC    237
208   GNSQESVTEQDSKDSTYSLSSTLTLSKADYEKHKVYACEVTHQGLSSPVTKSFNRGEC    237
209   GNSQESVTEQDSKDSTYSLSSTLTLSKADYEKHKVYACEVTHQGLSSPVTKSFNRGEC    238
212   GNSQESVTEQDSKDSTYSLSSTLTLSKADYEKHKVYACEVTHQGLSSPVTKSFNRGEC    237
213   GNSQESVTEQDSKDSTYSLSSTLTLSKADYEKHKVYACEVTHQGLSSPVTKSFNRGEC    237
214   GNSQESVTEQDSKDSTYSLSSTLTLSKADYEKHKVYACEVTHQGLSSPVTKSFNRGEC    237
215   GNSQESVTEQDSKDSTYSLSSTLTLSKADYEKHKVYACEVTHQGLSSPVTKSFNRGEC    237
```

TABLE 5a-continued

Multiple sequence alignment for light chain of variants 201-220
as indicated in right-hand column (CDR sequences
defined in accordance with IMGT ® are underlined)

```
216   GNSQESVTEQDSKDSTYSLSSTLTLSKADYEKHKVYACEVTHQGLSSPVTKSFNRGEC   237
217   GNSQESVTEQDSKDSTYSLSSTLTLSKADYEKHKVYACEVTHQGLSSPVTKSFNRGEC   237
218   GNSQESVTEQDSKDSTYSLSSTLTLSKADYEKHKVYACEVTHQGLSSPVTKSFNRGEC   237
219   GNSQESVTEQDSKDSTYSLSSTLTLSKADYEKHKVYACEVTHQGLSSPVTKSFNRGEC   237
220   GNSQESVTEQDSKDSTYSLSSTLTLSKADYEKHKVYACEVTHQGLSSPVTKSFNRGEC   237
      **********************************************************
```

TABLE 5b

Multiple sequence alignment for heavy chain of variants 201-220
as indicated in right-hand column (CDR sequences defined in
accordance with IMGT ® are underlined)

```
201   MKKNIAFLLASMFVFSIATNAYAEVQLVESGGGLVQPGGSLRLSCAASGFDLFHYSIHWV    60
202   MKKNIAFLLASMFVFSIATNAYAEVQLVESGGGLVQPGGSLRLSCAASGFDLFHYSIHWV    60
203   MKKNIAFLLASMFVFSIATNAYAEVQLVESGGGLVQPGGSLRLSCAASGFDLFHYSIHWV    60
204   MKKNIAFLLASMFVFSIATNAYAEVQLVESGGGLVQPGGSLRLSCAASGFDLFHYSIHWV    60
205   MKKNIAFLLASMFVFSIATNAYAEVQLVESGGGLVQPGGSLRLSCAASGFDLFHYSIHWV    60
206   MKKNIAFLLASMFVFSIATNAYAEVQLVESGGGLVQPGGSLRLSCAASGFDLFHYSIHWV    60
207   MKKNIAFLLASMFVFSIATNAYAEVQLVESGGGLVQPGGSLRLSCAASGFDLFHYSIHWV    60
208   MKKNIAFLLASMFVFSIATNAYAEVQLVESGGGLVQPGGSLRLSCAASGFDLFHYSIHWV    60
209   MKKNIAFLLASMFVFSIATNAYAEVQLVESGGGLVQPGGSLRLSCAASGFDLFHYSIHWV    60
212   MKKNIAFLLASMFVFSIATNAYAEVQLVESGGGLVQPGGSLRLSCAASGFDLFHYSIHWV    60
213   MKKNIAFLLASMFVFSIATNAYAEVQLVESGGGLVQPGGSLRLSCAASGFDLFHYDIHWV    60
214   MKKNIAFLLASMFVFSIATNAYAEVQLVESGGGLVQPGGSLRLSCAASGFDLFHDSIHWV    60
215   MKKNIAFLLASMFVFSIATNAYAEVQLVESGGGLVQPGGSLRLSCAASGFDLFDYSIHWV    60
216   MKKNIAFLLASMFVFSIATNAYAEVQLVESGGGLVQPGGSLRLSCAASGFDLFDHYSIHWV   60
217   MKKNIAFLLASMFVFSIATNAYAEVQLVESGGGLVQPGGSLRLSCAASGFDLFHYSIHWV    60
218   MKKNIAFLLASMFVFSIATNAYAEVQLVESGGGLVQPGGSLRLSCAASGFDLFHYSIHWV    60
219   MKKNIAFLLASMFVFSIATNAYAEVQLVESGGGLVQPGGSLRLSCAASGFDLFHYSIHWV    60
220   MKKNIAFLLASMFVFSIATNAYAEVQLVESGGGLVQPGGSLRLSCAASGFDLFHYSIHWV    60
      *****************************************************   .  .*.**
```

```
201   RQAPGKGLEWVAYIYPSYGYTYYADSVKGRFTISADTSKNTAYLQMNSLRAEDTAVYYCA   120
202   RQAPGKGLEWVAYIYPSYGYTYYADSVKGRFTISADTSKNTAYLQMNSLRAEDTAVYYCA   120
203   RQAPGKGLEWVAYIYPSYGYTYYADSVKGRFTISADTSKNTAYLQMNSLRAEDTAVYYCA   120
204   RQAPGKGLEWVAYIYPSYGYTYYADSVKGRFTISADTSKNTAYLQMNSLRAEDTAVYYCA   120
205   RQAPGKGLEWVAYIYPSYGYTYYADSVKGRFTISADTSKNTAYLQMNSLRAEDTAVYYCA   120
206   RQAPGKGLEWVAYIYPSYGYTYYADSVKGRFTISADTSKNTAYLQMNSLRAEDTAVYYCA   120
207   RQAPGKGLEWVAYIYPSYGYTYYADSVKGRFTISADTSKNTAYLQMNSLRAEDTAVYYCA   120
208   RQAPGKGLEWVAYIYPSYGYTYYADSVKGRFTISADTSKNTAYLQMNSLRAEDTAVYYCA   120
209   RQAPGKGLEWVAYIYPSYGYTYYADSVKGRFTISADTSKNTAYLQMNSLRAEDTAVYYCA   120
212   RQAPGKGLEWVAYIYPSYGYTYYADSVKGRFTISADTSKNTAYLQMNSLRAEDTAVYYCA   120
213   RQAPGKGLEWVAYIYPSYGYTYYADSVKGRFTISADTSKNTAYLQMNSLRAEDTAVYYCA   120
214   RQAPGKGLEWVAYIYPSYGYTYYADSVKGRFTISADTSKNTAYLQMNSLRAEDTAVYYCA   120
215   RQAPGKGLEWVAYIYPSYGYTYYADSVKGRFTISADTSKNTAYLQMNSLRAEDTAVYYCA   120
216   RQAPGKGLEWVAYIYPSYGYTYYADSVKGRFTISADTSKNTAYLQMNSLRAEDTAVYYCA   120
217   RQAPGKGLEWVAYIYPSYGYTYYADSVKGRFTISADTSKNTAYLQMNSLRAEDTAVYYCA   120
218   RQAPGKGLEWVAYIYPSYGYTYYADSVKGRFTISADTSKNTAYLQMNSLRAEDTAVYYCA   120
219   RQAPGKGLEWVAYIYPSYGYTYYADSVKGRFTISADTSKNTAYLQMNSLRAEDTAVYYCA   120
220   RQAPGKGLEWVAYIYPSYGYTYYADSVKGRFTISADTSKNTAYLQMNSLRAEDTAVYYCA   120
      ***********************************************************
```

```
201   RHAWYYGWGLDYWGQGTLVTVSSASTKGPSVFPLAPSSKSTSGGTAALGCLVKDYFPEPV   180
202   RHAWYYGWGLDYWGQGTLVTVSSASTKGPSVFPLAPSSKSTSGGTAALGCLVKDYFPEPV   180
203   RHAWYYGWGLDYWGQGTLVTVSSASTKGPSVFPLAPSSKSTSGGTAALGCLVKDYFPEPV   180
204   RHAWYYGWGLDYWGQGTLVTVSSASTKGPSVFPLAPSSKSTSGGTAALGCLVKDYFPEPV   180
205   RHAWYYGWGLDYWGQGTLVTVSSASTKGPSVFPLAPSSKSTSGGTAALGCLVKDYFPEPV   180
206   RHAWYYGWGLDYWGQGTLVTVSSASTKGPSVFPLAPSSKSTSGGTAALGCLVKDYFPEPV   180
207   RHAWYYGWGLDYWGQGTLVTVSSASTKGPSVFPLAPSSKSTSGGTAALGCLVKDYFPEPV   180
208   RHAWYYGWGLDYWGQGTLVTVSSASTKGPSVFPLAPSSKSTSGGTAALGCLVKDYFPEPV   180
209   RHAWYYGWGLDYWGQGTLVTVSSASTKGPSVFPLAPSSKSTSGGTAALGCLVKDYFPEPV   180
212   RHAWYYGWGLDYWGQGTLVTVSSASTKGPSVFPLAPSSKSTSGGTAALGCLVKDYFPEPV   180
213   RHAWYYGWGLDYWGQGTLVTVSSASTKGPSVFPLAPSSKSTSGGTAALGCLVKDYFPEPV   180
214   RHAWYYGWGLDYWGQGTLVTVSSASTKGPSVFPLAPSSKSTSGGTAALGCLVKDYFPEPV   180
215   RHAWYYGWGLDYWGQGTLVTVSSASTKGPSVFPLAPSSKSTSGGTAALGCLVKDYFPEPV   180
216   RHAWYYGWGLDYWGQGTLVTVSSASTKGPSVFPLAPSSKSTSGGTAALGCLVKDYFPEPV   180
217   RHAWYYGWGLDYWGQGTLVTVSSASTKGPSVFPLAPSSKSTSGGTAALGCLVKDYFPEPV   180
218   RHAWYYGWGLDYWGQGTLVTVSSASTKGPSVFPLAPSSKSTSGGTAALGCLVKDYFPEPV   180
219   RHAWYYGWGLDYWGQGTLVTVSSASTKGPSVFPLAPSSKSTSGGTAALGCLVKDYFPEPV   180
220   RHAWYYGWGLDYWGQGTLVTVSSASTKGPSVFPLAPSSKSTSGGTAALGCLVKDYFPEPV   180
      ***********************************************************
```

TABLE 5b-continued

Multiple sequence alignment for heavy chain of variants 201-220
as indicated in right-hand column (CDR sequences defined in
accordance with IMGT ® are underlined)

```
201  TVSWNSGALTSGVHTFPAVLQSSGLYSLSSVVTVPSSSLGTQTYICNVNHKPSNTKVDKK  240
202  TVSWNSGALTSGVHTFPAVLQSSGLYSLSSVVTVPSSSLGTQTYICNVNHKPSNTKVDKK  240
203  TVSWNSGALTSGVHTFPAVLQSSGLYSLSSVVTVPSSSLGTQTYICNVNHKPSNTKVDKK  240
204  TVSWNSGALTSGVHTFPAVLQSSGLYSLSSVVTVPSSSLGTQTYICNVNHKPSNTKVDKK  240
205  TVSWNSGALTSGVHTFPAVLQSSGLYSLSSVVTVPSSSLGTQTYICNVNHKPSNTKVDKK  240
206  TVSWNSGALTSGVHTFPAVLQSSGLYSLSSVVTVPSSSLGTQTYICNVNHKPSNTKVDKK  240
207  TVSWNSGALTSGVHTFPAVLQSSGLYSLSSVVTVPSSSLGTQTYICNVNHKPSNTKVDKK  240
208  TVSWNSGALTSGVHTFPAVLQSSGLYSLSSVVTVPSSSLGTQTYICNVNHKPSNTKVDKK  240
209  TVSWNSGALTSGVHTFPAVLQSSGLYSLSSVVTVPSSSLGTQTYICNVNHKPSNTKVDKK  240
212  TVSWNSGALTSGVHTFPAVLQSSGLYSLSSVVTVPSSSLGTQTYICNVNHKPSNTKVDKK  240
213  TVSWNSGALTSGVHTFPAVLQSSGLYSLSSVVTVPSSSLGTQTYICNVNHKPSNTKVDKK  240
214  TVSWNSGALTSGVHTFPAVLQSSGLYSLSSVVTVPSSSLGTQTYICNVNHKPSNTKVDKK  240
215  TVSWNSGALTSGVHTFPAVLQSSGLYSLSSVVTVPSSSLGTQTYICNVNHKPSNTKVDKK  240
216  TVSWNSGALTSGVHTFPAVLQSSGLYSLSSVVTVPSSSLGTQTYICNVNHKPSNTKVDKK  240
217  TVSWNSGALTSGVHTFPAVLQSSGLYSLSSVVTVPSSSLGTQTYICNVNHKPSNTKVDKK  240
218  TVSWNSGALTSGVHTFPAVLQSSGLYSLSSVVTVPSSSLGTQTYICNVNHKPSNTKVDKK  240
219  TVSWNSGALTSGVHTFPAVLQSSGLYSLSSVVTVPSSSLGTQTYICNVNHKPSNTKVDKK  240
220  TVSWNSGALTSGVHTFPAVLQSSGLYSLSSVVTVPSSSLGTQTYICNVNHKPSNTKVDKK  240
     ************************************************************

201  VEPKSCDKTHT  251
202  VEPKSCDKTHT  251
203  VEPKSCDKTHT  251
204  VEPKSCDKTHT  251
205  VEPKSCDKTHT  251
206  VEPKSCDKTHT  251
207  VEPKSCDKTHT  251
208  VEPKSCDKTHT  251
209  VEPKSCDKTHT  251
212  VEPKSCDKTHT  251
213  VEPKSCDKTHT  251
214  VEPKSCDKTHT  251
215  VEPKSCDKTHT  251
216  VEPKSCDKTHT  251
217  VEPKSCDKTHT  251
218  VEPKSCDKTHT  251
219  VEPKSCDKTHT  251
220  VEPKSCDKTHT  251
     ***********
```

TABLE 5c

Multiple sequence alignment for light chain of variants 201-220
as indicated in right-hand column (CDR sequences defined in
accordance with Kabat are underlined)

```
201  MKKNIAFLLASMFVFSIATNAYADIQMTQSPSSLSASVGDRVTITCRASQ-AAYGRVAWY  59
202  MKKNIAFLLASMFVFSIATNAYADIQMTQSPSSLSASVGDRVTITCRASQ-AAYGRVAWY  59
203  MKKNIAFLLASMFVFSIATNAYADIQMTQSPSSLSASVGDRVTITCRASQ-AAYGRVAWY  59
204  MKKNIAFLLASMFVFSIATNAYADIQMTQSPSSLSASVGDRVTITCRASQ-AAYGRVAWY  59
205  MKKNIAFLLASMFVFSIATNAYADIQMTQSPSSLSASVGDRVTITCRASQ-AAYGRVAWY  59
206  MKKNIAFLLASMFVFSIATNAYADIQMTQSPSSLSASVGDRVTITCRASQ-AAYGRVAWY  59
207  MKKNIAFLLASMFVFSIATNAYADIQMTQSPSSLSASVGDRVTITCRASQ-AAYGRVAWY  59
208  MKKNIAFLLASMFVFSIATNAYADIQMTQSPSSLSASVGDRVTITCDASQ-AAYGRVAWY  59
209  MKKNIAFLLASMFVFSIATNAYADIQMTQSPSSLSASVGDRVTITCRASQDAAYGRVAWY  60
212  MKKNIAFLLASMFVFSIATNAYADIQMTQSPSSLSASVGDRVTITCRASQ-AAYGRVAWY  59
213  MKKNIAFLLASMFVFSIATNAYADIQMTQSPSSLSASVGDRVTITCRASQ-AAYGRVAWY  59
214  MKKNIAFLLASMFVFSIATNAYADIQMTQSPSSLSASVGDRVTITCRASQ-AAYGRVAWY  59
215  MKKNIAFLLASMFVFSIATNAYADIQMTQSPSSLSASVGDRVTITCRASQ-AAYGRVAWY  59
216  MKKNIAFLLASMFVFSIATNAYADIQMTQSPSSLSASVGDRVTITCRASQ-AAYGRVAWY  59
217  MKKNIAFLLASMFVFSIATNAYADIQMTQSPSSLSASVGDRVTITCRASQ-DAYGRVAWY  59
218  MKKNIAFLLASMFVFSIATNAYADIQMTQSPSSLSASVGDRVTITCRASQ-AADGRVAWY  59
219  MKKNIAFLLASMFVFSIATNAYADIQMTQSPSSLSASVGDRVTITCRASQ-AAYDRVAWY  59
220  MKKNIAFLLASMFVFSIATNAYADIQMTQSPSSLSASVGDRVTITCRASQ-AAYGRVAWY  59
     ********************************************** ***  *  ****

201  QQKPGKAPKLLIYKASELYAGVPSRFSGSRSGTDFTLTISSLQPEDFATYYCQQRGWYLF  119
202  QQKPGKAPKLLIYKASELDAGVPSRFSGSRSGTDFTLTISSLQPEDFATYYCQQRGWYLF  119
203  QQKPGKAPKLLIYKASDLYAGVPSRFSGSRSGTDFTLTISSLQPEDFATYYCQQRGWYLF  119
204  QQKPGKAPKLLIYKADELYAGVPSRFSGSRSGTDFTLTISSLQPEDFATYYCQQRGWYLF  119
205  QQKPGKAPKLLIYKDSELYAGVPSRFSGSRSGTDFTLTISSLQPEDFATYYCQQRGWYLF  119
206  QQKPGKAPKLLIYDASELYAGVPSRFSGSRSGTDFTLTISSLQPEDFATYYCQQRGWYLF  119
207  QQKPGKAPKLLIDKASELYAGVPSRFSGSRSGTDFTLTISSLQPEDFATYYCQQRGWYLF  119
```

TABLE 5c-continued

Multiple sequence alignment for light chain of variants 201-220
as indicated in right-hand column (CDR sequences defined in
accordance with Kabat are underlined)

```
208  QQKPGKAPKLLIYKASELYAGVPSRFSGSRSGTDFTLTISSLQPEDFATYYCQQRGWYLF   119
209  QQKPGKAPKLLIYKASELYAGVPSRFSGSRSGTDFTLTISSLQPEDFATYYCQQRGWYLF   120
212  QQKPGKAPKLLIYKASELYAGVPSRFSGSRSGTDFTLTISSLQPEDFATYYCQQRGWYLF   119
213  QQKPGKAPKLLIYKASELYAGVPSRFSGSRSGTDFTLTISSLQPEDFATYYCQQRGWYLF   119
214  QQKPGKAPKLLIYKASELYAGVPSRFSGSRSGTDFTLTISSLQPEDFATYYCQQRGWYLF   119
215  QQKPGKAPKLLIYKASELYAGVPSRFSGSRSGTDFTLTISSLQPEDFATYYCQQRGWYLF   119
216  QQKPGKAPKLLIYKASELYAGVPSRFSGSRSGTDFTLTISSLQPEDFATYYCQQRGWYLF   119
217  QQKPGKAPKLLIYKASELYAGVPSRFSGSRSGTDFTLTISSLQPEDFATYYCQQRGWYLF   119
218  QQKPGKAPKLLIYKASELYAGVPSRFSGSRSGTDFTLTISSLQPEDFATYYCQQRGWYLF   119
219  QQKPGKAPKLLIYKASELYAGVPSRFSGSRSGTDFTLTISSLQPEDFATYYCQQRGWYLF   119
220  QQKPGKAPKLLIYKASELYAGVPSRFSGSRSGTDFTLTISSLQPEDFATYYCQQRGWYLF   119
     ***********  . .:* ****************************************

201  TFGQGTKVEIKRTVAAPSVFIFPPPSDSQLKSGTASVVCLLNNFYPREAKVQWKVDNALQS   179
202  TFGQGTKVEIKRTVAAPSVFIFPPPSDSQLKSGTASVVCLLNNFYPREAKVQWKVDNALQS   179
203  TFGQGTKVEIKRTVAAPSVFIFPPPSDSQLKSGTASVVCLLNNFYPREAKVQWKVDNALQS   179
204  TFGQGTKVEIKRTVAAPSVFIFPPPSDSQLKSGTASVVCLLNNFYPREAKVQWKVDNALQS   179
205  TFGQGTKVEIKRTVAAPSVFIFPPPSDSQLKSGTASVVCLLNNFYPREAKVQWKVDNALQS   179
206  TFGQGTKVEIKRTVAAPSVFIFPPPSDSQLKSGTASVVCLLNNFYPREAKVQWKVDNALQS   179
207  TFGQGTKVEIKRTVAAPSVFIFPPPSDSQLKSGTASVVCLLNNFYPREAKVQWKVDNALQS   179
208  TFGQGTKVEIKRTVAAPSVFIFPPPSDSQLKSGTASVVCLLNNFYPREAKVQWKVDNALQS   179
209  TFGQGTKVEIKRTVAAPSVFIFPPPSDSQLKSGTASVVCLLNNFYPREAKVQWKVDNALQS   180
212  TFGQGTKVEIKRTVAAPSVFIFPPPSDSQLKSGTASVVCLLNNFYPREAKVQWKVDNALQS   179
213  TFGQGTKVEIKRTVAAPSVFIFPPPSDSQLKSGTASVVCLLNNFYPREAKVQWKVDNALQS   179
214  TFGQGTKVEIKRTVAAPSVFIFPPPSDSQLKSGTASVVCLLNNFYPREAKVQWKVDNALQS   179
215  TFGQGTKVEIKRTVAAPSVFIFPPPSDSQLKSGTASVVCLLNNFYPREAKVQWKVDNALQS   179
216  TFGQGTKVEIKRTVAAPSVFIFPPPSDSQLKSGTASVVCLLNNFYPREAKVQWKVDNALQS   179
217  TFGQGTKVEIKRTVAAPSVFIFPPPSDSQLKSGTASVVCLLNNFYPREAKVQWKVDNALQS   179
218  TFGQGTKVEIKRTVAAPSVFIFPPPSDSQLKSGTASVVCLLNNFYPREAKVQWKVDNALQS   179
219  TFGQGTKVEIKRTVAAPSVFIFPPPSDSQLKSGTASVVCLLNNFYPREAKVQWKVDNALQS   179
220  TFGQGTKVEIKRTVAAPSVFIFPPPSDSQLKSGTASVVCLLNNFYPREAKVQWKVDNALQS   179
     ************************************************************

201  GNSQESVTEQDSKDSTYSLSSTLTLSKADYEKHKVYACEVTHQGLSSPVTKSFNRGEC   237
202  GNSQESVTEQDSKDSTYSLSSTLTLSKADYEKHKVYACEVTHQGLSSPVTKSFNRGEC   237
203  GNSQESVTEQDSKDSTYSLSSTLTLSKADYEKHKVYACEVTHQGLSSPVTKSFNRGEC   237
204  GNSQESVTEQDSKDSTYSLSSTLTLSKADYEKHKVYACEVTHQGLSSPVTKSFNRGEC   237
205  GNSQESVTEQDSKDSTYSLSSTLTLSKADYEKHKVYACEVTHQGLSSPVTKSFNRGEC   237
206  GNSQESVTEQDSKDSTYSLSSTLTLSKADYEKHKVYACEVTHQGLSSPVTKSFNRGEC   237
207  GNSQESVTEQDSKDSTYSLSSTLTLSKADYEKHKVYACEVTHQGLSSPVTKSFNRGEC   237
208  GNSQESVTEQDSKDSTYSLSSTLTLSKADYEKHKVYACEVTHQGLSSPVTKSFNRGEC   237
209  GNSQESVTEQDSKDSTYSLSSTLTLSKADYEKHKVYACEVTHQGLSSPVTKSFNRGEC   238
212  GNSQESVTEQDSKDSTYSLSSTLTLSKADYEKHKVYACEVTHQGLSSPVTKSFNRGEC   237
213  GNSQESVTEQDSKDSTYSLSSTLTLSKADYEKHKVYACEVTHQGLSSPVTKSFNRGEC   237
214  GNSQESVTEQDSKDSTYSLSSTLTLSKADYEKHKVYACEVTHQGLSSPVTKSFNRGEC   237
215  GNSQESVTEQDSKDSTYSLSSTLTLSKADYEKHKVYACEVTHQGLSSPVTKSFNRGEC   237
216  GNSQESVTEQDSKDSTYSLSSTLTLSKADYEKHKVYACEVTHQGLSSPVTKSFNRGEC   237
217  GNSQESVTEQDSKDSTYSLSSTLTLSKADYEKHKVYACEVTHQGLSSPVTKSFNRGEC   237
218  GNSQESVTEQDSKDSTYSLSSTLTLSKADYEKHKVYACEVTHQGLSSPVTKSFNRGEC   237
219  GNSQESVTEQDSKDSTYSLSSTLTLSKADYEKHKVYACEVTHQGLSSPVTKSFNRGEC   237
220  GNSQESVTEQDSKDSTYSLSSTLTLSKADYEKHKVYACEVTHQGLSSPVTKSFNRGEC   237
     *********************************************************
```

TABLE 5d

Multiple sequence alignment for heavy chain
(CDR sequences defined in accordance with Kabat are underlined)

```
201  MKKNIAFLLASMFVFSIATNAYAEVQLVESGGGLVQPGGSLRLSCAASGFDLFHYSIHWV   60
202  MKKNIAFLLASMFVFSIATNAYAEVQLVESGGGLVQPGGSLRLSCAASGFDLFHYSIHWV   60
203  MKKNIAFLLASMFVFSIATNAYAEVQLVESGGGLVQPGGSLRLSCAASGFDLFHYSIHWV   60
204  MKKNIAFLLASMFVFSIATNAYAEVQLVESGGGLVQPGGSLRLSCAASGFDLFHYSIHWV   60
205  MKKNIAFLLASMFVFSIATNAYAEVQLVESGGGLVQPGGSLRLSCAASGFDLFHYSIHWV   60
206  MKKNIAFLLASMFVFSIATNAYAEVQLVESGGGLVQPGGSLRLSCAASGFDLFHYSIHWV   60
207  MKKNIAFLLASMFVFSIATNAYAEVQLVESGGGLVQPGGSLRLSCAASGFDLFHYSIHWV   60
208  MKKNIAFLLASMFVFSIATNAYAEVQLVESGGGLVQPGGSLRLSCAASGFDLFHYSIHWV   60
209  MKKNIAFLLASMFVFSIATNAYAEVQLVESGGGLVQPGGSLRLSCAASGFDLFHYSIHWV   60
212  MKKNIAFLLASMFVFSIATNAYAEVQLVESGGGLVQPGGSLRLSCAASGFDLFHYSIDWV   60
213  MKKNIAFLLASMFVFSIATNAYAEVQLVESGGGLVQPGGSLRLSCAASGFDLFHYDIHWV   60
214  MKKNIAFLLASMFVFSIATNAYAEVQLVESGGGLVQPGGSLRLSCAASGFDLFHDSIHWV   60
215  MKKNIAFLLASMFVFSIATNAYAEVQLVESGGGLVQPGGSLRLSCAASGFDLFDYSIHWV   60
216  MKKNIAFLLASMFVFSIATNAYAEVQLVESGGGLVQPGGSLRLSCAASGFDLDHYSIHWV   60
217  MKKNIAFLLASMFVFSIATNAYAEVQLVESGGGLVQPGGSLRLSCAASGFDLFHYSIHWV   60
```

TABLE 5d-continued

Multiple sequence alignment for heavy chain
(CDR sequences defined in accordance with Kabat are underlined)

```
218  MKKNIAFLLASMFVFSIATNAYAEVQLVESGGGLVQPGGSLRLSCAASGFDLFHYSIHWV   60
219  MKKNIAFLLASMFVFSIATNAYAEVQLVESGGGLVQPGGSLRLSCAASGFDLFHYSIHWV   60
220  MKKNIAFLLASMFVFSIATNAYAEVQLVESGGGLVQPGGSLRLSCAASGFDLFHYSIHWV   60
     ***************************************************  .*.**
```

```
201  RQAPGKGLEWVAYIYPSYGYTYYADSVKGRFTISADTSKNTAYLQMNSLRAEDTAVYYCA  120
202  RQAPGKGLEWVAYIYPSYGYTYYADSVKGRFTISADTSKNTAYLQMNSLRAEDTAVYYCA  120
203  RQAPGKGLEWVAYIYPSYGYTYYADSVKGRFTISADTSKNTAYLQMNSLRAEDTAVYYCA  120
204  RQAPGKGLEWVAYIYPSYGYTYYADSVKGRFTISADTSKNTAYLQMNSLRAEDTAVYYCA  120
205  RQAPGKGLEWVAYIYPSYGYTYYADSVKGRFTISADTSKNTAYLQMNSLRAEDTAVYYCA  120
206  RQAPGKGLEWVAYIYPSYGYTYYADSVKGRFTISADTSKNTAYLQMNSLRAEDTAVYYCA  120
207  RQAPGKGLEWVAYIYPSYGYTYYADSVKGRFTISADTSKNTAYLQMNSLRAEDTAVYYCA  120
208  RQAPGKGLEWVAYIYPSYGYTYYADSVKGRFTISADTSKNTAYLQMNSLRAEDTAVYYCA  120
209  RQAPGKGLEWVAYIYPSYGYTYYADSVKGRFTISADTSKNTAYLQMNSLRAEDTAVYYCA  120
212  RQAPGKGLEWVAYIYPSYGYTYYADSVKGRFTISADTSKNTAYLQMNSLRAEDTAVYYCA  120
213  RQAPGKGLEWVAYIYPSYGYTYYADSVKGRFTISADTSKNTAYLQMNSLRAEDTAVYYCA  120
214  RQAPGKGLEWVAYIYPSYGYTYYADSVKGRFTISADTSKNTAYLQMNSLRAEDTAVYYCA  120
215  RQAPGKGLEWVAYIYPSYGYTYYADSVKGRFTISADTSKNTAYLQMNSLRAEDTAVYYCA  120
216  RQAPGKGLEWVAYIYPSYGYTYYADSVKGRFTISADTSKNTAYLQMNSLRAEDTAVYYCA  120
217  RQAPGKGLEWVAYIYPSYGYTYYADSVKGRFTISADTSKNTAYLQMNSLRAEDTAVYYCA  120
218  RQAPGKGLEWVAYIYPSYGYTYYADSVKGRFTISADTSKNTAYLQMNSLRAEDTAVYYCA  120
219  RQAPGKGLEWVAYIYPSYGYTYYADSVKGRFTISADTSKNTAYLQMNSLRAEDTAVYYCA  120
220  RQAPGKGLEWVAYIYPSYGYTYYADSVKGRFTISADTSKNTAYLQMNSLRAEDTAVYYCA  120
     ************************************************************
```

```
201  RHAWYYGWGLDYWGQGTLVTVSSASTKGPSVFPLAPSSKSTSGGTAALGCLVKDYFPEPV  180
202  RHAWYYGWGLDYWGQGTLVTVSSASTKGPSVFPLAPSSKSTSGGTAALGCLVKDYFPEPV  180
203  RHAWYYGWGLDYWGQGTLVTVSSASTKGPSVFPLAPSSKSTSGGTAALGCLVKDYFPEPV  180
204  RHAWYYGWGLDYWGQGTLVTVSSASTKGPSVFPLAPSSKSTSGGTAALGCLVKDYFPEPV  180
205  RHAWYYGWGLDYWGQGTLVTVSSASTKGPSVFPLAPSSKSTSGGTAALGCLVKDYFPEPV  180
206  RHAWYYGWGLDYWGQGTLVTVSSASTKGPSVFPLAPSSKSTSGGTAALGCLVKDYFPEPV  180
207  RHAWYYGWGLDYWGQGTLVTVSSASTKGPSVFPLAPSSKSTSGGTAALGCLVKDYFPEPV  180
208  RHAWYYGWGLDYWGQGTLVTVSSASTKGPSVFPLAPSSKSTSGGTAALGCLVKDYFPEPV  180
209  RHAWYYGWGLDYWGQGTLVTVSSASTKGPSVFPLAPSSKSTSGGTAALGCLVKDYFPEPV  180
212  RHAWYYGWGLDYWGQGTLVTVSSASTKGPSVFPLAPSSKSTSGGTAALGCLVKDYFPEPV  180
213  RHAWYYGWGLDYWGQGTLVTVSSASTKGPSVFPLAPSSKSTSGGTAALGCLVKDYFPEPV  180
214  RHAWYYGWGLDYWGQGTLVTVSSASTKGPSVFPLAPSSKSTSGGTAALGCLVKDYFPEPV  180
215  RHAWYYGWGLDYWGQGTLVTVSSASTKGPSVFPLAPSSKSTSGGTAALGCLVKDYFPEPV  180
216  RHAWYYGWGLDYWGQGTLVTVSSASTKGPSVFPLAPSSKSTSGGTAALGCLVKDYFPEPV  180
217  RHAWYYGWGLDYWGQGTLVTVSSASTKGPSVFPLAPSSKSTSGGTAALGCLVKDYFPEPV  180
218  RHAWYYGWGLDYWGQGTLVTVSSASTKGPSVFPLAPSSKSTSGGTAALGCLVKDYFPEPV  180
219  RHAWYYGWGLDYWGQGTLVTVSSASTKGPSVFPLAPSSKSTSGGTAALGCLVKDYFPEPV  180
220  RHAWYYGWGLDYWGQGTLVTVSSASTKGPSVFPLAPSSKSTSGGTAALGCLVKDYFPEPV  180
     ************************************************************
```

```
201  TVSWNSGALTSGVHTFPAVLQSSGLYSLSSVVTVPSSSLGTQTYICNVNHKPSNTKVDKK  240
202  TVSWNSGALTSGVHTFPAVLQSSGLYSLSSVVTVPSSSLGTQTYICNVNHKPSNTKVDKK  240
203  TVSWNSGALTSGVHTFPAVLQSSGLYSLSSVVTVPSSSLGTQTYICNVNHKPSNTKVDKK  240
204  TVSWNSGALTSGVHTFPAVLQSSGLYSLSSVVTVPSSSLGTQTYICNVNHKPSNTKVDKK  240
205  TVSWNSGALTSGVHTFPAVLQSSGLYSLSSVVTVPSSSLGTQTYICNVNHKPSNTKVDKK  240
206  TVSWNSGALTSGVHTFPAVLQSSGLYSLSSVVTVPSSSLGTQTYICNVNHKPSNTKVDKK  240
207  TVSWNSGALTSGVHTFPAVLQSSGLYSLSSVVTVPSSSLGTQTYICNVNHKPSNTKVDKK  240
208  TVSWNSGALTSGVHTFPAVLQSSGLYSLSSVVTVPSSSLGTQTYICNVNHKPSNTKVDKK  240
209  TVSWNSGALTSGVHTFPAVLQSSGLYSLSSVVTVPSSSLGTQTYICNVNHKPSNTKVDKK  240
212  TVSWNSGALTSGVHTFPAVLQSSGLYSLSSVVTVPSSSLGTQTYICNVNHKPSNTKVDKK  240
213  TVSWNSGALTSGVHTFPAVLQSSGLYSLSSVVTVPSSSLGTQTYICNVNHKPSNTKVDKK  240
214  TVSWNSGALTSGVHTFPAVLQSSGLYSLSSVVTVPSSSLGTQTYICNVNHKPSNTKVDKK  240
215  TVSWNSGALTSGVHTFPAVLQSSGLYSLSSVVTVPSSSLGTQTYICNVNHKPSNTKVDKK  240
216  TVSWNSGALTSGVHTFPAVLQSSGLYSLSSVVTVPSSSLGTQTYICNVNHKPSNTKVDKK  240
217  TVSWNSGALTSGVHTFPAVLQSSGLYSLSSVVTVPSSSLGTQTYICNVNHKPSNTKVDKK  240
218  TVSWNSGALTSGVHTFPAVLQSSGLYSLSSVVTVPSSSLGTQTYICNVNHKPSNTKVDKK  240
219  TVSWNSGALTSGVHTFPAVLQSSGLYSLSSVVTVPSSSLGTQTYICNVNHKPSNTKVDKK  240
220  TVSWNSGALTSGVHTFPAVLQSSGLYSLSSVVTVPSSSLGTQTYICNVNHKPSNTKVDKK  240
     ************************************************************
```

```
201  VEPKSCDKTHT  251
202  VEPKSCDKTHT  251
203  VEPKSCDKTHT  251
204  VEPKSCDKTHT  251
205  VEPKSCDKTHT  251
206  VEPKSCDKTHT  251
207  VEPKSCDKTHT  251
208  VEPKSCDKTHT  251
209  VEPKSCDKTHT  251
212  VEPKSCDKTHT  251
213  VEPKSCDKTHT  251
214  VEPKSCDKTHT  251
```

TABLE 5d-continued

Multiple sequence alignment for heavy chain
(CDR sequences defined in accordance with Kabat are underlined)

```
215  VEPKSCDKTHT  251
216  VEPKSCDKTHT  251
217  VEPKSCDKTHT  251
218  VEPKSCDKTHT  251
219  VEPKSCDKTHT  251
220  VEPKSCDKTHT  251
     ***********
```

Example 4

Formulation 1 comprises the following excipients. Polysorbate 20 at 0.03%, sucrose at 5%, sodium chloride at 40 mM, phosphate buffer at 10 mM, and pH at 5.8. In alternate embodiments Polysorbate 20 may be used at a range of about 0.1% to 0.04%. Further, sucrose: may be used at a range of about 1% to about 20%. Sodium chloride may be used at a range; of about 10 to about 80 mM. Phosphate buffer may be used at a range of about 10 to about 100 mM. Also, the pH may be at a range of about 5 to 6.

Formulation 2 comprises the following excipients. Polysorbate 20 at 0.03%, sucrose at 0.05%, sodium chloride at 40 mM, histidine buffer at 10 mM, and pH at 5.5. In alternate embodiments Polysorbate 20 may be used at a range of about 1% to about 20%. Further, sucrose may be used at a range of about 1% to about 20%. Sodium chloride may be used at a range of about 10 to about 80 mM. Histidine buffer may be used at a range of about 5 to about 50 mM. Also, the pH may be at a range of about 5 to 5.5.

Formulation 3 comprises the following excipients. Polysorbate 20 at 0.03%, sucrose at 0.05%, sodium chloride at 40 mM sodium citrate buffer at 10 mM, and pH at 5. In alternate embodiments Polysorbate 20 may be used at a range of about 0.1% to 0.04%. Further, sucrose may be used at a range of about 1% to about 20%. Sodium chloride may be used at a range of about 10 to about 80 mM. Sodium citrate buffer may be used at a range of about 5 to about 20 mM. Also, the pH may be at a range of about 5 to 5.5.

Example 5

Variant 201 Biochemical Description

Variant 201 is a Fab antibody comprising human anti-VEGF variable domain shown in FIGS. 23 and 24 and is initially produced as a fusion protein (SEQ ID NO: 16) before being processed to remove the 23 amino-terminal secretory signal to produce the mature Fab 201 antibody fragment, with the heavy chain variable region-CH1 domain and part of a hinge region provided in FIG. 23 and the kappa light chain variable region-kappa light chain constant region provided in FIG. 24. Compared to other known anti-VEGF antibodies, like Lucentis, the variable domain of variant 201 contains multiple mutations (FIGS. 23 and 24), especially in the CDRs as defined either by Kabat nomenclature or IMGT® nomenclature. These mutations confer stronger binding of variant 201 to VEGF (FIG. 3).

Example 6

Upstream Process Information for Synthetic Antibodies Against VEGF
Transformation of Anti-VEGF Fab-201 Construct in E. coli BL21 by KCM Method The anti-VEGF Fab DNA construct was mixed with 10 ul of 1× KCM and prechilled on ice for 2-5 mins before adding the same volume of competent cells (10 ul). Tube was further incubated on ice for 20 mins, and then incubated at room temperature for 10 mins. 200 ul of Super Optimal Broth with Catabolite Repression (SOC) was added and the cells are incubated in orbital shaker 37° C. for 1 hour. 100 μl of above culture was plated in LB agar plate with adequate antibiotic (Carbenicillin), incubated the plate at 37° C. for 14 hours.
Expression of Anti-VEGF Fab-201 in the Shake Flask Culture
Pre-Inoculum Preparation:

Inoculated 10 μl from frozen working cell bank of E. coli BL21-201 in 10 ml sterile LB broth containing carbenicillin antibiotic (10 μl from 100 mg/ml stock). Incubated the culture in orbital shaker at 37° C. at 210 rpm for 16 hours (overnight).
Growth and Induction in Minimal Medium:

Prepared the minimal salt medium for growth and production as mentioned in Table 5. pH of the medium was adjusted to 7.0±0.3. The growth and production medium was autoclaved at 121° C. at 15 psi for 15 min.

Before inoculation, 500 μL carbenicillin (from 100 mg/mL stocks), 500 μL Thiamine HCL (from 1 M sterile stocks), 2.5 mL sterile glucose (from 40% sterile stocks) and 320 μL potassium phosphate (from 1M KH2PO4) was added. 8% of overnight grown culture (Pre-inoculum) was transferred to Growth medium. Initial OD (at 600 nm), Glucose concentration and Phosphate concentration of the culture were measured in the Growth medium.

The culture flask was incubated at 37° C., 210 rpm for 7-8 hours (till the OD reached in between 2-2.5). The OD (at 600 nm), Glucose concentration and Phosphate concentration of the culture was checked in the Growth medium after 8 hours of growth. Spun the culture at 4000 rpm, +30° C. for 15 mins. The cell pellet was washed with minimal medium (without phosphate) and spun it again at 4000 rpm for 15 mins. The supernatant was drained slowly. Suspended the cell pellet in 500 mL. Production medium with low phosphate concentration. The culture flask was incubated at 30° C., 210 rpm for 16 hours. OD (at 600 nm), Glucose concentration and Phosphate concentration of the harvest culture was checked. The expressed culture was spun at 4300 G, +4° C. for 30 mins. Anti-VEGF Fab expression was checked by SDS-PAGE and quantified the expression level by ELISA.
Expression of Anti-VEGF Fab-201 in 2.5 L Fermentation Salt Medium
Expression in 2.5 L Fermenter:

Anti-VEGF antibody was produced in large scale using fermentation process in 3.7 L fermenter.
Inoculum Preparation:

For each 2.5 L fermentation, inoculated 20 pd of frozen working cell bank of E. coli BL21-201 in 250 ml sterile LB broth containing carbenicillin antibiotic (250 μl from 100 mg/ml stock). The culture flask was incubated in orbital shaker at 37° C. at 210 rpm for 16 hours (overnight).
High Cell Density Fermentation in Minimal Salt Medium:

The minimal salt medium for 2.5 L fermentation culture was prepared. Adjusted the medium pH to 7.0±0.3 by Ammonium hydroxide (25%). The minimal salt medium was sterilized in 3.7 L fermenter at 121° C. at 15 psi for 20 mins.

Before inoculation, 2.5 mL carbenicillin (from 100 mg/mL stocks), 2.5 mL Thiamine HCL (from 1 M sterile stocks), 2.5 mL trace elements, 300 μl L-61 antifoam, and 100 mL sterile glucose solution (containing 40 g of glucose) were added. Calibrated and set the DO level to 100% before inoculum transfer. After Do calibration, transferred 10% (250 mL) of overnight grown culture (Inoculum) in the fermenter medium. The initial OD (at 600 nm), Glucose concentration and Phosphate concentration of the culture in the fermentation medium were checked.

Fermentation was performed at 37° C. at 3 lpm of air flow and was controlled at a pH of 7.0±0.3 by ammonium hydroxide (25%). The back pressure of the fermenter was maintained at 0.5 bar gauge and the agitation rate was set to 500 rpm. Maintained the minimum DO level to 30% during the fermentation by increasing agitation from 500 to 1200 rpm (agitation was increased in a gradual manner), and by keeping the back pressure in the fermenter. The Culture OD (at 600 nm) reached to 1812 in 12 hours, at this point the computer-based feeding was started to achieve the high cell density culture. The concentrated feed contained glucose (450 g), 25 ml of 1 M magnesium sulphate, 25 ml of 20× salt medium and 50 ml of 1M potassium phosphate. The concentrated feed was added to the fermenter and started at a flow rate of 1 ml/min for 18 hours. When the fermenter culture reached the OD (at 600 nm) around 120±10, in-parallel the phosphate concentration was measured. At 21±2 hours the phosphate concentration in the fermentation culture was below 0.05 mM, at this point the fermentation temperature was gradually changed from 37° C. to 30° C. The Induction was started, when the phosphate concentration in the fermentation culture was below than 0.05 mM. The post induction was carried out for 10 hours at 30° C. and 1200 rpm. Minimum dissolved oxygen level (30%) was maintained for high cell density culture with the addition of pure oxygen. The mixture of air and pure oxygen was pumped at the flow of 4 lpm at 30° C. to maintained the dissolved oxygen set point. OD (at 600 nm), Glucose concentration and Phosphate concentration of the fermentation culture were measured after induction. Spun the culture at 4300 G, +4° C. for 30 mins and discarded the supernatant. The anti-VEGF Fab-201 purifications were performed and expression was checked by SDS-PAGE and quantified by ELISA.

Fermentation data and expression yield are shown in FIG. 21.

Example 7

Downstream Process Information for Synthetic Antibodies Against VEGF
Cell Pellet Suspension and Lysis:

Lysis of *E. coli* cell pellet was carried out using lysis buffer (Lysis Buffer—200 mM Phosphate buffer, pH 7.4, 400 mM Sodium Chloride, 10 mM Phenyl Methane Sulfonyl Fluoride (PMSF), 2 mM EDTA, 5% Sucrose, 1% Triton X-100. About 446 grams of wet weight of cell pellet was suspended in 4.0 L of lysis buffer (approx. at 1:10 ratio) at room temperature and the cell pellet was mixed vigorously until a homogeneous cell suspension is obtained. Since the pellet was taken from –80° C. and lysis performed at room temperature, due to extreme temperature difference and high buffer strength coupled with salt concentration results in the formation of osmotic shock on the bacterial cell wall making it highly porous for free flow of molecules from periplasmic region. This method is not sufficient to release the proteins and requires further treatment with high pressure homogenizer.

The cell paste so obtained was passed through GIA-homogenizer for three continuous passes at 800 bar pressure at 4° C. temperature. Microscopic examination was carried out after each pass to make sure about complete lysis has happened.
Heating and Centrifugation:

The homogenized lysate was heated at 65° C. for an hour in waterbath and then, chilled on ice for 20 minutes. The chilled lysate was clarified by centrifuging at 17,000 g for 30 minutes under 4° C. Further, the clarified lysate was concentrated by 6 times the initial volume of the lysate using 10 KDa by Tangential Flow Filtration.
Step 1 Purification by Capto-L:

A volume of 20 ml of GE Capto L was packed in XK16/20 column was equilibrated with 0.2 M sodium phosphate, pH 7.4, containing 0.4M sodium chloride. The concentrated lysate was loaded at flowrate of 4 mL/minute and washed with the equilibration buffer. Saksin Fab-201 was eluted using buffer containing 0.2 M glycine-Cl/2% sucrose, pH 2.0 and collected eluate was immediately neutralized with 1.5 M Tris-Cl, pH 8.8.
Step 2 Purification by Q-Sepharose:

The first elution from capto-L chromatography was dialysed against 20 mM sodium phosphate buffer, at pH 7.3 and polished using 10 mL of anion exchange resin GE Q sepharose in order to remove endotoxins and HCDNAs. The purified fab was collected as flowthrough.
Step 3 Purification by SP-Sepharose:

The flowthrough from Q-sepharose was loaded onto 15 mL of cation exchange GE SP sepharose resin packed in XK26/20. Resin was washed with slightly increased conductivity, and elution of bound proteins including Fab was carried out by gradient elution at a conductivity of 14-16 mS/cm. Tightly bound proteins were eluted with 1 M sodium chloride with buffer. The drug substance was dialysed against 20 mM PB pH-5.6 and sterile (0.22 μm) filtered finally.

Example 8

Stability of Formulated FAB 201 as a Drug

Drug substance Fab 201, was subjected to formulation (Drug product) to increase the stability characteristics to facilitate intravitreal injections for wet AMD. The drug product DP_201 was formulated in a concentration range between 5 to 10 mg/mL In addition to the API, the formulation contains in 10 mM phosphate buffer/40 mM NaCl/ 0.03% polysorbate 20/5% sucrose solution at pH 5.8. The osmolarity of the formulation is approx. 276 mOsm, comparable to human intra-vitreal fluid.

The stability was analysed with respect to quantitative ELISA and SDS PAGE. The data suggests that the Drug product is stable for 8 months (240 days) at 4° C., as depicted in FIG. 22.

Example 9

Anti-Angiogenic Chronic Study in Rabbit Eye

A study was conducted to evaluate efficacy and sustainability of an anti VEGF (Vascular Endothelial Growth Factor) Fab (Fragment Antigen Binding) protein (Test Molecule #201) discovered by Saksin Lifesciences Pvt. Ltd., TICEL Bio-Park Facility, Taramani, Chennai, India in the VEGF induced retinal leakage model rabbits (Dutch Belted, 3-4 months old males, body weight—1.0-1.3 kg) compared to commercially available Lucentis. The study was conducted at PharmOptima, LLC, Portage MI, USA. Groups of the rabbits were treated with test Molecule #201 (150 μg in 50 μL Formulation buffer), Lucentis (150 μg in 50 μL Formulation buffer), or Vehicle (50 μL Formulation buffer) on Day 0 by intravitreal administration (IVT). Animals from each group then received VEGF challenge on Days 7, 21 or 37 by IVT to determine whether the efficacy was sustained over time.

Prior to IVT administrations (Test Molecule #201, Lucentis, Vehicle or VEGF), the rabbit was anaesthetized with Isoflurane vapors to effect. Prior to injection, each eye was moistened with an ophthalmic Betadine solution and rinsed. Proparacaine (0.5%) was applied to the ocular surface, the eye was held open with an eye speculum and the pars plana was marked ~4.0 mm from the limbus with calipers. The test Molecule was then delivered through the pars plana into the mid vitreous at an angle to avoid the lens.

Fluorescein Angiograms (FAs) were conducted on all animals on 3rd day after VEGF challenge. Eyes were anesthetized with proparacaine and pupils dilated with tropicamide and EyePrim. Animals were anesthetized with isoflurane vapors to effect, and 0.1 mL of 10% ophthalmic sodium fluorescein was administered in the rabbit ear vein and allowed to circulate for at least 2 minutes prior to imaging. Images were graded using a standard scoring system given below (Table 6):

TABLE 6

Scoring System for Fluorescein Imaging

| Score | Description |
|---|---|
| 0 | Major vessels very straight, with some tortuosity of smaller vessels |
| 1 | Increased tortuosity of major vessels and or vessel dilation |
| 2 | Leakage between major vessels |
| 3 | Leakage between major and minor vessels. Minor vessels still visible. |
| 4 | Leakage between major and minor vessels. Minor vessels not visible. |

Following terminal FAs, animals were euthanized by intravenous barbiturate overdose. Eyes were harvested and vitreous, aqueous humor and retina was collected. All samples were stored at −80° C. for further analysis.

Scores of both the eyes were subjected to Kruskal-Wallis one way ANOVA to find the significant difference among the Groups. Data showing significant difference were subjected to Dunn's test for determining significant difference between the Groups.

VEGF challenge 1 week after test Molecule #201 administration resulted in the expected amount of leakage in the vehicle injected group and full protection from both Lucentis and Test Molecule #201. VEGF challenge 3 weeks after Test Molecule #201 administration resulted in the expected amount of leakage in the vehicle treated group, and a significantly greater protection in the Test Molecule #201 treated rabbits than that of Lucentis treated rabbits. VEGF challenge 5 weeks after test Molecule #201 administration resulted in the expected amount of leakage in the vehicle injected group, but no protection from both Lucentis and test Molecule #201 (Table 7).

TABLE 7

Fluorescein Imaging Scores of VEGF Challenged Rabbits after 1, 3 and 5 Weeks Test Molecule Administration

| Treatment | Week 1 | Week 3 | Week 5 |
|---|---|---|---|
| Test Molecule #201 | $0.17 \pm 0.39^a$ | $1.25 \pm 0.89^a$ | $3.25 \pm 0.45^a$ |
| Lucentis | $0.00 \pm 0.00^a$ | $2.88 \pm 0.35^b$ | $3.08 \pm 0.51^a$ |
| Vehicle | $3.50 \pm 0.47^b$ | $3.67 \pm 0.49^c$ | $3.50 \pm 0.52^a$ |

Values are expressed as mean±SD. Values showing similar superscripts in any single column are statistically the same (Dunn's test).

Conclusion

From the study, it may be concluded that sustainability of efficacy of Test Molecule #201 was significantly greater than that of Lucentis in the VEGF-induced retinal leakage model rabbits, following VEGF challenge 3 weeks after test Molecule #201 administration. The molecular basis for this efficacy may be attributable to the differences in the CDRs of Fab 201 compared to Lucentis as shown in FIGS. 23 and 24.

What is claimed is:

1. An isolated anti-VEGF antibody or antigen-binding portion thereof that specifically recognizes and binds a VEGF comprising CDRH 1-3 from a heavy chain fragment comprising the amino acid sequence: EVQLVESGGGL-VQPGGSLRLSCAASGFDLFHYSIHWVRQAPGKGLE-WVAYIYPS YGYTYYADSVKGRFTISADTSKNTAYLQ-MNSLRAEDTAVYYCARHAWYYGWGLDYWGQGT-LVTVSSASTKGPSVFPLAPSSKSTSGGTAALGCLVK-DYFPEPVTVS WNSGALTSGVHTFPAVLQSSGLYSLS-SVVTVPSSSLGTQTYICNVNHKPSNTKVD KKVEPKS-CDKTHT of SEQ ID NO: 2 and CDRL1-3 from a light chain comprising the amino acid sequence: DIQMTQS-PSSLSASVGDRVTITCRASQAAYGRVAWYQQKPGK-APKLLIYKASEL YAGVPSRFSGSRSGTDFTLTISSLQ-PEDFATYYCQQRGWYLFTFGQGTKVEIKRT VAAPS-VFIFPPSDEQLKSGTASVVCLLNNFYPREAKVQWKV-DNALQSGNSQESV TEQDSKDSTYSLSSTLTLSKAD-YEKHKVYACEVTHQGLSSPVTKSFNRGEC of SEQ ID NO: 4; or CDRH 1-3 from a heavy chain fragment comprising the amino acid sequence: EVQLVESGGGLVQPG-GSLRLSCAASGFDLDHYSIHWVRQAPGKGLEW-VAYIYPS YGYTYYADSVKGRFTISADTSKNTAY-LQMNSLRAEDTAVYYCARHAWYYGWG LDYW-GQGTLVTVSSASTKGPSVFPLAPSSKSTSGGT-AALGCLVKDYFPEPVTVS WNSGALTSGVHTFP-AVLQSSGLYSLSSVVTVPSSSLGTQTYICNVNH-KPSNTKVD KKVEPKSCDKTHT of SEQ ID NO: 78 and CDRL1-3 from a light chain comprising the amino acid sequence: DIQMTQSPSSLSASVGDRVTIT-CRASQAAYGRVAWYQQKPGKAPKLLIYKASEL YAGVPSRFSGSRSGTDFTLTISSLQPEDFATYY-CQQRGWYLFTFGQGTKVEIKRT VAAPSV- FIFPP-SDSQLKSGTASVVCLLNNFYPREAKVQWKVD-NALQSGNSQESV TEQDSKDSTYSLSSTLTLSKA-DYEKHKVYACEVTHQGLSSPVTKSFNRGEC of SEQ ID NO: 76.

2. The anti-VEGF antibody of claim 1 which is a full length antibody.

3. The anti-VEGF antibody of claim 2, wherein the full length antibody comprises (a) a light chain comprising the amino acid sequence shown in SEQ ID NO: 4 and a heavy chain shown in SEQ ID NO: 2; (b) a light chain comprising the aspartic acid at amino acid position 24 to cysteine at amino acid position 237 of SEQ ID NO:17 and a heavy chain comprising the glutamic acid at amino acid position 24 to threonine at amino acid position 251 of SEQ ID NO:18; or (c) a light chain comprising the sequences shown in SEQ ID NO:76 and a heavy chain comprising sequences shown in SEQ ID NO:78.

4. The anti-VEGF antibody of claim 1 which is human or humanized.

5. The anti-VEGF antibody of claim 1 wherein the antigen-binding portion of the antibody is an antibody fragment.

6. The anti-VEGF antibody of claim 5, wherein the antibody fragment is a Fab.

7. The anti-VEGF antibody of claim 6, wherein the Fab is joined to a Fc region.

8. The anti-VEGF antibody of claim 5, wherein the antibody fragment is a scFv.

9. A bispecific antibody with a binding specificity for two different antigens, one of the antigens being that with which the antibody of claim 1 binds and wherein the bispecific antibody comprises an amino acid sequence comprising the amino acid sequence for CDRH1 of claim 1, CDRH2 of claim 1, CDRH3 of claim 1, CDRL1 of claim 1, CDRL2 of claim 1, and CDRL3 of claim 1.

10. The anti-VEGF antibody of claim 1 which is a monoclonal antibody, a chimeric antibody, a humanized antibody, a human antibody, a synthetic antibody, a single chain antibody or an antigen-binding fragment thereof.

11. A composition comprising the anti-VEGF antibody of claim 1 and a pharmaceutically acceptable carrier.

12. A method for inhibiting VEGF-induced angiogenesis in a mammal comprising administering a therapeutically effective amount of the anti-VEGF antibody or antigen-binding portion thereof of claim 1 that specifically recognizes and binds a VEGF comprising a heavy chain variable domain comprising the following hypervariable region or complementarity determining region (CDR) amino acid sequences: CDRH1 comprising histidine at amino acid position 31 to histidine at amino acid position 35 of SEQ ID NO: 2, CDRH2 comprising tyrosine at amino acid position 50 to glycine at amino acid position 66 of SEQ ID NO: 2 and CDRH3 comprising histidine at amino acid position 99 to tyrosine at amino acid position 109 of SEQ ID NO: 2 to the mammal.

13. The method of claim 12, wherein the mammal has a disease selected from retinal disorder, wet age-related macular degeneration, diabetic maculopathy, proliferative diabetic retinopathy, macular edema in retinal vein occlusion (RVO), iris neovascularization, choroidal neovascularization caused by pathological myopia, retinopathy of prematurity (ROP), retinopathy of maturity, neovascular glaucoma, and cancer.

14. The method of claim 13, wherein the retinal disorder is associated with poor vision at night (night blindness), trouble adjusting from brightly lit to dim areas, sudden or unexplained loss of vision, loss of peripheral vision, loss of vision in a particular visual field, a rapid, involuntary oscillatory motion of the eyeball (nystagmus), abnormal sensitivity to or intolerance of light (photophobia) or a combination thereof.

15. A method for inhibiting a cell proliferative disorder in a mammal comprising administering a therapeutically effective amount of the anti-VEGF antibody or antigen-binding portion thereof of claim 1 to the mammal.

16. The method of claim 15, wherein the cell proliferative disorder is selected from the group consisting of wet age related macular degeneration, diabetic maculopathy, proliferative diabetic retinopathy, macular edema in retinal vein occlusion (RVO), iris neovascularization, choroidal neovascularization caused by pathological myopia, retinopathy of maturity, neovascular glaucoma, diabetic retinopathy, retinal neovascularization, pars plana vitrectomy (PPV), diabetic macular edema (DME) and cancer.

17. A method for inhibiting macular degeneration in a mammal comprising administering a therapeutically effective amount of the humanized anti-VEGF antibody or antigen-binding portion thereof of claim 4 to the mammal.

* * * * *

SEQUENCE LISTING

```
<160> NUMBER OF SEQ ID NOS: 156

<210> SEQ ID NO 1
<211> LENGTH: 684
<212> TYPE: DNA
<213> ORGANISM: Artificial Sequence
<220> FEATURE:
<223> OTHER INFORMATION: Ig heavy chain of a synthetic humanized anti-
      VEGF Fab antibody fragment, Fab FF03046-2, comprising a variable
      region with an optimized human framework & affinity matured
      CDR-H1, -H2 and -H3 against mouse & human VEGF & a constant region
      with a CH1 domain
<220> FEATURE:
<221> NAME/KEY: CDS
<222> LOCATION: (1)..(684)
<223> OTHER INFORMATION: Coding sequence for Ig heavy chain fragment of
      Fab FF03046-2 antibody comprising a variable region with an
      optimized human framework and affinity matured CDR-H1, -H2 & -H3
      against mouse and human VEGF and a constant region with a CH1
      domain and a
<220> FEATURE:
<221> NAME/KEY: misc_feature
```

-continued

<222> LOCATION: (1)..(360)
<223> OTHER INFORMATION: Coding sequence of variable region of Fab
      FF03046-2 antibody heavy chain
<220> FEATURE:
<221> NAME/KEY: misc_feature
<222> LOCATION: (76)..(99)
<223> OTHER INFORMATION: coding sequence of complementarity determining
      region, CDR-H1, as defined in accordance with IMGT
<220> FEATURE:
<221> NAME/KEY: misc_feature
<222> LOCATION: (91)..(105)
<223> OTHER INFORMATION: coding sequence of complementarity determining
      region, CDR-H1, as defined in accordance with Kabat
<220> FEATURE:
<221> NAME/KEY: misc_feature
<222> LOCATION: (148)..(198)
<223> OTHER INFORMATION: coding sequence of complementarity determining
      region, CDR-H2, as defined in accordance with Kabat
<220> FEATURE:
<221> NAME/KEY: misc_feature
<222> LOCATION: (151)..(174)
<223> OTHER INFORMATION: coding sequence of complementarity determining
      region, CDR-H2, as defined in accordance with IMGT
<220> FEATURE:
<221> NAME/KEY: misc_feature
<222> LOCATION: (289)..(327)
<223> OTHER INFORMATION: coding sequence of complementarity determining
      region, CDR-H3, as defined in accordance with IMGT
<220> FEATURE:
<221> NAME/KEY: misc_feature
<222> LOCATION: (295)..(327)
<223> OTHER INFORMATION: coding sequence of complementarity determining
      region, CDR-H3, as defined in accordance with Kabat
<220> FEATURE:
<221> NAME/KEY: misc_feature
<222> LOCATION: (361)..(684)
<223> OTHER INFORMATION: Coding sequence of Fab FF03046-2 antibody heavy
      chain constant region comprising a CH1 domain and part of a hinge
      region
<220> FEATURE:
<221> NAME/KEY: misc_feature
<222> LOCATION: (361)..(654)
<223> OTHER INFORMATION: Coding sequence of CH1 domain of Fab FF03046-2
      antibody heavy chain constant region
<220> FEATURE:
<221> NAME/KEY: misc_feature
<222> LOCATION: (655)..(684)
<223> OTHER INFORMATION: Coding sequence for portion of the hinge region
      of Fab FF03046-2 antibody heavy chain constant region <400> SEQUENCE: 1 gag gtt cag ctg gtg gag tct ggc ggt ggc ctg gtg cag cca ggg ggc        48
Glu Val Gln Leu Val Glu Ser Gly Gly Gly Leu Val Gln Pro Gly Gly
1               5                   10                  15 tca ctc cgt ttg tcc tgt gca gct tct ggc ttc gat tta ttt cat tat        96
Ser Leu Arg Leu Ser Cys Ala Ala Ser Gly Phe Asp Leu Phe His Tyr
            20                  25                  30 tct ata cac tgg gtg cgt cag gcc ccg ggt aag ggc ctg gaa tgg gtt       144
Ser Ile His Trp Val Arg Gln Ala Pro Gly Lys Gly Leu Glu Trp Val
        35                  40                  45 gca tac att tac ccg tct tat ggc tat act tat tat gcc gat agc gtc       192
Ala Tyr Ile Tyr Pro Ser Tyr Gly Tyr Thr Tyr Tyr Ala Asp Ser Val
    50                  55                  60 aag ggc cgt ttc act ata agc gca gac aca tcc aaa aac aca gcc tac       240
Lys Gly Arg Phe Thr Ile Ser Ala Asp Thr Ser Lys Asn Thr Ala Tyr
65                  70                  75                  80 cta caa atg aac agc tta aga gct gag gac act gcc gtc tat tat tgt       288
Leu Gln Met Asn Ser Leu Arg Ala Glu Asp Thr Ala Val Tyr Tyr Cys
                85                  90                  95 gct cgc cat gcg tgg tat tat ggg tgg ggt ttg gac tac tgg ggt caa       336
Ala Arg His Ala Trp Tyr Tyr Gly Trp Gly Leu Asp Tyr Trp Gly Gln
            100                 105                 110

-continued

```
gga acc ctg gtc acc gtc tcc tcg gct agc acc aag ggc cca tcg gtc      384
Gly Thr Leu Val Thr Val Ser Ser Ala Ser Thr Lys Gly Pro Ser Val
        115             120             125 ttc ccc ctg gca ccc tcc tcc aag agc acc tct ggg ggc aca gcg gcc      432
Phe Pro Leu Ala Pro Ser Ser Lys Ser Thr Ser Gly Gly Thr Ala Ala
    130             135             140 ctg ggc tgc ctg gtc aag gac tac ttc ccc gaa ccg gtg acg gtg tcg      480
Leu Gly Cys Leu Val Lys Asp Tyr Phe Pro Glu Pro Val Thr Val Ser
145             150             155             160 tgg aac tca ggc gcc ctg acc agc ggc gtg cac acc ttc ccg gct gtc      528
Trp Asn Ser Gly Ala Leu Thr Ser Gly Val His Thr Phe Pro Ala Val
            165             170             175 cta cag tcc tca gga ctc tac tcc ctc agc agc gtg gtg acc gtg ccc      576
Leu Gln Ser Ser Gly Leu Tyr Ser Leu Ser Ser Val Val Thr Val Pro
            180             185             190 tcc agc agc ttg ggc acc cag acc tac atc tgc aac gtg aat cac aag      624
Ser Ser Ser Leu Gly Thr Gln Thr Tyr Ile Cys Asn Val Asn His Lys
            195             200             205 ccc agc aac acc aag gtg gac aag aaa gtt gag ccc aaa tct tgt gac      672
Pro Ser Asn Thr Lys Val Asp Lys Lys Val Glu Pro Lys Ser Cys Asp
    210             215             220 aaa act cac aca                                                       684
Lys Thr His Thr
225
```

```
<210> SEQ ID NO 2
<211> LENGTH: 228
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5               10              15

Ser Leu Arg Leu Ser Cys Ala Ala Ser Gly Phe Asp Leu Phe His Tyr
            20              25              30

Ser Ile His Trp Val Arg Gln Ala Pro Gly Lys Gly Leu Glu Trp Val
            35              40              45

Ala Tyr Ile Tyr Pro Ser Tyr Gly Tyr Thr Tyr Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ala Arg His Ala Trp Tyr Tyr Gly Trp Gly Leu Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190
```

-continued

---

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225

<210> SEQ ID NO 3
<211> LENGTH: 642
<212> TYPE: DNA
<213> ORGANISM: Artificial Sequence
<220> FEATURE:
<223> OTHER INFORMATION: Ig light chain of a synthetic humanized anti-
      VEGF Fab antibody fragment, Fab FF03046-2, comprising a variable
      region with an optimized human framework and affinity matured
      CDR-L1, L2 and L3 against mouse and human VEGF and a kappa light
      chain constant
<220> FEATURE:
<221> NAME/KEY: CDS
<222> LOCATION: (1)..(642)
<223> OTHER INFORMATION: Coding sequence for immunoglobulin kappa light
      chain of Fab FF03046-2 antibody comprising a variable region with
      an optimized human framework and affinity matured CDR-L1, CDR-L2
      and CDR-L3 against mouse and human VEGF and a kappa light chain
      constant
<220> FEATURE:
<221> NAME/KEY: misc_feature
<222> LOCATION: (1)..(321)
<223> OTHER INFORMATION: coding sequence of variable region of Fab
      FF03046-2 antibody kappa light chain
<220> FEATURE:
<221> NAME/KEY: misc_feature
<222> LOCATION: (70)..(102)
<223> OTHER INFORMATION: coding sequence of complementarity determining
      region, CDR-L1, as defined in accordance with Kabat
<220> FEATURE:
<221> NAME/KEY: misc_feature
<222> LOCATION: (79)..(96)
<223> OTHER INFORMATION: coding sequence of complementarity determining
      region, CDR-L1, as defined in accordance with IMGT
<220> FEATURE:
<221> NAME/KEY: misc_feature
<222> LOCATION: (148)..(168)
<223> OTHER INFORMATION: coding sequence of complementarity determining
      region, CDR-L2, as defined in accordance with Kabat
<220> FEATURE:
<221> NAME/KEY: misc_feature
<222> LOCATION: (148)..(156)
<223> OTHER INFORMATION: coding sequence of complementarity determining
      region, CDR-L2, as defined in accordance with IMGT
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with Kabat
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with IMGT
<220> FEATURE:
<221> NAME/KEY: misc_feature
<222> LOCATION: (322)..(642)
<223> OTHER INFORMATION: coding sequence of constant region of Fab
      FF03046-2 antibody kappa light chain
<220> FEATURE:
<221> NAME/KEY: misc_feature
<222> LOCATION: (367)..(369)
<223> OTHER INFORMATION: GAG codon encoding amino acid glutamic acid at
      amino acid position 123 of kappa light chain constant region of
      Fab FF03046-2, which differs from TCA codon encoding serine in
      Clone #201

<400> SEQUENCE: 3 gat atc cag atg acc cag tcc ccg agc tcc ctg tcc gcc tct gtg ggc          48

```
Asp Ile Gln Met Thr Gln Ser Pro Ser Ser Leu Ser Ala Ser Val Gly
1               5                   10                  15 gat agg gtc acc atc acc tgc cgt gcc agt cag gcc gcc tac ggc cgc      96
Asp Arg Val Thr Ile Thr Cys Arg Ala Ser Gln Ala Ala Tyr Gly Arg
            20                  25                  30 gta gcc tgg tat caa cag aaa cca gga aaa gct ccg aag ctt ctg att     144
Val Ala Trp Tyr Gln Gln Lys Pro Gly Lys Ala Pro Lys Leu Leu Ile
        35                  40                  45 tac aaa gca tcc gaa ctc tac gcc gga gtc cct tct cgc ttc tct ggt     192
Tyr Lys Ala Ser Glu Leu Tyr Ala Gly Val Pro Ser Arg Phe Ser Gly
    50                  55                  60 agc cgt tcc ggg acg gat ttc act ctg acc atc agc agt ctg cag ccg     240
Ser Arg Ser Gly Thr Asp Phe Thr Leu Thr Ile Ser Ser Leu Gln Pro
65                  70                  75                  80 gaa gac ttc gca act tat tac tgt cag caa cgt ggc tgg tat ctg ttc     288
Glu Asp Phe Ala Thr Tyr Tyr Cys Gln Gln Arg Gly Trp Tyr Leu Phe
                85                  90                  95 acg ttc gga cag ggt acc aag gtg gag atc aaa cgt acg gtg gct gca     336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tgt                                              642
Phe Asn Arg Gly Glu Cys
    210
```

```
<210> SEQ ID NO 4
<211> LENGTH: 214
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ala Tyr Gly Arg
            20                  25                  30

Val Ala Trp Tyr Gln Gln Lys Pro Gly Lys Ala Pro Lys Leu Leu Ile
        35                  40                  45

Tyr Lys Ala Ser Glu Leu Tyr Ala Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Arg Gly Trp Tyr Leu Phe
             85              90              95

Thr Phe Gly Gln Gly Thr Lys Val Glu Ile Lys Arg Thr Val Ala Ala
             100             105             110

Pro Ser Val Phe Ile Phe Pro Pro Ser Asp Glu Gln Leu Lys Ser Gly
         115             120             125

Thr Ala Ser Val Val Cys Leu Leu Asn Asn Phe Tyr Pro Arg Glu Ala
     130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
             165             170             175

Ser Thr Leu Thr Leu Ser Lys Ala Asp Tyr Glu Lys His Lys Val Tyr
         180             185             190

Ala Cys Glu Val Thr His Gln Gly Leu Ser Ser Pro Val Thr Lys Ser
     195             200             205

Phe Asn Arg Gly Glu Cys
     210
```

```
<210> SEQ ID NO 5
<211> LENGTH: 1404
<212> TYPE: DNA
<213> ORGANISM: Artificial Sequence
<220> FEATURE:
<223> OTHER INFORMATION: Synthetic humanized antibody FF03092-1 heavy
      chain used to form a humanized anti-VEGF Fc-Fab fusion comprising
      an amino terminal humanized immunoglobulin Fc fragment fused to a
      humanized Fab fragment
<220> FEATURE:
<221> NAME/KEY: CDS
<222> LOCATION: (1)..(1404)
<223> OTHER INFORMATION: Synthetic humanized antibody FF03092-1 heavy
      chain fusion used to form a humanized anti-VEGF Fc-Fab fusion
      comprising an amino terminal humanized immunoglobulin Fc fragment
      fused to a humanized Fab fragment
<220> FEATURE:
<221> NAME/KEY: misc_feature
<222> LOCATION: (1)..(666)
<223> OTHER INFORMATION: coding sequence for Fc fragment of synthetic
      humanized anti-VEGF antibody FF03092-1, a humanized anti-VEGF
      Fc-Fab fusion comprising an amino terminal humanized
      immunoglobulin Fc fragment fused to a humanized Fab fragment
<220> FEATURE:
<221> NAME/KEY: misc_feature
<222> LOCATION: (1)..(15)
<223> OTHER INFORMATION: coding sequence for the hinge region of the Fc
      fragment of synthetic humanized anti-VEGF antibody FF03092-1, as
      defined in accordance with IMGT
<220> FEATURE:
<221> NAME/KEY: misc_feature
<222> LOCATION: (16)..(345)
<223> OTHER INFORMATION: coding sequence for the CH2 domain of the Fc
      fragment of synthetic humanized anti-VEGF antibody FF03092-1, as
      defined in accordance with IMGT
<220> FEATURE:
<221> NAME/KEY: misc_feature
<222> LOCATION: (346)..(666)
<223> OTHER INFORMATION: coding sequence for the CH3 domain of the Fc
      fragment of synthetic humanized anti-VEGF antibody FF03092-1, as
      defined in accordance with IMGT
<220> FEATURE:
<221> NAME/KEY: misc_feature
<222> LOCATION: (667)..(720)
<223> OTHER INFORMATION: coding sequence for a linker between Fc
      fragment and Fab heavy chain of synthetic humanized anti-VEGF
      antibody FF03092-1, a humanized anti-VEGF Fc-Fab fusion comprising
      an amino terminal humanized immunoglobulin Fc fragment fused to a
      humanized Fab
<220> FEATURE:
```

-continued

```
<221> NAME/KEY: misc_feature
<222> LOCATION: (721)..(1404)
<223> OTHER INFORMATION: coding sequence for Fab heavy chain of
      synthetic humanized anti-VEGF antibody FF03092-1, a humanized
      anti-VEGF Fc-Fab fusion comprising an amino terminal humanized
      immunoglobulin Fc fragment fused to a humanized Fab fragment
<220> FEATURE:
<221> NAME/KEY: misc_feature
<222> LOCATION: (721)..(1080)
<223> OTHER INFORMATION: coding sequence for variable region of Fab
      heavy chain of synthetic humanized anti-VEGF antibody FF03092-1,
      as defined in accordance with IMGT
<220> FEATURE:
<221> NAME/KEY: misc_feature
<222> LOCATION: (796)..(819)
<223> OTHER INFORMATION: coding sequence of complementarity determining
      region, CDR-H1, as defined in accordance with IMGT
<220> FEATURE:
<221> NAME/KEY: misc_feature
<222> LOCATION: (811)..(825)
<223> OTHER INFORMATION: coding sequence of complementarity determining
      region, CDR-H1, as defined in accordance with Kabat
<220> FEATURE:
<221> NAME/KEY: misc_feature
<222> LOCATION: (868)..(918)
<223> OTHER INFORMATION: coding sequence of complementarity determining
      region, CDR-H2, as defined in accordance with Kabat
<220> FEATURE:
<221> NAME/KEY: misc_feature
<222> LOCATION: (871)..(894)
<223> OTHER INFORMATION: coding sequence of complementarity determining
      region, CDR-H2, as defined in accordance with IMGT
<220> FEATURE:
<221> NAME/KEY: misc_feature
<222> LOCATION: (1009)..(1047)
<223> OTHER INFORMATION: coding sequence of complementarity determining
      region, CDR-H3, as defined in accordance with IMGT
<220> FEATURE:
<221> NAME/KEY: misc_feature
<222> LOCATION: (1015)..(1047)
<223> OTHER INFORMATION: coding sequence of complementarity determining
      region, CDR-H3, as defined in accordance with Kabat
<220> FEATURE:
<221> NAME/KEY: misc_feature
<222> LOCATION: (1081)..(1374)
<223> OTHER INFORMATION: coding sequence for CH1 domain of the constant
      region of Fab heavy chain of synthetic humanized anti-VEGF
      antibody FF03092-1, as defined in accordance with IMGT
<220> FEATURE:
<221> NAME/KEY: misc_feature
<222> LOCATION: (1375)..(1404)
<223> OTHER INFORMATION: coding sequence for portion of the hinge region
      comprising a cysteine at amino acid position 463 (TGC at
      nucleotide position 1387-1389) that participates in interstrand
      disulfide crosslink with the light chain in FF03092-1 antibody, as
      defined iby IMGT

<400> SEQUENCE: 5 tgc cca ccg tgc cca gca cct gaa ctc ctg ggg gga ccg tca gtc ttc        48
Cys Pro Pro Cys Pro Ala Pro Glu Leu Leu Gly Gly Pro Ser Val Phe
1               5                   10                  15 ctc ttc ccc cca aaa ccc aag gac acc ctc atg atc tcc cgg acc cct        96
Leu Phe Pro Pro Lys Pro Lys Asp Thr Leu Met Ile Ser Arg Thr Pro
                20                  25                  30 gag gtc aca tgc gtg gtg gtg gac gtg agc cac gaa gac cct gag gtc       144
Glu Val Thr Cys Val Val Val Asp Val Ser His Glu Asp Pro Glu Val
            35                  40                  45 aag ttc aac tgg tac gtg gac ggc gtg gag gtg cat aat gcc aag aca       192
Lys Phe Asn Trp Tyr Val Asp Gly Val Glu Val His Asn Ala Lys Thr
        50                  55                  60 aag ccg cgg gag gag cag tac aac agc acg tac cgt gtg gtc agc gtc       240
Lys Pro Arg Glu Glu Gln Tyr Asn Ser Thr Tyr Arg Val Val Ser Val
65                  70                  75                  80
```

-continued

```
ctc acc gtc ctg cac cag gac tgg ctg aat ggc aag gag tac aag tgc       288
Leu Thr Val Leu His Gln Asp Trp Leu Asn Gly Lys Glu Tyr Lys Cys
            85              90                  95 aag gtc tcc aac aaa gcc ctc cca gcc ccc atc gag aaa acc atc tcc       336
Lys Val Ser Asn Lys Ala Leu Pro Ala Pro Ile Glu Lys Thr Ile Ser
            100             105                 110 aaa gcc aaa ggg cag ccc cga gaa cca cag gtg tac acc ctg ccc cca       384
Lys Ala Lys Gly Gln Pro Arg Glu Pro Gln Val Tyr Thr Leu Pro Pro
            115             120                 125 tcc cgg gag gag atg acc aag aac cag gtc agc ctg acc tgc ctg gtc       432
Ser Arg Glu Glu Met Thr Lys Asn Gln Val Ser Leu Thr Cys Leu Val
            130             135                 140 aaa ggc ttc tat ccc agc gac atc gcc gtg gag tgg gag agc aat ggg       480
Lys Gly Phe Tyr Pro Ser Asp Ile Ala Val Glu Trp Glu Ser Asn Gly
145             150             155                 160 cag ccg gag aac aac tac aag acc acg cct ccc gtg ctg gac tcc gac       528
Gln Pro Glu Asn Asn Tyr Lys Thr Thr Pro Pro Val Leu Asp Ser Asp
            165             170                 175 ggc tcc ttc ttc ctc tac agc aag ctc acc gtg gac aag agc agg tgg       576
Gly Ser Phe Phe Leu Tyr Ser Lys Leu Thr Val Asp Lys Ser Arg Trp
            180             185                 190 cag cag ggg aac gtc ttc tca tgc tcc gtg atg cat gag gct ctg cac       624
Gln Gln Gly Asn Val Phe Ser Cys Ser Val Met His Glu Ala Leu His
            195             200                 205 aac cac tac acg cag aag agc ctc tcg ctg agc cct gga aaa ggt ggc       672
Asn His Tyr Thr Gln Lys Ser Leu Ser Leu Ser Pro Gly Lys Gly Gly
            210             215                 220 gga gga tct ggc ggc gga gga agc ggt gga ggc gga agc gga ggc gga       720
Gly Gly Ser Gly Gly Gly Gly Ser Gly Gly Gly Gly Ser Gly Gly Gly
225             230             235                 240 gaa gtg cag ctg gtg gaa tca ggc ggt gga ctg gtg cag cct ggc gga       768
Glu Val Gln Leu Val Glu Ser Gly Gly Gly Leu Val Gln Pro Gly Gly
            245             250                 255 agc tta aga ctg agc tgc gcc gcc agc ggc ttc gac ctg ttc cac tac       816
Ser Leu Arg Leu Ser Cys Ala Ala Ser Gly Phe Asp Leu Phe His Tyr
            260             265                 270 tct atc cac tgg gtc cga cag gcc cct ggc aag gga ctg gaa tgg gtg       864
Ser Ile His Trp Val Arg Gln Ala Pro Gly Lys Gly Leu Glu Trp Val
            275             280                 285 gcc tac atc tac ccc agc tac ggc tac acc tac tac gcc gac agc gtg       912
Ala Tyr Ile Tyr Pro Ser Tyr Gly Tyr Thr Tyr Tyr Ala Asp Ser Val
290             295                 300 aag ggc cgg ttc acc atc agc gcc gac acc agc aag aac acc gcc tac       960
Lys Gly Arg Phe Thr Ile Ser Ala Asp Thr Ser Lys Asn Thr Ala Tyr
305             310             315                 320 ctg cag atg aac agc ctg aga gcc gag gac acc gcc gtg tac tac tgt      1008
Leu Gln Met Asn Ser Leu Arg Ala Glu Asp Thr Ala Val Tyr Tyr Cys
            325             330                 335 gcc aga cac gcc tgg tac tac ggc tgg ggc ctg gat tat tgg ggc cag      1056
Ala Arg His Ala Trp Tyr Tyr Gly Trp Gly Leu Asp Tyr Trp Gly Gln
            340             345                 350 ggc acc ctg gtc acc gtg tct agc gcc tct aca aag ggc ccc agc gtg      1104
Gly Thr Leu Val Thr Val Ser Ser Ala Ser Thr Lys Gly Pro Ser Val
            355             360                 365 ttc cct ctg gcc cct agc agc aag agc aca tct ggc gga aca gcc gcc      1152
Phe Pro Leu Ala Pro Ser Ser Lys Ser Thr Ser Gly Gly Thr Ala Ala
            370             375                 380 ctg ggc tgc ctg gtc aag gac tac ttt ccc gag ccc gtg acc gtg tcc      1200
Leu Gly Cys Leu Val Lys Asp Tyr Phe Pro Glu Pro Val Thr Val Ser
385             390             395                 400
```

```
tgg aac tct ggt gcc ctg acc agc ggc gtg cac acc ttt cca gct gtg      1248
Trp Asn Ser Gly Ala Leu Thr Ser Gly Val His Thr Phe Pro Ala Val
            405                 410                 415 ctg cag agc agc ggc ctg tac agc ctg tcc agc gtg gtc aca gtg cca      1296
Leu Gln Ser Ser Gly Leu Tyr Ser Leu Ser Ser Val Val Thr Val Pro
            420                 425                 430 agc agc agc ctg ggc acc cag acc tac atc tgc aac gtg aac cac aag      1344
Ser Ser Ser Leu Gly Thr Gln Thr Tyr Ile Cys Asn Val Asn His Lys
            435                 440                 445 ccc agc aac acc aag gtg gac aag aag gtg gaa ccc aag agc tgc gac      1392
Pro Ser Asn Thr Lys Val Asp Lys Lys Val Glu Pro Lys Ser Cys Asp
    450                 455                 460 aag acc cac acc                                                      1404
Lys Thr His Thr
465

<210> SEQ ID NO 6
<211> LENGTH: 468
<212> TYPE: PRT
<213> ORGANISM: Artificial Sequence
<220> FEATURE:
<223> OTHER INFORMATION: Synthetic Construct

<400> SEQUENCE: 6

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
            195                 200                 205

Asn His Tyr Thr Gln Lys Ser Leu Ser Leu Ser Pro Gly Lys Gly Gly
    210                 215                 220

Gly Gly Ser Gly Gly Gly Gly Ser Gly Gly Gly Ser Gly Gly Gly
225                 230                 235                 240

Glu Val Gln Leu Val Glu Ser Gly Gly Gly Leu Val Gln Pro Gly Gly
                245                 250                 255
```

-continued

```
Ser Leu Arg Leu Ser Cys Ala Ala Ser Gly Phe Asp Leu Phe His Tyr
        260             265             270

Ser Ile His Trp Val Arg Gln Ala Pro Gly Lys Gly Leu Glu Trp Val
        275             280             285

Ala Tyr Ile Tyr Pro Ser Tyr Gly Tyr Thr Tyr Tyr Ala Asp Ser Val
    290             295             300

Lys Gly Arg Phe Thr Ile Ser Ala Asp Thr Ser Lys Asn Thr Ala Tyr
305             310             315             320

Leu Gln Met Asn Ser Leu Arg Ala Glu Asp Thr Ala Val Tyr Tyr Cys
            325             330             335

Ala Arg His Ala Trp Tyr Tyr Gly Trp Gly Leu Asp Tyr Trp Gly Gln
        340             345             350

Gly Thr Leu Val Thr Val Ser Ser Ala Ser Thr Lys Gly Pro Ser Val
        355             360             365

Phe Pro Leu Ala Pro Ser Ser Lys Ser Thr Ser Gly Gly Thr Ala Ala
    370             375             380

Leu Gly Cys Leu Val Lys Asp Tyr Phe Pro Glu Pro Val Thr Val Ser
385             390             395             400

Trp Asn Ser Gly Ala Leu Thr Ser Gly Val His Thr Phe Pro Ala Val
            405             410             415

Leu Gln Ser Ser Gly Leu Tyr Ser Leu Ser Ser Val Val Thr Val Pro
        420             425             430

Ser Ser Ser Leu Gly Thr Gln Thr Tyr Ile Cys Asn Val Asn His Lys
        435             440             445

Pro Ser Asn Thr Lys Val Asp Lys Lys Val Glu Pro Lys Ser Cys Asp
    450             455             460

Lys Thr His Thr
465
```

```
<210> SEQ ID NO 7
<211> LENGTH: 642
<212> TYPE: DNA
<213> ORGANISM: Artificial Sequence
<220> FEATURE:
<223> OTHER INFORMATION: Synthetic humanized antibody FF03092-1 kappa
      light chain used to form a humanized anti-VEGF Fc-Fab fusion
      comprising an amino terminal humanized immunoglobulin Fc fragment
      fused to a humanized Fab fragment
<220> FEATURE:
<221> NAME/KEY: CDS
<222> LOCATION: (1)..(642)
<223> OTHER INFORMATION: coding sequence for synthetic humanized
      antibody FF03092-1 kappa light chain
<220> FEATURE:
<221> NAME/KEY: misc_feature
<222> LOCATION: (1)..(321)
<223> OTHER INFORMATION: coding sequence for synthetic humanized
      antibody FF03092-1 kappa light chain variable domain
<220> FEATURE:
<221> NAME/KEY: misc_feature
<222> LOCATION: (70)..(102)
<223> OTHER INFORMATION: coding sequence of complementarity determining
      region, CDR-L1, as defined in accordance with Kabat
<220> FEATURE:
<221> NAME/KEY: misc_feature
<222> LOCATION: (79)..(96)
<223> OTHER INFORMATION: coding sequence of complementarity determining
      region, CDR-L1, as defined in accordance with IMGT
<220> FEATURE:
<221> NAME/KEY: misc_feature
<222> LOCATION: (148)..(168)
<223> OTHER INFORMATION: coding sequence of complementarity determining
      region, CDR-L2, as defined in accordance with Kabat
<220> FEATURE:
<221> NAME/KEY: misc_feature
```

<222> LOCATION: (148)..(156)
<223> OTHER INFORMATION: coding sequence of complementarity determining
      region, CDR-L2, as defined in accordance with IMGT
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with Kabat
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with IMGT
<220> FEATURE:
<221> NAME/KEY: misc_feature
<222> LOCATION: (322)..(642)
<223> OTHER INFORMATION: coding sequence for synthetic humanized
      antibody FF03092-1 kappa light chain constant domain
<220> FEATURE:
<221> NAME/KEY: misc_feature
<222> LOCATION: (640)..(642)
<223> OTHER INFORMATION: codon for cysteine at amino acid position 214
      which participates in interstrand disulfide crosslink formation
      with Ig heavy chain

<400> SEQUENCE: 7 gat atc cag atg acc cag tcc ccg agc tcc ctg tcc gcc tct gtg ggc          48
Asp Ile Gln Met Thr Gln Ser Pro Ser Ser Leu Ser Ala Ser Val Gly
1               5                   10                  15 gat agg gtc acc atc acc tgc cgt gcc agt cag gcc gcc tac ggc cgc          96
Asp Arg Val Thr Ile Thr Cys Arg Ala Ser Gln Ala Ala Tyr Gly Arg
            20                  25                  30 gta gcc tgg tat caa cag aaa cca gga aaa gct ccg aag ctt ctg att          144
Val Ala Trp Tyr Gln Gln Lys Pro Gly Lys Ala Pro Lys Leu Leu Ile
        35                  40                  45 tac aaa gca tcc gaa ctc tac gcc gga gtc cct tct cgc ttc tct ggt          192
Tyr Lys Ala Ser Glu Leu Tyr Ala Gly Val Pro Ser Arg Phe Ser Gly
    50                  55                  60 agc cgt tcc ggg acg gat ttc act ctg acc atc agc agt ctg cag ccg          240
Ser Arg Ser Gly Thr Asp Phe Thr Leu Thr Ile Ser Ser Leu Gln Pro
65                  70                  75                  80 gaa gac ttc gca act tat tac tgt cag caa cgt ggc tgg tat ctg ttc          288
Glu Asp Phe Ala Thr Tyr Tyr Cys Gln Gln Arg Gly Trp Tyr Leu Phe
                85                  90                  95 acg ttc gga cag ggt acc aag gtg gag atc aaa cgt acg gtg gct gca          336
Thr Phe Gly Gln Gly Thr Lys Val Glu Ile Lys Arg Thr Val Ala Ala
                100                 105                 110 cca tct gtc ttc atc ttc ccg cca tct gat gag cag ttg aaa tct gga          384
Pro Ser Val Phe Ile Phe Pro Pro Ser Asp Glu Gln Leu Lys Ser Gly
                115                 120                 125 act gcc tct gtt gtg tgc ctg ctg aat aac ttc tat ccc aga gag gcc          432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag          480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc          528
Glu Ser Val Thr Glu Gln Asp Ser Lys Asp Ser Thr Tyr Ser Leu Ser
                165                 170                 175 agc acc ctg acg ctg agc aaa gca gac tac gaa aaa cat aaa gtc tac          576
Ser Thr Leu Thr Leu Ser Lys Ala Asp Tyr Glu Lys His Lys Val Tyr
                180                 185                 190 gcc tgc gaa gtc acc cat cag ggc ctg agc tcg ccc gtc aca aag agc          624
Ala Cys Glu Val Thr His Gln Gly Leu Ser Ser Pro Val Thr Lys Ser
                195                 200                 205

-continued

```
ttc aac agg gga gag tgt                                          642
Phe Asn Arg Gly Glu Cys
    210
```

<210> SEQ ID NO 8
<211> LENGTH: 214
<212> TYPE: PRT
<213> ORGANISM: Artificial Sequence
<220> FEATURE:
<223> OTHER INFORMATION: Synthetic Construct

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ala Tyr Gly Arg
                20                  25                  30

Val Ala Trp Tyr Gln Gln Lys Pro Gly Lys Ala Pro Lys Leu Leu Ile
            35                  40                  45

Tyr Lys Ala Ser Glu Leu Tyr Ala Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Gly Trp Tyr Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 9
<211> LENGTH: 1449
<212> TYPE: DNA
<213> ORGANISM: Artificial Sequence
<220> FEATURE:
<223> OTHER INFORMATION: Synthetic humanized antibody FF03077-4
      comprising an amino-terminal humanized Fc fragment fused to a
      humanized anti-VEGF single chain Fv (scFv) directed against human
      and mouse VEGF
<220> FEATURE:
<221> NAME/KEY: CDS
<222> LOCATION: (1)..(1449)
<223> OTHER INFORMATION: Synthetic humanized antibody FF03077-4
      comprising an amino-terminal humanized Fc fragment fused to a
      humanized anti-VEGF single chain Fv (scFv) directed against human
      and mouse VEGF
<220> FEATURE:
<221> NAME/KEY: misc_feature
<222> LOCATION: (1)..(666)
<223> OTHER INFORMATION: coding sequence for Fc fragment of synthetic
      humanized anti-VEGF antibody FF03077-4, comprising an amino-
      terminal humanized Fc fragment fused to a humanized anti-VEGF single chain Fv (scFv) directed against human and mouse VEGF
<220> FEATURE:
<221> NAME/KEY: misc_feature
<222> LOCATION: (1)..(15)
<223> OTHER INFORMATION: coding sequence for the hinge region of the Fc
      fragment of synthetic humanized anti-VEGF antibody FF03077-4, as
      defined in accordance with IMGT
<220> FEATURE:
<221> NAME/KEY: misc_feature
<222> LOCATION: (16)..(345)
<223> OTHER INFORMATION: coding sequencefor the CH2 domain of the Fc
      fragment of synthetic humanized anti-VEGF antibody FF03077-4, as
      defined in accordance with IMGT
<220> FEATURE:
<221> NAME/KEY: misc_feature
<222> LOCATION: (346)..(666)
<223> OTHER INFORMATION: coding sequencefor the CH3 domain of the Fc
      fragment of synthetic humanized anti-VEGF antibody FF03077-4, as
      defined in accordance with IMGT
<220> FEATURE:
<221> NAME/KEY: misc_feature
<222> LOCATION: (667)..(720)
<223> OTHER INFORMATION: coding sequence for a linker between Fc
      fragment and scFv of synthetic humanized anti-VEGF antibody
      FF03077-4, comprising an amino-terminal humanized Fc fragment
      fused to a humanized anti-VEGF single chain Fv (scFv) directed
      against human and mouse
<220> FEATURE:
<221> NAME/KEY: misc_feature
<222> LOCATION: (721)..(1449)
<223> OTHER INFORMATION: coding sequence for scFv of synthetic humanized
      anti-VEGF antibody FF03077-4, comprising an amino-terminal
      humanized Fc fragment fused to a humanized anti-VEGF single chain
      Fv (scFv) directed against human and mouse VEGF
<220> FEATURE:
<221> NAME/KEY: misc_feature
<222> LOCATION: (790)..(822)
<223> OTHER INFORMATION: coding sequence of complementarity determining
      region, CDR-L1, as defined in accordance with Kabat
<220> FEATURE:
<221> NAME/KEY: misc_feature
<222> LOCATION: (799)..(816)
<223> OTHER INFORMATION: coding sequence of complementarity determining
      region, CDR-L1, as defined in accordance with IMGT
<220> FEATURE:
<221> NAME/KEY: misc_feature
<222> LOCATION: (868)..(876)
<223> OTHER INFORMATION: coding sequence of complementarity determining
      region, CDR-L2, as defined in accordance with IMGT
<220> FEATURE:
<221> NAME/KEY: misc_feature
<222> LOCATION: (868)..(888)
<223> OTHER INFORMATION: coding sequence of complementarity determining
      region, CDR-L2, as defined in accordance with Kabat
<220> FEATURE:
<221> NAME/KEY: misc_feature
<222> LOCATION: (985)..(1011)
<223> OTHER INFORMATION: coding sequence of complementarity determining
      region, CDR-L3, as defined in accordance with IMGT
<220> FEATURE:
<221> NAME/KEY: misc_feature
<222> LOCATION: (985)..(1011)
<223> OTHER INFORMATION: coding sequence of complementarity determining
      region, CDR-L3, as defined in accordance with Kabat
<220> FEATURE:
<221> NAME/KEY: misc_feature
<222> LOCATION: (1162)..(1188)
<223> OTHER INFORMATION: coding sequence of complementarity determining
      region, CDR-H1, as defined in accordance with IMGT
<220> FEATURE:
<221> NAME/KEY: misc_feature
<222> LOCATION: (1180)..(1194)
<223> OTHER INFORMATION: coding sequence of complementarity determining
      region, CDR-H1, as defined in accordance with Kabat
<220> FEATURE:
<221> NAME/KEY: misc_feature
<222> LOCATION: (1237)..(1287)
<223> OTHER INFORMATION: coding sequence of complementarity determining
      region, CDR-H2, as defined in accordance with Kabat

```
<220> FEATURE:
<221> NAME/KEY: misc_feature
<222> LOCATION: (1240)..(1263)
<223> OTHER INFORMATION: coding sequence of complementarity determining
      region, CDR-H2, as defined in accordance with IMGT
<220> FEATURE:
<221> NAME/KEY: misc_feature
<222> LOCATION: (1378)..(1416)
<223> OTHER INFORMATION: coding sequence of complementarity determining
      region, CDR-H3, as defined in accordance with IMGT
<220> FEATURE:
<221> NAME/KEY: misc_feature
<222> LOCATION: (1384)..(1416)
<223> OTHER INFORMATION: coding sequence of complementarity determining
      region, CDR-H3, as defined in accordance with Kabat

<400> SEQUENCE: 9 tgc cca ccg tgc cca gca cct gaa ctc ctg ggg gga ccg tca gtc ttc        48
Cys Pro Pro Cys Pro Ala Pro Glu Leu Leu Gly Gly Pro Ser Val Phe
1               5                   10                  15 ctc ttc ccc cca aaa ccc aag gac acc ctc atg atc tcc cgg acc cct        96
Leu Phe Pro Pro Lys Pro Lys Asp Thr Leu Met Ile Ser Arg Thr Pro
                20                  25                  30 gag gtc aca tgc gtg gtg gtg gac gtg agc cac gaa gac cct gag gtc       144
Glu Val Thr Cys Val Val Val Asp Val Ser His Glu Asp Pro Glu Val
            35                  40                  45 aag ttc aac tgg tac gtg gac ggc gtg gag gtg cat aat gcc aag aca       192
Lys Phe Asn Trp Tyr Val Asp Gly Val Glu Val His Asn Ala Lys Thr
        50                  55                  60 aag ccg cgg gag gag cag tac aac agc acg tac cgt gtg gtc agc gtc       240
Lys Pro Arg Glu Glu Gln Tyr Asn Ser Thr Tyr Arg Val Val Ser Val
65                  70                  75                  80 ctc acc gtc ctg cac cag gac tgg ctg aat ggc aag gag tac aag tgc       288
Leu Thr Val Leu His Gln Asp Trp Leu Asn Gly Lys Glu Tyr Lys Cys
                85                  90                  95 aag gtc tcc aac aaa gcc ctc cca gcc ccc atc gag aaa acc atc tcc       336
Lys Val Ser Asn Lys Ala Leu Pro Ala Pro Ile Glu Lys Thr Ile Ser
                100                 105                 110 aaa gcc aaa ggg cag ccc cga gaa cca cag gtg tac acc ctg ccc cca       384
Lys Ala Lys Gly Gln Pro Arg Glu Pro Gln Val Tyr Thr Leu Pro Pro
            115                 120                 125 tcc cgg gag gag atg acc aag aac cag gtc agc ctg acc tgc ctg gtc       432
Ser Arg Glu Glu Met Thr Lys Asn Gln Val Ser Leu Thr Cys Leu Val
            130                 135                 140 aaa ggc ttc tat ccc agc gac atc gcc gtg gag tgg gag agc aat ggg       480
Lys Gly Phe Tyr Pro Ser Asp Ile Ala Val Glu Trp Glu Ser Asn Gly
145                 150                 155                 160 cag ccg gag aac aac tac aag acc acg cct ccc gtg ctg gac tcc gac       528
Gln Pro Glu Asn Asn Tyr Lys Thr Thr Pro Pro Val Leu Asp Ser Asp
                165                 170                 175 ggc tcc ttc ttc ctc tac agc aag ctc acc gtg gac aag agc agg tgg       576
Gly Ser Phe Phe Leu Tyr Ser Lys Leu Thr Val Asp Lys Ser Arg Trp
                180                 185                 190 cag cag ggg aac gtc ttc tca tgc tcc gtg atg cat gag gct ctg cac       624
Gln Gln Gly Asn Val Phe Ser Cys Ser Val Met His Glu Ala Leu His
            195                 200                 205 aac cac tac acg cag aag agc ctc tcg ctg agc cct gga aaa ggt ggc       672
Asn His Tyr Thr Gln Lys Ser Leu Ser Leu Ser Pro Gly Lys Gly Gly
        210                 215                 220 gga gga tct ggc ggc gga gga agc ggt gga ggc gga agc gga ggc ggc       720
Gly Gly Ser Gly Gly Gly Gly Ser Gly Gly Gly Gly Ser Gly Gly Gly
225                 230                 235                 240 gat atc cag atg aca cag agc cct agc agc ctg agc gcc agc gtg ggc       768
Asp Ile Gln Met Thr Gln Ser Pro Ser Ser Leu Ser Ala Ser Val Gly
```

```
Asp Ile Gln Met Thr Gln Ser Pro Ser Ser Leu Ser Ala Ser Val Gly
                245                 250                 255 gac aga gtg acc atc acc tgt aga gcc agc cag gcc gcc tat ggc aga        816
Asp Arg Val Thr Ile Thr Cys Arg Ala Ser Gln Ala Ala Tyr Gly Arg
            260                 265                 270 gtg gcc tgg tat cag cag aag ccc ggc aag gcc cct aag ctg ctg atc        864
Val Ala Trp Tyr Gln Gln Lys Pro Gly Lys Ala Pro Lys Leu Leu Ile
        275                 280                 285 tac aag gcc agc gag ctg tat gcc ggc gtg ccc agc aga ttc agc ggc        912
Tyr Lys Ala Ser Glu Leu Tyr Ala Gly Val Pro Ser Arg Phe Ser Gly
    290                 295                 300 agc aga tcc ggc acc gac ttc acc ctg acc atc agc agc ctg cag ccc        960
Ser Arg Ser Gly Thr Asp Phe Thr Leu Thr Ile Ser Ser Leu Gln Pro
305                 310                 315                 320 gag gac ttc gcc acc tac tac tgc cag cag cgg ggc tgg tat ctg ttc       1008
Glu Asp Phe Ala Thr Tyr Tyr Cys Gln Gln Arg Gly Trp Tyr Leu Phe
                325                 330                 335 acc ttc ggc cag ggc acc aag gtg gaa atc aag ggc aca aca gcc gcc       1056
Thr Phe Gly Gln Gly Thr Lys Val Glu Ile Lys Gly Thr Thr Ala Ala
            340                 345                 350 agc ggc tct agc ggc gga tct tct agc gga gcc gag gtg cag ctg gtg       1104
Ser Gly Ser Ser Gly Gly Ser Ser Ser Gly Ala Glu Val Gln Leu Val
        355                 360                 365 gaa tca ggc ggt gga ctg gtg cag cct ggc gga agc ctg aga ctg tct       1152
Glu Ser Gly Gly Gly Leu Val Gln Pro Gly Gly Ser Leu Arg Leu Ser
    370                 375                 380 tgc gcc gcc tct ggc ttc gac ctg ttc cac tac agc atc cac tgg gtc       1200
Cys Ala Ala Ser Gly Phe Asp Leu Phe His Tyr Ser Ile His Trp Val
385                 390                 395                 400 cga cag gcc cct ggc aag gga ctg gaa tgg gtg gcc tac atc tac ccc       1248
Arg Gln Ala Pro Gly Lys Gly Leu Glu Trp Val Ala Tyr Ile Tyr Pro
                405                 410                 415 agc tac ggc tac acc tat tac gcc gac agc gtg aag ggc cgg ttc acc       1296
Ser Tyr Gly Tyr Thr Tyr Tyr Ala Asp Ser Val Lys Gly Arg Phe Thr
                420                 425                 430 atc agc gcc gac acc agc aag aac acc gcc tac ctg cag atg aac agc       1344
Ile Ser Ala Asp Thr Ser Lys Asn Thr Ala Tyr Leu Gln Met Asn Ser
            435                 440                 445 ctg aga gcc gag gac acc gcc gtg tac tac tgt gcc aga cac gcc tgg       1392
Leu Arg Ala Glu Asp Thr Ala Val Tyr Tyr Cys Ala Arg His Ala Trp
        450                 455                 460 tac tac ggc tgg ggc ctg gat tac tgg ggc cag gga acc ctg gtc acc       1440
Tyr Tyr Gly Trp Gly Leu Asp Tyr Trp Gly Gln Gly Thr Leu Val Thr
465                 470                 475                 480 gtg tcc tct                                                            1449
Val Ser Ser
```

```
<210> SEQ ID NO 10
<211> LENGTH: 483
<212> TYPE: PRT
<213> ORGANISM: Artificial Sequence
<220> FEATURE:
<223> OTHER INFORMATION: Synthetic Construct

<400> SEQUENCE: 10

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
```

-continued

```
              35                    40                    45
Lys Phe Asn Trp Tyr Val Asp Gly Val Glu Val His Asn Ala Lys Thr
    50                    55                    60
Lys Pro Arg Glu Glu Gln Tyr Asn Ser Thr Tyr Arg Val Val Ser Val
65                    70                    75                    80
Leu Thr Val Leu His Gln Asp Trp Leu Asn Gly Lys Glu Tyr Lys Cys
                85                    90                    95
Lys Val Ser Asn Lys Ala Leu Pro Ala Pro Ile Glu Lys Thr Ile Ser
                100                   105                   110
Lys Ala Lys Gly Gln Pro Arg Glu Pro Gln Val Tyr Thr Leu Pro Pro
                115                   120                   125
Ser Arg Glu Glu Met Thr Lys Asn Gln Val Ser Leu Thr Cys Leu Val
    130                   135                   140
Lys Gly Phe Tyr Pro Ser Asp Ile Ala Val Glu Trp Glu Ser Asn Gly
145                   150                   155                   160
Gln Pro Glu Asn Asn Tyr Lys Thr Thr Pro Pro Val Leu Asp Ser Asp
                165                   170                   175
Gly Ser Phe Phe Leu Tyr Ser Lys Leu Thr Val Asp Lys Ser Arg Trp
                180                   185                   190
Gln Gln Gly Asn Val Phe Ser Cys Ser Val Met His Glu Ala Leu His
    195                   200                   205
Asn His Tyr Thr Gln Lys Ser Leu Ser Leu Ser Pro Gly Lys Gly Gly
    210                   215                   220
Gly Gly Ser Gly Gly Gly Gly Ser Gly Gly Gly Gly Ser Gly Gly Gly
225                   230                   235                   240
Asp Ile Gln Met Thr Gln Ser Pro Ser Ser Leu Ser Ala Ser Val Gly
                245                   250                   255
Asp Arg Val Thr Ile Thr Cys Arg Ala Ser Gln Ala Ala Tyr Gly Arg
                260                   265                   270
Val Ala Trp Tyr Gln Gln Lys Pro Gly Lys Ala Pro Lys Leu Leu Ile
                275                   280                   285
Tyr Lys Ala Ser Glu Leu Tyr Ala Gly Val Pro Ser Arg Phe Ser Gly
    290                   295                   300
Ser Arg Ser Gly Thr Asp Phe Thr Leu Thr Ile Ser Ser Leu Gln Pro
305                   310                   315                   320
Glu Asp Phe Ala Thr Tyr Tyr Cys Gln Gln Arg Gly Trp Tyr Leu Phe
                325                   330                   335
Thr Phe Gly Gln Gly Thr Lys Val Glu Ile Lys Gly Thr Thr Ala Ala
                340                   345                   350
Ser Gly Ser Ser Gly Gly Ser Ser Ser Gly Ala Glu Val Gln Leu Val
                355                   360                   365
Glu Ser Gly Gly Gly Leu Val Gln Pro Gly Gly Ser Leu Arg Leu Ser
    370                   375                   380
Cys Ala Ala Ser Gly Phe Asp Leu Phe His Tyr Ser Ile His Trp Val
385                   390                   395                   400
Arg Gln Ala Pro Gly Lys Gly Leu Glu Trp Val Ala Tyr Ile Tyr Pro
                405                   410                   415
Ser Tyr Gly Tyr Thr Tyr Tyr Ala Asp Ser Val Lys Gly Arg Phe Thr
                420                   425                   430
Ile Ser Ala Asp Thr Ser Lys Asn Thr Ala Tyr Leu Gln Met Asn Ser
                435                   440                   445
Leu Arg Ala Glu Asp Thr Ala Val Tyr Tyr Cys Ala Arg His Ala Trp
    450                   455                   460
```

-continued

```
Tyr Tyr Gly Trp Gly Leu Asp Tyr Trp Gly Gln Gly Thr Leu Val Thr
465                 470                 475                 480

Val Ser Ser
```

```
<210> SEQ ID NO 11
<211> LENGTH: 1350
<212> TYPE: DNA
<213> ORGANISM: Artificial Sequence
<220> FEATURE:
<223> OTHER INFORMATION: Synthetic humanized anti-VEGF full length
      mature IgG1 antibody, FF03092-3, heavy chain comprising an
      optimized human framework and affinity matured CDR-H1, CDR-H2 and
      CDR-H3 directed against mouse and human VEGF
<220> FEATURE:
<221> NAME/KEY: CDS
<222> LOCATION: (1)..(1350)
<223> OTHER INFORMATION: Coding sequence for IgG1 heavy chain of a
      synthetic humanized anti-VEGF full length mature antibody,
      FF03092-3
<220> FEATURE:
<221> NAME/KEY: misc_feature
<222> LOCATION: (1)..(360)
<223> OTHER INFORMATION: Coding sequence for IgG1 heavy chain variable
      domain of a synthetic humanized anti-VEGF full length mature
      antibody, FF03092-3
<220> FEATURE:
<221> NAME/KEY: misc_feature
<222> LOCATION: (76)..(99)
<223> OTHER INFORMATION: coding sequence of complementarity determining
      region, CDR-H1, as defined in accordance with IMGT
<220> FEATURE:
<221> NAME/KEY: misc_feature
<222> LOCATION: (91)..(105)
<223> OTHER INFORMATION: coding sequence of complementarity determining
      region, CDR-H1, as defined in accordance with Kabat
<220> FEATURE:
<221> NAME/KEY: misc_feature
<222> LOCATION: (148)..(198)
<223> OTHER INFORMATION: coding sequence of complementarity determining
      region, CDR-H2, as defined in accordance with Kabat
<220> FEATURE:
<221> NAME/KEY: misc_feature
<222> LOCATION: (151)..(174)
<223> OTHER INFORMATION: coding sequence of complementarity determining
      region, CDR-H2, as defined in accordance with IMGT
<220> FEATURE:
<221> NAME/KEY: misc_feature
<222> LOCATION: (289)..(327)
<223> OTHER INFORMATION: coding sequence of complementarity determining
      region, CDR-H3, as defined in accordance with IMGT
<220> FEATURE:
<221> NAME/KEY: misc_feature
<222> LOCATION: (295)..(327)
<223> OTHER INFORMATION: coding sequence of complementarity determining
      region, CDR-H3, as defined in accordance with Kabat
<220> FEATURE:
<221> NAME/KEY: misc_feature
<222> LOCATION: (361)..(1350)
<223> OTHER INFORMATION: Coding sequence for IgG1 heavy chain constant
      domain of a synthetic humanized anti-VEGF full length mature
      antibody, FF03092-3
<220> FEATURE:
<221> NAME/KEY: misc_feature
<222> LOCATION: (361)..(654)
<223> OTHER INFORMATION: Coding sequence for CH1 domain of FF03092-3
      antibody IgG1 heavy chain constant region based on IMGT
<220> FEATURE:
<221> NAME/KEY: misc_feature
<222> LOCATION: (655)..(699)
<223> OTHER INFORMATION: Coding sequence for the hinge region of
      FF03092-3 antibody IgG1 heavy chain constant region, based on IMGT
<220> FEATURE:
<221> NAME/KEY: misc_feature
<222> LOCATION: (667)..(669)
<223> OTHER INFORMATION: codon for cysteine at amino acid position 223
      of full length mature IgG1 heavy chain which forms a disulfide
```

```
      bridge with an immunoglobulin light chain in FF03092-3 antibody
<220> FEATURE:
<221> NAME/KEY: misc_feature
<222> LOCATION: (700)..(1029)
<223> OTHER INFORMATION: Coding sequence for CH2 domain of FF03092-3
      antibody IgG1 heavy chain constant region based on IMGT
<220> FEATURE:
<221> NAME/KEY: misc_feature
<222> LOCATION: (1030)..(1350)
<223> OTHER INFORMATION: Coding sequence for CH3 domain of FF03092-3
      antibody IgG1 heavy chain constant region based on IMGT

<400> SEQUENCE: 11 gag gtt cag ctg gtg gag tct ggc ggt ggc ctg gtg cag cca ggg ggc         48
Glu Val Gln Leu Val Glu Ser Gly Gly Gly Leu Val Gln Pro Gly Gly
1               5                   10                  15 tca ctc cgt ttg tcc tgt gca gct tct ggc ttc gat tta ttt cat tat         96
Ser Leu Arg Leu Ser Cys Ala Ala Ser Gly Phe Asp Leu Phe His Tyr
                20                  25                  30 tct ata cac tgg gtg cgt cag gcc ccg ggt aag ggc ctg gaa tgg gtt        144
Ser Ile His Trp Val Arg Gln Ala Pro Gly Lys Gly Leu Glu Trp Val
            35                  40                  45 gca tac att tac ccg tct tat ggc tat act tat tat gcc gat agc gtc        192
Ala Tyr Ile Tyr Pro Ser Tyr Gly Tyr Thr Tyr Tyr Ala Asp Ser Val
        50                  55                  60 aag ggc cgt ttc act ata agc gca gac aca tcc aaa aac aca gcc tac        240
Lys Gly Arg Phe Thr Ile Ser Ala Asp Thr Ser Lys Asn Thr Ala Tyr
65                  70                  75                  80 cta caa atg aac agc tta aga gct gag gac act gcc gtc tat tat tgt        288
Leu Gln Met Asn Ser Leu Arg Ala Glu Asp Thr Ala Val Tyr Tyr Cys
                85                  90                  95 gct cgc cat gcg tgg tat tat ggg tgg ggt ttg gac tac tgg ggt caa        336
Ala Arg His Ala Trp Tyr Tyr Gly Trp Gly Leu Asp Tyr Trp Gly Gln
            100                 105                 110 gga acc ctg gtc acc gtc tcc tcg gct agc acc aag ggc cca tcg gtc        384
Gly Thr Leu Val Thr Val Ser Ser Ala Ser Thr Lys Gly Pro Ser Val
            115                 120                 125 ttc ccc ctg gca ccc tcc tcc aag agc acc tct ggg ggc aca gcg gcc        432
Phe Pro Leu Ala Pro Ser Ser Lys Ser Thr Ser Gly Gly Thr Ala Ala
        130                 135                 140 ctg ggc tgc ctg gtc aag gac tac ttc ccc gaa ccg gtg acg gtg tcg        480
Leu Gly Cys Leu Val Lys Asp Tyr Phe Pro Glu Pro Val Thr Val Ser
145                 150                 155                 160 tgg aac tca ggc gcc ctg acc agc ggc gtg cac acc ttc ccg gct gtc        528
Trp Asn Ser Gly Ala Leu Thr Ser Gly Val His Thr Phe Pro Ala Val
                165                 170                 175 cta cag tcc tca gga ctc tac tcc ctc agc agc gtg gtg acc gtg ccc        576
Leu Gln Ser Ser Gly Leu Tyr Ser Leu Ser Ser Val Val Thr Val Pro
            180                 185                 190 tcc agc agc ttg ggc acc cag acc tac atc tgc aac gtg aat cac aag        624
Ser Ser Ser Leu Gly Thr Gln Thr Tyr Ile Cys Asn Val Asn His Lys
            195                 200                 205 ccc agc aac acc aag gtg gac aag aaa gtt gag ccc aaa tct tgt gac        672
Pro Ser Asn Thr Lys Val Asp Lys Lys Val Glu Pro Lys Ser Cys Asp
        210                 215                 220 aaa act cac aca tgc cca ccg tgc cca gca cct gaa ctc ctg ggg gga        720
Lys Thr His Thr Cys Pro Pro Cys Pro Ala Pro Glu Leu Leu Gly Gly
225                 230                 235                 240 ccg tca gtc ttc ctc ttc ccc cca aaa ccc aag gac acc ctc atg atc        768
Pro Ser Val Phe Leu Phe Pro Pro Lys Pro Lys Asp Thr Leu Met Ile
                245                 250                 255 tcc cgg acc cct gag gtc aca tgc gtg gtg gtg gac gtg agc cac gaa        816
```

-continued

```
Ser Arg Thr Pro Glu Val Thr Cys Val Val Asp Val Ser His Glu
            260                 265                 270 gac cct gag gtc aag ttc aac tgg tac gtg gac ggc gtg gag gtg cat        864
Asp Pro Glu Val Lys Phe Asn Trp Tyr Val Asp Gly Val Glu Val His
        275                 280                 285 aat gcc aag aca aag ccg cgg gag gag cag tac aac agc acg tac cgt        912
Asn Ala Lys Thr Lys Pro Arg Glu Glu Gln Tyr Asn Ser Thr Tyr Arg
    290                 295                 300 gtg gtc agc gtc ctc acc gtc ctg cac cag gac tgg ctg aat ggc aag        960
Val Val Ser Val Leu Thr Val Leu His Gln Asp Trp Leu Asn Gly Lys
305                 310                 315                 320 gag tac aag tgc aag gtc tcc aac aaa gcc ctc cca gcc ccc atc gag       1008
Glu Tyr Lys Cys Lys Val Ser Asn Lys Ala Leu Pro Ala Pro Ile Glu
                325                 330                 335 aaa acc atc tcc aaa gcc aaa ggg cag ccc cga gaa cca cag gtg tac       1056
Lys Thr Ile Ser Lys Ala Lys Gly Gln Pro Arg Glu Pro Gln Val Tyr
            340                 345                 350 acc ctg ccc cca tcc cgg gag gag atg acc aag aac cag gtc agc ctg       1104
Thr Leu Pro Pro Ser Arg Glu Glu Met Thr Lys Asn Gln Val Ser Leu
        355                 360                 365 acc tgc ctg gtc aaa ggc ttc tat ccc agc gac atc gcc gtg gag tgg       1152
Thr Cys Leu Val Lys Gly Phe Tyr Pro Ser Asp Ile Ala Val Glu Trp
        370                 375                 380 gag agc aat ggg cag ccg gag aac aac tac aag acc acg cct ccc gtg       1200
Glu Ser Asn Gly Gln Pro Glu Asn Asn Tyr Lys Thr Thr Pro Pro Val
385                 390                 395                 400 ctg gac tcc gac ggc tcc ttc ttc ctc tac agc aag ctc acc gtg gac       1248
Leu Asp Ser Asp Gly Ser Phe Phe Leu Tyr Ser Lys Leu Thr Val Asp
                405                 410                 415 aag agc agg tgg cag cag ggg aac gtc ttc tca tgc tcc gtg atg cat       1296
Lys Ser Arg Trp Gln Gln Gly Asn Val Phe Ser Cys Ser Val Met His
            420                 425                 430 gag gct ctg cac aac cac tac acg cag aag agc ctc tcc ctg tct ccg       1344
Glu Ala Leu His Asn His Tyr Thr Gln Lys Ser Leu Ser Leu Ser Pro
            435                 440                 445 ggt aaa                                                                1350
Gly Lys
    450
```

```
<210> SEQ ID NO 12
<211> LENGTH: 450
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Phe His Tyr
            20                  25                  30

Ser Ile His Trp Val Arg Gln Ala Pro Gly Lys Gly Leu Glu Trp Val
        35                  40                  45

Ala Tyr Ile Tyr Pro Ser Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

-continued

```
Ala Arg His Ala Trp Tyr Tyr Gly Trp Gly Leu Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 13
<211> LENGTH: 642
<212> TYPE: DNA
<213> ORGANISM: Artificial Sequence
<220> FEATURE:
<223> OTHER INFORMATION: Synthetic humanized full length mature IgG1
      antibody, FF03092-3, kappa light chain comprising an optimized
      human framework and affinity matured CDR-L1, CDR-L2 and CDR-L3
      directed against mouse and human VEGF
```

```
<220> FEATURE:
<221> NAME/KEY: CDS
<222> LOCATION: (1)..(642)
<223> OTHER INFORMATION: Coding sequence for immunoglobulin kappa light
      chain of a synthetic humanized anti-VEGF antibody, FF03092-3
<220> FEATURE:
<221> NAME/KEY: misc_feature
<222> LOCATION: (1)..(321)
<223> OTHER INFORMATION: coding sequence of variable domain of
      immunoglobulin kappa light chain of a synthetic humanized anti-
      VEGF antibody, FF03092-3
<220> FEATURE:
<221> NAME/KEY: misc_feature
<222> LOCATION: (70)..(102)
<223> OTHER INFORMATION: coding sequence of complementarity determining
      region, CDR-L1, as defined in accordance with Kabat
<220> FEATURE:
<221> NAME/KEY: misc_feature
<222> LOCATION: (79)..(96)
<223> OTHER INFORMATION: coding sequence of complementarity determining
      region, CDR-L1, as defined in accordance with IMGT
<220> FEATURE:
<221> NAME/KEY: misc_feature
<222> LOCATION: (148)..(168)
<223> OTHER INFORMATION: coding sequence of complementarity determining
      region, CDR-L2, as defined in accordance with Kabat
<220> FEATURE:
<221> NAME/KEY: misc_feature
<222> LOCATION: (148)..(156)
<223> OTHER INFORMATION: coding sequence of complementarity determining
      region, CDR-L2, as defined in accordance with IMGT
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with Kabat
<220> FEATURE:
<221> NAME/KEY: misc_feature
<222> LOCATION: (265)..(291)
<223> OTHER INFORMATION: coding sequence of complementarity determining
      region, CDR-L3, as defined in accordance with IMGT
<220> FEATURE:
<221> NAME/KEY: misc_feature
<222> LOCATION: (322)..(642)
<223> OTHER INFORMATION: coding sequence of constant domain of
      immunoglobulin kappa light chain of a synthetic humanized anti-
      VEGF antibody, FF03092-3
<220> FEATURE:
<221> NAME/KEY: misc_feature
<222> LOCATION: (640)..(642)
<223> OTHER INFORMATION: codon for cysteine residue at amino acid 214 of
      kappa light chain which forms a disulfide bond with the
      immunoglobulin heavy chain in FF03092-3 antibody

<400> SEQUENCE: 13 gat atc cag atg acc cag tcc ccg agc tcc ctg tcc gcc tct gtg ggc        48
Asp Ile Gln Met Thr Gln Ser Pro Ser Ser Leu Ser Ala Ser Val Gly
1               5                   10                  15 gat agg gtc acc atc acc tgc cgt gcc agt cag gcc gcc tac ggc cgc        96
Asp Arg Val Thr Ile Thr Cys Arg Ala Ser Gln Ala Ala Tyr Gly Arg
                20                  25                  30 gta gcc tgg tat caa cag aaa cca gga aaa gct ccg aag ctt ctg att       144
Val Ala Trp Tyr Gln Gln Lys Pro Gly Lys Ala Pro Lys Leu Leu Ile
        35                  40                  45 tac aaa gca tcc gaa ctc tac gcc gga gtc cct tct cgc ttc tct ggt       192
Tyr Lys Ala Ser Glu Leu Tyr Ala Gly Val Pro Ser Arg Phe Ser Gly
    50                  55                  60 agc cgt tcc ggg acg gat ttc act ctg acc atc agc agt ctg cag ccg       240
Ser Arg Ser Gly Thr Asp Phe Thr Leu Thr Ile Ser Ser Leu Gln Pro
65                  70                  75                  80 gaa gac ttc gca act tat tac tgt cag caa cgt ggc tgg tat ctg ttc       288
Glu Asp Phe Ala Thr Tyr Tyr Cys Gln Gln Arg Gly Trp Tyr Leu Phe
                85                  90                  95
```

-continued

```
acg ttc gga cag ggt acc aag gtg gag atc aaa cgt acg gtg gct gca      336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga      384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc      432
Thr Ala Ser Val Val Cys Leu Leu Asn Asn Phe Tyr Pro Arg Glu Ala
            130                 135                 140 aaa gta cag tgg aag gtg gat aac gcc ctc caa tcg ggt aac tcc cag      480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc      528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac      576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc      624
Ala Cys Glu Val Thr His Gln Gly Leu Ser Ser Pro Val Thr Lys Ser
            195                 200                 205 ttc aac agg gga gag tgt                                              642
Phe Asn Arg Gly Glu Cys
    210
```

```
<210> SEQ ID NO 14
<211> LENGTH: 214
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ala Tyr Gly Arg
                20                  25                  30

Val Ala Trp Tyr Gln Gln Lys Pro Gly Lys Ala Pro Lys Leu Leu Ile
            35                  40                  45

Tyr Lys Ala Ser Glu Leu Tyr Ala Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Gly Trp Tyr Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
<211> LENGTH: 268
<212> TYPE: DNA
<213> ORGANISM: Escherichia coli
<220> FEATURE:
<221> NAME/KEY: promoter
<222> LOCATION: (1)..(217)
<223> OTHER INFORMATION: E. coli Pho A promoter

<400> SEQUENCE: 15
gaccaacagc ggttgattga tcaggtagag ggggcgctgt acgaggtaaa gcccgatgcc      60
agcattcctg acgacgatac ggagctgctg cgcgattacg taaagaagtt attgaagcat     120
cctcgtcagt aaaaagttaa tcttttcaac agctgtcata aagttgtcac ggccgagact     180
tatagtcgct ttgttttat tttttaatgt atttgtaact agtacgcaag ttcacgtaaa     240
aagggtatgt agaggttgag gtgatttt                                       268

<210> SEQ ID NO 16
<211> LENGTH: 1583
<212> TYPE: DNA
<213> ORGANISM: Artificial Sequence
<220> FEATURE:
<223> OTHER INFORMATION: Coding sequence for synthetic humanized Fab
      anti-VEGF antibody fragment directed against mouse and human VEGF
      used in expression plasmid Clone #201
<220> FEATURE:
<221> NAME/KEY: CDS
<222> LOCATION: (1)..(714)
<223> OTHER INFORMATION: anti-VEGF kappa light chain derived from
      FF03046-2 antibody comprising amino terminal sequence coding for
      MKKNIAFLLASMFVFSIATNAYA
<220> FEATURE:
<221> NAME/KEY: misc_feature
<222> LOCATION: (1)..(3)
<223> OTHER INFORMATION: translation start codon, AUG
<220> FEATURE:
<221> NAME/KEY: misc_feature
<222> LOCATION: (1)..(69)
<223> OTHER INFORMATION: coding sequence for secretory signal cleaved
      during secretion of Ig light chain
<220> FEATURE:
<221> NAME/KEY: misc_feature
<222> LOCATION: (70)..(390)
<223> OTHER INFORMATION: coding sequence for variable region of an
      immunoglobulin kappa light chain of a synthetic humanized anti-
      VEGF antibody
<220> FEATURE:
<221> NAME/KEY: misc_feature
<222> LOCATION: (70)..(711)
<223> OTHER INFORMATION: coding sequence for the mature Ig kappa light
      chain of a synthetic humanized anti-VEGF Fab antibody lacking the
      secretory signal
<220> FEATURE:
<221> NAME/KEY: misc_feature
<222> LOCATION: (139)..(171)
<223> OTHER INFORMATION: coding sequence of complementarity determining
      region, CDR-L1, as defined in accordance with Kabat
<220> FEATURE:
<221> NAME/KEY: misc_feature
<222> LOCATION: (148)..(165)
<223> OTHER INFORMATION: coding sequence of complementarity determining
      region, CDR-L1, as defined in accordance with IMGT
<220> FEATURE:
<221> NAME/KEY: misc_feature
<222> LOCATION: (217)..(237)
<223> OTHER INFORMATION: coding sequence of complementarity determining
      region, CDR-L2, as defined in accordance with Kabat

```
<220> FEATURE:
<221> NAME/KEY: misc_feature
<222> LOCATION: (217)..(225)
<223> OTHER INFORMATION: coding sequence of complementarity determining
      region, CDR-L2, as defined in accordance with IMGT
<220> FEATURE:
<221> NAME/KEY: misc_feature
<222> LOCATION: (334)..(360)
<223> OTHER INFORMATION: coding sequence of complementarity determining
      region, CDR-L3, as defined in accordance with Kabat
<220> FEATURE:
<221> NAME/KEY: misc_feature
<222> LOCATION: (334)..(360)
<223> OTHER INFORMATION: coding sequence of complementarity determining
      region, CDR-L3, as defined in accordance with IMGT
<220> FEATURE:
<221> NAME/KEY: misc_feature
<222> LOCATION: (391)..(711)
<223> OTHER INFORMATION: coding sequence for constant region of an
      immunoglobulin kappa light chain of a synthetic humanized anti-
      VEGF antibody
<220> FEATURE:
<221> NAME/KEY: misc_feature
<222> LOCATION: (436)..(438)
<223> OTHER INFORMATION: TCA codon encoding amino acid serine at amino
      acid position 146 of kappa light chain constant region in Clone
      #201 parent, which differs from GAG codon encoding glutamic acid
      in kappa light chain of parent Fab FF03046-2
<220> FEATURE:
<221> NAME/KEY: misc_feature
<222> LOCATION: (709)..(711)
<223> OTHER INFORMATION: codon for cysteine residue at the end of kappa
      light chain constant region that participates in disulfide bond
      formation with a heavy chain
<220> FEATURE:
<221> NAME/KEY: misc_feature
<222> LOCATION: (712)..(714)
<223> OTHER INFORMATION: translational termination codon
<220> FEATURE:
<221> NAME/KEY: misc_feature
<222> LOCATION: (715)..(827)
<223> OTHER INFORMATION: non coding spacer region between the light
      chain and heavy chain coding sequences
<220> FEATURE:
<221> NAME/KEY: CDS
<222> LOCATION: (828)..(1583)
<223> OTHER INFORMATION: anti-VEGF Fab antibody heavy chain derived from
      FF03046-2 antibody comprising amino terminal sequence coding for
      MKKNIAFLLASMFVFSIATNAYA
<220> FEATURE:
<221> NAME/KEY: misc_feature
<222> LOCATION: (828)..(830)
<223> OTHER INFORMATION: translational start codon for an immunoglobulin
      heavy chain fragment of a synthetic humanized anti-VEGF Fab
      antibody
<220> FEATURE:
<221> NAME/KEY: misc_feature
<222> LOCATION: (828)..(896)
<223> OTHER INFORMATION: coding sequence for secretory signal cleaved
      during secretion of Ig heavy chain fragment of a synthetic
      humanized anti-VEGF Fab antibody
<220> FEATURE:
<221> NAME/KEY: misc_feature
<222> LOCATION: (897)..(1580)
<223> OTHER INFORMATION: coding sequence for the mature Ig heavy chain
      fragment of a synthetic humanized anti-VEGF Fab antibody lacking
      the secretory signal
<220> FEATURE:
<221> NAME/KEY: misc_feature
<222> LOCATION: (897)..(1256)
<223> OTHER INFORMATION: coding sequence for Ig heavy chain variable
      region of a synthetic humanized anti-VEGF Fab antibody
<220> FEATURE:
<221> NAME/KEY: misc_feature
<222> LOCATION: (972)..(995)
<223> OTHER INFORMATION: coding sequence of complementarity determining
      region, CDR-H1, as defined in accordance with IMGT
<220> FEATURE:
<221> NAME/KEY: misc_feature
```

```
<222> LOCATION: (987)..(1001)
<223> OTHER INFORMATION: coding sequence of complementarity determining
      region, CDR-H1, as defined in accordance with Kabat
<220> FEATURE:
<221> NAME/KEY: misc_feature
<222> LOCATION: (1044)..(1094)
<223> OTHER INFORMATION: coding sequence of complementarity determining
      region, CDR-H2, as defined in accordance with Kabat
<220> FEATURE:
<221> NAME/KEY: misc_feature
<222> LOCATION: (1047)..(1070)
<223> OTHER INFORMATION: coding sequence of complementarity determining
      region, CDR-H2, as defined in accordance with IMGT
<220> FEATURE:
<221> NAME/KEY: misc_feature
<222> LOCATION: (1185)..(1223)
<223> OTHER INFORMATION: coding sequence of complementarity determining
      region, CDR-H3, as defined in accordance with IMGT
<220> FEATURE:
<221> NAME/KEY: misc_feature
<222> LOCATION: (1191)..(1223)
<223> OTHER INFORMATION: coding sequence of complementarity determining
      region, CDR-H3, as defined in accordance with Kabat
<220> FEATURE:
<221> NAME/KEY: misc_feature
<222> LOCATION: (1257)..(1550)
<223> OTHER INFORMATION: coding sequence for CH1 domain of Ig heavy
      chain constant region of a synthetic humanized anti-VEGF Fab
      antibody
<220> FEATURE:
<221> NAME/KEY: misc_feature
<222> LOCATION: (1281)..(1583)
<223> OTHER INFORMATION: translational stop codon
<220> FEATURE:
<221> NAME/KEY: misc_feature
<222> LOCATION: (1551)..(1580)
<223> OTHER INFORMATION: coding sequence for part of the hinge region of
      an immunoglobulin heavy chain fragment of a synthetic humanized
      anti-VEGF Fab antibody
<220> FEATURE:
<221> NAME/KEY: misc_feature
<222> LOCATION: (1563)..(1565)
<223> OTHER INFORMATION: codon for cysteine residue within the hinge
      region which participates in interstrand disulfide bond formation
      with a light chain in a synthetic humanized anti-VEGF Fab antibody

<400> SEQUENCE: 16 atg aaa aag aat atc gca ttt ctt ctt gca tct atg ttc gtt ttt tct        48
Met Lys Lys Asn Ile Ala Phe Leu Leu Ala Ser Met Phe Val Phe Ser
1               5                   10                  15 att gct aca aat gcc tat gca gat atc cag atg acc cag tcc ccg agc        96
Ile Ala Thr Asn Ala Tyr Ala Asp Ile Gln Met Thr Gln Ser Pro Ser
                20                  25                  30 tcc ctg tcc gcc tct gtg ggc gat agg gtc acc atc acc tgc cgt gcc       144
Ser Leu Ser Ala Ser Val Gly Asp Arg Val Thr Ile Thr Cys Arg Ala
            35                  40                  45 agt cag gcc gcc tac ggc cgc gta gcc tgg tat caa cag aaa cca gga       192
Ser Gln Ala Ala Tyr Gly Arg Val Ala Trp Tyr Gln Gln Lys Pro Gly
        50                  55                  60 aaa gct ccg aag ctt ctg att tac aaa gca tcc gaa ctc tac gcc gga       240
Lys Ala Pro Lys Leu Leu Ile Tyr Lys Ala Ser Glu Leu Tyr Ala Gly
65                  70                  75                  80 gtc cct tct cgc ttc tct ggt agc cgt tcc ggg acg gat ttc act ctg       288
Val Pro Ser Arg Phe Ser Gly Ser Arg Ser Gly Thr Asp Phe Thr Leu
                85                  90                  95 acc atc agc agt ctg cag ccg gaa gac ttc gca act tat tac tgt cag       336
Thr Ile Ser Ser Leu Gln Pro Glu Asp Phe Ala Thr Tyr Tyr Cys Gln
                100                 105                 110 caa cgt ggc tgg tat ctg ttc acg ttc gga cag ggt acc aag gtg gag       384
Gln Arg Gly Trp Tyr Leu Phe Thr Phe Gly Gln Gly Thr Lys Val Glu
            115                 120                 125
```

-continued

```
atc aaa cga act gtg gct gca cca tct gtc ttc atc ttc ccg cca tct        432
Ile Lys Arg Thr Val Ala Ala Pro Ser Val Phe Ile Phe Pro Pro Ser
    130             135                 140 gat tca cag ttg aaa tct gga act gcc tct gtt gtg tgc ctg ctg aat        480
Asp Ser Gln Leu Lys Ser Gly Thr Ala Ser Val Val Cys Leu Leu Asn
145             150                 155                 160 aac ttc tat ccc aga gag gcc aaa gta cag tgg aag gtg gat aac gcc        528
Asn Phe Tyr Pro Arg Glu Ala Lys Val Gln Trp Lys Val Asp Asn Ala
                165                 170                 175 ctc caa tcg ggt aac tcc cag gag agt gtc aca gag cag gac agc aag        576
Leu Gln Ser Gly Asn Ser Gln Glu Ser Val Thr Glu Gln Asp Ser Lys
                180                 185                 190 gac agc acc tac agc ctc agc agc acc ctg acg ctg agc aaa gca gac        624
Asp Ser Thr Tyr Ser Leu Ser Ser Thr Leu Thr Leu Ser Lys Ala Asp
            195                 200                 205 tac gaa aaa cat aaa gtc tac gcc tgc gaa gtc acc cat cag ggc ctg        672
Tyr Glu Lys His Lys Val Tyr Ala Cys Glu Val Thr His Gln Gly Leu
    210                 215                 220 agc tcg ccc gtc aca aag agc ttc aac agg gga gag tgt taa              714
Ser Ser Pro Val Thr Lys Ser Phe Asn Arg Gly Glu Cys
225                 230                 235 tactcgaggc tgagcaaagc agactactaa taacataaag tctacgccgg acgcatcgtg     774
gccctagtac gcaagttcac gtaaaaaggg taactagagg ttgaggtgat ttt atg       830
                                                            Met aaa aag aat atc gca ttt ctt ctt gca tct atg ttc gtt ttt tct att        878
Lys Lys Asn Ile Ala Phe Leu Leu Ala Ser Met Phe Val Phe Ser Ile
    240                 245                 250 gct aca aac gcg tac gct gag gtt cag ctg gtg gag tct ggc ggt ggc        926
Ala Thr Asn Ala Tyr Ala Glu Val Gln Leu Val Glu Ser Gly Gly Gly
255                 260                 265                 270 ctg gtg cag cca ggg ggc tca ctc cgt ttg tcc tgt gca gct tct ggc        974
Leu Val Gln Pro Gly Gly Ser Leu Arg Leu Ser Cys Ala Ala Ser Gly
                275                 280                 285 ttc gat tta ttt cat tat tct ata cac tgg gtg cgt cag gcc ccg ggt       1022
Phe Asp Leu Phe His Tyr Ser Ile His Trp Val Arg Gln Ala Pro Gly
                290                 295                 300 aag ggc ctg gaa tgg gtt gca tac att tac ccg tct tat ggc tat act       1070
Lys Gly Leu Glu Trp Val Ala Tyr Ile Tyr Pro Ser Tyr Gly Tyr Thr
    305                 310                 315 tat tat gcc gat agc gtc aag ggc cgt ttc act ata agc gca gac aca       1118
Tyr Tyr Ala Asp Ser Val Lys Gly Arg Phe Thr Ile Ser Ala Asp Thr
    320                 325                 330 tcc aaa aac aca gcc tac cta caa atg aac agc tta aga gct gag gac       1166
Ser Lys Asn Thr Ala Tyr Leu Gln Met Asn Ser Leu Arg Ala Glu Asp
335                 340                 345                 350 act gcc gtc tat tat tgt gct cgc cat gcg tgg tat tat ggg tgg ggt       1214
Thr Ala Val Tyr Tyr Cys Ala Arg His Ala Trp Tyr Tyr Gly Trp Gly
                355                 360                 365 ttg gac tac tgg ggt caa gga acc ctg gtc acc gtc tcc tcg gcc tcc       1262
Leu Asp Tyr Trp Gly Gln Gly Thr Leu Val Thr Val Ser Ser Ala Ser
                370                 375                 380 acc aag ggt cca tcg gtc ttc ccc ctg gca ccc tcc tcc aag agc acc       1310
Thr Lys Gly Pro Ser Val Phe Pro Leu Ala Pro Ser Ser Lys Ser Thr
                385                 390                 395 tct ggg ggc aca gcg gcc ctg ggc tgc ctg gtc aag gac tac ttc ccc       1358
Ser Gly Gly Thr Ala Ala Leu Gly Cys Leu Val Lys Asp Tyr Phe Pro
    400                 405                 410 gaa ccg gtg acg gtg tcg tgg aac tca ggc gcc ctg acc agc ggc gtg       1406
Glu Pro Val Thr Val Ser Trp Asn Ser Gly Ala Leu Thr Ser Gly Val
```

-continued

```
Glu Pro Val Thr Val Ser Trp Asn Ser Gly Ala Leu Thr Ser Gly Val
415                 420                 425                 430 cac acc ttc ccg gct gtc cta cag tcc tca gga ctc tac tcc ctc agc          1454
His Thr Phe Pro Ala Val Leu Gln Ser Ser Gly Leu Tyr Ser Leu Ser
                    435                 440                 445 agc gtg gtg acc gtg ccc tcc agc agc ttg ggc acc cag acc tac atc          1502
Ser Val Val Thr Val Pro Ser Ser Ser Leu Gly Thr Gln Thr Tyr Ile
                450                 455                 460 tgc aac gtg aat cac aag ccc agc aac acc aag gtc gac aag aaa gtt          1550
Cys Asn Val Asn His Lys Pro Ser Asn Thr Lys Val Asp Lys Lys Val
                465                 470                 475 gag ccc aaa tct tgt gac aaa act cac aca taa                              1583
Glu Pro Lys Ser Cys Asp Lys Thr His Thr
    480                 485
```

```
<210> SEQ ID NO 17
<211> LENGTH: 237
<212> TYPE: PRT
<213> ORGANISM: Artificial Sequence
<220> FEATURE:
<223> OTHER INFORMATION: Synthetic Construct

<400> SEQUENCE: 17

Met Lys Lys Asn Ile Ala Phe Leu Leu Ala Ser Met Phe Val Phe Ser
1                 5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

```
<210> SEQ ID NO 18
<211> LENGTH: 251
<212> TYPE: PRT
<213> ORGANISM: Artificial Sequence
```

```
<220> FEATURE:
<223> OTHER INFORMATION: Synthetic Construct

<400> SEQUENCE: 18

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

```
<210> SEQ ID NO 19
<211> LENGTH: 274
<212> TYPE: DNA
<213> ORGANISM: Escherichia coli
<220> FEATURE:
<221> NAME/KEY: terminator
<222> LOCATION: (1)..(274)
<223> OTHER INFORMATION: rrnB terminator

<400> SEQUENCE: 19
cgttttacaa cgtcgtgact gggaaaacat ccatgcgtta acgcgagagt agggaactgc     60
caggcatcaa ataaaacgaa aggctcagtc ggaagactgg gcctttcgtt ttatctgttg    120
tttgtcggtg aacgctctcc tgagtaggac aaatccgccg ggagcggatt tgaacgttgt    180
gaagcaacgg cccggagggt ggcgggcagg acgcccgcca taaactgcca ggcatcaaac    240
taagcagaag gccatcctga cggatggcct tttt                                274
```

```
<210> SEQ ID NO 20
<211> LENGTH: 3012
<212> TYPE: DNA
```

```
<213> ORGANISM: Escherichia coli
<220> FEATURE:
<221> NAME/KEY: misc_feature
<222> LOCATION: (1)..(3009)
<223> OTHER INFORMATION: vector sequences corresponding to pBR322
      (GenBank Accession No: J01749.1) from nucleotide position 1353 to
      4361 in which the tetracycline resistance gene of pBR322 has been
      deleted
<220> FEATURE:
<221> NAME/KEY: misc_feature
<222> LOCATION: (1944)..(2801)
<223> OTHER INFORMATION: beta-lactamase coding sequences with start of
      translation at nucleotide position 2801 and end of translation at
      nucleotide position 1944

<400> SEQUENCE: 20
gaatgcgcaa accaacccctt ggcagaacat atccatcgcg tccgccatct ccagcagccg      60
cacgcggcgc atctcgggca gcgttgggtc ctggccacgg gtgcgcatga tcgtgctcct     120
gtcgttgagg acccggctag gctggcgggg ttgccttact ggttagcaga atgaatcacc     180
gatacgcgag cgaacgtgaa gcgactgctg ctgcaaaacg tctgcgacct gagcaacaac     240
atgaatggtc ttcggtttcc gtgtttcgta aagtctggaa acgcggaagt cagcgccctg     300
caccattatg ttccggatct gcatcgcagg atgctgctgg ctaccctgtg gaacacctac     360
atctgtatta cgaagcgct ggcattgacc ctgagtgatt tttctctggt cccgccgcat     420
ccataccgcc agttgtttac cctcacaacg ttccagtaac cgggcatgtt catcatcagt     480
aacccgtatc gtgagcatcc tctctcgttt catcggtatc attaccccca tgaacagaaa     540
tcccccttac acgaggcat cagtgaccaa acaggaaaaa accgccctta acatggcccg     600
ctttatcaga agccagacat taacgcttct ggagaaactc aacgagctgg acgcggatga     660
acaggcagac atctgtgaat cgcttcacga ccacgctgat gagctttacc gcagctgcct     720
cgcgcgtttc ggtgatgacg gtgaaaacct ctgacacatg cagctcccgg agacggtcac     780
agcttgtctg taagcggatg ccgggagcag acaagcccgt cagggcgcgt cagcgggtgt     840
tggcgggtgt cggggcgcag ccatgaccca gtcacgtagc gatagcggag tgtatactgg     900
cttaactatg cggcatcaga gcagattgta ctgagagtgc accatatgcg gtgtgaaata     960
ccgcacagat gcgtaaggag aaaataccgc atcaggcgct cttccgcttc ctcgctcact    1020
gactcgctgc gctcggtcgt tcggctgcgg cgagcggtat cagctcactc aaaggcggta    1080
atacggttat ccacagaatc aggggataac gcaggaaaga acatgtgagc aaaaggccag    1140
caaaaggcca ggaaccgtaa aaaggccgcg ttgctggcgt ttttccatag gctccgcccc    1200
cctgacgagc atcacaaaaa tcgacgctca agtcagaggt ggcgaaaccc gacaggacta    1260
taaagatacc aggcgtttcc ccctggaagc tccctcgtgc gctctcctgt tccgaccctg    1320
ccgcttaccg gatacctgtc cgcctttctc ccttcgggaa gcgtggcgct ttctcatagc    1380
tcacgctgta ggtatctcag ttcggtgtag tcgttcgct ccaagctggg ctgtgtgcac    1440 gaacccccg ttcagcccga ccgctgcgcc ttatccggta actatcgtct tgagtccaac    1500
ccggtaagac acgacttatc gccactggca gcagccactg gtaacaggat tagcagagcg    1560
aggtatgtag gcggtgctac agagttcttg aagtggtggc ctaactacgg ctacactaga    1620
aggacagtat ttggtatctg cgctctgctg aagccagtta ccttcggaaa aagagttggt    1680
agctcttgat ccggcaaaca aaccaccgct ggtagcggtg gtttttttgt ttgcaagcag    1740
cagattacgc gcagaaaaaa aggatctcaa gaagatcctt tgatcttttc tacggggtct    1800
gacgctcagt ggaacgaaaa ctcacgttaa gggattttgg tcatgagatt atcaaaaagg    1860
```

```
atcttcacct agatcctttt aaattaaaaa tgaagtttta aatcaatcta aagtatatat    1920
gagtaaactt ggtctgacag ttaccaatgc ttaatcagtg aggcacctat ctcagcgatc    1980
tgtctatttc gttcatccat agttgcctga ctccccgtcg tgtagataac tacgatacgg    2040
gagggcttac catctggccc cagtgctgca atgataccgc gagacccacg ctcaccggct    2100
ccagatttat cagcaataaa ccagccagcc ggaagggccg agcgcagaag tggtcctgca    2160
actttatccg cctccatcca gtctattaat tgttgccggg aagctagagt aagtagttcg    2220
ccagttaata gtttgcgcaa cgttgttgcc attgctgcag gcatcgtggt gtcacgctcg    2280
tcgtttggta tggcttcatt cagctccggt tcccaacgat caaggcgagt tacatgatcc    2340
cccatgttgt gcaaaaaagc ggttagctcc ttcggtcctc cgatcgttgt cagaagtaag    2400
ttggccgcag tgttatcact catggttatg gcagcactgc ataattctct tactgtcatg    2460
ccatccgtaa gatgcttttc tgtgactggt gagtactcaa ccaagtcatt ctgagaatag    2520
tgtatgcggc gaccgagttg ctcttgcccg gcgtcaacac gggataatac cgcgccacat    2580
agcagaactt taaaagtgct catcattgga aaacgttctt cggggcgaaa actctcaagg    2640
atcttaccgc tgttgagatc cagttcgatg taacccactc gtgcacccaa ctgatcttca    2700
gcatctttta ctttcaccag cgtttctggg tgagcaaaaa caggaaggca aaatgccgca    2760
aaaaagggaa taagggcgac acggaaatgt tgaatactca tactcttcct ttttcaatat    2820
tattgaagca tttatcaggg ttattgtctc atgagcggat acatatttga atgtatttag    2880
aaaaataaac aaataggggt tccgcgcaca tttccccgaa aagtgccacc tgacgtctaa    2940
gaaaccatta ttatcatgac attaacctat aaaaataggc gtatcacgag gccctttcgt    3000
cttcaagaat tc                                                        3012

<210> SEQ ID NO 21
<211> LENGTH: 1583
<212> TYPE: DNA
<213> ORGANISM: Artificial Sequence
<220> FEATURE:
<223> OTHER INFORMATION: Variant 201 Sequence of  Example 3
<220> FEATURE:
<221> NAME/KEY: misc_feature
<222> LOCATION: (1)..(1583)

<400> SEQUENCE: 21
atgaaaaaga atatcgcatt tcttcttgca tctatgttcg ttttttctat tgctacaaat      60
gcctatgcag atatccagat gacccagtcc ccgagctccc tgtccgcctc tgtgggcgat     120
agggtcacca tcacctgccg tgccagtcag gccgcctacg gccgcgtagc ctggtatcaa     180
cagaaaccag gaaaagctcc gaagcttctg atttacaaag catccgaact ctacgccgga     240
gtcccttctc gcttctctgg tagccgttcc gggacggatt tcactctgac catcagcagt     300
ctgcagccgg aagacttcgc aacttattac tgtcagcaac gtggctggta tctgttcacg     360
ttcggacagg gtaccaaggt ggagatcaaa cgaactgtgg ctgcaccatc tgtcttcatc     420
ttcccgccat ctgattcaca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgaa aaacataaag tctacgcctg cgaagtcacc     660
catcagggcc tgagctcgcc cgtcacaaag agcttcaaca ggggagagtg ttaatactcg     720
aggctgagca aagcagacta ctaataacat aaagtctacg ccggacgcat cgtggcccta     780
```

-continued

```
gtacgcaagt tcacgtaaaa agggtaacta gaggttgagg tgattttatg aaaaagaata      840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
gtgcagcttc tggcttcgat ttatttcatt attctataca ctgggtgcgt caggccccgg     1020
gtaagggcct ggaatgggtt gcatacattt acccgtctta tggctatact tattatgccg     1080
atagcgtcaa gggccgtttc actataagcg cagacacatc caaaaacaca gcctacctac     1140
aaatgaacag cttaagagct gaggacactg ccgtctatta ttgtgctcgc catgcgtggt     1200
attatgggtg gggtttggac tactggggtc aaggaaccct ggtcaccgtc tcctcggcct     1260
ccaccaaggg tccatcggtc ttccccctgg caccctcctc caagagcacc tctgggggca     1320
cagcggccct gggctgcctg gtcaaggact acttccccga accggtgacg gtgtcgtgga     1380
actcaggcgc cctgaccagc ggcgtgcaca ccttcccggc tgtcctacag tcctcaggac     1440
tctactccct cagcagcgtg gtgaccgtgc cctccagcag cttgggcacc cagacctaca     1500
tctgcaacgt gaatcacaag cccagcaaca ccaaggtcga caagaaagtt gagcccaaat     1560
cttgtgacaa aactcacaca taa                                            1583
```

```
<210> SEQ ID NO 22
<211> LENGTH: 1583
<212> TYPE: DNA
<213> ORGANISM: Artificial Sequence
<220> FEATURE:
<223> OTHER INFORMATION: Variant 202 Sequence of Example 3
<220> FEATURE:
<221> NAME/KEY: misc_feature
<222> LOCATION: (1)..(1583)

<400> SEQUENCE: 22
```

```
atgaaaaaga atatcgcatt tcttcttgca tctatgttcg tttttttctat tgctacaaat       60 gcctatgcag atatccagat gacccagtcc ccgagctccc tgtccgcctc tgtgggcgat      120
agggtcacca tcacctgccg tgccagtcag gccgcctacg gccgcgtagc ctggtatcaa      180
cagaaaccag gaaaagctcc gaagcttctg atttacaaag catccgaact cgacgccgga      240
gtcccttctc gcttctctgg tagccgttcc gggacggatt tcactctgac catcagcagt      300
ctgcagccgg aagacttcgc aacttattac tgtcagcaac gtggctggta tctgttcacg      360
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
aggctgagca aagcagacta ctaataacat aaagtctacg ccggacgcat cgtggcccta      780
gtacgcaagt tcacgtaaaa agggtaacta gaggttgagg tgattttatg aaaaagaata      840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
gtgcagcttc tggcttcgat ttatttcatt attctataca ctgggtgcgt caggccccgg     1020
gtaagggcct ggaatgggtt gcatacattt acccgtctta tggctatact tattatgccg     1080
atagcgtcaa gggccgtttc actataagcg cagacacatc caaaaacaca gcctacctac     1140
```

-continued

```
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                             1583
```

```
<210> SEQ ID NO 23
<211> LENGTH: 1583
<212> TYPE: DNA
<213> ORGANISM: Artificial Sequence
<220> FEATURE:
<223> OTHER INFORMATION: Variant 203 Sequence of Example 3
<220> FEATURE:
<221> NAME/KEY: misc_feature
<222> LOCATION: (1)..(1583)

<400> SEQUENCE: 23
```

```
atgaaaaaga atatcgcatt tcttcttgca tctatgttcg ttttttctat tgctacaaat        60
gcctatgcag atatccagat gacccagtcc ccgagctccc tgtccgcctc tgtgggcgat       120
agggtcacca tcacctgccg tgccagtcag gccgcctacg gccgcgtagc ctggtatcaa       180
cagaaaccag gaaaagctcc gaagcttctg atttacaaag catccgatct ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
ttcggacagg gtaccaaggt ggagatcaaa cgaactgtgg ctgcaccatc tgtcttcatc       420
ttcccgccat ctgattcaca gttgaaatct ggaactgcct ctgttgtgtg cctgctgaat       480
aacttctatc ccagagaggc caaagtacag tggaaggtgg ataacgccct ccaatcgggt       540
aactcccagg agagtgtcac agagcaggac agcaaggaca gcacctacag cctcagcagc       600
accctgacgc tgagcaaagc agactacgaa aaacataaag tctacgcctg cgaagtcacc       660
catcagggcc tgagctcgcc cgtcacaaag agcttcaaca ggggagagtg ttaatactcg       720
aggctgagca aagcagacta ctaataacat aaagtctacg ccggacgcat cgtggcccta       780
gtacgcaagt tcacgtaaaa agggtaacta gaggttgagg tgattttatg aaaaagaata       840
tcgcatttct tcttgcatct atgttcgttt tttctattgc tacaaacgcg tacgctgagg       900
ttcagctggt ggagtctggc ggtggcctgg tgcagccagg gggctcactc cgtttgtcct       960
gtgcagcttc tggcttcgat ttatttcatt attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
```

```
tctgcaacgt gaatcacaag cccagcaaca ccaaggtcga caagaaagtt gagcccaaat    1560
cttgtgacaa aactcacaca taa                                            1583
```

<210> SEQ ID NO 24
<211> LENGTH: 1583
<212> TYPE: DNA
<213> ORGANISM: Artificial Sequence
<220> FEATURE:
<223> OTHER INFORMATION: Variant Sequence of Example 3
<220> FEATURE:
<221> NAME/KEY: misc_feature
<222> LOCATION: (1)..(1583)

<400> SEQUENCE: 24

```
atgaaaaaga atatcgcatt tcttcttgca tctatgttcg ttttttctat tgctacaaat      60
gcctatgcag atatccagat gacccagtcc ccgagctccc tgtccgcctc tgtgggcgat     120
agggtcacca tcacctgccg tgccagtcag gccgcctacg gccgcgtagc ctggtatcaa     180
cagaaaccag gaaaagctcc gaagcttctg atttacaaag cagacgaact ctacgccgga     240
gtcccttctc gcttctctgg tagccgttcc gggacggatt tcactctgac catcagcagt     300
ctgcagccgg aagacttcgc aacttattac tgtcagcaac gtggctggta tctgttcacg     360
ttcggacagg gtaccaaggt ggagatcaaa cgaactgtgg ctgcaccatc tgtcttcatc     420
ttcccgccat ctgattcaca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgaa aaacataaag tctacgcctg cgaagtcacc     660
catcagggcc tgagctcgcc cgtcacaaag agcttcaaca ggggagagtg ttaatactcg     720
aggctgagca aagcagacta ctaataacat aaagtctacg ccggacgcat cgtggcccta     780
gtacgcaagt tcacgtaaaa agggtaacta gaggttgagg tgattttatg aaaaagaata     840
tcgcatttct tcttgcatct atgttcgttt tttctattgc tacaaacgcg tacgctgagg     900
ttcagctggt ggagtctggc ggtggcctgg tgcagccagg gggctcactc cgtttgtcct     960
gtgcagcttc tggcttcgat ttatttcatt attctataca ctgggtgcgt caggccccgg    1020
gtaagggcct ggaatgggtt gcatacattt acccgtctta tggctatact tattatgccg    1080
atagcgtcaa gggccgtttc actataagcg cagacacatc caaaaacaca gcctacctac    1140
aaatgaacag cttaagagct gaggacactg ccgtctatta ttgtgctcgc catgcgtggt    1200
attatgggtg gggtttggac tactggggtc aaggaaccct ggtcaccgtc tcctcggcct    1260
ccaccaaggg tccatcggtc ttccccctgg caccctcctc caagagcacc tctgggggca    1320
cagcggccct gggctgcctg gtcaaggact acttccccga accggtgacg gtgtcgtgga    1380
actcaggcgc cctgaccagc ggcgtgcaca ccttcccggc tgtcctacag tcctcaggac    1440
tctactccct cagcagcgtg gtgaccgtgc cctccagcag cttgggcacc cagacctaca    1500
tctgcaacgt gaatcacaag cccagcaaca ccaaggtcga caagaaagtt gagcccaaat    1560
cttgtgacaa aactcacaca taa                                            1583
```

<210> SEQ ID NO 25
<211> LENGTH: 1583
<212> TYPE: DNA
<213> ORGANISM: Artificial Sequence
<220> FEATURE:
<223> OTHER INFORMATION: Variant 205 Sequence of Example 3
<220> FEATURE:

```
<221> NAME/KEY: misc_feature
<222> LOCATION: (1)..(1583)

<400> SEQUENCE: 25
atgaaaaaga atatcgcatt tcttcttgca tctatgttcg ttttttctat tgctacaaat      60
gcctatgcag atatccagat gacccagtcc ccgagctccc tgtccgcctc tgtgggcgat     120
agggtcacca tcacctgccg tgccagtcag gccgcctacg gccgcgtagc ctggtatcaa     180
cagaaaccag gaaaagctcc gaagcttctg atttacaaag attccgaact ctacgccgga     240
gtcccttctc gcttctctgg tagccgttcc gggacggatt tcactctgac catcagcagt     300
ctgcagccgg aagacttcgc aacttattac tgtcagcaac gtggctggta tctgttcacg     360
ttcggacagg gtaccaaggt ggagatcaaa cgaactgtgg ctgcaccatc tgtcttcatc     420
ttcccgccat ctgattcaca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgaa aaacataaag tctacgcctg cgaagtcacc     660
catcagggcc tgagctcgcc cgtcacaaag agcttcaaca ggggagagtg ttaatactcg     720
aggctgagca aagcagacta ctaataacat aaagtctacg ccggacgcat cgtggcccta     780
gtacgcaagt tcacgtaaaa agggtaacta gaggttgagg tgattttatg aaaaagaata     840
tcgcatttct tcttgcatct atgttcgttt tttctattgc tacaaacgcg tacgctgagg     900
ttcagctggt ggagtctggc ggtggcctgg tgcagccagg gggctcactc cgtttgtcct     960
gtgcagcttc tggcttcgat ttatttcatt attctataca ctgggtgcgt caggccccgg    1020
gtaagggcct ggaatgggtt gcatacattt acccgtctta tggctatact tattatgccg    1080
atagcgtcaa gggccgtttc actataagcg cagacacatc caaaaacaca gcctacctac    1140
aaatgaacag cttaagagct gaggacactg ccgtctatta ttgtgctcgc catgcgtggt    1200
attatgggtg gggtttggac tactggggtc aaggaaccct ggtcaccgtc tcctcggcct    1260
ccaccaaggg tccatcggtc ttccccctgg caccctcctc caagagcacc tctgggggca    1320
cagcggccct gggctgcctg gtcaaggact acttccccga accggtgacg gtgtcgtgga    1380
actcaggcgc cctgaccagc ggcgtgcaca ccttcccggc tgtcctacag tcctcaggac    1440
tctactccct cagcagcgtg gtgaccgtgc cctccagcag cttgggcacc cagacctaca    1500
tctgcaacgt gaatcacaag cccagcaaca ccaaggtcga caagaaagtt gagcccaaat    1560
cttgtgacaa aactcacaca taa                                            1583

<210> SEQ ID NO 26
<211> LENGTH: 1583
<212> TYPE: DNA
<213> ORGANISM: Artificial Sequence
<220> FEATURE:
<223> OTHER INFORMATION: Variant 206 Sequence of Example 3
<220> FEATURE:
<221> NAME/KEY: misc_feature
<222> LOCATION: (1)..(1583)

<400> SEQUENCE: 26
atgaaaaaga atatcgcatt tcttcttgca tctatgttcg ttttttctat tgctacaaat      60
gcctatgcag atatccagat gacccagtcc ccgagctccc tgtccgcctc tgtgggcgat     120
agggtcacca tcacctgccg tgccagtcag gccgcctacg gccgcgtagc ctggtatcaa     180
cagaaaccag gaaaagctcc gaagcttctg atttacgatg catccgaact ctacgccgga     240
```

-continued

```
gtcccttctc gcttctctgg tagccgttcc gggacggatt tcactctgac catcagcagt      300
ctgcagccgg aagacttcgc aacttattac tgtcagcaac gtggctggta tctgttcacg      360
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
aggctgagca aagcagacta ctaataacat aaagtctacg ccggacgcat cgtggcccta      780
gtacgcaagt tcacgtaaaa agggtaacta gaggttgagg tgattttatg aaaaagaata      840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
gtgcagcttc tggcttcgat ttatttcatt attctataca ctgggtgcgt caggccccgg     1020
gtaagggcct ggaatgggtt gcatacattt acccgtctta tggctatact tattatgccg     1080
atagcgtcaa gggccgtttc actataagcg cagacacatc caaaaacaca gcctacctac     1140
aaatgaacag cttaagagct gaggacactg ccgtctatta ttgtgctcgc catgcgtggt     1200
attatgggtg gggtttggac tactggggtc aaggaacccct ggtcaccgtc tcctcggcct     1260
ccaccaaggg tccatcggtc ttccccctgg caccctcctc caagagcacc tctgggggca     1320
cagcggccct gggctgcctg gtcaaggact acttccccga accggtgacg gtgtcgtgga     1380
actcaggcgc cctgaccagc ggcgtgcaca ccttccccggc tgtcctacag tcctcaggac     1440
tctactccct cagcagcgtg gtgaccgtgc cctccagcag cttgggcacc cagacctaca     1500
tctgcaacgt gaatcacaag cccagcaaca ccaaggtcga caagaaagtt gagcccaaat     1560
cttgtgacaa aactcacaca taa                                             1583
```

```
<210> SEQ ID NO 27
<211> LENGTH: 1583
<212> TYPE: DNA
<213> ORGANISM: Artificial Sequence
<220> FEATURE:
<223> OTHER INFORMATION: Variant 207 Sequence of Example 3
<220> FEATURE:
<221> NAME/KEY: misc_feature
<222> LOCATION: (1)..(1583)

<400> SEQUENCE: 27
```

```
atgaaaaaga atatcgcatt tcttcttgca tctatgttcg ttttttctat tgctacaaat       60
gcctatgcag atatccagat gacccagtcc ccgagctccc tgtccgcctc tgtgggcgat      120
agggtcacca tcacctgccg tgccagtcag gccgcctacg gccgcgtagc ctggtatcaa      180
cagaaaccag gaaaagctcc gaagcttctg attgacaaag catccgaact ctacgccgga      240
gtcccttctc gcttctctgg tagccgttcc gggacggatt tcactctgac catcagcagt      300
ctgcagccgg aagacttcgc aacttattac tgtcagcaac gtggctggta tctgttcacg      360
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
```

```
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
aggctgagca aagcagacta ctaataacat aaagtctacg ccggacgcat cgtggccta      780 gtacgcaagt tcacgtaaaa agggtaacta gaggttgagg tgattttatg aaaaagaata     840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
gtgcagcttc tggcttcgat ttatttcatt attctataca ctgggtgcgt caggccccgg     1020
gtaagggcct ggaatgggtt gcatacattt acccgtctta tggctatact tattatgccg     1080
atagcgtcaa gggccgtttc actataagcg cagacacatc caaaaacaca gcctacctac     1140
aaatgaacag cttaagagct gaggacactg ccgtctatta ttgtgctcgc catgcgtggt     1200
attatgggtg gggtttggac tactggggtc aaggaaccct ggtcaccgtc tcctcggcct     1260
ccaccaaggg tccatcggtc ttcccccctgg caccctcctc caagagcacc tctgggggca     1320
cagcggccct gggctgcctg gtcaaggact acttccccga accggtgacg gtgtcgtgga     1380
actcaggcgc cctgaccagc ggcgtgcaca ccttccccggc tgtcctacag tcctcaggac     1440
tctactccct cagcagcgtg gtgaccgtgc cctccagcag cttgggcacc cagacctaca     1500
tctgcaacgt gaatcacaag cccagcaaca ccaaggtcga caagaaagtt gagcccaaat     1560
cttgtgacaa aactcacaca taa                                            1583
```

```
<210> SEQ ID NO 28
<211> LENGTH: 1583
<212> TYPE: DNA
<213> ORGANISM: Artificial Sequence
<220> FEATURE:
<223> OTHER INFORMATION: Variant 208 Sequence of Example 3
<220> FEATURE:
<221> NAME/KEY: misc_feature
<222> LOCATION: (1)..(1583)

<400> SEQUENCE: 28
atgaaaaaga atatcgcatt tcttcttgca tctatgttcg tttttttctat tgctacaaat      60 gcctatgcag atatccagat gacccagtcc ccgagctccc tgtccgcctc tgtgggcgat      120
agggtcacca tcacctgcga tgccagtcag gccgcctacg gccgcgtagc ctggtatcaa      180
cagaaaccag gaaaagctcc gaagcttctg atttacaaag catccgaact ctacgccgga      240
gtcccttctc gcttctctgg tagccgttcc gggacggatt tcactctgac catcagcagt      300
ctgcagccgg aagacttcgc aacttattac tgtcagcaac gtggctggta tctgttcacg      360
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
aggctgagca aagcagacta ctaataacat aaagtctacg ccggacgcat cgtggccta      780 gtacgcaagt tcacgtaaaa agggtaacta gaggttgagg tgattttatg aaaaagaata     840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
```

```
gtgcagcttc tggcttcgat ttatttcatt attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                             1583
```

<210> SEQ ID NO 29
<211> LENGTH: 1586
<212> TYPE: DNA
<213> ORGANISM: Artificial Sequence
<220> FEATURE:
<223> OTHER INFORMATION: Variant 209 Sequence of Example 3
<220> FEATURE:
<221> NAME/KEY: misc_feature
<222> LOCATION: (1)..(1583)

<400> SEQUENCE: 29

```
atgaaaaaga atatcgcatt tcttcttgca tctatgttcg tttttttctat tgctacaaat        60 gcctatgcag atatccagat gacccagtcc ccgagctccc tgtccgcctc tgtgggcgat       120
agggtcacca tcacctgccg tgccagtcag gatgccgcct acggccgcgt agcctggtat       180
caacagaaac caggaaaagc tccgaagctt ctgatttaca aagcatccga actctacgcc       240
ggagtcccct ctcgcttctc tggtagccgt tccgggacgg atttcactct gaccatcagc       300
agtctgcagc cggaagactt cgcaacttat tactgtcagc aacgtggctg gtatctgttc       360
acgttcggac agggtaccaa ggtggagatc aaacgaactg tggctgcacc atctgtcttc       420
atcttcccgc catctgattc acagttgaaa tctggaactg cctctgttgt gtgcctgctg       480
aataacttct atcccagaga ggccaaagta cagtggaagg tggataacgc cctccaatcg       540
ggtaactccc aggagagtgt cacagagcag gacagcaagg acagcaccta cagcctcagc       600
agcaccctga cgctgagcaa agcagactac gaaaaacata agtctacgc ctgcgaagtc       660 acccatcagg gcctgagctc gcccgtcaca aagagcttca cagggggaga gtgttaatac       720
tcgaggctga gcaaagcaga ctactaataa cataaagtct acgccggacg catcgtggcc       780
ctagtacgca agttcacgta aaaagggtaa ctagaggttg aggtgatttt atgaaaaaga       840
atatcgcatt tcttcttgca tctatgttcg tttttttctat tgctacaaac gcgtacgctg       900
aggttcagct ggtggagtct ggcggtggcc tggtgcagcc agggggctca ctccgtttgt       960
cctgtgcagc ttctggcttc gatttatttc attattctat acactgggtg cgtcaggccc      1020
cgggtaaggg cctggaatgg gttgcataca tttacccgtc ttatggctat acttattatg      1080
ccgatagcgt caagggccgt ttcactataa gcgcagacac atccaaaaac acagcctacc      1140
tacaaatgaa cagcttaaga gctgaggaca ctgccgtcta ttattgtgct cgccatgcgt      1200
ggtattatgg gtggggtttg gactactggg gtcaaggaac cctggtcacc gtctcctcgg      1260
cctccaccaa gggtccatcg gtcttccccc tggcaccctc ctccaagagc acctctgggg      1320
```

```
gcacagcggc cctgggctgc ctggtcaagg actacttccc cgaaccggtg acggtgtcgt   1380
ggaactcagg cgccctgacc agcggcgtgc acaccttccc ggctgtccta cagtcctcag   1440
gactctactc cctcagcagc gtggtgaccg tgccctccag cagcttgggc acccagacct   1500
acatctgcaa cgtgaatcac aagcccagca acaccaaggt cgacaagaaa gttgagcccca   1560 aatcttgtga caaaactcac acataa                                        1586
```

```
<210> SEQ ID NO 30
<211> LENGTH: 1583
<212> TYPE: DNA
<213> ORGANISM: Artificial Sequence
<220> FEATURE:
<223> OTHER INFORMATION: Variant 212 Sequence of Example 3
<220> FEATURE:
<221> NAME/KEY: misc_feature
<222> LOCATION: (1)..(1583)

<400> SEQUENCE: 30
```

```
atgaaaaaga atatcgcatt tcttcttgca tctatgttcg ttttttctat tgctacaaat     60
gcctatgcag atatccagat gacccagtcc ccgagctccc tgtccgcctc tgtgggcgat    120
agggtcacca tcacctgccg tgccagtcag gccgcctacg gccgcgtagc ctggtatcaa    180
cagaaaccag gaaaagctcc gaagcttctg atttacaaag catccgaact ctacgccgga    240
gtcccttctc gcttctctgg tagccgttcc gggacggatt tcactctgac catcagcagt    300
ctgcagccgg aagacttcgc aacttattac tgtcagcaac gtggctggta tctgttcacg    360
ttcggacagg gtaccaaggt ggagatcaaa cgaactgtgg ctgcaccatc tgtcttcatc    420
ttcccgccat ctgattcaca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgaa aaacataaag tctacgcctg cgaagtcacc    660
catcagggcc tgagctcgcc cgtcacaaag agcttcaaca ggggagagtg ttaatactcg    720
aggctgagca aagcagacta ctaataacat aaagtctacg ccggacgcat cgtggcccta    780
gtacgcaagt tcacgtaaaa agggtaacta gaggttgagg tgattttatg aaaaagaata    840
tcgcatttct tcttgcatct atgttcgttt tttctattgc tacaaacgcg tacgctgagg    900
ttcagctggt ggagtctggc ggtggcctgg tgcagccagg gggctcactc cgtttgtcct    960
gtgcagcttc tggcttcgat ttatttcatt attctataga ctgggtgcgt caggccccgg   1020
gtaagggcct ggaatgggtt gcatacattt acccgtctta tggctatact tattatgccg   1080
atagcgtcaa gggccgtttc actataagcg cagacacatc caaaaacaca gcctacctac   1140
aaatgaacag cttaagagct gaggacactg ccgtctatta ttgtgctcgc catgcgtggt   1200
attatgggtg gggtttggac tactggggtc aaggaaccct ggtcaccgtc tcctcggcct   1260
ccaccaaggg tccatcggtc ttcccccctgg caccctcctc caagagcacc tctgggggca   1320
cagcggccct gggctgcctg gtcaaggact acttccccga accggtgacg gtgtcgtgga   1380
actcaggcgc cctgaccagc ggcgtgcaca ccttcccggc tgtcctacag tcctcaggac   1440
tctactccct cagcagcgtg gtgaccgtgc cctccagcag cttgggcacc cagacctaca   1500
tctgcaacgt gaatcacaag cccagcaaca ccaaggtcga caagaaagtt gagcccaaat   1560
cttgtgacaa aactcacaca taa                                          1583
```

-continued

```
<210> SEQ ID NO 31
<211> LENGTH: 1583
<212> TYPE: DNA
<213> ORGANISM: Artificial Sequence
<220> FEATURE:
<223> OTHER INFORMATION: Variant 213 Sequence of Example 3
<220> FEATURE:
<221> NAME/KEY: misc_feature
<222> LOCATION: (1)..(1583)

<400> SEQUENCE: 31
atgaaaaaga atatcgcatt tcttcttgca tctatgttcg tttttttctat tgctacaaat        60 gcctatgcag atatccagat gacccagtcc ccgagctccc tgtccgcctc tgtgggcgat       120
agggtcacca tcacctgccg tgccagtcag gccgcctacg gccgcgtagc ctggtatcaa       180
cagaaaccag gaaaagctcc gaagcttctg atttacaaag catccgaact ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
ttcggacagg gtaccaaggt ggagatcaaa cgaactgtgg ctgcaccatc tgtcttcatc       420
ttcccgccat ctgattcaca gttgaaatct ggaactgcct ctgttgtgtg cctgctgaat       480
aacttctatc ccagagaggc caaagtacag tggaaggtgg ataacgccct ccaatcgggt       540
aactcccagg agagtgtcac agagcaggac agcaaggaca gcacctacag cctcagcagc       600
accctgacgc tgagcaaagc agactacgaa aaacataaag tctacgcctg cgaagtcacc       660
catcagggcc tgagctcgcc cgtcacaaag agcttcaaca ggggagagtg ttaatactcg       720
aggctgagca aagcagacta ctaataacat aaagtctacg ccggacgcat cgtggcccta       780
gtacgcaagt tcacgtaaaa agggtaacta gaggttgagg tgattttatg aaaaagaata       840
tcgcatttct tcttgcatct atgttcgttt tttctattgc tacaaacgcg tacgctgagg       900
ttcagctggt ggagtctggc ggtggcctgg tgcagccagg gggctcactc cgtttgtcct       960
gtgcagcttc tggcttcgat ttatttcatt atgatataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                             1583

<210> SEQ ID NO 32
<211> LENGTH: 1583
<212> TYPE: DNA
<213> ORGANISM: Artificial Sequence
<220> FEATURE:
<223> OTHER INFORMATION: Variant 214 Sequence of Example 3
<220> FEATURE:
<221> NAME/KEY: misc_feature
<222> LOCATION: (1)..(1583)

<400> SEQUENCE: 32
```

-continued

```
atgaaaaaga atatcgcatt tcttcttgca tctatgttcg ttttttctat tgctacaaat        60
gcctatgcag atatccagat gacccagtcc ccgagctccc tgtccgcctc tgtgggcgat       120
agggtcacca tcacctgccg tgccagtcag gccgcctacg gccgcgtagc ctggtatcaa       180
cagaaaccag gaaaagctcc gaagcttctg atttacaaag catccgaact ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
ttcggacagg gtaccaaggt ggagatcaaa cgaactgtgg ctgcaccatc tgtcttcatc       420
ttcccgccat ctgattcaca gttgaaatct ggaactgcct ctgttgtgtg cctgctgaat       480
aacttctatc ccagagaggc caaagtacag tggaaggtgg ataacgccct ccaatcgggt       540
aactcccagg agagtgtcac agagcaggac agcaaggaca gcacctacag cctcagcagc       600
accctgacgc tgagcaaagc agactacgaa aaacataaag tctacgcctg cgaagtcacc       660
catcagggcc tgagctcgcc cgtcacaaag agcttcaaca ggggagagtg ttaatactcg       720
aggctgagca aagcagacta ctaataacat aaagtctacg ccggacgcat cgtggcccta       780
gtacgcaagt tcacgtaaaa agggtaacta gaggttgagg tgattttatg aaaaagaata       840
tcgcatttct tcttgcatct atgttcgttt tttctattgc tacaaacgcg tacgctgagg       900
ttcagctggt ggagtctggc ggtggcctgg tgcagccagg gggctcactc cgtttgtcct       960
gtgcagcttc tggcttcgat ttatttcatg attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctggggca       1320 cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                             1583
```

```
<210> SEQ ID NO 33
<211> LENGTH: 1583
<212> TYPE: DNA
<213> ORGANISM: Artificial Sequence
<220> FEATURE:
<223> OTHER INFORMATION: Variant 215 Seuence of Example 3
<220> FEATURE:
<221> NAME/KEY: misc_feature
<222> LOCATION: (1)..(1583)

<400> SEQUENCE: 33
```

```
atgaaaaaga atatcgcatt tcttcttgca tctatgttcg ttttttctat tgctacaaat        60
gcctatgcag atatccagat gacccagtcc ccgagctccc tgtccgcctc tgtgggcgat       120
agggtcacca tcacctgccg tgccagtcag gccgcctacg gccgcgtagc ctggtatcaa       180
cagaaaccag gaaaagctcc gaagcttctg atttacaaag catccgaact ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
```

```
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
aggctgagca aagcagacta ctaataacat aaagtctacg ccggacgcat cgtggcccta      780
gtacgcaagt tcacgtaaaa agggtaacta gaggttgagg tgattttatg aaaaagaata      840
tcgcatttct tcttgcatct atgttcgttt tttctattgc tacaaacgcg tacgctgagg      900
ttcagctggt ggagtctggc ggtggcctgg tgcagccagg gggctcactc cgtttgtcct      960
gtgcagcttc tggcttcgat ttatttgatt attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg cacctcctc caagagcacc tctggggca       1320 cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                              1583
```

```
<210> SEQ ID NO 34
<211> LENGTH: 1583
<212> TYPE: DNA
<213> ORGANISM: Artificial Sequence
<220> FEATURE:
<223> OTHER INFORMATION: Variant 216 Sequence of Example 3
<220> FEATURE:
<221> NAME/KEY: misc_feature
<222> LOCATION: (1)..(1583)

<400> SEQUENCE: 34
atgaaaaaga atatcgcatt tcttcttgca tctatgttcg tttttttctat tgctacaaat      60 gcctatgcag atatccagat gacccagtcc ccgagctccc tgtccgcctc tgtgggcgat      120
agggtcacca tcacctgccg tgccagtcag gccgcctacg gccgcgtagc ctggtatcaa      180
cagaaaccag gaaaagctcc gaagcttctg atttacaaag catccgaact ctacgccgga      240
gtcccttctc gcttctctgg tagccgttcc gggacggatt tcactctgac catcagcagt      300
ctgcagccga agacttcgc aacttattac tgtcagcaac gtggctggta tctgttcacg      360
ttcggacagg gtaccaaggt ggagatcaaa cgaactgtgg ctgcaccatc tgtcttcatc      420
ttcccgccat ctgattcaca gttgaaatct ggaactgcct ctgttgtgtg cctgctgaat      480
aacttctatc ccagagaggc caaagtacag tggaaggtgg ataacgccct ccaatcgggt      540
aactcccagg agagtgtcac agagcaggac agcaaggaca gcacctacag cctcagcagc      600
accctgacgc tgagcaaagc agactacgaa aaacataaag tctacgcctg cgaagtcacc      660
catcagggcc tgagctcgcc cgtcacaaag agcttcaaca ggggagagtg ttaatactcg      720
```

-continued

```
aggctgagca aagcagacta ctaataacat aaagtctacg ccggacgcat cgtggcccta        780
gtacgcaagt tcacgtaaaa agggtaacta gaggttgagg tgattttatg aaaaagaata        840
tcgcatttct tcttgcatct atgttcgttt tttctattgc tacaaacgcg tacgctgagg        900
ttcagctggt ggagtctggc ggtggcctgg tgcagccagg gggctcactc cgtttgtcct        960
gtgcagcttc tggcttcgat ttagatcatt attctataca ctgggtgcgt caggccccgg       1020
gtaagggcct ggaatgggtt gcatacattt acccgtctta tggctatact tattatgccg       1080
atagcgtcaa gggccgtttc actataagcg cagacacatc caaaaacaca gcctacctac       1140
aaatgaacag cttaagagct gaggacactg ccgtctatta ttgtgctcgc catgcgtggt       1200
attatgggtg gggtttggac tactggggtc aaggaaccct ggtcaccgtc tcctcggcct       1260
ccaccaaggg tccatcggtc ttccccctgg caccctcctc caagagcacc tctggggca        1320 cagcggccct gggctgcctg gtcaaggact acttccccga accggtgacg gtgtcgtgga       1380
actcaggcgc cctgaccagc ggcgtgcaca ccttccccggc tgtcctacag tcctcaggac      1440
tctactccct cagcagcgtg gtgaccgtgc cctccagcag cttgggcacc cagacctaca       1500
tctgcaacgt gaatcacaag cccagcaaca ccaaggtcga caagaaagtt gagcccaaat       1560
cttgtgacaa aactcacaca taa                                              1583
```

```
<210> SEQ ID NO 35
<211> LENGTH: 1583
<212> TYPE: DNA
<213> ORGANISM: Artificial Sequence
<220> FEATURE:
<223> OTHER INFORMATION: Variant 217 Sequence of Example 3
<220> FEATURE:
<221> NAME/KEY: misc_feature
<222> LOCATION: (1)..(1583)

<400> SEQUENCE: 35
```

```
atgaaaaaga atatcgcatt tcttcttgca tctatgttcg ttttttctat tgctacaaat         60
gcctatgcag atatccagat gacccagtcc ccgagctccc tgtccgcctc tgtgggcgat        120
agggtcacca tcacctgccg tgccagtcag gacgcctacg gccgcgtagc ctggtatcaa        180
cagaaaccag gaaaagctcc gaagcttctg atttacaaag catccgaact ctacgccgga        240
gtcccttctc gcttctctgg tagccgttcc gggacggatt tcactctgac catcagcagt        300
ctgcagccgg aagacttcgc aacttattac tgtcagcaac gtggctggta tctgttcacg        360
ttcggacagg gtaccaaggt ggagatcaaa cgaactgtgg ctgcaccatc tgtcttcatc        420
ttcccgccat ctgattcaca gttgaaatct ggaactgcct ctgttgtgtg cctgctgaat        480
aacttctatc ccagagaggc caaagtacag tggaaggtgg ataacgccct ccaatcgggt        540
aactcccagg agagtgtcac agagcaggac agcaaggaca gcacctacag cctcagcagc        600
accctgacgc tgagcaaagc agactacgaa aaacataaag tctacgcctg cgaagtcacc        660
catcagggcc tgagctcgcc cgtcacaaag agcttcaaca ggggagagtg ttaatactcg        720
aggctgagca aagcagacta ctaataacat aaagtctacg ccggacgcat cgtggcccta        780
gtacgcaagt tcacgtaaaa agggtaacta gaggttgagg tgattttatg aaaaagaata        840
tcgcatttct tcttgcatct atgttcgttt tttctattgc tacaaacgcg tacgctgagg        900
ttcagctggt ggagtctggc ggtggcctgg tgcagccagg gggctcactc cgtttgtcct        960
gtgcagcttc tggcttcgat ttatttcatt attctataca ctgggtgcgt caggccccgg       1020
gtaagggcct ggaatgggtt gcatacattt acccgtctta tggctatact tattatgccg       1080
```

-continued

```
atagcgtcaa gggccgtttc actataagcg cagacacatc caaaaacaca gcctacctac    1140
aaatgaacag cttaagagct gaggacactg ccgtctatta ttgtgctcgc catgcgtggt    1200
attatgggtg gggtttggac tactgggtc aaggaaccct ggtcaccgtc tcctcggcct    1260
ccaccaaggg tccatcggtc ttcccctgg caccctcctc caagagcacc tctgggggca    1320
cagcggccct gggctgcctg gtcaaggact acttccccga accggtgacg gtgtcgtgga    1380
actcaggcgc cctgaccagc ggcgtgcaca ccttcccggc tgtcctacag tcctcaggac    1440
tctactccct cagcagcgtg gtgaccgtgc cctccagcag cttgggcacc cagacctaca    1500
tctgcaacgt gaatcacaag cccagcaaca ccaaggtcga caagaaagtt gagcccaaat    1560
cttgtgacaa aactcacaca taa                                            1583
```

```
<210> SEQ ID NO 36
<211> LENGTH: 1583
<212> TYPE: DNA
<213> ORGANISM: Artificial Sequence
<220> FEATURE:
<223> OTHER INFORMATION: Variant 218 Sequence of Example 3
<220> FEATURE:
<221> NAME/KEY: misc_feature
<222> LOCATION: (1)..(1583)

<400> SEQUENCE: 36
```

```
atgaaaaaga atatcgcatt tcttcttgca tctatgttcg tttttttctat tgctacaaat      60 gcctatgcag atatccagat gacccagtcc ccgagctccc tgtccgcctc tgtgggcgat    120
agggtcacca tcacctgccg tgccagtcag gccgccgacg gccgcgtagc ctggtatcaa    180
cagaaaccag gaaaagctcc gaagcttctg atttacaaag catccgaact ctacgccgga    240
gtcccttctc gcttctctgg tagccgttcc gggacggatt tcactctgac catcagcagt    300
ctgcagccgg aagacttcgc aacttattac tgtcagcaac gtggctggta tctgttcacg    360
ttcggacagg gtaccaaggt ggagatcaaa cgaactgtgg ctgcaccatc tgtcttcatc    420
ttcccgccat ctgattcaca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgaa aaacataaag tctacgcctg cgaagtcacc    660
catcagggcc tgagctcgcc cgtcacaaag agcttcaaca ggggagagtg ttaatactcg    720
aggctgagca aagcagacta ctaataacat aaagtctacg ccggacgcat cgtggcccta    780
gtacgcaagt tcacgtaaaa agggtaacta gaggttgagg tgattttatg aaaaagaata    840
tcgcatttct tcttgcatct atgttcgttt tttctattgc tacaaacgcg tacgctgagg    900
ttcagctggt ggagtctggc ggtggcctgg tgcagccagg gggctcactc cgtttgtcct    960
gtgcagcttc tggcttcgat ttatttcatt attctataca ctgggtgcgt caggccccgg   1020
gtaagggcct ggaatgggtt gcatacattt accgtctta tggctatact tattatgccg    1080
atagcgtcaa gggccgtttc actataagcg cagacacatc caaaaacaca gcctacctac   1140
aaatgaacag cttaagagct gaggacactg ccgtctatta ttgtgctcgc catgcgtggt   1200
attatgggtg gggtttggac tactgggtc aaggaaccct ggtcaccgtc tcctcggcct    1260
ccaccaaggg tccatcggtc ttcccctgg caccctcctc caagagcacc tctgggggca    1320
cagcggccct gggctgcctg gtcaaggact acttccccga accggtgacg gtgtcgtgga    1380
actcaggcgc cctgaccagc ggcgtgcaca ccttcccggc tgtcctacag tcctcaggac    1440
```

-continued

```
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                            1583

<210> SEQ ID NO 37
<211> LENGTH: 1583
<212> TYPE: DNA
<213> ORGANISM: Artificial Sequence
<220> FEATURE:
<223> OTHER INFORMATION: Variant 219 Sequence of Example 3
<220> FEATURE:
<221> NAME/KEY: misc_feature
<222> LOCATION: (1)..(1583)

<400> SEQUENCE: 37
atgaaaaaga atatcgcatt tcttcttgca tctatgttcg tttttttctat tgctacaaat        60 gcctatgcag atatccagat gacccagtcc ccgagctccc tgtccgcctc tgtgggcgat       120
agggtcacca tcacctgccg tgccagtcag gccgcctacg accgcgtagc ctggtatcaa       180
cagaaaccag gaaaagctcc gaagcttctg atttacaaag catccgaact ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
ttcggacagg gtaccaaggt ggagatcaaa cgaactgtgg ctgcaccatc tgtcttcatc       420
ttcccgccat ctgattcaca gttgaaatct ggaactgcct ctgttgtgtg cctgctgaat       480
aacttctatc ccagagaggc caaagtacag tggaaggtgg ataacgccct ccaatcgggt       540
aactcccagg agagtgtcac agagcaggac agcaaggaca gcacctacag cctcagcagc       600
accctgacgc tgagcaaagc agactacgaa aaacataaag tctacgcctg cgaagtcacc       660
catcagggcc tgagctcgcc cgtcacaaag agcttcaaca ggggagagtg ttaatactcg       720
aggctgagca aagcagacta ctaataacat aaagtctacg ccggacgcat cgtggcccta       780
gtacgcaagt tcacgtaaaa agggtaacta gaggttgagg tgattttatg aaaaagaata       840
tcgcatttct tcttgcatct atgttcgttt tttctattgc tacaaacgcg tacgctgagg       900
ttcagctggt ggagtctggc ggtggcctgg tgcagccagg gggctcactc cgtttgtcct       960
gtgcagcttc tggcttcgat ttatttcatt attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                            1583

<210> SEQ ID NO 38
<211> LENGTH: 1583
<212> TYPE: DNA
<213> ORGANISM: Artificial Sequence
<220> FEATURE:
```

<223> OTHER INFORMATION: Variant 220 Sequence of Example 3
<220> FEATURE:
<221> NAME/KEY: misc_feature
<222> LOCATION: (1)..(1583)

<400> SEQUENCE: 38

```
atgaaaaaga atatcgcatt tcttcttgca tctatgttcg tttttttctat tgctacaaat        60 gcctatgcag atatccagat gacccagtcc ccgagctccc tgtccgcctc tgtgggcgat       120
agggtcacca tcacctgccg tgccagtcag gccgcctacg gcgacgtagc ctggtatcaa       180
cagaaaccag gaaaagctcc gaagcttctg atttacaaag catccgaact ctacgccgga       240
gtcccttctc gcttctctgg tagccgttcc gggacggatt tcactctgac catcagcagt       300
ctgcagccgg aagacttcgc aacttattac tgtcagcaac gtggctggta tctgttcacg       360
ttcggacagg gtaccaaggt ggagatcaaa cgaactgtgg ctgcaccatc tgtcttcatc       420
ttcccgccat ctgattcaca gttgaaatct ggaactgcct ctgttgtgtg cctgctgaat       480
aacttctatc ccagagaggc caaagtacag tggaaggtgg ataacgccct ccaatcgggt       540
aactcccagg agagtgtcac agagcaggac agcaaggaca gcacctacag cctcagcagc       600
accctgacgc tgagcaaagc agactacgaa aaacataaag tctacgcctg cgaagtcacc       660
catcagggcc tgagctcgcc cgtcacaaag agcttcaaca ggggagagtg ttaatactcg       720
aggctgagca aagcagacta ctaataacat aaagtctacg ccggacgcat cgtggcccta       780
gtacgcaagt tcacgtaaaa agggtaacta gaggttgagg tgattttatg aaaaagaata       840
tcgcatttct tcttgcatct atgttcgttt tttctattgc tacaaacgcg tacgctgagg       900
ttcagctggt ggagtctggc ggtggcctgg tgcagccagg gggctcactc cgtttgtcct       960
gtgcagcttc tggcttcgat ttatttcatt attctataca ctgggtgcgt caggccccgg      1020
gtaagggcct ggaatgggtt gcatacattt acccgtctta tggctatact tattatgccg      1080
atagcgtcaa gggccgtttc actataagcg cagacacatc caaaaacaca gcctacctac      1140
aaatgaacag cttaagagct gaggacactg ccgtctatta ttgtgctcgc catgcgtggt      1200
attatgggtg gggtttggac tactggggtc aaggaaccct ggtcaccgtc tcctcggcct      1260
ccaccaaggg tccatcggtc ttccccctgg caccctcctc caagagcacc tctgggggca      1320
cagcggccct gggctgcctg gtcaaggact acttccccga accggtgacg gtgtcgtgga      1380
actcaggcgc cctgaccagc ggcgtgcaca ccttcccggc tgtcctacag tcctcaggac      1440
tctactccct cagcagcgtg gtgaccgtgc cctccagcag cttgggcacc cagacctaca      1500
tctgcaacgt gaatcacaag cccagcaaca ccaaggtcga caagaaagtt gagcccaaat      1560
cttgtgacaa aactcacaca taa                                             1583
```

<210> SEQ ID NO 39
<211> LENGTH: 63
<212> TYPE: PRT
<213> ORGANISM: Artificial Sequence
<220> FEATURE:
<223> OTHER INFORMATION: FF0124-1 F2078 of Figures 4 and 7
<220> FEATURE:
<221> NAME/KEY: MISC_FEATURE
<222> LOCATION: (1)..(63)

<400> SEQUENCE: 39

```
Arg Ala Ser Gln Ser Val Ser Ser Ala Val Ala Ser Ala Ser Ser Leu
1               5                   10                  15

Tyr Ser Gln Gln Gly Gly Trp Trp Leu Ile Thr Asp Leu Tyr Tyr Tyr
                20                  25                  30
```

```
Ser Ile His Tyr Ile Tyr Pro Ser Tyr Gly Tyr Thr Tyr Tyr Ala Asp
        35                  40                  45

Ser Val Lys Gly His Ala Trp Tyr Ser Gly Trp Ala Met Asp Tyr
        50                  55                  60

<210> SEQ ID NO 40
<211> LENGTH: 67
<212> TYPE: PRT
<213> ORGANISM: Artificial Sequence
<220> FEATURE:
<223> OTHER INFORMATION: FF0124-2 F2083 Sequence of Figures 4 and 7
<220> FEATURE:
<221> NAME/KEY: MISC_FEATURE
<222> LOCATION: (1)..(67)

<400> SEQUENCE: 40

Arg Ala Ser Gln Ser Val Ser Ser Ala Val Ala Ser Ala Ser Ser Leu
1               5                   10                  15

Tyr Ser Gln Gln Ser Gly Pro Leu Phe Thr Asp Leu Tyr Tyr Ser Ser
                20                  25                  30

Met His Ser Ile Ser Pro Ser Ser Ser Tyr Thr Tyr Tyr Ala Asp Ser
        35                  40                  45

Val Lys Gly Tyr Tyr Trp Trp His Ser Pro Phe Trp Ala Tyr Ser Gly
        50                  55                  60

Leu Asp Tyr
65

<210> SEQ ID NO 41
<211> LENGTH: 64
<212> TYPE: PRT
<213> ORGANISM: Artificial Sequence
<220> FEATURE:
<223> OTHER INFORMATION: FF0124-3 F2086 Sequence of Figures 4 and 7
<220> FEATURE:
<221> NAME/KEY: MISC_FEATURE
<222> LOCATION: (1)..(64)

<400> SEQUENCE: 41

Arg Ala Ser Gln Ser Val Ser Ser Ala Val Ala Ser Ala Ser Ser Leu
1               5                   10                  15

Tyr Ser Gln Gln Ser Ser Tyr Ser Leu Ile Thr Asp Leu Ser Tyr Ser
                20                  25                  30

Ser Ile His Ser Ile Ser Ser Tyr Tyr Ser Tyr Thr Tyr Tyr Ala Asp
        35                  40                  45

Ser Val Lys Gly Ser Phe Gly Trp Pro Trp Gly Trp Ala Met Asp Tyr
        50                  55                  60

<210> SEQ ID NO 42
<211> LENGTH: 63
<212> TYPE: PRT
<213> ORGANISM: Artificial Sequence
<220> FEATURE:
<223> OTHER INFORMATION: FF0124-4 F2088 Sequence of Figures 4 and 7
<220> FEATURE:
<221> NAME/KEY: MISC_FEATURE
<222> LOCATION: (1)..(63)

<400> SEQUENCE: 42

Arg Ala Ser Gln Ser Val Ser Ser Ala Val Ala Ser Ala Ser Ser Leu
1               5                   10                  15

Tyr Ser Gln Gln Gly Tyr Gly Pro Phe Tyr Ser Leu Ile Thr Asp Leu
                20                  25                  30
```

```
Tyr Ser Tyr Ser Ile His Ser Ile Tyr Ser Tyr Ser Gly Tyr Thr Tyr
        35              40              45

Tyr Ala Asp Ser Val Lys Gly Gly Gly Trp Tyr Ala Leu Asp Tyr
    50              55              60

<210> SEQ ID NO 43
<211> LENGTH: 74
<212> TYPE: PRT
<213> ORGANISM: Artificial Sequence
<220> FEATURE:
<223> OTHER INFORMATION: FF0124-5 F2091 Sequence of Figures 4 and 7
<220> FEATURE:
<221> NAME/KEY: MISC_FEATURE
<222> LOCATION: (1)..(74)

<400> SEQUENCE: 43

Arg Ala Ser Gln Ser Val Ser Ser Ala Val Ala Ser Ala Ser Ser Leu
1               5               10              15

Tyr Ser Gln Gln Phe Trp Ala Gly Tyr Gly Leu Ile Thr Asp Ile Ser
            20              25              30

Ser Tyr Tyr Met His Ser Ile Tyr Ser Tyr Ser Gly Tyr Thr Tyr Tyr
        35              40              45

Ala Asp Ser Val Lys Gly His Ser Val Tyr Tyr Trp Tyr Gly Ser Tyr
    50              55              60

Trp Tyr Tyr Pro Ser Ser Ala Met Asp Tyr
65              70

<210> SEQ ID NO 44
<211> LENGTH: 64
<212> TYPE: PRT
<213> ORGANISM: Artificial Sequence
<220> FEATURE:
<223> OTHER INFORMATION: FF0124-6 F2094 Sequences of Figures 4 and 7
<220> FEATURE:
<221> NAME/KEY: MISC_FEATURE
<222> LOCATION: (1)..(64)

<400> SEQUENCE: 44

Arg Ala Ser Gln Ser Val Ser Ser Ala Val Ala Ser Ala Ser Ser Leu
1               5               10              15

Tyr Ser Gln Gln Ser Gly His Tyr His Tyr Pro Phe Thr Asp Ile Tyr
            20              25              30

Tyr Tyr Ser Met His Ser Ile Ser Ser Tyr Ser Gly Tyr Thr Ser Tyr
        35              40              45

Ala Asp Ser Val Lys Gly Tyr Pro Tyr Tyr Tyr Trp Ala Phe Asp Tyr
    50              55              60

<210> SEQ ID NO 45
<211> LENGTH: 63
<212> TYPE: PRT
<213> ORGANISM: Artificial Sequence
<220> FEATURE:
<223> OTHER INFORMATION: FF0124-7 F2116 Sequence of Figures 4 and 7
<220> FEATURE:
<221> NAME/KEY: MISC_FEATURE
<222> LOCATION: (1)..(63)

<400> SEQUENCE: 45

Arg Ala Ser Gln Ser Val Ser Ser Ala Val Ala Ser Ala Ser Ser Leu
1               5               10              15

Tyr Ser Gln Gln His Tyr Gly Pro Ile Thr Asp Leu Tyr Tyr Ser Tyr
            20              25              30

Met His Ser Ile Ser Ser Tyr Ser Gly Tyr Thr Ser Tyr Ala Asp Ser
```

```
       35                40                45

Val Lys Gly Gly Phe Tyr Tyr Gly Gly Trp Tyr Gly Ile Asp Tyr
   50                55                60

<210> SEQ ID NO 46
<211> LENGTH: 45
<212> TYPE: PRT
<213> ORGANISM: Artificial Sequence
<220> FEATURE:
<223> OTHER INFORMATION: FF0158-C4 Sequence of Figure 6
<220> FEATURE:
<221> NAME/KEY: MISC_FEATURE
<222> LOCATION: (1)..(45)

<400> SEQUENCE: 46

Gln Gln Arg Gly Trp Tyr Leu Phe Thr Asn Leu Tyr Tyr Tyr Ser Ile
1                5                10                15

His Tyr Ile Tyr Pro Ser Tyr Gly Tyr Thr Tyr Tyr Ala Asp Ser Val
            20                25                30

Lys Gly His Ala Trp Tyr Ser Gly Trp Ala Met Asp Tyr
         35                40                45

<210> SEQ ID NO 47
<211> LENGTH: 45
<212> TYPE: PRT
<213> ORGANISM: Artificial Sequence
<220> FEATURE:
<223> OTHER INFORMATION: FF0158-F11 Sequence of Figure 6
<220> FEATURE:
<221> NAME/KEY: MISC_FEATURE
<222> LOCATION: (1)..(45)

<400> SEQUENCE: 47

Gln Gln Gly Gly Trp Trp Leu Ile Thr Asn Leu Tyr Tyr Tyr Ser Ile
1                5                10                15

His Tyr Ile Tyr Pro Ser Tyr Gly Tyr Thr Tyr Tyr Ala Asp Ser Val
            20                25                30

Lys Gly His Ala Trp Tyr Tyr Arg Trp Ala Phe Asp Tyr
         35                40                45

<210> SEQ ID NO 48
<211> LENGTH: 45
<212> TYPE: PRT
<213> ORGANISM: Artificial Sequence
<220> FEATURE:
<223> OTHER INFORMATION: FF0158-C11 Sequence of Figure 6
<220> FEATURE:
<221> NAME/KEY: MISC_FEATURE
<222> LOCATION: (1)..(45)

<400> SEQUENCE: 48

Gln Gln Gly Gly Trp Tyr Leu Ile Thr Asn Leu Tyr Tyr Tyr Ser Ile
1                5                10                15

His Tyr Ile Tyr Pro Ser Tyr Gly Tyr Thr Tyr Tyr Ala Asp Ser Val
            20                25                30

Lys Gly His Ala Trp Tyr Ser Gly Trp Ala Met Asp Tyr
         35                40                45

<210> SEQ ID NO 49
<211> LENGTH: 45
<212> TYPE: PRT
<213> ORGANISM: Artificial Sequence
<220> FEATURE:
<223> OTHER INFORMATION: FF0158-F2 Sequence of Figure 6
<220> FEATURE:
```

<221> NAME/KEY: MISC_FEATURE
<222> LOCATION: (1)..(45)

<400> SEQUENCE: 49

Gln Gln Gly Gly Trp Trp Leu Ile Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Tyr Tyr Gly Trp Ala Met Asp Tyr
        35                  40                  45

<210> SEQ ID NO 50
<211> LENGTH: 45
<212> TYPE: PRT
<213> ORGANISM: Artificial Sequence
<220> FEATURE:
<223> OTHER INFORMATION: FF0158-E2 Sequence of FIgure 6
<220> FEATURE:
<221> NAME/KEY: MISC_FEATURE
<222> LOCATION: (1)..(45)

<400> SEQUENCE: 50

Gln Gln Gly Gly Trp Trp Leu Ile Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Tyr Phe Gly Trp Ala Met Asp Tyr
        35                  40                  45

<210> SEQ ID NO 51
<211> LENGTH: 45
<212> TYPE: PRT
<213> ORGANISM: Artificial Sequence
<220> FEATURE:
<223> OTHER INFORMATION: FF0158-C3 Sequence of Figure 6
<220> FEATURE:
<221> NAME/KEY: MISC_FEATURE
<222> LOCATION: (1)..(45)

<400> SEQUENCE: 51

Gln Gln Arg Asp Trp Arg Leu Phe Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Tyr Ser Gly Trp Ala Met Asp Tyr
        35                  40                  45

<210> SEQ ID NO 52
<211> LENGTH: 45
<212> TYPE: PRT
<213> ORGANISM: Artificial Sequence
<220> FEATURE:
<223> OTHER INFORMATION: FF0158-B10 Sequence of Figure 6
<220> FEATURE:
<221> NAME/KEY: MISC_FEATURE
<222> LOCATION: (1)..(45)

<400> SEQUENCE: 52

Gln Gln Gly Gly Trp Tyr Leu Phe Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Tyr Ser Gly Trp Ala Met Asp Tyr
        35                  40                  45

<210> SEQ ID NO 53
<211> LENGTH: 45
<212> TYPE: PRT
<213> ORGANISM: Artificial Sequence
<220> FEATURE:
<223> OTHER INFORMATION: FF0158-C2 Sequence of Figure 6
<220> FEATURE:
<221> NAME/KEY: MISC_FEATURE
<222> LOCATION: (1)..(45)

<400> SEQUENCE: 53

Gln Gln Gly Gly Trp Trp Leu Ile Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Phe Phe Gly Trp Gly Leu Asp Tyr
        35                  40                  45

<210> SEQ ID NO 54
<211> LENGTH: 45
<212> TYPE: PRT
<213> ORGANISM: Artificial Sequence
<220> FEATURE:
<223> OTHER INFORMATION: FF0128-1 Sequence of Figure 6
<220> FEATURE:
<221> NAME/KEY: MISC_FEATURE
<222> LOCATION: (1)..(45)

<400> SEQUENCE: 54

Gln Gln Gly Gly Trp Trp Leu Ile Thr Asn Leu Tyr Tyr Tyr Ser Ile
1               5                   10                  15

His Tyr Ile Tyr Pro Ser Tyr Gly Tyr Thr Tyr Tyr Ala Asp Ser Val
            20                  25                  30

Lys Gly His Ala Trp Tyr Ser Gly Trp Ala Met Asp Tyr
        35                  40                  45

<210> SEQ ID NO 55
<211> LENGTH: 47
<212> TYPE: PRT
<213> ORGANISM: Artificial Sequence
<220> FEATURE:
<223> OTHER INFORMATION: FF0117-A3 Sequence of Figure 8
<220> FEATURE:
<221> NAME/KEY: MISC_FEATURE
<222> LOCATION: (1)..(47)

<400> SEQUENCE: 55

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Phe Gly Trp Ala Leu Asp Tyr
        35                  40                  45

<210> SEQ ID NO 56
<211> LENGTH: 47
<212> TYPE: PRT
<213> ORGANISM: Artificial Sequence
<220> FEATURE:
<223> OTHER INFORMATION: FF0117-A5 Sequence of Figure 8
<220> FEATURE:
<221> NAME/KEY: MISC_FEATURE
<222> LOCATION: (1)..(47)

<400> SEQUENCE: 56

-continued

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Tyr Gly Trp Gly Leu Asp Tyr
        35                  40                  45
```

```
<210> SEQ ID NO 57
<211> LENGTH: 47
<212> TYPE: PRT
<213> ORGANISM: Artificial Sequence
<220> FEATURE:
<223> OTHER INFORMATION: FF0117-A8 Sequence of Figure 8
<220> FEATURE:
<221> NAME/KEY: MISC_FEATURE
<222> LOCATION: (1)..(47)

<400> SEQUENCE: 57
```

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Leu Asp Tyr
        35                  40                  45
```

```
<210> SEQ ID NO 58
<211> LENGTH: 47
<212> TYPE: PRT
<213> ORGANISM: Artificial Sequence
<220> FEATURE:
<223> OTHER INFORMATION: FF0117-A10 Sequence of Figure 8
<220> FEATURE:
<221> NAME/KEY: MISC_FEATURE
<222> LOCATION: (1)..(47)

<400> SEQUENCE: 58
```

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Tyr Gly Trp Ala Leu Asp Tyr
        35                  40                  45
```

```
<210> SEQ ID NO 59
<211> LENGTH: 47
<212> TYPE: PRT
<213> ORGANISM: Artificial Sequence
<220> FEATURE:
<223> OTHER INFORMATION: FF0117-A11 Sequence of Figure 8
<220> FEATURE:
<221> NAME/KEY: MISC_FEATURE
<222> LOCATION: (1)..(47)

<400> SEQUENCE: 59
```

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Trp Gly Trp Ala Leu Asp Tyr
        35                  40                  45
```

```
<210> SEQ ID NO 60
<211> LENGTH: 47
```

```
<212> TYPE: PRT
<213> ORGANISM: Artificial Sequence
<220> FEATURE:
<223> OTHER INFORMATION: FF0117-A12 Sequence of Figure 8
<220> FEATURE:
<221> NAME/KEY: MISC_FEATURE
<222> LOCATION: (1)..(47)

<400> SEQUENCE: 60

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Phe Arg Trp Ala Leu Asp Tyr
        35                  40                  45

<210> SEQ ID NO 61
<211> LENGTH: 47
<212> TYPE: PRT
<213> ORGANISM: Artificial Sequence
<220> FEATURE:
<223> OTHER INFORMATION: FF0117-B5 Sequence of Figure 8
<220> FEATURE:
<221> NAME/KEY: MISC_FEATURE
<222> LOCATION: (1)..(47)

<400> SEQUENCE: 61

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Phe Tyr Gly Trp Gly Leu Asp Tyr
        35                  40                  45

<210> SEQ ID NO 62
<211> LENGTH: 47
<212> TYPE: PRT
<213> ORGANISM: Artificial Sequence
<220> FEATURE:
<223> OTHER INFORMATION: FF0117-B9 Sequence of Figure 8
<220> FEATURE:
<221> NAME/KEY: MISC_FEATURE
<222> LOCATION: (1)..(47)

<400> SEQUENCE: 62

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Tyr Gly Trp Ala Met Asp Tyr
        35                  40                  45

<210> SEQ ID NO 63
<211> LENGTH: 47
<212> TYPE: PRT
<213> ORGANISM: Artificial Sequence
<220> FEATURE:
<223> OTHER INFORMATION: FF0117-B11 Sequence of Figure 8
<220> FEATURE:
<221> NAME/KEY: MISC_FEATURE
<222> LOCATION: (1)..(47)

<400> SEQUENCE: 63

Gln Gln Arg Gly Trp Tyr Leu Phe Thr Gly Phe Asp Leu Phe His Tyr
1               5                   10                  15
```

-continued

```
Ser Ile His Tyr Ile Tyr Pro Ser Tyr Gly Tyr Thr Tyr Tyr Ala Asp
            20                  25                  30

Ser Val Lys Gly His Ala Trp Tyr Tyr Gly Trp Ala Met Asp Tyr
        35                  40                  45
```

<210> SEQ ID NO 64
<211> LENGTH: 47
<212> TYPE: PRT
<213> ORGANISM: Artificial Sequence
<220> FEATURE:
<223> OTHER INFORMATION: FF0188-H5 (2) Sequence of Figure 8
<220> FEATURE:
<221> NAME/KEY: MISC_FEATURE
<222> LOCATION: (1)..(47)

<400> SEQUENCE: 64

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45
```

<210> SEQ ID NO 65
<211> LENGTH: 64
<212> TYPE: PRT
<213> ORGANISM: Artificial Sequence
<220> FEATURE:
<223> OTHER INFORMATION: FF03033-1 Sequence of Figure 9A
<220> FEATURE:
<221> NAME/KEY: MISC_FEATURE
<222> LOCATION: (1)..(64)

<400> SEQUENCE: 65

```
Arg Ala Ser Gln Tyr Met Asn Ser Asn Val Ala Ala Ala Ser Val Leu
1               5                   10                  15

Val Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60
```

<210> SEQ ID NO 66
<211> LENGTH: 64
<212> TYPE: PRT
<213> ORGANISM: Artificial Sequence
<220> FEATURE:
<223> OTHER INFORMATION: FF03033-2 Sequence of Figure 9A
<220> FEATURE:
<221> NAME/KEY: MISC_FEATURE
<222> LOCATION: (1)..(64)

<400> SEQUENCE: 66

```
Arg Ala Ser Gln Val Ala Phe Tyr Asn Val Ala Asp Ala Ser Ile Leu
1               5                   10                  15

Asn Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60
```

<210> SEQ ID NO 67
<211> LENGTH: 64
<212> TYPE: PRT
<213> ORGANISM: Artificial Sequence
<220> FEATURE:
<223> OTHER INFORMATION: FF03033-3 Sequence of Figrure 9A
<220> FEATURE:
<221> NAME/KEY: MISC_FEATURE
<222> LOCATION: (1)..(64)

<400> SEQUENCE: 67

Arg Ala Ser Gln Phe Val Gly Tyr Asn Val Ala Gln Ala Ser Ser Leu
1               5                   10                  15

Ala Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60

<210> SEQ ID NO 68
<211> LENGTH: 64
<212> TYPE: PRT
<213> ORGANISM: Artificial Sequence
<220> FEATURE:
<223> OTHER INFORMATION: FF03033-4 Sequence of Figure 9A
<220> FEATURE:
<221> NAME/KEY: MISC_FEATURE
<222> LOCATION: (1)..(64)

<400> SEQUENCE: 68

Arg Ala Ser Gln Glu Gly Trp Asp Arg Val Ala Ser Ala Ser Gln Leu
1               5                   10                  15

Ala Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60

<210> SEQ ID NO 69
<211> LENGTH: 64
<212> TYPE: PRT
<213> ORGANISM: Artificial Sequence
<220> FEATURE:
<223> OTHER INFORMATION: FF03033-5 Sequence of Figure 9A
<220> FEATURE:
<221> NAME/KEY: MISC_FEATURE
<222> LOCATION: (1)..(64)

<400> SEQUENCE: 69

Arg Ala Ser Gln Gly Val Gly Glu Arg Val Ala Asn Ala Ser His Leu
1               5                   10                  15

Ala Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60

<210> SEQ ID NO 70
<211> LENGTH: 64
<212> TYPE: PRT
<213> ORGANISM: Artificial Sequence -continued

```
<220> FEATURE:
<223> OTHER INFORMATION: FF03033-6 Sequence of Figure 9A
<220> FEATURE:
<221> NAME/KEY: MISC_FEATURE
<222> LOCATION: (1)..(64)

<400> SEQUENCE: 70

Arg Ala Ser Gln Pro Arg Glu Asp Arg Val Ala Arg Ala Ser Thr Leu
1               5                   10                  15

Ala Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60

<210> SEQ ID NO 71
<211> LENGTH: 64
<212> TYPE: PRT
<213> ORGANISM: Artificial Sequence
<220> FEATURE:
<223> OTHER INFORMATION: FF03033-8 Sequence of Figure 9A
<220> FEATURE:
<221> NAME/KEY: MISC_FEATURE
<222> LOCATION: (1)..(64)

<400> SEQUENCE: 71

Arg Ala Ser Gln Ala Ala Tyr Gly Arg Val Ala Lys Ala Ser Glu Leu
1               5                   10                  15

Ala Gln Gln Arg Gly Trp Tyr Leu Phe Thr Gly Phe Asp Leu Phe His
            20                  25                  30

Tyr Ser Ile His Tyr Ile Tyr Pro Ser Tyr Gly Tyr Thr Tyr Tyr Ala
        35                  40                  45

Asp Ser Val Lys Gly His Ala Trp Tyr Tyr Gly Trp Gly Leu Asp Tyr
    50                  55                  60

<210> SEQ ID NO 72
<211> LENGTH: 65
<212> TYPE: PRT
<213> ORGANISM: Artificial Sequence
<220> FEATURE:
<223> OTHER INFORMATION: FF03046-2 Sequence of Figure 9A
<220> FEATURE:
<221> NAME/KEY: MISC_FEATURE
<222> LOCATION: (1)..(65)

<400> SEQUENCE: 72

Arg Ala Ser Gln Ala Ala Tyr Gly Arg Val Ala Lys Ala Ser Glu Leu
1               5                   10                  15

Tyr Ala Gln Gln Arg Gly Trp Tyr Leu Phe Thr Gly Phe Asp Leu Phe
            20                  25                  30

His Tyr Ser Ile His Tyr Ile Tyr Pro Ser Tyr Gly Tyr Thr Tyr Tyr
        35                  40                  45

Ala Asp Ser Val Lys Gly His Ala Trp Tyr Tyr Gly Trp Gly Leu Asp
    50                  55                  60

Tyr
65

<210> SEQ ID NO 73
<211> LENGTH: 65
<212> TYPE: PRT
<213> ORGANISM: Artificial Sequence
<220> FEATURE:
```

-continued

```
<223> OTHER INFORMATION: FF0117-A5 (2) Sequence of Figure 9A
<220> FEATURE:
<221> NAME/KEY: MISC_FEATURE
<222> LOCATION: (1)..(65)

<400> SEQUENCE: 73

Arg Ala Ser Gln Ser Val Ser Ser Ala Val Ala Ser Ala Ser Ser Leu
1               5                   10                  15

Tyr Ser Gln Gln Arg Gly Trp Tyr Leu Phe Thr Gly Phe Asp Leu Phe
                20                  25                  30

His Tyr Ser Ile His Tyr Ile Tyr Pro Ser Tyr Gly Tyr Thr Tyr Tyr
            35                  40                  45

Ala Asp Ser Val Lys Gly His Ala Trp Tyr Tyr Gly Trp Gly Leu Asp
    50                  55                  60

Tyr
65

<210> SEQ ID NO 74
<211> LENGTH: 1449
<212> TYPE: DNA
<213> ORGANISM: Artificial Sequence
<220> FEATURE:
<223> OTHER INFORMATION: Single chain nucleic acid sequence of Figure 13
<220> FEATURE:
<221> NAME/KEY: misc_feature
<222> LOCATION: (1)..(1449)

<400> SEQUENCE: 74
tgcccaccgt gcccagcacc tgaactcctg gggggaccgt cagtcttcct cttcccccca      60
aaacccaagg acaccctcat gatctcccgg acccctgagg tcacatgcgt ggtggtggac     120
gtgagccacg aagaccctga ggtcaagttc aactggtacg tggacggcgt ggaggtgcat     180
aatgccaaga caaagccgcg ggaggagcag tacaacagca cgtaccgtgt ggtcagcgtc     240
ctcaccgtcc tgcaccagga ctggctgaat ggcaaggagt acaagtgcaa ggtctccaac     300
aaagccctcc cagcccccat cgagaaaacc atctccaaag ccaaagggca gccccgagaa     360
ccacaggtgt acaccctgcc cccatcccgg gaggagatga ccaagaacca ggtcagcctg     420
acctgcctgg tcaaaggctt ctatcccagc gacatcgccg tggagtggga gagcaatggg     480
cagccggaga acaactacaa gaccacgcct cccgtgctgg actccgacgg ctccttcttc     540
ctctacagca agctcaccgt ggacaagagc aggtggcagc aggggaacgt cttctcatgc     600
tccgtgatgc atgaggctct gcacaaccac tacacgcaga gagcctctc gctgagccct     660 ggaaaaggtg gcggaggatc tggcggcgga ggaagcggtg gaggcggaag cggaggcggc     720
gatatccaga tgacacagag ccctagcagc ctgagcgcca gcgtgggcga cagagtgacc     780
atcacctgta gagccagcca ggccgcctat ggcagagtgg cctggtatca gcagaagccc     840
ggcaaggccc ctaagctgct gatctacaag gccagcgagc tgtatgccgg cgtgcccagc     900
agattcagcg gcagcagatc cggcaccgac ttcaccctga ccatcagcag cctgcagccc     960
gaggacttcg ccacctacta ctgccagcag cggggctggt atctgttcac cttcggccag    1020
ggcaccaagg tggaaatcaa gggcacaaca gccgccagcg gctctagcgg cggatcttct    1080
agcggagcca aggtgcagct ggtggaatca ggcggtggac tggtgcagcc tggcggaagc    1140
ctgagactgt cttgcgccgc ctctggcttc gacctgttcc actacagcat ccactgggtc    1200
cgacaggccc ctggcaaggg actggaatgg gtggcctaca tctaccccag ctacggctac    1260
acctattacg ccgacagcgt gaagggccgg ttcaccatca gcgccgacac cagcaagaac    1320
```

-continued

```
accgcctacc tgcagatgaa cagcctgaga gccgaggaca ccgccgtgta ctactgtgcc     1380
agacacgcct ggtactacgg ctggggcctg gattactggg gccagggaac cctggtcacc     1440
gtgtcctct                                                             1449
```

<210> SEQ ID NO 75
<211> LENGTH: 483
<212> TYPE: PRT
<213> ORGANISM: Artificial Sequence
<220> FEATURE:
<223> OTHER INFORMATION: Single chain amino acid sequence of Figure 13
<220> FEATURE:
<221> NAME/KEY: MISC_FEATURE
<222> LOCATION: (1)..(483)

<400> SEQUENCE: 75

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys Gly Gly
    210                 215                 220

Gly Gly Ser Gly Gly Gly Gly Ser Gly Gly Gly Gly Ser Gly Gly Gly
225                 230                 235                 240

Asp Ile Gln Met Thr Gln Ser Pro Ser Ser Leu Ser Ala Ser Val Gly
                245                 250                 255

Asp Arg Val Thr Ile Thr Cys Arg Ala Ser Gln Ala Ala Tyr Gly Arg
                260                 265                 270

Val Ala Trp Tyr Gln Gln Lys Pro Gly Lys Ala Pro Lys Leu Leu Ile
            275                 280                 285

Tyr Lys Ala Ser Glu Leu Tyr Ala Gly Val Pro Ser Arg Phe Ser Gly
        290                 295                 300

Ser Arg Ser Gly Thr Asp Phe Thr Leu Thr Ile Ser Ser Leu Gln Pro
305                 310                 315                 320
```

-continued

Glu Asp Phe Ala Thr Tyr Tyr Cys Gln Gln Arg Gly Trp Tyr Leu Phe
                325                     330                     335

Thr Phe Gly Gln Gly Thr Lys Val Glu Ile Lys Gly Thr Thr Ala Ala
                340                     345                     350

Ser Gly Ser Ser Gly Gly Ser Ser Ser Gly Ala Glu Val Gln Leu Val
                355                     360                     365

Glu Ser Gly Gly Gly Leu Val Gln Pro Gly Gly Ser Leu Arg Leu Ser
    370                     375                     380

Cys Ala Ala Ser Gly Phe Asp Leu Phe His Tyr Ser Ile His Trp Val
385                     390                     395                     400

Arg Gln Ala Pro Gly Lys Gly Leu Glu Trp Val Ala Tyr Ile Tyr Pro
                405                     410                     415

Ser Tyr Gly Tyr Thr Tyr Tyr Ala Asp Ser Val Lys Gly Arg Phe Thr
                420                     425                     430

Ile Ser Ala Asp Thr Ser Lys Asn Thr Ala Tyr Leu Gln Met Asn Ser
                435                     440                     445

Leu Arg Ala Glu Asp Thr Ala Val Tyr Tyr Cys Ala Arg His Ala Trp
    450                     455                     460

Tyr Tyr Gly Trp Gly Leu Asp Tyr Trp Gly Gln Gly Thr Leu Val Thr
465                     470                     475                     480

Val Ser Ser

<210> SEQ ID NO 76
<211> LENGTH: 214
<212> TYPE: PRT
<213> ORGANISM: Artificial Sequence
<220> FEATURE:
<223> OTHER INFORMATION: Light chain (hK) amino acid sequence of Figure
      16
<220> FEATURE:
<221> NAME/KEY: MISC_FEATURE
<222> LOCATION: (1)..(214)

<400> SEQUENCE: 76

Asp Ile Gln Met Thr Gln Ser Pro Ser Ser Leu Ser Ala Ser Val Gly
1               5                       10                      15

Asp Arg Val Thr Ile Thr Cys Arg Ala Ser Gln Ala Ala Tyr Gly Arg
                20                      25                      30

Val Ala Trp Tyr Gln Gln Lys Pro Gly Lys Ala Pro Lys Leu Leu Ile
                35                      40                      45

Tyr Lys Ala Ser Glu Leu Tyr Ala Gly Val Pro Ser Arg Phe Ser Gly
    50                      55                      60

Ser Arg Ser Gly Thr Asp Phe Thr Leu Thr Ile Ser Ser Leu Gln Pro
65                      70                      75                      80

Glu Asp Phe Ala Thr Tyr Tyr Cys Gln Gln Arg Gly Trp Tyr Leu Phe
                85                      90                      95

Thr Phe Gly Gln Gly Thr Lys Val Glu Ile Lys Arg Thr Val Ala Ala
                100                     105                     110

Pro Ser Val Phe Ile Phe Pro Pro Ser Asp Ser Gln Leu Lys Ser Gly
                115                     120                     125

Thr Ala Ser Val Val Cys Leu Leu Asn Asn Phe Tyr Pro Arg Glu Ala
    130                     135                     140

Lys Val Gln Trp Lys Val Asp Asn Ala Leu Gln Ser Gly Asn Ser Gln
145                     150                     155                     160

Glu Ser Val Thr Glu Gln Asp Ser Lys Asp Ser Thr Tyr Ser Leu Ser
                165                     170                     175

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210
```

```
<210> SEQ ID NO 77
<211> LENGTH: 642
<212> TYPE: DNA
<213> ORGANISM: Artificial Sequence
<220> FEATURE:
<223> OTHER INFORMATION: Light chain (hK) nucleic acid sequence of
      Figure 16
<220> FEATURE:
<221> NAME/KEY: misc_feature
<222> LOCATION: (1)..(642)

<400> SEQUENCE: 77
gatatccaga tgacccagtc cccgagctcc ctgtccgcct ctgtgggcga tagggtcacc      60
atcacctgcc gtgccagtca ggccgcctac ggccgcgtag cctggtatca acagaaacca     120
ggaaaagctc cgaagcttct gatttacaaa gcatccgaac tctacgccgg agtcccttct     180
cgcttctctg gtagccgttc cgggacggat ttcactctga ccatcagcag tctgcagccg     240
gaagacttcg caacttatta ctgtcagcaa cgtggctggt atctgttcac gttcggacag     300
ggtaccaagg tggagatcaa acgtacggtg gctgcaccat ctgtcttcat cttcccgcca     360
tctgattcac agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642
```

```
<210> SEQ ID NO 78
<211> LENGTH: 228
<212> TYPE: PRT
<213> ORGANISM: Artificial Sequence
<220> FEATURE:
<223> OTHER INFORMATION: Heavy chain amino acid sequence of Figure 16
<220> FEATURE:
<221> NAME/KEY: MISC_FEATURE
<222> LOCATION: (1)..(228)

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Asp His Tyr
            20                  25                  30

Ser Ile His Trp Val Arg Gln Ala Pro Gly Lys Gly Leu Glu Trp Val
        35                  40                  45

Ala Tyr Ile Tyr Pro Ser Tyr Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Ala Trp Tyr Tyr Gly Trp Gly Leu Asp Tyr Trp Gly Gln
            100                 105                 110
```

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225
```

<210> SEQ ID NO 79
<211> LENGTH: 684
<212> TYPE: DNA
<213> ORGANISM: Artificial Sequence
<220> FEATURE:
<223> OTHER INFORMATION: Heavy chain Nucleic acid sequence of Figure 16

<400> SEQUENCE: 79

```
gaggttcagc tggtggagtc tggcggtggc ctggtgcagc caggggggctc actccgtttg     60 tcctgtgcag cttctggctt cgatttagat cattattcta tacactgggt gcgtcaggcc    120
ccgggtaagg gcctggaatg ggttgcatac atttacccgt cttatggcta tacttattat    180
gccgatagcg tcaagggccg tttcactata agcgcagaca catccaaaaa cacagcctac    240
ctacaaatga acagcttaag agctgaggac actgccgtct attattgtgc tcgccatgcg    300
tggtattatg gtgggggttt ggactactgg ggtcaaggaa ccctggtcac cgtctcctcg    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca caca                                          684
```

<210> SEQ ID NO 80
<211> LENGTH: 231
<212> TYPE: PRT
<213> ORGANISM: Artificial Sequence
<220> FEATURE:
<223> OTHER INFORMATION: Lucentis (Ranibizumab) Heavy Chain Sequence of
      Figure 23
<220> FEATURE:
<221> NAME/KEY: MISC_FEATURE
<222> LOCATION: (1)..(231)

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
```

-continued

```
        35                  40                  45
Gly Trp Ile Asn Thr Tyr Thr Gly Glu Pro Thr Tyr Ala Ala Asp Phe
    50                  55                  60
Lys Arg Arg Phe Thr Phe Ser Leu Asp Thr Ser Lys Ser Thr Ala Tyr
65                  70                  75                  80
Leu Gln Met Asn Ser Leu Arg Ala Glu Asp Thr Ala Val Tyr Tyr Cys
                85                  90                  95
Ala Lys Tyr Pro Tyr Tyr Tyr Gly Thr Ser His Trp Tyr Phe Asp Val
            100                 105                 110
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Lys Val Glu Pro Lys
    210                 215                 220
Ser Cys Asp Lys Thr His Leu
225                 230
```

```
<210> SEQ ID NO 81
<211> LENGTH: 228
<212> TYPE: PRT
<213> ORGANISM: Artificial Sequence
<220> FEATURE:
<223> OTHER INFORMATION: Fab 201 Heavy Chain Sequence of Figure 23
<220> FEATURE:
<221> NAME/KEY: MISC_FEATURE
<222> LOCATION: (1)..(228)

<400> SEQUENCE: 81
```

```
Glu Val Gln Leu Val Glu Ser Gly Gly Gly Leu Val Gln Pro Gly Gly
1                   5                   10                  15
Ser Leu Arg Leu Ser Cys Ala Ala Ser Gly Phe Asp Leu Phe His Tyr
                20                  25                  30
Ser Ile His Trp Val Arg Gln Ala Pro Gly Lys Gly Leu Glu Trp Val
                35                  40                  45
Ala Tyr Ile Tyr Pro Ser Tyr Gly Tyr Thr Tyr Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg His Ala Trp Tyr Tyr Gly Trp Gly Leu Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
```

```
145             150             155             160

Trp Asn Ser Gly Ala Leu Thr Ser Gly Val His Thr Phe Pro Ala Val
                165             170             175

Leu Gln Ser Ser Gly Leu Tyr Ser Leu Ser Ser Val Val Thr Val Pro
                180             185             190

Ser Ser Ser Leu Gly Thr Gln Thr Tyr Ile Cys Asn Val Asn His Lys
                195             200             205

Pro Ser Asn Thr Lys Val Asp Lys Lys Val Glu Pro Lys Ser Cys Asp
    210             215             220

Lys Thr His Thr
225

<210> SEQ ID NO 82
<211> LENGTH: 214
<212> TYPE: PRT
<213> ORGANISM: Artificial Sequence
<220> FEATURE:
<223> OTHER INFORMATION: Lucentis (Ranibizumab) Light Chain of Figure 24
<220> FEATURE:
<221> NAME/KEY: MISC_FEATURE
<222> LOCATION: (1)..(214)

<400> SEQUENCE: 82

Asp Ile Gln Leu Thr Gln Ser Pro Ser Ser Leu Ser Ala Ser Val Gly
1               5               10              15

Asp Arg Val Thr Ile Thr Cys Ser Ala Ser Gln Asp Ile Ser Asn Tyr
                20              25              30

Leu Asn Trp Tyr Gln Gln Lys Pro Gly Lys Ala Pro Lys Val Leu Ile
        35              40              45

Tyr Phe Thr Ser Ser Leu His Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Tyr Ser Thr Val Pro Trp
                85              90              95

Thr Phe Gly Gln Gly Thr Lys Val Glu Ile Lys Arg Thr Val Ala Ala
                100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
        130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
                180             185             190

Ala Cys Glu Val Thr His Gln Gly Leu Ser Ser Pro Val Thr Lys Ser
        195             200             205

Phe Asn Arg Gly Glu Cys
    210

<210> SEQ ID NO 83
<211> LENGTH: 214
<212> TYPE: PRT
<213> ORGANISM: Artificial Sequence
<220> FEATURE:
<223> OTHER INFORMATION: Fab 201 Light Chain Sequence of Figure 24
```

```
<220> FEATURE:
<221> NAME/KEY: MISC_FEATURE
<222> LOCATION: (1)..(214)

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ala Tyr Gly Arg
            20                  25                  30

Val Ala Trp Tyr Gln Gln Lys Pro Gly Lys Ala Pro Lys Leu Leu Ile
        35                  40                  45

Tyr Lys Ala Ser Glu Leu Tyr Ala Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Gly Trp Tyr Leu Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Ser Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 47
<212> TYPE: PRT
<213> ORGANISM: Artificial Sequence
<220> FEATURE:
<223> OTHER INFORMATION: FF0158-C4 (2) Sequence of Figure 7
<220> FEATURE:
<221> NAME/KEY: MISC_FEATURE
<222> LOCATION: (1)..(47)

<400> SEQUENCE: 84

Gln Gln Arg Gly Trp Tyr Leu Phe Thr Gly Phe Asn Leu Tyr Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 85
<211> LENGTH: 47
<212> TYPE: PRT
<213> ORGANISM: Artificial Sequence
<220> FEATURE:
<223> OTHER INFORMATION: FF0187-B3 Sequence of Figure 7
<220> FEATURE:
<221> NAME/KEY: MISC_FEATURE
```

<222> LOCATION: (1)..(47)

<400> SEQUENCE: 85

Gln Gln Arg Gly Trp Tyr Leu Phe Thr Gly Phe Asp Leu Trp Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 86
<211> LENGTH: 47
<212> TYPE: PRT
<213> ORGANISM: Artificial Sequence
<220> FEATURE:
<223> OTHER INFORMATION: FF0187-C1 Sequence of Figure 7
<220> FEATURE:
<221> NAME/KEY: MISC_FEATURE
<222> LOCATION: (1)..(47)

<400> SEQUENCE: 86

Gln Gln Arg Gly Trp Tyr Leu Phe Thr Gly Phe Asp Leu Trp Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 87
<211> LENGTH: 47
<212> TYPE: PRT
<213> ORGANISM: Artificial Sequence
<220> FEATURE:
<223> OTHER INFORMATION: FF0187-A12 Sequence of Figure 7
<220> FEATURE:
<221> NAME/KEY: MISC_FEATURE
<222> LOCATION: (1)..(47)

<400> SEQUENCE: 87

Gln Gln Arg Gly Trp Tyr Leu Phe Thr Gly Phe Asp Leu Trp Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 88
<211> LENGTH: 47
<212> TYPE: PRT
<213> ORGANISM: Artificial Sequence
<220> FEATURE:
<223> OTHER INFORMATION: FF0187-H3 Sequence of Figure 7
<220> FEATURE:
<221> NAME/KEY: MISC_FEATURE
<222> LOCATION: (1)..(47)

<400> SEQUENCE: 88

Gln Gln Arg Gly Trp Tyr Leu Phe Thr Gly Phe Asp Leu Trp Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

```
<210> SEQ ID NO 89
<211> LENGTH: 47
<212> TYPE: PRT
<213> ORGANISM: Artificial Sequence
<220> FEATURE:
<223> OTHER INFORMATION: FF0188-H5 Sequence of Figure 7
<220> FEATURE:
<221> NAME/KEY: MISC_FEATURE
<222> LOCATION: (1)..(47)

<400> SEQUENCE: 89

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 90
<211> LENGTH: 47
<212> TYPE: PRT
<213> ORGANISM: Artificial Sequence
<220> FEATURE:
<223> OTHER INFORMATION: FF0188-B10 Sequence of Figure 7
<220> FEATURE:
<221> NAME/KEY: MISC_FEATURE
<222> LOCATION: (1)..(47)

<400> SEQUENCE: 90

Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 91
<211> LENGTH: 47
<212> TYPE: PRT
<213> ORGANISM: Artificial Sequence
<220> FEATURE:
<223> OTHER INFORMATION: FF0188-F12 Sequence of Figure 7
<220> FEATURE:
<221> NAME/KEY: MISC_FEATURE
<222> LOCATION: (1)..(47)

<400> SEQUENCE: 91

Gln Gln Arg Gly Trp Tyr Leu Phe Thr Gly Phe Asp Leu Tyr His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45

<210> SEQ ID NO 92
<211> LENGTH: 47
<212> TYPE: PRT
<213> ORGANISM: Artificial Sequence
<220> FEATURE:
<223> OTHER INFORMATION: FF0188-B6 Sequence of Figure 7
<220> FEATURE:
<221> NAME/KEY: MISC_FEATURE
<222> LOCATION: (1)..(47)

<400> SEQUENCE: 92
```

```
Gln Gln Arg Gly Trp Tyr Leu Phe Thr Gly Phe Asp Leu Trp Tyr Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45
```

```
<210> SEQ ID NO 93
<211> LENGTH: 47
<212> TYPE: PRT
<213> ORGANISM: Artificial Sequence
<220> FEATURE:
<223> OTHER INFORMATION: FF0188-A2 Sequence of Figure 7
<220> FEATURE:
<221> NAME/KEY: MISC_FEATURE
<222> LOCATION: (1)..(47)

<400> SEQUENCE: 93
```

```
Gln Gln Arg Gly Trp Tyr Leu Phe Thr Gly Phe Asp Leu Phe Phe Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45
```

```
<210> SEQ ID NO 94
<211> LENGTH: 47
<212> TYPE: PRT
<213> ORGANISM: Artificial Sequence
<220> FEATURE:
<223> OTHER INFORMATION: FF0188-A9 Sequence of Figure 7
<220> FEATURE:
<221> NAME/KEY: MISC_FEATURE
<222> LOCATION: (1)..(47)

<400> SEQUENCE: 94
```

```
Gln Gln Arg Gly Trp Tyr Leu Phe Thr Gly Phe Asp Leu Phe His Tyr
1               5                   10                  15

Ser Ile His Tyr Ile Tyr Pro Ser Tyr Gly Tyr Thr Tyr Tyr Ala Asp
            20                  25                  30

Ser Val Lys Gly His Ala Trp Tyr Ser Gly Trp Ala Met Asp Tyr
        35                  40                  45
```

```
<210> SEQ ID NO 95
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      202 found in Table 5A and 5C
<220> FEATURE:
<221> NAME/KEY: MISC_FEATURE
<222> LOCATION: (2)..(237)

<400> SEQUENCE: 95
```

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Ala Ala Tyr Gly Arg Val Ala Trp Tyr Gln Gln Lys Pro Gly
    50                  55                  60
```

```
Lys Ala Pro Lys Leu Leu Ile Tyr Lys Ala Ser Glu Leu Asp Ala Gly
65              70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
                100                 105                 110

Gln Arg Gly Trp Tyr Leu Phe Thr Phe Gly Gln Gly Thr Lys Val Glu
                115                 120                 125

Ile Lys Arg Thr Val Ala Ala Pro Ser Val Phe Ile Phe Pro Pro Ser
                130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
                180                 185                 190

Asp Ser Thr Tyr Ser Leu Ser Ser Thr Leu Thr Leu Ser Lys Ala Asp
                195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

```
<210> SEQ ID NO 96
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      203 found in Table 5A and 5C
<220> FEATURE:
<221> NAME/KEY: MISC_FEATURE
<222> LOCATION: (1)..(237)

<400> SEQUENCE: 96
```

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
                35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Lys Ala Ser Asp Leu Tyr Ala Gly
65              70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
                100                 105                 110

Gln Arg Gly Trp Tyr Leu Phe Thr Phe Gly Gln Gly Thr Lys Val Glu
                115                 120                 125

Ile Lys Arg Thr Val Ala Ala Pro Ser Val Phe Ile Phe Pro Pro Ser
                130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175
```

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 97
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
     204 found in Table 5A and 5C
<220> FEATURE:
<221> NAME/KEY: MISC_FEATURE
<222> LOCATION: (1)..(237)

<400> SEQUENCE: 97

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Asp Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235

<210> SEQ ID NO 98
<211> LENGTH: 237
<212> TYPE: PRT
<213> ORGANISM: Artificial Sequence
<220> FEATURE:
<223> OTHER INFORMATION: Amino Acid Sequence (Light Chain) of Variant 205 found in Table 5A and 5C
<220> FEATURE:
<221> NAME/KEY: MISC_FEATURE
<222> LOCATION: (1)..(237)

<400> SEQUENCE: 98

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
        35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Lys Asp Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 99
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
     206 found in Table 5A and 5C
<220> FEATURE:
<221> NAME/KEY: MISC_FEATURE
<222> LOCATION: (1)..(237)

<400> SEQUENCE: 99

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
        35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Asp Ala Ser Glu Leu Tyr Ala Gly

-continued

```
65              70              75              80

Val Pro Ser Arg Phe Ser Gly Ser Arg Ser Gly Thr Asp Phe Thr Leu
                85              90              95

Thr Ile Ser Ser Leu Gln Pro Glu Asp Phe Ala Thr Tyr Tyr Cys Gln
            100             105             110

Gln Arg Gly Trp Tyr Leu Phe Thr Phe Gly Gln Gly Thr Lys Val Glu
            115             120             125

Ile Lys Arg Thr Val Ala Ala Pro Ser Val Phe Ile Phe Pro Pro Ser
        130             135             140

Asp Ser Gln Leu Lys Ser Gly Thr Ala Ser Val Val Cys Leu Leu Asn
145             150             155             160

Asn Phe Tyr Pro Arg Glu Ala Lys Val Gln Trp Lys Val Asp Asn Ala
                165             170             175

Leu Gln Ser Gly Asn Ser Gln Glu Ser Val Thr Glu Gln Asp Ser Lys
            180             185             190

Asp Ser Thr Tyr Ser Leu Ser Ser Thr Leu Thr Leu Ser Lys Ala Asp
            195             200             205

Tyr Glu Lys His Lys Val Tyr Ala Cys Glu Val Thr His Gln Gly Leu
        210             215             220

Ser Ser Pro Val Thr Lys Ser Phe Asn Arg Gly Glu Cys
225             230             235
```

<210> SEQ ID NO 100
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
    207 found in Table 5A and 5C
<220> FEATURE:
<221> NAME/KEY: MISC_FEATURE
<222> LOCATION: (1)..(237)

<400> SEQUENCE: 100

```
Met Lys Lys Asn Ile Ala Phe Leu Leu Ala Ser Met Phe Val Phe Ser
1               5               10              15

Ile Ala Thr Asn Ala Tyr Ala Asp Ile Gln Met Thr Gln Ser Pro Ser
            20              25              30

Ser Leu Ser Ala Ser Val Gly Asp Arg Val Thr Ile Thr Cys Arg Ala
        35              40              45

Ser Gln Ala Ala Tyr Gly Arg Val Ala Trp Tyr Gln Gln Lys Pro Gly
    50              55              60

Lys Ala Pro Lys Leu Leu Ile Asp Lys Ala Ser Glu Leu Tyr Ala Gly
65              70              75              80

Val Pro Ser Arg Phe Ser Gly Ser Arg Ser Gly Thr Asp Phe Thr Leu
                85              90              95

Thr Ile Ser Ser Leu Gln Pro Glu Asp Phe Ala Thr Tyr Tyr Cys Gln
            100             105             110

Gln Arg Gly Trp Tyr Leu Phe Thr Phe Gly Gln Gly Thr Lys Val Glu
            115             120             125

Ile Lys Arg Thr Val Ala Ala Pro Ser Val Phe Ile Phe Pro Pro Ser
        130             135             140

Asp Ser Gln Leu Lys Ser Gly Thr Ala Ser Val Val Cys Leu Leu Asn
145             150             155             160

Asn Phe Tyr Pro Arg Glu Ala Lys Val Gln Trp Lys Val Asp Asn Ala
                165             170             175
```

```
Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

```
<210> SEQ ID NO 101
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      208 found in Table 5A and 5C
<220> FEATURE:
<221> NAME/KEY: MISC_FEATURE
<222> LOCATION: (1)..(237)

<400> SEQUENCE: 101
```

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
            115                 120                 125

Ile Lys Arg Thr Val Ala Ala Pro Ser Val Phe Ile Phe Pro Pro Ser
        130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
            195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

```
<210> SEQ ID NO 102
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      209 found in Table 5A and 5C
```

```
<220> FEATURE:
<221> NAME/KEY: MISC_FEATURE
<222> LOCATION: (1)..(237)

<400> SEQUENCE: 102

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Asp Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 103
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      212 found in Table 5A and 5C
<220> FEATURE:
<221> NAME/KEY: MISC_FEATURE
<222> LOCATION: (1)..(237)

<400> SEQUENCE: 103

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Ser Glu Leu Tyr Ala Gly
65                  70                  75                  80
```

```
Val Pro Ser Arg Phe Ser Gly Ser Arg Ser Gly Thr Asp Phe Thr Leu
             85                  90                  95

Thr Ile Ser Ser Leu Gln Pro Glu Asp Phe Ala Thr Tyr Tyr Cys Gln
             100                 105                 110

Gln Arg Gly Trp Tyr Leu Phe Thr Phe Gly Gln Gly Thr Lys Val Glu
             115                 120                 125

Ile Lys Arg Thr Val Ala Ala Pro Ser Val Phe Ile Phe Pro Pro Ser
     130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
             165                 170                 175

Leu Gln Ser Gly Asn Ser Gln Glu Ser Val Thr Glu Gln Asp Ser Lys
             180                 185                 190

Asp Ser Thr Tyr Ser Leu Ser Ser Thr Leu Thr Leu Ser Lys Ala Asp
             195                 200                 205

Tyr Glu Lys His Lys Val Tyr Ala Cys Glu Val Thr His Gln Gly Leu
     210                 215                 220

Ser Ser Pro Val Thr Lys Ser Phe Asn Arg Gly Glu Cys
225                 230                 235
```

<210> SEQ ID NO 104
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      213 found in Table 5A and 5C
<220> FEATURE:
<221> NAME/KEY: MISC_FEATURE
<222> LOCATION: (1)..(237)

<400> SEQUENCE: 104

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
             20                  25                  30

Ser Leu Ser Ala Ser Val Gly Asp Arg Val Thr Ile Thr Cys Arg Ala
             35                  40                  45

Ser Gln Ala Ala Tyr Gly Arg Val Ala Trp Tyr Gln Gln Lys Pro Gly
     50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
             85                  90                  95

Thr Ile Ser Ser Leu Gln Pro Glu Asp Phe Ala Thr Tyr Tyr Cys Gln
             100                 105                 110

Gln Arg Gly Trp Tyr Leu Phe Thr Phe Gly Gln Gly Thr Lys Val Glu
             115                 120                 125

Ile Lys Arg Thr Val Ala Ala Pro Ser Val Phe Ile Phe Pro Pro Ser
     130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
             165                 170                 175

Leu Gln Ser Gly Asn Ser Gln Glu Ser Val Thr Glu Gln Asp Ser Lys
```

-continued

```
                180                    185                    190

Asp Ser Thr Tyr Ser Leu Ser Ser Thr Leu Thr Leu Ser Lys Ala Asp
                195                    200                    205

Tyr Glu Lys His Lys Val Tyr Ala Cys Glu Val Thr His Gln Gly Leu
        210                    215                    220

Ser Ser Pro Val Thr Lys Ser Phe Asn Arg Gly Glu Cys
225                    230                    235
```

```
<210> SEQ ID NO 105
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      214 found in Table 5A and 5C
<220> FEATURE:
<221> NAME/KEY: MISC_FEATURE
<222> LOCATION: (1)..(237)

<400> SEQUENCE: 105
```

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
        35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
        210                 215                 220

Ser Ser Pro Val Thr Lys Ser Phe Asn Arg Gly Glu Cys
225                 230                 235
```

```
<210> SEQ ID NO 106
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      215 found in Table 5A and 5C
<220> FEATURE:
```

-continued

```
<221> NAME/KEY: MISC_FEATURE
<222> LOCATION: (1)..(237)

<400> SEQUENCE: 106

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 107
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      216 found in Table 5A and 5C
<220> FEATURE:
<221> NAME/KEY: MISC_FEATURE
<222> LOCATION: (1)..(237)

<400> SEQUENCE: 107

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
                20                  25                  30

Ser Leu Ser Ala Ser Val Gly Asp Arg Val Thr Ile Thr Cys Arg Ala
            35                  40                  45

Ser Gln Ala Ala Tyr Gly Arg Val Ala Trp Tyr Gln Gln Lys Pro Gly
        50                  55                  60

Lys Ala Pro Lys Leu Leu Ile Tyr Lys Ala Ser Glu Leu Tyr Ala Gly
65                  70                  75                  80
```

```
Val Pro Ser Arg Phe Ser Gly Ser Arg Ser Gly Thr Asp Phe Thr Leu
                85              90              95

Thr Ile Ser Ser Leu Gln Pro Glu Asp Phe Ala Thr Tyr Tyr Cys Gln
            100             105             110

Gln Arg Gly Trp Tyr Leu Phe Thr Phe Gly Gln Gly Thr Lys Val Glu
        115             120             125

Ile Lys Arg Thr Val Ala Ala Pro Ser Val Phe Ile Phe Pro Pro Ser
    130             135             140

Asp Ser Gln Leu Lys Ser Gly Thr Ala Ser Val Val Cys Leu Leu Asn
145             150             155             160

Asn Phe Tyr Pro Arg Glu Ala Lys Val Gln Trp Lys Val Asp Asn Ala
                165             170             175

Leu Gln Ser Gly Asn Ser Gln Glu Ser Val Thr Glu Gln Asp Ser Lys
            180             185             190

Asp Ser Thr Tyr Ser Leu Ser Ser Thr Leu Thr Leu Ser Lys Ala Asp
            195             200             205

Tyr Glu Lys His Lys Val Tyr Ala Cys Glu Val Thr His Gln Gly Leu
    210             215             220

Ser Ser Pro Val Thr Lys Ser Phe Asn Arg Gly Glu Cys
225             230             235
```

```
<210> SEQ ID NO 108
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      217 found in Table 5A and 5C
<220> FEATURE:
<221> NAME/KEY: MISC_FEATURE
<222> LOCATION: (1)..(237)

<400> SEQUENCE: 108
```

```
Met Lys Lys Asn Ile Ala Phe Leu Leu Ala Ser Met Phe Val Phe Ser
1               5               10              15

Ile Ala Thr Asn Ala Tyr Ala Asp Ile Gln Met Thr Gln Ser Pro Ser
            20              25              30

Ser Leu Ser Ala Ser Val Gly Asp Arg Val Thr Ile Thr Cys Arg Ala
        35              40              45

Ser Gln Asp Ala Tyr Gly Arg Val Ala Trp Tyr Gln Gln Lys Pro Gly
    50              55              60

Lys Ala Pro Lys Leu Leu Ile Tyr Lys Ala Ser Glu Leu Tyr Ala Gly
65              70              75              80

Val Pro Ser Arg Phe Ser Gly Ser Arg Ser Gly Thr Asp Phe Thr Leu
                85              90              95

Thr Ile Ser Ser Leu Gln Pro Glu Asp Phe Ala Thr Tyr Tyr Cys Gln
            100             105             110

Gln Arg Gly Trp Tyr Leu Phe Thr Phe Gly Gln Gly Thr Lys Val Glu
        115             120             125

Ile Lys Arg Thr Val Ala Ala Pro Ser Val Phe Ile Phe Pro Pro Ser
    130             135             140

Asp Ser Gln Leu Lys Ser Gly Thr Ala Ser Val Val Cys Leu Leu Asn
145             150             155             160

Asn Phe Tyr Pro Arg Glu Ala Lys Val Gln Trp Lys Val Asp Asn Ala
                165             170             175

Leu Gln Ser Gly Asn Ser Gln Glu Ser Val Thr Glu Gln Asp Ser Lys
            180             185             190
```

```
Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 109
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      218 found in Table 5A and 5C
<220> FEATURE:
<221> NAME/KEY: MISC_FEATURE
<222> LOCATION: (1)..(237)

<400> SEQUENCE: 109

```
Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
        20                  25                  30

Ser Leu Ser Ala Ser Val Gly Asp Arg Val Thr Ile Thr Cys Arg Ala
        35                  40                  45

Ser Gln Ala Ala Asp Gly Arg Val Ala Trp Tyr Gln Gln Lys Pro Gly
    50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
        100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
        180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 110
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      219 found in Table 5A and 5C
<220> FEATURE:
<221> NAME/KEY: MISC_FEATURE -continued

```
<222> LOCATION: (1)..(237)

<400> SEQUENCE: 110

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Ala Ala Tyr Gly Arg Val Ala Trp Tyr Gln Gln Lys Pro Gly
    50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
                85                  90                  95

Thr Ile Ser Ser Leu Gln Pro Glu Asp Phe Ala Thr Tyr Tyr Cys Gln
            100                 105                 110

Gln Arg Gly Trp Tyr Leu Phe Thr Phe Gly Gln Gly Thr Lys Val Glu
        115                 120                 125

Ile Lys Arg Thr Val Ala Ala Pro Ser Val Phe Ile Phe Pro Pro Ser
    130                 135                 140

Asp Ser Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 111
<211> LENGTH: 237
<212> TYPE: PRT
<213> ORGANISM: Artificial Sequence
<220> FEATURE:
<223> OTHER INFORMATION: Amino Acid Sequence (Light Chain) of Variant
      220 found in Table 5A and 5C
<220> FEATURE:
<221> NAME/KEY: MISC_FEATURE
<222> LOCATION: (1)..(237)

<400> SEQUENCE: 111

Met Lys Lys Asn Ile Ala Phe Leu Leu Ala Ser Met Phe Val Phe Ser
1               5                   10                  15

Ile Ala Thr Asn Ala Tyr Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Ala Ala Tyr Gly Asp Val Ala Trp Tyr Gln Gln Lys Pro Gly
    50                  55                  60

Lys Ala Pro Lys Leu Leu Ile Tyr Lys Ala Ser Glu Leu Tyr Ala Gly
65                  70                  75                  80

Val Pro Ser Arg Phe Ser Gly Ser Arg Ser Gly Thr Asp Phe Thr Leu
```

-continued

```
                85              90              95
Thr Ile Ser Ser Leu Gln Pro Glu Asp Phe Ala Thr Tyr Tyr Cys Gln
            100             105             110

Gln Arg Gly Trp Tyr Leu Phe Thr Phe Gly Gln Gly Thr Lys Val Glu
        115             120             125

Ile Lys Arg Thr Val Ala Ala Pro Ser Val Phe Ile Phe Pro Pro Ser
    130             135             140

Asp Ser Gln Leu Lys Ser Gly Thr Ala Ser Val Val Cys Leu Leu Asn
145             150             155             160

Asn Phe Tyr Pro Arg Glu Ala Lys Val Gln Trp Lys Val Asp Asn Ala
            165             170             175

Leu Gln Ser Gly Asn Ser Gln Glu Ser Val Thr Glu Gln Asp Ser Lys
        180             185             190

Asp Ser Thr Tyr Ser Leu Ser Ser Thr Leu Thr Leu Ser Lys Ala Asp
        195             200             205

Tyr Glu Lys His Lys Val Tyr Ala Cys Glu Val Thr His Gln Gly Leu
    210             215             220

Ser Ser Pro Val Thr Lys Ser Phe Asn Arg Gly Glu Cys
225             230             235
```

<210> SEQ ID NO 112
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 202
    found in Table 5B and 5D
<220> FEATURE:
<221> NAME/KEY: MISC_FEATURE
<222> LOCATION: (1)..(251)

<400> SEQUENCE: 112

```
Met Lys Lys Asn Ile Ala Phe Leu Leu Ala Ser Met Phe Val Phe Ser
1               5               10              15

Ile Ala Thr Asn Ala Tyr Ala Glu Val Gln Leu Val Glu Ser Gly Gly
            20              25              30

Gly Leu Val Gln Pro Gly Gly Ser Leu Arg Leu Ser Cys Ala Ala Ser
        35              40              45

Gly Phe Asp Leu Phe His Tyr Ser Ile His Trp Val Arg Gln Ala Pro
    50              55              60

Gly Lys Gly Leu Glu Trp Val Ala Tyr Ile Tyr Pro Ser Tyr Gly Tyr
65              70              75              80

Thr Tyr Tyr Ala Asp Ser Val Lys Gly Arg Phe Thr Ile Ser Ala Asp
            85              90              95

Thr Ser Lys Asn Thr Ala Tyr Leu Gln Met Asn Ser Leu Arg Ala Glu
            100             105             110

Asp Thr Ala Val Tyr Tyr Cys Ala Arg His Ala Trp Tyr Tyr Gly Trp
        115             120             125

Gly Leu Asp Tyr Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
            165             170             175

Pro Glu Pro Val Thr Val Ser Trp Asn Ser Gly Ala Leu Thr Ser Gly
        180             185             190
```

```
Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

<210> SEQ ID NO 113
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 203
      found in Table 5B and 5D

<400> SEQUENCE: 113

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe His Tyr Ser Ile His Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

<210> SEQ ID NO 114
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 204
      found in Table 5B and 5D

```
<220> FEATURE:
<221> NAME/KEY: MISC_FEATURE
<222> LOCATION: (1)..(251)

<400> SEQUENCE: 114

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
            115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250

<210> SEQ ID NO 115
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 205
      found in Table 5B and 5D
<220> FEATURE:
<221> NAME/KEY: MISC_FEATURE
<222> LOCATION: (1)..(251)

<400> SEQUENCE: 115

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60
```

```
Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
            115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

```
<210> SEQ ID NO 116
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 206
      found in Table 5B and 5D
<220> FEATURE:
<221> NAME/KEY: MISC_FEATURE
<222> LOCATION: (1)..(251)

<400> SEQUENCE: 116
```

```
Met Lys Lys Asn Ile Ala Phe Leu Leu Ala Ser Met Phe Val Phe Ser
1                   5                   10                  15

Ile Ala Thr Asn Ala Tyr Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
            115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
```

-continued

```
145                150                155                160

Thr Ser Gly Gly Thr Ala Ala Leu Gly Cys Leu Val Lys Asp Tyr Phe
                165                170                175

Pro Glu Pro Val Thr Val Ser Trp Asn Ser Gly Ala Leu Thr Ser Gly
                180                185                190

Val His Thr Phe Pro Ala Val Leu Gln Ser Ser Gly Leu Tyr Ser Leu
                195                200                205

Ser Ser Val Val Thr Val Pro Ser Ser Ser Leu Gly Thr Gln Thr Tyr
        210                215                220

Ile Cys Asn Val Asn His Lys Pro Ser Asn Thr Lys Val Asp Lys Lys
225                230                235                240

Val Glu Pro Lys Ser Cys Asp Lys Thr His Thr
                245                250

<210> SEQ ID NO 117
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 207
      found in Table 5B and 5D
<220> FEATURE:
<221> NAME/KEY: MISC_FEATURE
<222> LOCATION: (1)..(251)

<400> SEQUENCE: 117

Met Lys Lys Asn Ile Ala Phe Leu Leu Ala Ser Met Phe Val Phe Ser
1                5                10                15

Ile Ala Thr Asn Ala Tyr Ala Glu Val Gln Leu Val Glu Ser Gly Gly
                20                25                30

Gly Leu Val Gln Pro Gly Gly Ser Leu Arg Leu Ser Cys Ala Ala Ser
        35                40                45

Gly Phe Asp Leu Phe His Tyr Ser Ile His Trp Val Arg Gln Ala Pro
        50                55                60

Gly Lys Gly Leu Glu Trp Val Ala Tyr Ile Tyr Pro Ser Tyr Gly Tyr
65                70                75                80

Thr Tyr Tyr Ala Asp Ser Val Lys Gly Arg Phe Thr Ile Ser Ala Asp
                85                90                95

Thr Ser Lys Asn Thr Ala Tyr Leu Gln Met Asn Ser Leu Arg Ala Glu
                100                105                110

Asp Thr Ala Val Tyr Tyr Cys Ala Arg His Ala Trp Tyr Tyr Gly Trp
        115                120                125

Gly Leu Asp Tyr Trp Gly Gln Gly Thr Leu Val Thr Val Ser Ser Ala
        130                135                140

Ser Thr Lys Gly Pro Ser Val Phe Pro Leu Ala Pro Ser Ser Lys Ser
145                150                155                160

Thr Ser Gly Gly Thr Ala Ala Leu Gly Cys Leu Val Lys Asp Tyr Phe
                165                170                175

Pro Glu Pro Val Thr Val Ser Trp Asn Ser Gly Ala Leu Thr Ser Gly
                180                185                190

Val His Thr Phe Pro Ala Val Leu Gln Ser Ser Gly Leu Tyr Ser Leu
                195                200                205

Ser Ser Val Val Thr Val Pro Ser Ser Ser Leu Gly Thr Gln Thr Tyr
        210                215                220

Ile Cys Asn Val Asn His Lys Pro Ser Asn Thr Lys Val Asp Lys Lys
225                230                235                240
```

-continued

```
Val Glu Pro Lys Ser Cys Asp Lys Thr His Thr
            245                 250

<210> SEQ ID NO 118
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 208
      found in Table 5B and 5D
<220> FEATURE:
<221> NAME/KEY: MISC_FEATURE
<222> LOCATION: (1)..(251)

<400> SEQUENCE: 118

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe His Tyr Ser Ile His Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
            245                 250

<210> SEQ ID NO 119
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 209
      found in Table 5B and 5D
<220> FEATURE:
<221> NAME/KEY: MISC_FEATURE
<222> LOCATION: (1)..(251)

<400> SEQUENCE: 119
```

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe His Tyr Ser Ile His Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

<210> SEQ ID NO 120
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 212
    found in Table 5B and 5D
<220> FEATURE:
<221> NAME/KEY: MISC_FEATURE
<222> LOCATION: (1)..(251)

<400> SEQUENCE: 120

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe His Tyr Ser Ile Asp Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95
```

-continued

```
Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
            115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250
```

```
<210> SEQ ID NO 121
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 213
      found in Table 5B and 5D
<220> FEATURE:
<221> NAME/KEY: MISC_FEATURE
<222> LOCATION: (1)..(251)

<400> SEQUENCE: 121
```

```
Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe His Tyr Asp Ile His Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
            115                 120                 125

Gly Leu Asp Tyr Trp Gly Gln Gly Thr Leu Val Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
```

```
                180              185              190

Val His Thr Phe Pro Ala Val Leu Gln Ser Ser Gly Leu Tyr Ser Leu
        195              200              205

Ser Ser Val Val Thr Val Pro Ser Ser Ser Leu Gly Thr Gln Thr Tyr
        210              215              220

Ile Cys Asn Val Asn His Lys Pro Ser Asn Thr Lys Val Asp Lys Lys
225              230              235              240

Val Glu Pro Lys Ser Cys Asp Lys Thr His Thr
                245              250

<210> SEQ ID NO 122
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 214
      found in Table 5B and 5D
<220> FEATURE:
<221> NAME/KEY: MISC_FEATURE
<222> LOCATION: (1)..(251)

<400> SEQUENCE: 122

Met Lys Lys Asn Ile Ala Phe Leu Leu Ala Ser Met Phe Val Phe Ser
1               5               10              15

Ile Ala Thr Asn Ala Tyr Ala Glu Val Gln Leu Val Glu Ser Gly Gly
                20              25              30

Gly Leu Val Gln Pro Gly Gly Ser Leu Arg Leu Ser Cys Ala Ala Ser
        35              40              45

Gly Phe Asp Leu Phe His Asp Ser Ile His Trp Val Arg Gln Ala Pro
        50              55              60

Gly Lys Gly Leu Glu Trp Val Ala Tyr Ile Tyr Pro Ser Tyr Gly Tyr
65              70              75              80

Thr Tyr Tyr Ala Asp Ser Val Lys Gly Arg Phe Thr Ile Ser Ala Asp
                85              90              95

Thr Ser Lys Asn Thr Ala Tyr Leu Gln Met Asn Ser Leu Arg Ala Glu
                100             105             110

Asp Thr Ala Val Tyr Tyr Cys Ala Arg His Ala Trp Tyr Tyr Gly Trp
        115             120             125

Gly Leu Asp Tyr Trp Gly Gln Gly Thr Leu Val Thr Val Ser Ser Ala
        130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
                165             170             175

Pro Glu Pro Val Thr Val Ser Trp Asn Ser Gly Ala Leu Thr Ser Gly
                180             185             190

Val His Thr Phe Pro Ala Val Leu Gln Ser Ser Gly Leu Tyr Ser Leu
        195             200             205

Ser Ser Val Val Thr Val Pro Ser Ser Ser Leu Gly Thr Gln Thr Tyr
        210             215             220

Ile Cys Asn Val Asn His Lys Pro Ser Asn Thr Lys Val Asp Lys Lys
225             230             235             240

Val Glu Pro Lys Ser Cys Asp Lys Thr His Thr
                245             250

<210> SEQ ID NO 123
<211> LENGTH: 251
```

```
<212> TYPE: PRT
<213> ORGANISM: Artificial Sequence
<220> FEATURE:
<223> OTHER INFORMATION: Amino Acid Sequence (Heavy Chain) Variant 215
      found in Table 5B and 5D
<220> FEATURE:
<221> NAME/KEY: MISC_FEATURE
<222> LOCATION: (1)..(251)

<400> SEQUENCE: 123

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Asp Leu Phe Asp Tyr Ser Ile His Trp Val Arg Gln Ala Pro
    50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250

<210> SEQ ID NO 124
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 216
      found in Table 5B and 5D
<220> FEATURE:
<221> NAME/KEY: MISC_FEATURE
<222> LOCATION: (1)..(251)

<400> SEQUENCE: 124

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
            20                  25                  30
```

-continued

```
Gly Leu Val Gln Pro Gly Gly Ser Leu Arg Leu Ser Cys Ala Ala Ser
        35              40              45

Gly Phe Asp Leu Asp His Tyr Ser Ile His Trp Val Arg Gln Ala Pro
    50              55              60

Gly Lys Gly Leu Glu Trp Val Ala Tyr Ile Tyr Pro Ser Tyr Gly Tyr
65              70              75              80

Thr Tyr Tyr Ala Asp Ser Val Lys Gly Arg Phe Thr Ile Ser Ala Asp
                85              90              95

Thr Ser Lys Asn Thr Ala Tyr Leu Gln Met Asn Ser Leu Arg Ala Glu
            100             105             110

Asp Thr Ala Val Tyr Tyr Cys Ala Arg His Ala Trp Tyr Tyr Gly Trp
            115             120             125

Gly Leu Asp Tyr Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
            165             170             175

Pro Glu Pro Val Thr Val Ser Trp Asn Ser Gly Ala Leu Thr Ser Gly
            180             185             190

Val His Thr Phe Pro Ala Val Leu Gln Ser Ser Gly Leu Tyr Ser Leu
            195             200             205

Ser Ser Val Val Thr Val Pro Ser Ser Ser Leu Gly Thr Gln Thr Tyr
    210             215             220

Ile Cys Asn Val Asn His Lys Pro Ser Asn Thr Lys Val Asp Lys Lys
225             230             235             240

Val Glu Pro Lys Ser Cys Asp Lys Thr His Thr
            245             250
```

```
<210> SEQ ID NO 125
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 217
      found in Table 5B and 5D
<220> FEATURE:
<221> NAME/KEY: MISC_FEATURE
<222> LOCATION: (1)..(251)

<400> SEQUENCE: 125
```

```
Met Lys Lys Asn Ile Ala Phe Leu Leu Ala Ser Met Phe Val Phe Ser
1               5               10              15

Ile Ala Thr Asn Ala Tyr Ala Glu Val Gln Leu Val Glu Ser Gly Gly
            20              25              30

Gly Leu Val Gln Pro Gly Gly Ser Leu Arg Leu Ser Cys Ala Ala Ser
        35              40              45

Gly Phe Asp Leu Phe His Tyr Ser Ile His Trp Val Arg Gln Ala Pro
    50              55              60

Gly Lys Gly Leu Glu Trp Val Ala Tyr Ile Tyr Pro Ser Tyr Gly Tyr
65              70              75              80

Thr Tyr Tyr Ala Asp Ser Val Lys Gly Arg Phe Thr Ile Ser Ala Asp
                85              90              95

Thr Ser Lys Asn Thr Ala Tyr Leu Gln Met Asn Ser Leu Arg Ala Glu
            100             105             110

Asp Thr Ala Val Tyr Tyr Cys Ala Arg His Ala Trp Tyr Tyr Gly Trp
            115             120             125
```

-continued

```
Gly Leu Asp Tyr Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
            165             170             175

Pro Glu Pro Val Thr Val Ser Trp Asn Ser Gly Ala Leu Thr Ser Gly
            180             185             190

Val His Thr Phe Pro Ala Val Leu Gln Ser Ser Gly Leu Tyr Ser Leu
        195             200             205

Ser Ser Val Val Thr Val Pro Ser Ser Ser Leu Gly Thr Gln Thr Tyr
    210             215             220

Ile Cys Asn Val Asn His Lys Pro Ser Asn Thr Lys Val Asp Lys Lys
225             230             235             240

Val Glu Pro Lys Ser Cys Asp Lys Thr His Thr
            245             250
```

<210> SEQ ID NO 126
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 218
      found in Table 5B and 5D
<220> FEATURE:
<221> NAME/KEY: MISC_FEATURE
<222> LOCATION: (1)..(251)

<400> SEQUENCE: 126

```
Met Lys Lys Asn Ile Ala Phe Leu Leu Ala Ser Met Phe Val Phe Ser
1               5               10              15

Ile Ala Thr Asn Ala Tyr Ala Glu Val Gln Leu Val Glu Ser Gly Gly
            20              25              30

Gly Leu Val Gln Pro Gly Gly Ser Leu Arg Leu Ser Cys Ala Ala Ser
        35              40              45

Gly Phe Asp Leu Phe His Tyr Ser Ile His Trp Val Arg Gln Ala Pro
    50              55              60

Gly Lys Gly Leu Glu Trp Val Ala Tyr Ile Tyr Pro Ser Tyr Gly Tyr
65              70              75              80

Thr Tyr Tyr Ala Asp Ser Val Lys Gly Arg Phe Thr Ile Ser Ala Asp
            85              90              95

Thr Ser Lys Asn Thr Ala Tyr Leu Gln Met Asn Ser Leu Arg Ala Glu
            100             105             110

Asp Thr Ala Val Tyr Tyr Cys Ala Arg His Ala Trp Tyr Tyr Gly Trp
        115             120             125

Gly Leu Asp Tyr Trp Gly Gln Gly Thr Leu Val Thr Val Ser Ser Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
            165             170             175

Pro Glu Pro Val Thr Val Ser Trp Asn Ser Gly Ala Leu Thr Ser Gly
            180             185             190

Val His Thr Phe Pro Ala Val Leu Gln Ser Ser Gly Leu Tyr Ser Leu
        195             200             205

Ser Ser Val Val Thr Val Pro Ser Ser Ser Leu Gly Thr Gln Thr Tyr
```

-continued

```
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250

<210> SEQ ID NO 127
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 219
      found in Table 5B and 5D
<220> FEATURE:
<221> NAME/KEY: MISC_FEATURE
<222> LOCATION: (1)..(251)

<400> SEQUENCE: 127

Met Lys Lys Asn Ile Ala Phe Leu Leu Ala Ser Met Phe Val Phe Ser
1                 5                   10                  15

Ile Ala Thr Asn Ala Tyr Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250

<210> SEQ ID NO 128
<211> LENGTH: 251
<212> TYPE: PRT
<213> ORGANISM: Artificial Sequence
<220> FEATURE:
<223> OTHER INFORMATION: Amino Acid Sequence (Heavy Chain) Variant 220
      found in Table 5B and 5D
<220> FEATURE:
```

```
<221> NAME/KEY: MISC_FEATURE
<222> LOCATION: (1)..(251)

<400> SEQUENCE: 128

Met Lys Lys Asn Ile Ala Phe Leu Leu Ala Ser Met Phe Val Phe Ser
1               5                   10                  15

Ile Ala Thr Asn Ala Tyr Ala Glu Val Gln Leu Val Glu Ser Gly Gly
                20                  25                  30

Gly Leu Val Gln Pro Gly Gly Ser Leu Arg Leu Ser Cys Ala Ala Ser
            35                  40                  45

Gly Phe Asp Leu Phe His Tyr Ser Ile His Trp Val Arg Gln Ala Pro
        50                  55                  60

Gly Lys Gly Leu Glu Trp Val Ala Tyr Ile Tyr Pro Ser Tyr Gly Tyr
65                  70                  75                  80

Thr Tyr Tyr Ala Asp Ser Val Lys Gly Arg Phe Thr Ile Ser Ala Asp
                85                  90                  95

Thr Ser Lys Asn Thr Ala Tyr Leu Gln Met Asn Ser Leu Arg Ala Glu
            100                 105                 110

Asp Thr Ala Val Tyr Tyr Cys Ala Arg His Ala Trp Tyr Tyr Gly Trp
        115                 120                 125

Gly Leu Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr
                245                 250

<210> SEQ ID NO 129
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(11)

<400> SEQUENCE: 129

Arg Ala Ser Gln Ala Ala Tyr Gly Arg Val Ala
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(11)
```

-continued

<400> SEQUENCE: 130

Asp Ala Ser Gln Ala Ala Tyr Gly Arg Val Ala
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(12)

<400> SEQUENCE: 131

Arg Ala Ser Gln Asp Ala Ala Tyr Gly Arg Val Ala
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(11)

<400> SEQUENCE: 132

Arg Ala Ser Gln Asp Ala Tyr Gly Arg Val Ala
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(11)

<400> SEQUENCE: 133

Arg Ala Ser Gln Ala Ala Asp Gly Arg Val Ala
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE
<222> LOCATION: (1)..(11)

<400> SEQUENCE: 134

Arg Ala Ser Gln Ala Ala Tyr Asp Arg Val Ala
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Kabat CDRL1 of Table 5C
<220> FEATURE:
<221> NAME/KEY: MISC_FEATURE

```
<222> LOCATION: (1)..(11)

<400> SEQUENCE: 135

Arg Ala Ser Gln Ala Ala Tyr Gly Asp Val Ala
1               5                   10

<210> SEQ ID NO 136
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
<221> NAME/KEY: MISC_FEATURE
<222> LOCATION: (1)..(7)

<400> SEQUENCE: 136

Lys Ala Ser Glu Leu Tyr Ala
1               5

<210> SEQ ID NO 137
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
<221> NAME/KEY: MISC_FEATURE
<222> LOCATION: (1)..(7)

<400> SEQUENCE: 137

Lys Ala Ser Glu Leu Asp Ala
1               5

<210> SEQ ID NO 138
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
<221> NAME/KEY: MISC_FEATURE
<222> LOCATION: (1)..(7)

<400> SEQUENCE: 138

Lys Ala Ser Asp Leu Tyr Ala
1               5

<210> SEQ ID NO 139
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
<221> NAME/KEY: MISC_FEATURE
<222> LOCATION: (1)..(7)

<400> SEQUENCE: 139

Lys Ala Asp Glu Leu Tyr Ala
1               5

<210> SEQ ID NO 140
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
```

-continued

```
<221> NAME/KEY: MISC_FEATURE
<222> LOCATION: (1)..(7)

<400> SEQUENCE: 140

Lys Asp Ser Glu Leu Tyr Ala
1               5

<210> SEQ ID NO 141
<211> LENGTH: 7
<212> TYPE: PRT
<213> ORGANISM: Artificial Sequence
<220> FEATURE:
<223> OTHER INFORMATION: Kabat CDRL2 of Table 5C
<220> FEATURE:
<221> NAME/KEY: MISC_FEATURE
<222> LOCATION: (1)..(7)

<400> SEQUENCE: 141

Asp Ala Ser Glu Leu Tyr Ala
1               5

<210> SEQ ID NO 142
<211> LENGTH: 9
<212> TYPE: PRT
<213> ORGANISM: Artificial Sequence
<220> FEATURE:
<223> OTHER INFORMATION: Kabat CDRL3 of Table 5C
<220> FEATURE:
<221> NAME/KEY: MISC_FEATURE
<222> LOCATION: (1)..(9)

<400> SEQUENCE: 142

Gln Gln Arg Gly Trp Tyr Leu Phe Thr
1               5

<210> SEQ ID NO 143
<211> LENGTH: 5
<212> TYPE: PRT
<213> ORGANISM: Artificial Sequence
<220> FEATURE:
<223> OTHER INFORMATION: Kabat CDRH1 of Table 5D
<220> FEATURE:
<221> NAME/KEY: MISC_FEATURE
<222> LOCATION: (1)..(5)

<400> SEQUENCE: 143

His Tyr Ser Ile His
1               5

<210> SEQ ID NO 144
<211> LENGTH: 5
<212> TYPE: PRT
<213> ORGANISM: Artificial Sequence
<220> FEATURE:
<223> OTHER INFORMATION: Kabat CDRH1 of Table 5D
<220> FEATURE:
<221> NAME/KEY: MISC_FEATURE
<222> LOCATION: (1)..(5)

<400> SEQUENCE: 144

His Tyr Ser Ile Asp
1               5

<210> SEQ ID NO 145
<211> LENGTH: 5
<212> TYPE: PRT
<213> ORGANISM: Artificial Sequence
<220> FEATURE:
<223> OTHER INFORMATION: Kabat CDRH1 of Table 5D
```

```
<220> FEATURE:
<221> NAME/KEY: MISC_FEATURE
<222> LOCATION: (1)..(5)

<400> SEQUENCE: 145

His Tyr Asp Ile His
1               5

<210> SEQ ID NO 146
<211> LENGTH: 5
<212> TYPE: PRT
<213> ORGANISM: Artificial Sequence
<220> FEATURE:
<223> OTHER INFORMATION: Kabat CDRH1 of Table 5D
<220> FEATURE:
<221> NAME/KEY: MISC_FEATURE
<222> LOCATION: (1)..(5)

<400> SEQUENCE: 146

His Asp Ser Ile His
1               5

<210> SEQ ID NO 147
<211> LENGTH: 5
<212> TYPE: PRT
<213> ORGANISM: Artificial Sequence
<220> FEATURE:
<223> OTHER INFORMATION: Kabat CDRH1 of Table 5D
<220> FEATURE:
<221> NAME/KEY: MISC_FEATURE
<222> LOCATION: (1)..(5)

<400> SEQUENCE: 147

Asp Tyr Ser Ile His
1               5

<210> SEQ ID NO 148
<211> LENGTH: 17
<212> TYPE: PRT
<213> ORGANISM: Artificial Sequence
<220> FEATURE:
<223> OTHER INFORMATION: Kabat CDRH2 of Table 5D
<220> FEATURE:
<221> NAME/KEY: MISC_FEATURE
<222> LOCATION: (1)..(17)

<400> SEQUENCE: 148

Tyr Ile Tyr Pro Ser Tyr Gly Tyr Thr Tyr Tyr Ala Asp Ser Val Lys
1               5                   10                  15

Gly

<210> SEQ ID NO 149
<211> LENGTH: 11
<212> TYPE: PRT
<213> ORGANISM: Artificial Sequence
<220> FEATURE:
<223> OTHER INFORMATION: Kabat CDRH3 of Table 5D
<220> FEATURE:
<221> NAME/KEY: MISC_FEATURE
<222> LOCATION: (1)..(11)

<400> SEQUENCE: 149

His Ala Trp Tyr Tyr Gly Trp Gly Leu Asp Tyr
1               5                   10

<210> SEQ ID NO 150
<211> LENGTH: 11
<212> TYPE: PRT
```

-continued

```
<213> ORGANISM: Artificial Sequence
<220> FEATURE:
<223> OTHER INFORMATION: CDR-H3 Defined by Kabat
<220> FEATURE:
<221> NAME/KEY: MISC_FEATURE
<222> LOCATION: (1)..(11)

<400> SEQUENCE: 150

His Ala Trp Tyr Tyr Gly Trp Ala Phe Asp Tyr
1               5                   10

<210> SEQ ID NO 151
<211> LENGTH: 11
<212> TYPE: PRT
<213> ORGANISM: Artificial Sequence
<220> FEATURE:
<223> OTHER INFORMATION: CDR-H3 defined by Kabat
<220> FEATURE:
<221> NAME/KEY: MISC_FEATURE
<222> LOCATION: (1)..(11)

<400> SEQUENCE: 151

His Ala Trp Tyr Tyr Gly Trp Ala Leu Asp Tyr
1               5                   10

<210> SEQ ID NO 152
<211> LENGTH: 8
<212> TYPE: PRT
<213> ORGANISM: Artificial Sequence
<220> FEATURE:
<223> OTHER INFORMATION: IMGT- CDR H1 of Seq ID No. 78
<220> FEATURE:
<221> NAME/KEY: MISC_FEATURE
<222> LOCATION: (1)..(8)

<400> SEQUENCE: 152

Gly Phe Asp Leu Asp His Tyr Ser
1               5

<210> SEQ ID NO 153
<211> LENGTH: 8
<212> TYPE: PRT
<213> ORGANISM: Artificial Sequence
<220> FEATURE:
<223> OTHER INFORMATION: IMGT- CDR H2 of Seq ID No. 78.
<220> FEATURE:
<221> NAME/KEY: MISC_FEATURE
<222> LOCATION: (1)..(8)

<400> SEQUENCE: 153

Ile Tyr Pro Ser Tyr Gly Tyr Thr
1               5

<210> SEQ ID NO 154
<211> LENGTH: 13
<212> TYPE: PRT
<213> ORGANISM: Artificial Sequence
<220> FEATURE:
<223> OTHER INFORMATION: IMGT- CDR H3 of Seq ID No. 78
<220> FEATURE:
<221> NAME/KEY: MISC_FEATURE
<222> LOCATION: (1)..(13)

<400> SEQUENCE: 154

Ala Arg His Ala Trp Tyr Tyr Gly Trp Gly Leu Asp Tyr
1               5                   10

<210> SEQ ID NO 155
<211> LENGTH: 6
```

```
<212> TYPE: PRT
<213> ORGANISM: Artificial Sequence
<220> FEATURE:
<223> OTHER INFORMATION: IMGT- CDR L1 of Seq ID No. 76
<220> FEATURE:
<221> NAME/KEY: MISC_FEATURE
<222> LOCATION: (1)..(6)

<400> SEQUENCE: 155

Gln Ala Ala Tyr Gly Arg
1               5

<210> SEQ ID NO 156
<211> LENGTH: 8
<212> TYPE: PRT
<213> ORGANISM: Artificial Sequence
<220> FEATURE:
<223> OTHER INFORMATION: IMGT- CDR H1 of Seq ID No. 2
<220> FEATURE:
<221> NAME/KEY: MISC_FEATURE
<222> LOCATION: (1)..(8)

<400> SEQUENCE: 156

Gly Phe Asp Leu Phe His Tyr Ser
1               5
```